United States Patent
Soares Da Silva et al.

(10) Patent No.: US 10,975,083 B2
(45) Date of Patent: Apr. 13, 2021

(54) BLOOD-BRAIN BARRIER-PENETRANT DOPAMINE-β-HYDROXYLASE INHIBITORS

(71) Applicant: BIAL—PORTELA & Cª, S.A., S. Mamede do Coronado (PT)

(72) Inventors: Patrício Soares Da Silva, S. Mamede do Coronado (PT); Tino Rossi, S. Mamede do Coronado (PT); Laszlo Erno Kiss, S. Mamede do Coronado (PT); Alexander Beliaev, S. Mamede do Coronado (PT); Pedro Nuno Leal Palma, S. Mamede do Coronado (PT)

(73) Assignee: BIAL—PORTELA & CA, S.A., São Mamede do Coronado (PT)

( * ) Notice: Subject to any disclaimer, the term of this patent is extended or adjusted under 35 U.S.C. 154(b) by 0 days.

(21) Appl. No.: 16/335,521

(22) PCT Filed: Sep. 22, 2017

(86) PCT No.: PCT/PT2017/050022
§ 371 (c)(1),
(2) Date: Mar. 21, 2019

(87) PCT Pub. No.: WO2018/056854
PCT Pub. Date: Mar. 29, 2018

(65) Prior Publication Data
US 2019/0337950 A1    Nov. 7, 2019

(30) Foreign Application Priority Data

Sep. 23, 2016 (GB) .................................. 1616201
Aug. 29, 2017 (GB) .................................. 1713779

(51) Int. Cl.
| | | |
|---|---|---|
| C07D 487/04 | (2006.01) |
| C07D 207/06 | (2006.01) |
| C07D 207/08 | (2006.01) |
| C07D 207/27 | (2006.01) |
| C07D 405/04 | (2006.01) |
| C07D 409/04 | (2006.01) |
| A61P 25/34 | (2006.01) |
| A61P 25/36 | (2006.01) |
| A61P 25/32 | (2006.01) |
| A61P 9/12 | (2006.01) |
| A61P 9/04 | (2006.01) |

(52) U.S. Cl.
CPC .............. *C07D 487/04* (2013.01); *A61P 9/04* (2018.01); *A61P 9/12* (2018.01); *A61P 25/34* (2018.01); *C07D 207/06* (2013.01); *C07D 207/08* (2013.01); *C07D 207/27* (2013.01); *C07D 405/04* (2013.01); *C07D 409/04* (2013.01)

(58) Field of Classification Search
None
See application file for complete search history.

(56) References Cited

U.S. PATENT DOCUMENTS 3,647,790 A    3/1972  Potoski et al.
2020/0181148 A1  6/2020  Soares Da Silva et al.

FOREIGN PATENT DOCUMENTS

| WO | 1995/29165 A2 | 11/1995 | |
| WO | WO-02092019 A2 * | 11/2002 | ........... C07C 337/08 |
| WO | 2004/033447 A1 | 4/2004 | |
| WO | 2008/085008 A1 | 7/2008 | |
| WO | 2008/136695 A1 | 11/2008 | |
| WO | 2009/015248 A1 | 1/2009 | |
| WO | 2014/127350 A1 | 8/2014 | |
| WO | 2018/056854 A1 | 3/2018 | |
| WO | 2018/056855 A1 | 3/2018 | |

OTHER PUBLICATIONS

Koczka et al, Chemical Abstracts of 94:202456 (Abstract of Sejtosztodas Farmakologiaja , 8(1), 79-100) (Year: 1979).*
Koczka etal, Sejtosztodas Farmakologiaja , 8(1), 79-100 (Year: 1979).*
International Search Report for Application No. PCT/PT2017/050022, dated Nov. 24, 2017, 4 pages.
International Search Report for Application No. PCT/PT2017/050023, dated Dec. 15, 2017, 3 pages.
Beliaev et al., Dopamine beta-Monooxygenase: Mechanism, Substrates and Inhibitors. Current Enzyme Inhibition. 2009;5:27-43.
Goldstein et al., Inhibition of Dopamine-beta-Hydroxylase by Disulfiram. Life Sciences. 1964;3:763-767.
Hidaka, Fusaric (5-butylpicolinic) acid, an inhibitor of dopamine beta-hydroxylase, affects serotonin and noradrenaline. Nature. May 7, 1971;231(5297):54-5.

(Continued)

*Primary Examiner* — Zinna Northington Davis
(74) *Attorney, Agent, or Firm* — McCarter & English, LLP; Steven G. Davis; Wei Song

(57) ABSTRACT

This invention relates to: (a) compounds of formula (I) (with $R_1$ to $R_5$, n and A as defined herein) and pharmaceutically acceptable salts or solvates thereof that are useful as dopamine-β-hydroxylase inhibitors; (b) pharmaceutical compositions comprising such compounds, salts or solvates; (c) the use of such compounds, salts or solvates in therapy; (d) therapeutic methods of treatment using such compounds, salts or solvates; and (e) processes and intermediates useful for the synthesis of such compounds.

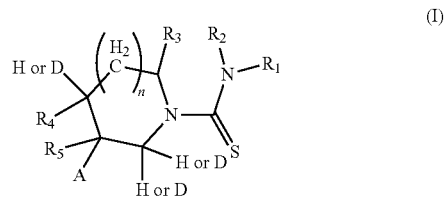

(I)

21 Claims, 4 Drawing Sheets

(56) References Cited

OTHER PUBLICATIONS

Johnson et al., In vivo inhibition of dopamine beta-hydroxylase by 1-phenyl-3-(2-thiazolyl)-2-thiourea (U-14,624). J Pharmacol Exp Ther. Jan. 1970;171(1):80-7.
Koczka et al., Adatok AZ 1,2,4-Triazol-Szarmazekok Antimikrobas Hatasahoz. (Antimicrobial Activity of 1,2,4-Triazole Derivatives.) Sejtosztodas Farmakologiaja. 1979;8(1):79-100.
Lippmann et al., Dopamine-hydroxylase inhibition by dimethyldithiocarbamate and related compounds. Biochem Pharmacol. Oct. 1969;18(10):2507-16.
Stanley et al., Catecholamine modulatory effects of nepicastat (RS-25560-197), a novel, potent and selective inhibitor of dopamine-beta-hydroxylase. Br J Pharmacol. Aug. 1997;121(8):1803-9.
U.S. Appl. No. 16/769,045, filed Jun. 2, 2020.
U.S. Appl. No. 16/335,529, filed Mar. 21, 2019, 2020-0181148.
International Search Report and Written Opinion for Application No. PCT/PT2018/050043, dated Feb. 15, 2019, 10 Pages.

\* cited by examiner

Fig. 2. Mean concentration-time profile of the compounds of Example 54, 61, 73, 74, 86 and 113 in rat plasma after oral administration of 10 mg/kg to Wistar rats. Each point represents mean ± SD of 4 rats.

Fig. 3. Mean concentration-time profile of the compounds of Example 54, 61, 73, 74, 86 and 113 in rat brain after oral administration of 10 mg/kg to Wistar rats. Each point represents mean ± SD of 4 rats.

Fig. 4. DβH activity in rat ADR after oral administration of 10 mg/kg of compounds of Example 54, 61, 73, 74, 86 and 113. Each point represents mean ± SD of 4 rats.

US 10,975,083 B2

BLOOD-BRAIN BARRIER-PENETRANT DOPAMINE-β-HYDROXYLASE INHIBITORS

CROSS-REFERENCE TO RELATED APPLICATIONS

This application is a U.S. national stage filing, under 35 U.S.C. § 371(c), of International Application No. PCT/PT2017/050022, filed on Sep. 22, 2017, which claims priority to United Kingdom Patent Application No. 1713779.5, filed on Aug. 29, 2017; and United Kingdom Patent Application No. 1616201.8, filed on Sep. 23, 2016. The entire contents of each of the aforementioned applications are incorporated herein by reference.

FIELD OF THE INVENTION

This invention relates to: (a) compounds and pharmaceutically acceptable salts or solvates thereof that are useful as dopamine-β-hydroxylase inhibitors; (b) pharmaceutical compositions comprising such compounds, salts or solvates; (c) the use of such compounds, salts or solvates in therapy; (d) therapeutic methods of treatment using such compounds, salts or solvates; and (e) processes and intermediates useful for the synthesis of such compounds.

BACKGROUND OF THE INVENTION

The enzyme dopamine-β-hydroxylase (DβH), also known as dopamine β-monooxygenase, is expressed both in the periphery and the central nervous system (CNS). DβH catalyses the specific hydroxylation of dopamine (DA) to produce norepinephrine, also known as noradrenaline (NA). As such, inhibitors of DβH can inhibit the biosynthesis of NA, limiting its concentration and increasing DA levels.

Conventionally, interest in the development of inhibitors of DβH had centred on the hypothesis that inhibition of this enzyme may provide significant clinical improvements in patients suffering from cardiovascular disorders such as hypertension or chronic heart failure.

The rationale for the use of DβH inhibitors is based on their capacity to inhibit the biosynthesis of NA, which is achieved via enzymatic hydroxylation of DA. Reduction of the biosynthesis of NA via inhibition of DβH can directly dampen sympathetic nerve function, the activation of which is the principal clinical manifestation of congestive heart failure (Parmley, W. W., Clin. Cardiol., 18: 440-445, 1995). Therefore, peripheral DβH inhibitors reduce sympathetic drive.

DβH inhibitors may also find application in disorders of the CNS, including drug addiction, psychiatric disorders, reduced cognition or dementia. For example, cocaine primarily acts through inhibition of presynaptic dopamine (DA) transporters as well as the serotonin and norepinephrine transporters. Increased levels of synaptic DA and, thereby, DA receptor binding following cocaine administration is a key mechanism through which cocaine is reinforcing. Cocaine also modulates the endogenous opioid system, especially μ-opioid receptors (MOR), κ-opioid receptors (KOR), and preprodynorphin. Whereas stimulation of dopaminergic pathways may be sufficient to cause the reinforcing effects of cocaine, DA transporter gene deletion studies have shown that this pathway is not essential to the development of cocaine self-administration. Selective gene disruption of the MOR will, however, prevent the development of cocaine self-administration.

Disulfiram (Antabuse), which inhibits aldehyde dehydrogenase (ALDH) and has been used for more than 50 years in the treatment of alcoholism (Fuller, R. K. et al., J. Amer. Med. Assoc., 256: 1449-55, 1986), was found to reduce alcohol and cocaine intake in co-dependent patient population (Carroll, K. M. et al., Arch. Gen. Psychiatry, 61: 264-72, 2000; Carroll, K. M. et al., Addiction, 93: 713-27, 1998; Carroll, K. M. et al., J. Stud. Alcohol, 54: 199-208, 1993). Surprisingly, further studies revealed that disulfiram was at least as effective at treating cocaine addicts who do not consume alcohol, and may even be more effective (Carroll, K. M. et al., Arch. Gen. Psychiatry, 61: 264-72, 2004; George, T. P. et al., Biol Psychiatry, 47: 1080-6, 2000; Petrakis, I. L. et al., Addiction, 95: 219-28, 2000). Therefore, an ALDH-independent mechanism must be responsible for the ability of disulfiram to promote cocaine abstinence (Gaval-Cruz, M. et al., Mol. Interv., 9: 175-87, 2009; Weinshenker, D. et al., Neuropsychopharmacology, 32: 1433-51, 2007). Subsequently, Schroeder et al. tested the effects of disulfiram on cocaine and food self-administration behaviour and drug-primed reinstatement of cocaine seeking in rats (Schroeder, J. P. et al., Neuropsychopharmacology, 35: 2440-9, 2010). Their results suggest that disulfiram's efficacy in the treatment of cocaine addiction is associated with the inhibition of DβH and interference with the ability of environmental stimuli to trigger relapse (Schroeder, J. P. et al., Neuropsychopharmacology, 35: 2440-9, 2010).

Furthermore, the noradrenergic system plays a role in a number of cognitive domains, including working memory, attention, and memory consolidation (Coull, J. T. et al., NeuroImage, 10: 705-15, 1999; McGaugh, J. L. et al., Psychopharmacology, 202: 3-14, 2009; Sara, S. J., Neuroscience, 10: 211-23, 2009). However, noradrenergic system activity in excess may impair cognition. Animal studies have shown associations between excess noradrenergic activity and impairments in attention and working memory (Arnsten, A. F., Nat. Rev. Neurosci., 10: 410-22, 2009; Sara, S. J., Neuroscience, 10: 211-23, 2009). Other studies show decreased cognitive performance in people placed under stress conditions, suggesting excess noradrenergic activity affects human cognition as well (Campbell, H. L. et al., Pharmacol. Biochem. Behav., 88: 222-9, 2008; Hermans, E. J. et al., Science, 334: 1151-3, 2011). Given this association between cognitive performance and noradrenergic system activity, there remains the question of whether differences in basal levels of activity may relate to differences in cognitive performance and whether this relationship is also influenced by age. Noradrenergic system activity appears higher in older compared with younger adults, both peripherally and in the CNS (Featherstone, J. A. et al., J. Gerontol., 42, 271-6, 1987; Lawlor, B. A. et al., Biol. Psychiatry, 38: 185-8, 1995; Supiano, M. A. et al., Am. J. Physiol., 259: E422-31, 1990). Previously it has been demonstrated that the concentration of cerebrospinal fluid NA was higher in older compared with younger adults, but it is not known whether noradrenergic system age differences may be a factor in cognitive differences. Numerous studies have linked excess noradrenergic activity with cognitive impairment. As such, DβH inhibitors may find application in enhancing cognition, especially in those suffering from dementia, including frontotemporal dementia (FTD), Parkinson disease and Alzheimer disease (AD), or Mild Cognitive Impairment (MCI).

Several inhibitors of DβH have been thus far reported in the literature. Early first and second generation examples such as disulfiram (Goldstein, M. et al., Life Sci., 3:763, 1964) and diethyldithiocarbamate (Lippmann, W. et al., Biochem. Pharmacol., 18: 2507, 1969) or fusaric acid (Hidaka, H. Nature, 231, 1971) and aromatic or alkyl thioureas (Johnson, G. A. et al, J. Pharmacol. Exp. Ther., 171: 80, 1970) were found to be of low potency, exhibited poor selectivity for DβH and caused toxic side effects. The third generation of DβH inhibitors, however, were found to have much greater potency, such as, for example, nepicastat (RS-25560-197, $IC_{50}$ 9 nM) (Stanley, W. C., et al., Br. J. Pharmacol., 121: 1803-1809, 1997), which was developed to early clinical trials. Although it was initially developed for peripheral indications (hypertension and congestive heart failure), an important discovery was that nepicastat was found to cross the blood-brain barrier (BBB), and was thereby able to cause central as well as peripheral effects.

Nepicastat and its analogues are disclosed in WO95/29165. Furthermore, WO 2004/033447 and WO 2008/136695 disclose DβH inhibitors having high potency and significantly reduced brain access, giving rise to potent and peripherally selective DβH inhibitors. However, these compounds would either not exhibit an effect in the CNS or would act primarily in the periphery, potentially resulting in unwanted secondary effects in the cardiovascular system or systemic tissues such as reduced sympathetic drive. A review of the mechanism, substrates and inhibitors of DβH, is given by Beliaev, A., et al. in Current Enzyme Inhibition, 5, 27-43, 2009.

Therefore, there remains an unfulfilled clinical requirement for a potent, non-toxic and CNS-penetrant/active inhibitor of DβH with suitable pharmacokinetic properties, which could be used for treatment of certain CNS disorders, including cocaine addiction, alcohol addiction, adjunct opioid addiction, cognition decline in FTD, cognition decline in MCI, cognition decline in AD, attention deficit-hyperactive disorder (ADHD), post-traumatic stress disorder (PTSD) and unipolar depression. A DβH inhibitor with similar or even greater potency than nepicastat and with beneficial CNS effects—including the ability to cross the BBB and exhibit a long residence time in the brain so as to provide a long duration of DβH inhibition in the CNS—would provide a significant improvement over all DβH inhibitor compounds thus far described in the prior art. Additionally, such compounds would preferably be orally bioavailable and easier and cheaper to synthesise.

During a SciFinder search, the following compounds were identified as commercially available. However, no reference was made to their disclosure in the scientific or patent literature.

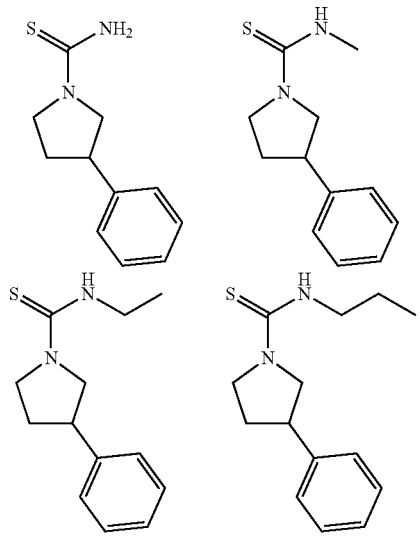

-continued

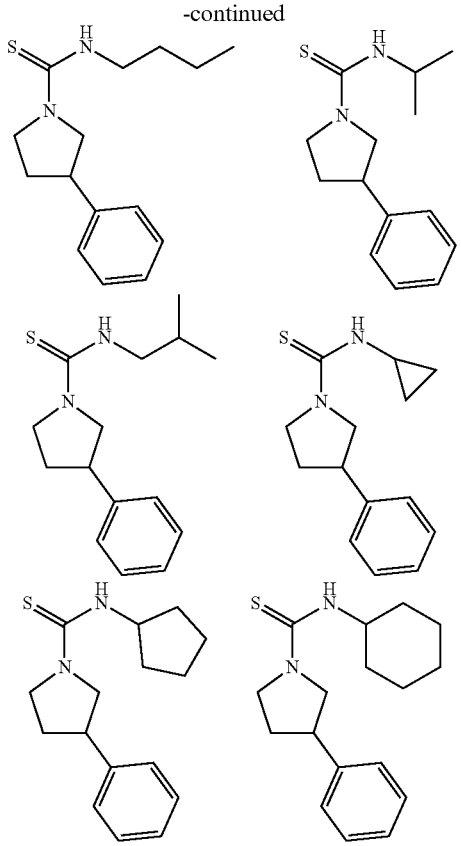

Sejtosztodas Farmakologiaja (1979), 8(1), 79-100 discusses the antimicrobial effect of certain 1,2,4-triazoles and discloses the compound 6-(4-chlorophenyl)-2,5,6,7-tetrahydro-3H-pyrrolo[2,1-c]-1,2,4-triazole-3-thione which is not within the scope of the present invention.

WO 2014/127350 A1 discloses a genus of compounds that are modulators, such as positive allosteric modulators, of one or more subclasses of vasopressin receptors. The genus disclosed in this publication overlaps to a small extent with the genus of the present invention. However, multiple selections of non-preferred embodiments within the genus of WO 2014/127350 A1 would be required to arrive at a compound of the present invention.

SUMMARY OF THE INVENTION

The present invention provides a compound of formula I, or a pharmaceutically acceptable salt or solvate thereof:

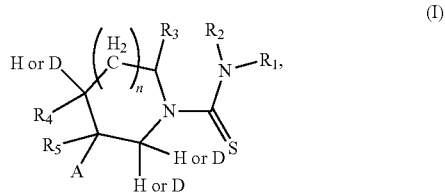

wherein:
$R_1$ is hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl or amino;

$R_2$ is hydrogen or $C_1$-$C_3$ alkyl;

$R_3$ is hydrogen or oxo;

or $R_2$ and $R_3$ combine to form a structure of formula Ia:

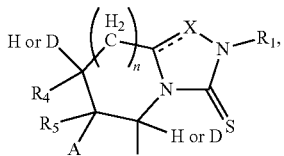

(Ia)

wherein:

X is $CH_2$, $CR_6$ or N;

≡≡≡≡ is a double bond when X is $CR_6$ or N and is a single bond when X is $CH_2$;

$R_4$ is hydrogen or $C_1$-$C_3$ alkyl;

$R_5$ is hydrogen or $C_1$-$C_2$ alkyl;

or $R_4$ and $R_5$ combine, together with the carbon atom to which they are attached, to form a cyclopropyl ring wherein the $CH_2$ moiety is optionally substituted with two deuterium (D) atoms;

$R_6$ is hydrogen;

A is $C_5$-$C_7$ cycloalkyl, furanyl, thiophenyl, methylthiophenyl or

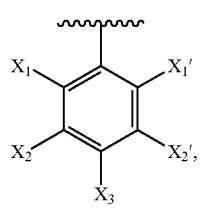

wherein:

$X_1$ is hydrogen, halo or methyl;

$X_1'$ is hydrogen or halo;

$X_2$ is hydrogen, halo or methyl;

$X_2'$ is hydrogen or halo;

$X_3$ is hydrogen or fluoro;

n is 0 or 1, and when n is 0 a single or double bond joins the carbon atoms to which $R_3$ and $R_4$ are attached;

for use in therapy.

This invention is also directed to compounds of formula I, as defined above, or a pharmaceutically acceptable salt or solvate thereof, per se, provided that the following compounds are excluded:

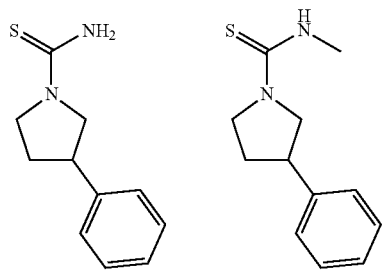

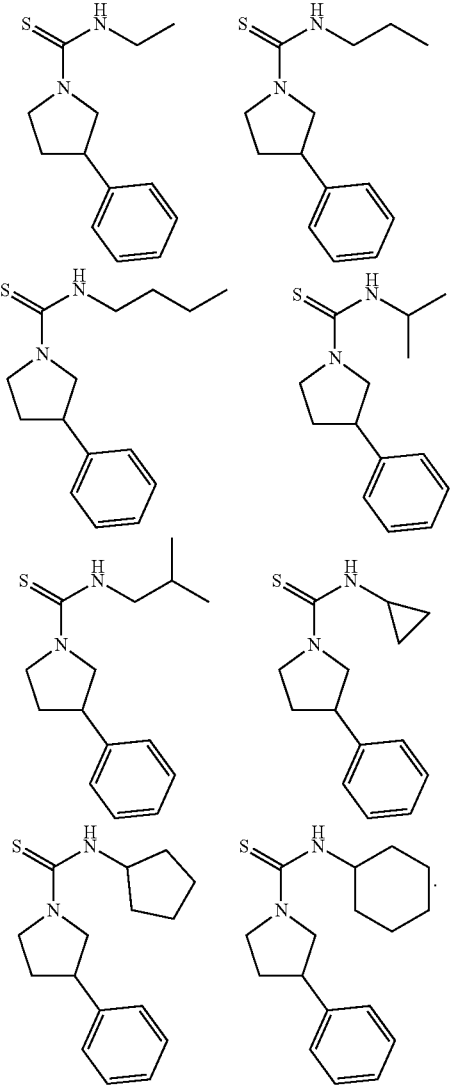

This invention is also directed to compounds of formula I, as defined above, or a pharmaceutically acceptable salt or solvate thereof, for use in the treatment of conditions ameliorated by inhibition of DβH within the CNS.

This invention is also directed to compounds of formula I, as defined above, or a pharmaceutically acceptable salt or solvate thereof, in the manufacture of a medicament for treatment of conditions ameliorated by inhibition of DβH within the CNS.

This invention is also directed to a method for treating or preventing conditions ameliorated by inhibition of DβH within the CNS comprising administering a therapeutically effective amount of a compound of formula I, as defined above, or a pharmaceutically acceptable salt or solvate thereof, to a patient in need thereof.

This invention is also directed to a pharmaceutical composition comprising (i) a therapeutically effective amount of a compound of formula I, as defined above, or a pharmaceutically acceptable salt or solvate thereof; and (ii) a pharmaceutically acceptable excipient.

DETAILED DESCRIPTION OF THE EMBODIMENTS

A. Definitions

Figure 1:
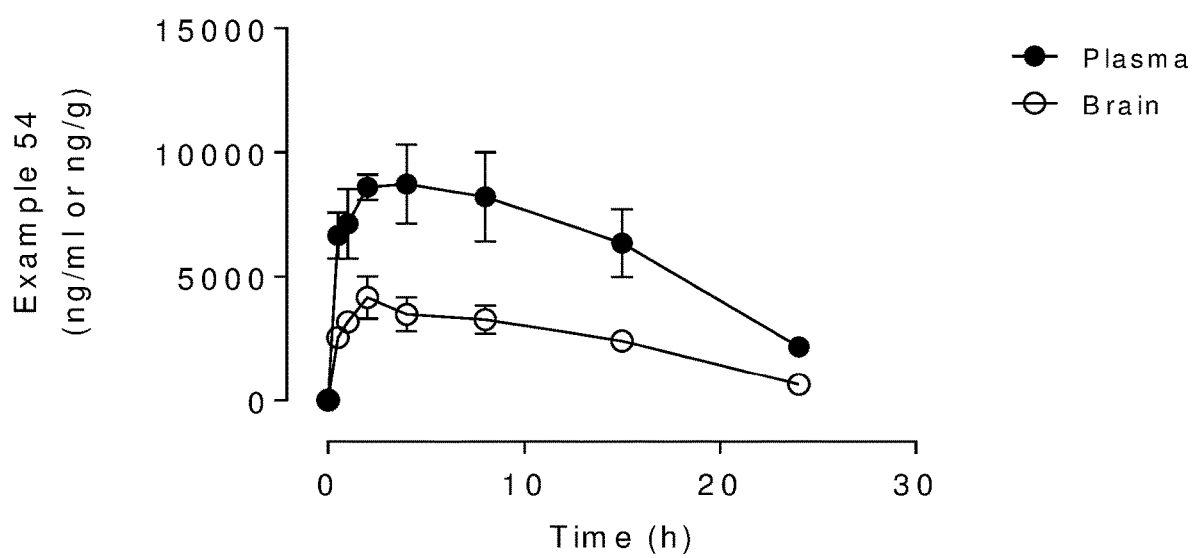
FIG. 1 shows mean concentration-time profile of the compound of Example 54 in plasma and brain after oral administration of 10 mg/kg to Wistar rats. Each point represents mean±SD of 4 rats.

"$C_1$-$C_6$ alkyl" means a monovalent unsubstituted saturated straight-chain or branched-chain hydrocarbon radical having from 1 to 6 carbon atoms. "$C_1$-$C_2$ alkyl", "$C_1$-$C_3$ alkyl", "$C_1$-$C_4$ alkyl" and "$C_1$-$C_5$ alkyl" have analogous meanings.

"partially or fully deuterated $C_1$-$C_6$ alkyl" means a $C_1$-$C_6$ alkyl wherein some or all of the hydrogen atoms, respectively, have been selectively replaced by deuterium.

"$C_3$-$C_6$ cycloalkyl" means a monovalent unsubstituted saturated cyclic hydrocarbon radical having from 3 to 6 carbon atoms. "$C_5$-$C_7$ cycloalkyl" has analogous meaning.

"$C_2$-$C_6$ cyanoalkyl" means a monovalent cyano-substituted saturated straight-chain or branched-chain hydrocarbon radical having from 2 to 6 carbon atoms including that which forms the cyano group.

"$C_1$-$C_6$ mercaptoalkyl" means a monovalent thiol-substituted saturated straight-chain or branched-chain hydrocarbon radical having from 1 to 6 carbon atoms.

"oxo" means an oxo radical, and may be depicted as =O.

"halo" means a fluorine (which may be depicted as —F), chlorine (which may be depicted as —Cl), bromine (which may be depicted as —Br) or iodine (which may be depicted as —I) radical.

"amino" means —$NH_2$.

"Pharmaceutically acceptable salt" means a salt such as those described in standard texts on salt formation, see for example: P. Stahl, et al., Handbook of Pharmaceutical Salts: Properties, Selection and Use (VCHA/Wiley-VCH, 2002), or S. M. Berge, et al., "Pharmaceutical Salts" (1977) *Journal of Pharmaceutical Sciences*, 66, 1-19.

"Pharmaceutically acceptable solvate" means a molecular complex comprising the compound of the invention and one or more pharmaceutically acceptable solvent molecules, for example, water or ethanol. The term "hydrate" may be employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

"Pharmaceutically acceptable excipient" means any ingredient of a pharmaceutical composition other than the compound(s) of the invention, or other known pharmacologically active components. The choice of excipient will to a large extent depend on factors such as the particular mode of administration, the effect of the excipient on solubility and stability, and the nature of the dosage form.

"Therapy", "treatment" and "treating" include both preventative and curative treatment of a condition, disease or disorder. It also includes slowing, interrupting, controlling or stopping the progression of a condition, disease or disorder. It also includes preventing, curing, slowing, interrupting, controlling or stopping the symptoms of a condition, disease or disorder.

Other variations to the disclosed embodiments can be understood and effected by those skilled in the art in practicing the claimed invention, from a study of the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

B. Compounds

The invention provides a compound of formula I, as defined above, or a pharmaceutically acceptable salt or solvate thereof:

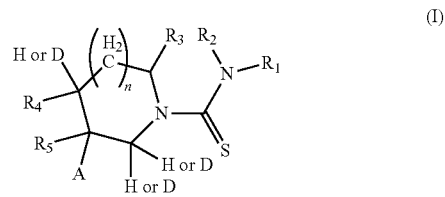

with the proviso that the following compounds are excluded:

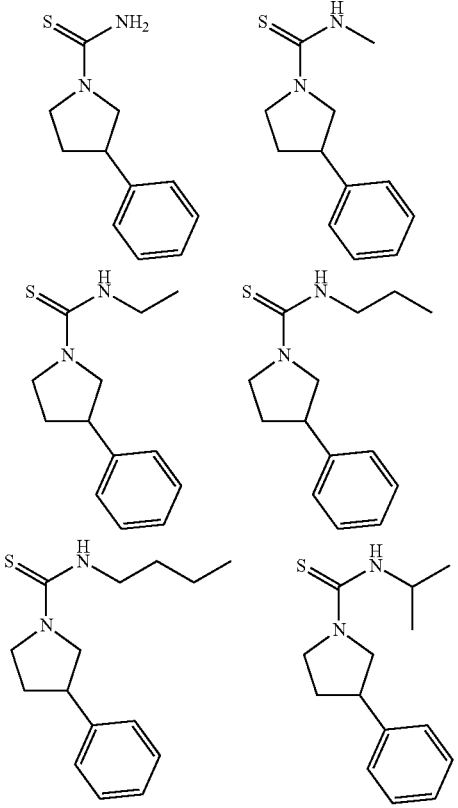

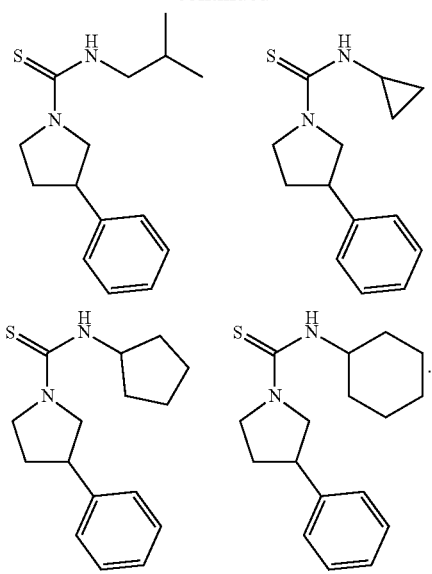

B0. Core Structures

In some embodiments $R_2$ is hydrogen or $C_1$-$C_3$ alkyl; and $R_3$ is hydrogen or oxo to form a structure of formula I1 to I4:

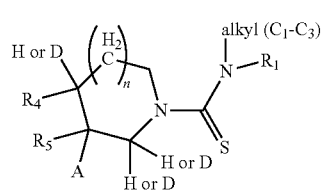

(I1)

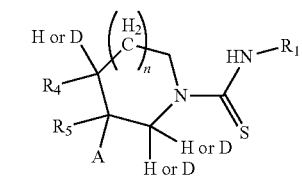

(I2)

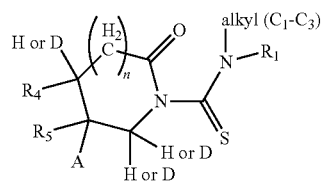

(I3)

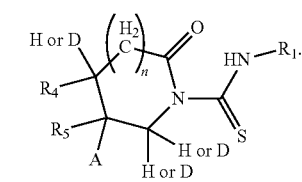

(I4)

Structure I2 is particularly preferred.

In some embodiments $R_2$ and $R_3$ of formula I combine to form a structure of formula Ia:

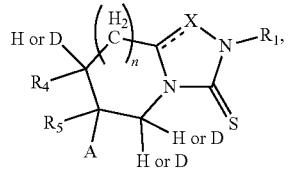

(Ia)

wherein:
X is $CH_2$, $CR_6$ or N;
▬▬▬ is a double bond when X is $CR_6$ or N and is a single bond when X is $CH_2$.

In some of these embodiments ▬▬▬ is a double bond and X is N.

In some of these embodiments ▬▬▬ is a double bond and X is $CR_6$. This embodiment is particularly preferred.

In some of these embodiments ▬▬▬ is a single bond and X is $CH_2$.

In some embodiments of formula I, n is 0 and a single bond joins the carbon atoms to which $R_3$ and $R_4$ are attached to form a structure of formula Ib

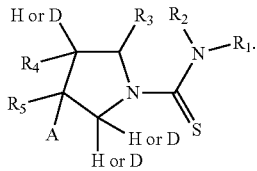

(Ib)

In some embodiments of formula I, $R_4$ and $R_5$ combine, together with the carbon atom to which they are attached, to form a structure of formula Ic having a cyclopropyl ring wherein the $CH_2$ moiety is optionally substituted with two deuterium atoms:

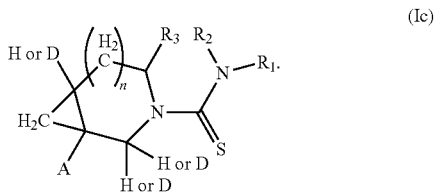

(Ic)

In some embodiments more than 50%, preferably more than 90%, more preferably more than 95% and even more preferably more than 99% of substituents $R_5$ and A of compounds of formula I have the stereochemical configuration of formula Id

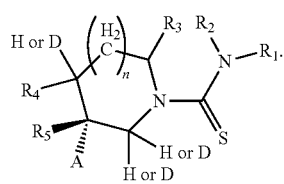

(Id)

In some embodiments more than 50%, preferably more than 90%, more preferably more than 95% and even more preferably more than 99% of substituents $R_5$ and A of compounds of formula I have the stereochemical configuration of formula Ie

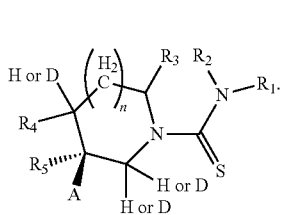

(Ie)

Preferred embodiments of formula I include compounds of formula If, Ig and Ih. Formula Ih is particularly preferred.

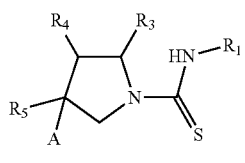

(If)

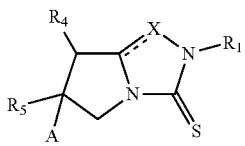

(Ig)

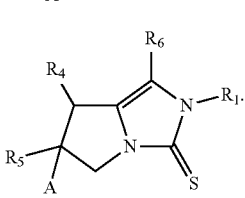

(Ih)

In some particularly preferred embodiments of formula If, Ig and Ih more than 50%, preferably more than 90%, more preferably more than 95% and even more preferably more than 99% have the stereochemical configuration of formulas Is, It and Iu. Formula Iu is particularly preferred.

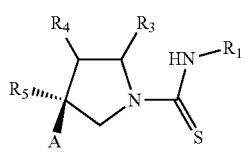

(Is)

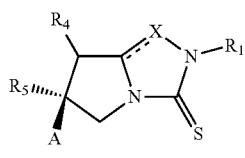

(It)

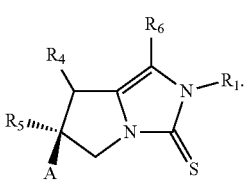

(Iu)

Other preferred embodiments of formula I include compounds of formula Ii, Ij and Ik. Formula Ik is particularly preferred.

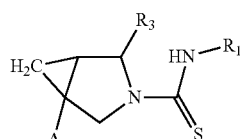

(Ii)

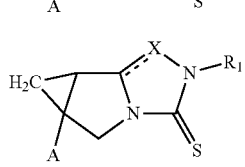

(Ij)

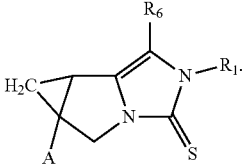

(Ik)

In some particularly preferred embodiments of formula Ii, Ij and Ik more than 50%, preferably more than 90%, more preferably more than 95% and even more preferably more than 99% have the stereochemical configuration of formulas Il, Im and In. Formula In is particularly preferred.

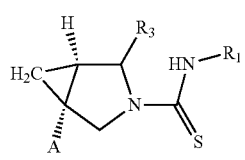

(Il)

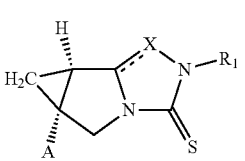

(Im)

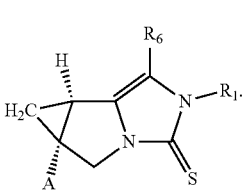

(In)

B1. Substituent $R_1$ $R_1$ is selected from the group consisting of hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl and amino.

$R_1$ is preferably selected from the group consisting of hydrogen and $C_1$-$C_6$ alkyl.

In some embodiments $R_1$ is hydrogen.

In some embodiments $R_1$ is $C_1$-$C_6$ alkyl.

In some embodiments $R_1$ is partially deuterated $C_1$-$C_6$ alkyl.

In some embodiments $R_1$ is fully deuterated $C_1$-$C_6$ alkyl.

In some embodiments $R_1$ is $C_3$-$C_6$ cycloalkyl.

In some embodiments $R_1$ is $C_2$-$C_6$ cyanoalkyl.
In some embodiments $R_1$ is $C_1$-$C_6$ mercaptoalkyl.
In some embodiments $R_1$ is amino.

$R_1$ is preferably selected from the group consisting of hydrogen, methyl, $d_3$-methyl, propyl, cyclopropyl, cyanomethyl, mercaptoethyl and amino.

$R_1$ is more preferably selected from the group consisting of hydrogen and methyl.

In some embodiments $R_1$ is preferably hydrogen.
In some embodiments $R_1$ is preferably methyl.
In some embodiments $R_1$ is preferably $d_3$-methyl.
In some embodiments $R_1$ is preferably propyl.
In some embodiments $R_1$ is preferably cyclopropyl.
In some embodiments $R_1$ is preferably cyanomethyl.
In some embodiments $R_1$ is preferably mercaptoethyl.
In some embodiments $R_1$ is preferably amino.
$R_1$ is most preferably hydrogen.

B2. Substituent $R_2$ (when not combined with $R_3$)
$R_2$ is selected from the group consisting of hydrogen and $C_1$-$C_3$ alkyl.
In some embodiments $R_2$ is hydrogen.
In some embodiments $R_2$ is $C_1$-$C_3$ alkyl.
$R_2$ is preferably selected from the group consisting of hydrogen and methyl.
In some embodiments $R_2$ is preferably hydrogen.
In some embodiments $R_2$ is preferably methyl.
$R_2$ is most preferably hydrogen.

B3. Substituent $R_3$ (when not combined with $R_2$)
$R_3$ is selected from the group consisting of hydrogen and oxo.
In some embodiments $R_3$ is hydrogen.
In some embodiments $R_3$ is oxo.
$R_3$ is preferably hydrogen.

B4. Substituent $R_4$ (when not combined with $R_5$)
$R_4$ is selected from the group consisting of hydrogen and $C_1$-$C_3$ alkyl.
In some embodiments $R_4$ is hydrogen.
In some embodiments $R_4$ is $C_1$-$C_3$ alkyl.
$R_4$ is preferably selected from the group consisting of hydrogen and methyl.
In some embodiments $R_4$ is preferably hydrogen.
In some embodiments $R_4$ is preferably methyl.
$R_4$ is most preferably hydrogen.

B5. Substituent $R_5$ (when not combined with $R_4$) $R_5$ is selected from the group consisting of hydrogen and $C_1$-$C_2$ alkyl.
In some embodiments $R_5$ is hydrogen.
In some embodiments $R_5$ is $C_1$-$C_2$ alkyl.
$R_5$ is preferably selected from the group consisting of hydrogen and methyl.
In some embodiments $R_5$ is preferably hydrogen.
In some embodiments $R_5$ is preferably methyl.
$R_5$ is most preferably hydrogen.

B6. Substituent $R_6$
$R_6$ is hydrogen.

B7. Substituent A
A is selected from the group consisting of $C_5$-$C_7$ cycloalkyl, furanyl, thiophenyl, methylthiophenyl and

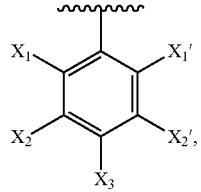

wherein:
$X_1$ is hydrogen, halo or methyl;
$X_1'$ is hydrogen or halo;
$X_2$ is hydrogen, halo or methyl;
$X_2'$ is hydrogen or halo; and
$X_3$ is hydrogen or fluoro.

Preferably A is

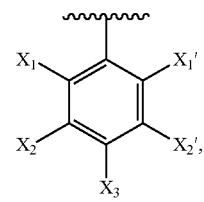

wherein $X_1$, $X_1'$, $X_2$, $X_2'$ and $X_3$ are as defined above.

More preferably A is

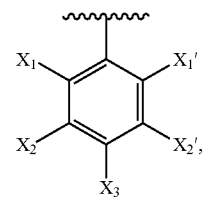

wherein:
$X_1$ is hydrogen, fluoro, chloro or methyl;
$X_1'$ is hydrogen, fluoro or chloro;
$X_2$ is hydrogen, fluoro, chloro, bromo or methyl;
$X_2'$ is hydrogen, fluoro, chloro or bromo; and
$X_3$ is hydrogen or fluoro.

In one preferred embodiment not all of $X_1$, $X_1'$, $X_2$, $X_2'$ and $X_3$ are hydrogen.

Preferably A is selected from the group consisting of

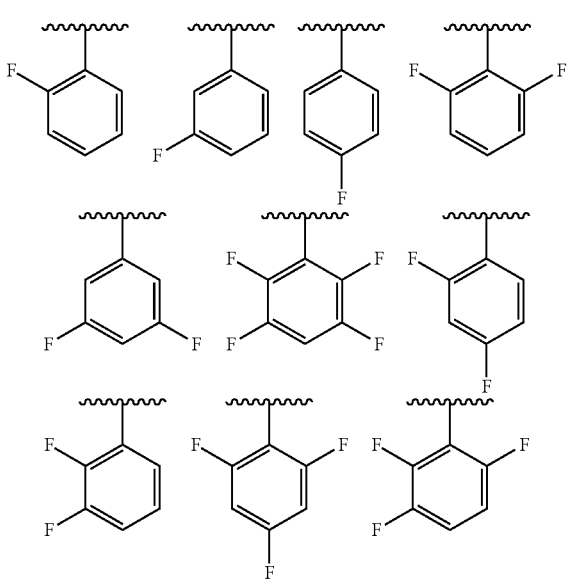

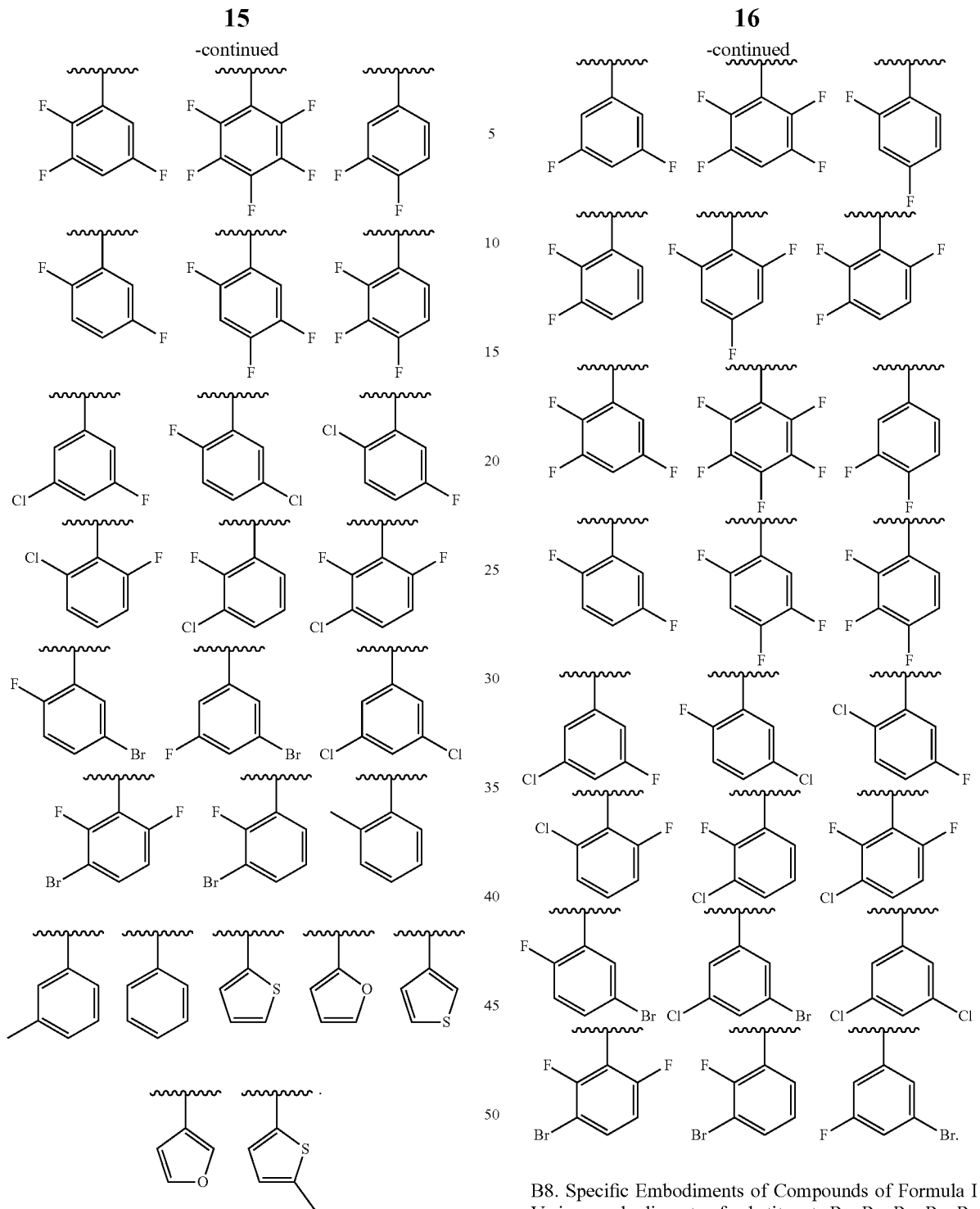

Most preferably A is selected from the group consisting of

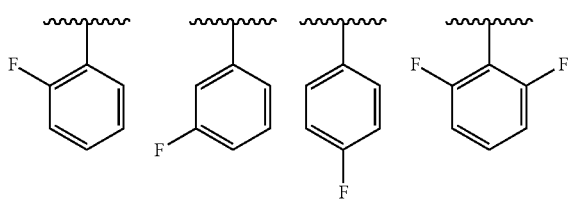

B8. Specific Embodiments of Compounds of Formula I

Various embodiments of substituents $R_1$, $R_2$, $R_3$, $R_4$, $R_5$, $R_6$, A, X, $X_1$, $X_1'$, $X_2$, $X_2'$ and $X_3$ have been discussed in B1 to B7 above. These "substituent" embodiments can be combined with any of the "core structure" embodiments, discussed in B0 above, to form further embodiments of compounds of formula I. All embodiments of compounds of formula I formed by combining the "substituent" embodiments and "core structure" embodiments, discussed above, are within the scope of Applicants' invention, and some preferred further embodiments of the compounds of formula I are provided below.

In some embodiments of formula I, structures of formula If, Ii, and Il are highly preferred

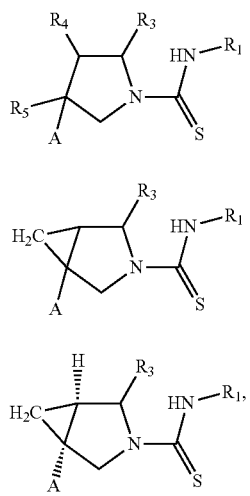

(If)

(Ii)

(II)

wherein:

R₁ is selected from the group consisting of hydrogen and methyl;

R₃ is selected from the group consisting of hydrogen and oxo;

R₄ (if present) is selected from the group consisting of hydrogen and methyl;

R₅ (if present) is selected from the group consisting of hydrogen and methyl; and A is selected from the group consisting of

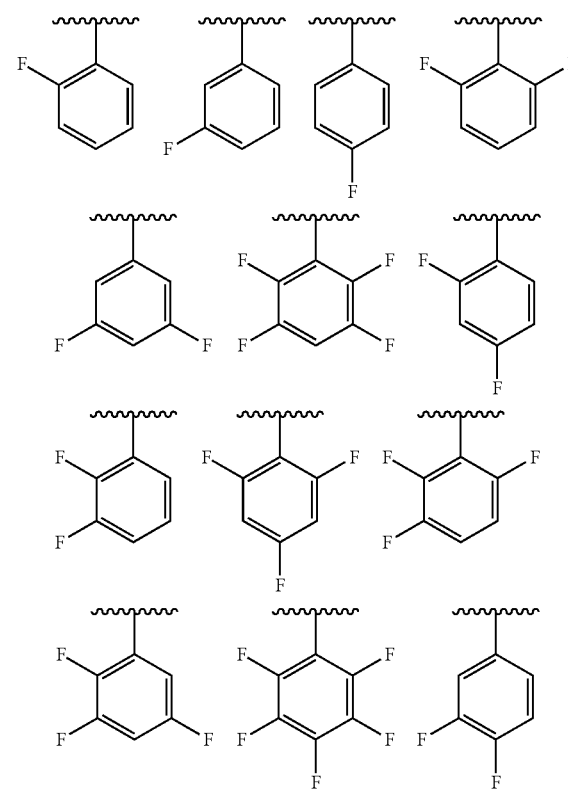

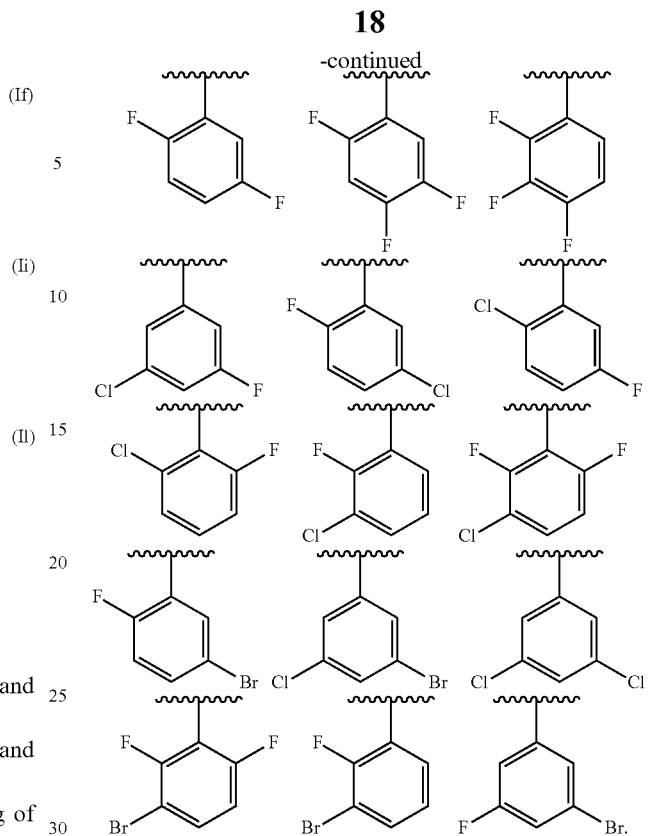

In some embodiments of formula I, structures of formula Ih, Ik, and In (in particular formula Ih) are highly preferred

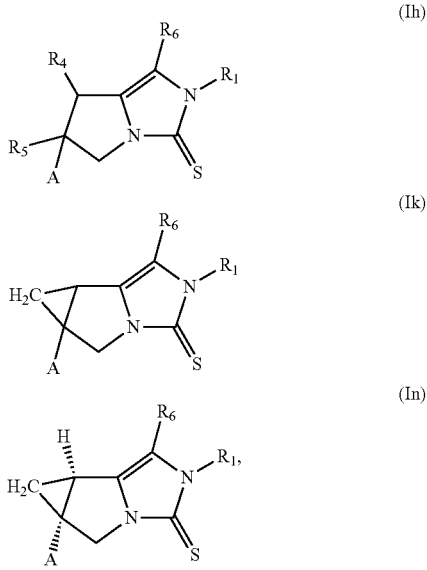

(Ih)

(Ik)

(In)

wherein:

R₁ is selected from the group consisting of hydrogen and methyl;

R₄ (if present) is selected from the group consisting of hydrogen and methyl;

R₅ (if present) is selected from the group consisting of hydrogen and methyl;

R₆ is hydrogen; and

A is selected from the group consisting of

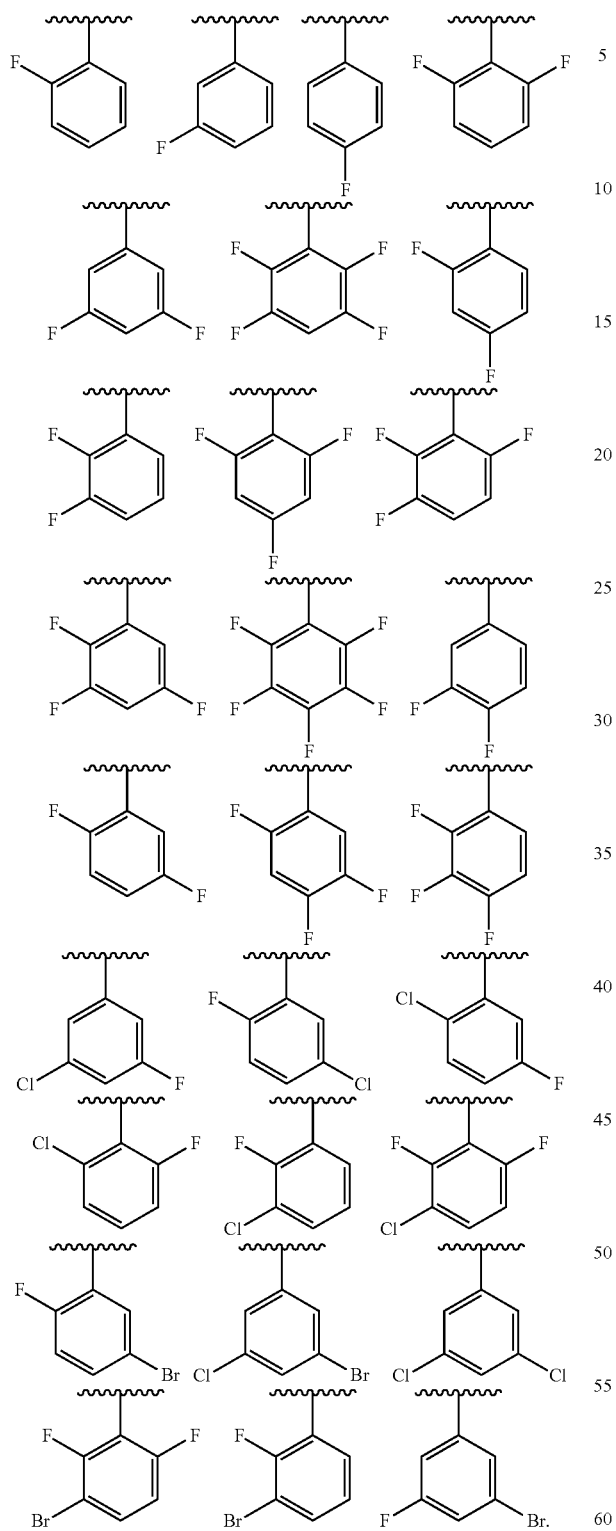

In some embodiments of formula I, structures of formula Ih wherein more than 50%, preferably more than 90%, more preferably more than 95% and even more preferably more than 99% have the stereochemical configuration of formula Iu are even more highly preferred

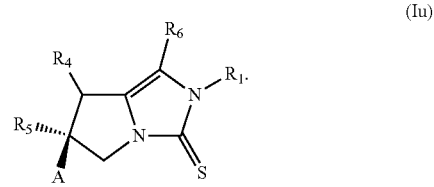

wherein:

$R_1$ is selected from the group consisting of hydrogen and methyl;

$R_4$ is selected from the group consisting of hydrogen and methyl;

$R_5$ is selected from the group consisting of hydrogen and methyl;

$R_6$ is hydrogen; and

A is selected from the group consisting of

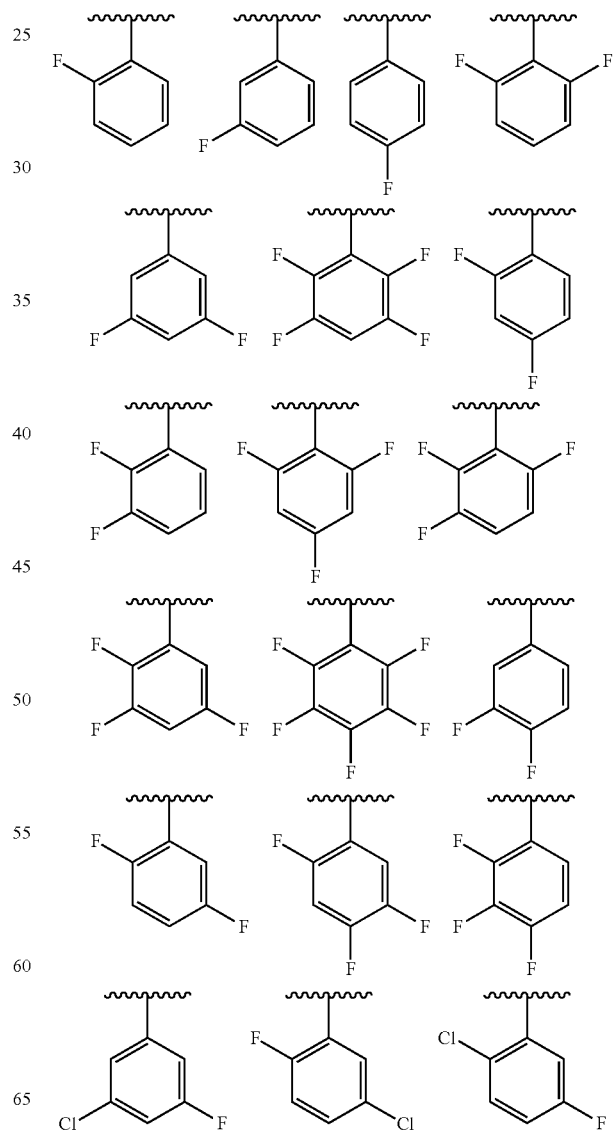

-continued

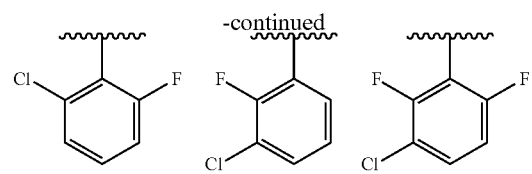

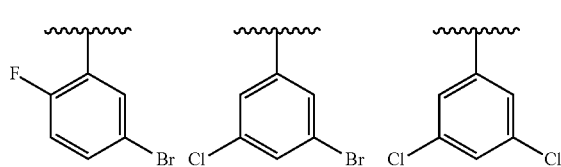

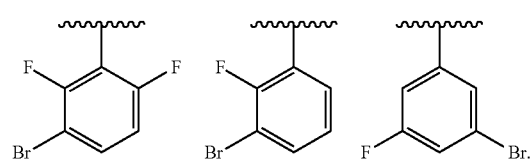

In some embodiments of formula I, structures of formula Io, Ip and Iq (in particular formula Io) are even more highly preferred

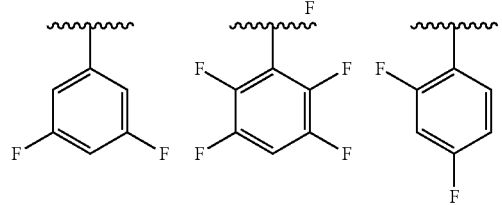

(Io)

(Ip)

(Iq)

wherein:

A is selected from the group consisting of

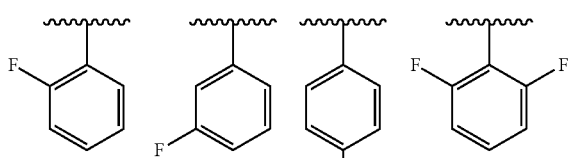

-continued

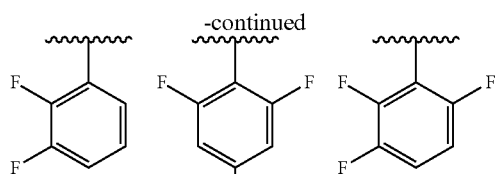

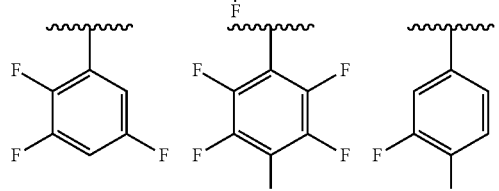

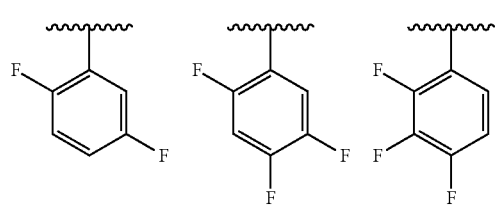

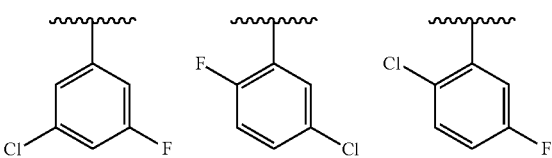

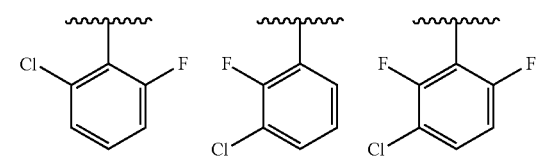

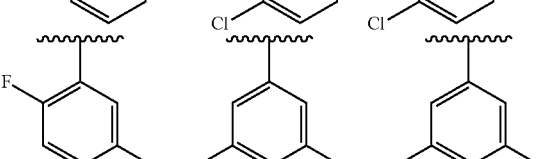

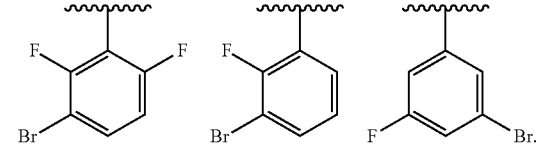

In some embodiments of formula I, structures of formula Io wherein more than 50%, preferably more than 90%, more preferably more than 95% and even more preferably more than 99% have the stereochemical configuration of formula Iv are even more highly preferred (Iv)

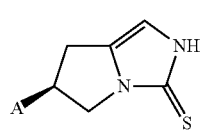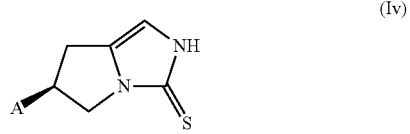

wherein:
A is selected from the group consisting of

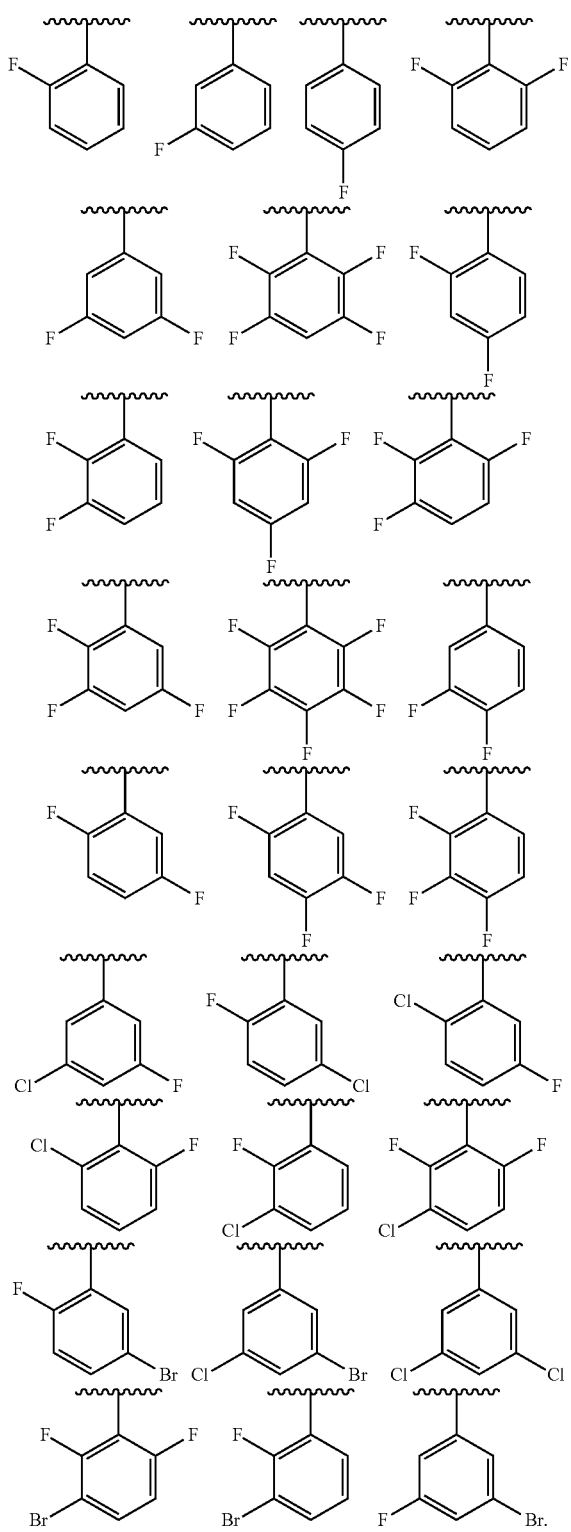

The following compounds represent specific embodiments of the invention:
3-Phenylpyrrolidine-1-carbothioamide;
3-(thiophen-2-yl)pyrrolidine-1-carbothioamide;
3-(4-Fluorophenyl)pyrrolidine-1-carbothioamide;
3-phenylpiperidine-1-carbothioamide;
3-(2,4-difluorophenyl)pyrrolidine-1-carbothioamide;
(S)-3-phenylpyrrolidine-1-carbothioamide;
3-methyl-3-phenylpyrrolidine-1-carbothioamide;
1-phenyl-3-azabicyclo[3.1.0]hexane-3-carbothioamide;
3-cyclohexylpyrrolidine-1-carbothioamide;
3-(5-methylthiophen-2-yl)pyrrolidine-1-carbothioamide;
(R)-3-phenylpyrrolidine-1-carbothioamide;
3-(3,5-Difluorophenyl)pyrrolidine-1-carbothioamide;
3-o-tolylpyrrolidine-1-carbothioamide;
3-m-tolylpyrrolidine-1-carbothioamide;
3-(thiophen-3-yl)pyrrolidine-1-carbothioamide;
3-(furan-3-yl)pyrrolidine-1-carbothioamide;
3-(furan-2-yl)pyrrolidine-1-carbothioamide;
3-(2,5-difluorophenyl)pyrrolidine-1-carbothioamide;
3-(2,4,5-trifluorophenyl)pyrrolidine-1-carbothioamide;
3-(3,4-difluorophenyl)pyrrolidine-1-carbothioamide;
(S)-3-(2,4,6-trifluorophenyl)pyrrolidine-1-carbothioamide;
3-(2,3,4-trifluorophenyl)pyrrolidine-1-carbothioamide;
3-(2,3,5,6-Tetrafluorophenyl)pyrrolidine-1-carbothioamide;
3-(2,3,5-trifluorophenyl)pyrrolidine-1-carbothioamide;
(S)-3-(3,5-difluorophenyl)pyrrolidine-1-carbothioamide;
(R)-3-(3,5-difluorophenyl)pyrrolidine-1-carbothioamide;
(1S,5S)-1-(thiophen-2-yl)-3-azabicyclo[3.1.0]hexane-3-carbothioamide;
(1R,5R)-1-(thiophen-2-yl)-3-azabicyclo[3.1.0]hexane-3-carbothioamide;
3-(perfluorophenyl)pyrrolidine-1-carbothioamide;
(1S,5R)-1-(3,5-Difluorophenyl)-N-methyl-3-azabicyclo[3.1.0]hexane-3-carbothioamide;
N-methyl-3-phenylpyrrolidine-1-carbothioamide;
3-(3,5-difluorophenyl)-N-methylpyrrolidine-1-carbothioamide;
N-methyl-3-(2,3,5,6-tetrafluorophenyl)pyrrolidine-1-carbothioamide;
1-(3,5-difluorophenyl)-3-azabicyclo[3.1.0]hexane-3-carbothioamide;
(1R,5S)-1-(3,5-difluorophenyl)-3-azabicyclo[3.1.0]hexane-3-carbothioamide;
(1S,5R)-1-(3,5-difluorophenyl)-3-azabicyclo[3.1.0]hexane-3-carbothioamide;
1-(2,4-difluorophenyl)-3-azabicyclo[3.1.0]hexane-3-carbothioamide;
1-(2,5-difluorophenyl)-3-azabicyclo[3.1.0]hexane-3-carbothioamide;
(1S,5R)-1-(3,5-Difluorophenyl)-N-propyl-3-azabicyclo[3.1.0]hexane-3-carbothioamide;
1-(2,5-difluorophenyl)-N-(2-mercaptoethyl)-3-azabicyclo[3.1.0]hexane-3-carbothioamide;
(1S,5R)-1-(3,5-difluorophenyl)-N-methyl-4-oxo-3-azabicyclo[3.1.0]hexane-3-carbothioamide;
4-(3,5-difluorophenyl)-N-methyl-2-oxopyrrolidine-1-carbothioamide;
1-(3,5-Difluorophenyl)-N-methyl-4-oxo-3-azabicyclo[3.1.0]hexane-3-carbothioamide;
6-Phenyltetrahydro-1H-pyrrolo[1,2-c]imidazole-3(2H)-thione;
1-(3,5-Difluorophenyl)-3-azabicyclo[3.1.0]hexane-3-carbothiohydrazide;
1-(3,5-Difluorophenyl)-N,N-dimethyl-3-azabicyclo[3.1.0]hexane-3-carbothioamide;
N-(cyanomethyl)-1-(2,5-difluorophenyl)-3-azabicyclo[3.1.0]hexane-3-carbothioamide;
3-(3,5-Difluorophenyl)-N-methyl-2,3-dihydro-1H-pyrrole-1-carbothioamide;

6-phenyl-6,7-dihydro-2H-pyrrolo[1,2-c]imidazole-3 (5H)-thione;
6-(3,5-difluorophenyl)-6,7-dihydro-2H-pyrrolo[1,2-c]imidazole-3 (5H)-thione;
6-(2,4-Difluorophenyl)-6,7-dihydro-2H-pyrrolo[1,2-c]imidazole-3 (5H)-thione;
6-(2,5-difluorophenyl)-6,7-dihydro-2H-pyrrolo[1,2-c]imidazole-3 (5H)-thione;
5a-(3,5-difluorophenyl)-5,5a,6,6a-tetrahydrocyclopropa[3,4]pyrrolo[1,2-c]imidazole-3(2H)-thione;
(5aS,6aR)-5a-(3,5-difluorophenyl)-5,5a,6,6a-tetrahydrocyclopropa[3,4]pyrrolo[1,2-c]imidazole-3 (2H)-thione;
(5aS,6aR)-5a-(2,5-difluorophenyl)-5,5a,6,6a-tetrahydrocyclopropa[3,4]pyrrolo[1,2-c]imidazole-3(2H)-thione;
(5aS,6aR)-5a-(2,5-difluorophenyl)-5,5a,6,6a-tetrahydrocyclopropa[3,4]pyrrolo[1,2-c]imidazole-3 (2H)-thione;
(5aR,6aS)-5a-(2,5-difluorophenyl)-5,5a,6,6a-tetrahydrocyclopropa[3,4]pyrrolo[1,2-c]imidazole-3 (2H)-thione;
(R)-6-(3,5-difluorophenyl)-6,7-dihydro-2H-pyrrolo[1,2-c]imidazole-3(5H)-thione;
(S)-6-(3,5-difluorophenyl)-6,7-dihydro-2H-pyrrolo[1,2-c]imidazole-3 (5H)-thione;
(5aS,6aR)-5a-(3,5-difluorophenyl)-5,5a,6,6a-tetrahydrocyclopropa[3,4]pyrrolo[2,1-c][1,2,4]triazole-3(2H)-thione;
(S)-6-(2,3,5,6-tetrafluorophenyl)-6,7-dihydro-2H-pyrrolo[1,2-c]imidazole-3 (5H)-thione;
(R)-6-(2,3,5,6-tetrafluorophenyl)-6,7-dihydro-2H-pyrrolo[1,2-c]imidazole-3(5H)-thione;
(5aS,6aR)-5a-(2,3,5-trifluorophenyl)-5,5a,6,6a-tetrahydrocyclopropa[3,4]pyrrolo[1,2-c]imidazole-3(2H)-thione;
(5aS,6aR)-5a-(2,6-difluorophenyl)-5,5a,6,6a-tetrahydrocyclopropa[3,4]pyrrolo[1,2-c]imidazole-3 (2H)-thione;
(5aR,6aS)-5a-(2,6-difluorophenyl)-5,5a,6,6a-tetrahydrocyclopropa[3,4]pyrrolo[1,2-c]imidazole-3(2H)-thione;
(5aS,6aR)-5a-(2,3-difluorophenyl)-5,5a,6,6a-tetrahydrocyclopropa[3,4]pyrrolo[1,2-c]imidazole-3 (2H)-thione;
(5aR,6aS)-5a-(2,3-difluorophenyl)-5,5a,6,6a-tetrahydrocyclopropa[3,4]pyrrolo[1,2-c]imidazole-3 (2H)-thione;
(5aS,6aR)-5a-(2,3,6-trifluorophenyl)-5,5a,6,6a-tetrahydrocyclopropa[3,4]pyrrolo[1,2-c]imidazole-3(2H)-thione;
(5aR,6aS)-5a-(2,3,6-trifluorophenyl)-5,5a,6,6a-tetrahydrocyclopropa[3,4]pyrrolo[1,2-c]imidazole-3(2H)-thione;
(5aS,6aR)-5a-(2,4-difluorophenyl)-5,5a,6,6a-tetrahydrocyclopropa[3,4]pyrrolo[1,2-c]imidazole-3(2H)-thione;
(5aS,6aR)-5a-(3,4-difluorophenyl)-5,5a,6,6a-tetrahydrocyclopropa[3,4]pyrrolo[1,2-c]imidazole-3 (2H)-thione;
(5aS,6aR)-5a-(2,4,5-trifluorophenyl)-5,5a,6,6a-tetrahydrocyclopropa[3,4]pyrrolo[1,2-c]imidazole-3(2H)-thione;
(5aS,6aR)-5a-(3-chloro-5-fluorophenyl)-5,5a,6,6a-tetrahydrocyclopropa[3,4]pyrrolo[1,2-c]imidazole-3(2H)-thione;
(5aS,6aR)-5a-(5-chloro-2-fluorophenyl)-5,5a,6,6a-tetrahydrocyclopropa[3,4]pyrrolo[1,2-c]imidazole-3(2H)-thione;
(5aS,6aR)-5a-(2-chloro-5-fluorophenyl)-5,5a,6,6a-tetrahydrocyclopropa[3,4]pyrrolo[1,2-c]imidazole-3(2H)-thione;
(5aS,6aR)-5a-(3,5-difluorophenyl)-2-methyl-5,5a,6,6a-tetrahydrocyclopropa[3,4]pyrrolo[1,2-c]imidazole-3(2H)-thione;
(5aS,6aR)-2-cyclopropyl-5 a-(3,5-difluorophenyl)-5,5a,6,6a-tetrahydrocyclopropa[3,4]pyrrolo[1,2-c]imidazole-3 (2H)-thione;
6-cyclohexyl-6,7-dihydro-2H-pyrrolo[1,2-c]imidazole-3 (5H)-thione;
(S)-6-(2,3,5-trifluorophenyl)-2,5,6,7-tetrahydro-3H-pyrrolo[1,2-c]imidazole-3-thione;
(R)-6-(2,3,5-trifluorophenyl)-2,5,6,7-tetrahydro-3H-pyrrolo[1,2-c]imidazole-3-thione;
(S)-6-(2,6-difluorophenyl)-2,5,6,7-tetrahydro-3H-pyrrolo[1,2-c]imidazole-3-thione;
(S)-6-(3-chloro-2,6-difluorophenyl)-2,5,6,7-tetrahydro-3H-pyrrolo[1,2-c]imidazole-3-thione;
(R)-6-(3-chloro-2,6-difluorophenyl)-2,5,6,7-tetrahydro-3H-pyrrolo[1,2-c]imidazole-3-thione;
(R)-6-(2,6-difluorophenyl)-2,5,6,7-tetrahydro-3H-pyrrolo[1,2-c]imidazole-3-thione;
(5aS,6aR)-5a-(3-chloro-2,6-difluorophenyl)-5,5a,6,6a-tetrahydrocyclopropa[3,4]pyrrolo[2,1-c][1,2,4]triazole-3(2H)-thione;
(5aS,6aR)-5a-(2-chloro-6-fluorophenyl)-5,5a,6,6a-tetrahydrocyclopropa[3,4]pyrrolo[1,2-c]imidazole-3(2H)-thione;
(5aS,6aR)-5a-(3-chloro-2,6-difluorophenyl)-5,5a,6,6a-tetrahydrocyclopropa[3,4]pyrrolo[1,2-c]imidazole-3(2H)-thione;
(5aS,6aR)-5a-(5-chloro-2-fluorophenyl)-5,5a,6,6a-tetrahydrocyclopropa[3,4]pyrrolo[1,2-c]imidazole-3(2H)-thione-5,5-$d_2$;
(5aS,6aR)-5a-(3-chloro-2-fluorophenyl)-5,5a,6,6a-tetrahydrocyclopropa[3,4]pyrrolo[1,2-c]imidazole-3(2H)-thione;
(5aS,6aR)-5a-(5-bromo-2-fluorophenyl)-5,5a,6,6a-tetrahydrocyclopropa[3,4]pyrrolo[1,2-c]imidazole-3(2H)-thione;
(5aS,6aR)-5a-(3-bromo-5-fluorophenyl)-5,5a,6,6a-tetrahydrocyclopropa[3,4]pyrrolo[1,2-c]imidazole-3(2H)-thione;
(5aS,6aR)-5a-(5-chloro-2-fluorophenyl)-2-(methyl-$d_3$)-5,5a,6,6a-tetrahydrocyclopropa[3,4]pyrrolo[1,2-c]imidazole-3 (2H)-thione;
5a-(5-chloro-2-fluorophenyl)-5,5a,6,6a-tetrahydrocyclopropa[3,4]pyrrolo[1,2-c]imidazole-3(2H)-thione-6,6,6a-$d_3$;
(5aR,6aS)-5a-(3-chloro-2,6-difluorophenyl)-5,5a,6,6a-tetrahydrocyclopropa[3,4]pyrrolo[1,2-c]imidazole-3(2H)-thione;
(5aS,6aS)-5a-(3,5-difluorophenyl)-2,5,5a,6,6a,7-hexahydro-3H-cyclopropa[d]imidazo[1,5-a]pyridine-3-thione;
(6R,7S)-7-methyl-6-(2,3,5,6-tetrafluorophenyl)-2,5,6,7-tetrahydro-3H-pyrrolo[1,2-c]imidazole-3-thione;
(6R,7R)-7-methyl-6-(2,3,5,6-tetrafluorophenyl)-2,5,6,7-tetrahydro-3H-pyrrolo[1,2-c]imidazole-3-thione;
(5aS,6aR)-5a-(3,5-dichlorophenyl)-5,5a,6,6a-tetrahydrocyclopropa[3,4]pyrrolo[1,2-c]imidazole-3 (2H)-thione;
(5aR,6aS)-5a-(5-chloro-2-fluorophenyl)-5,5a,6,6a-tetrahydrocyclopropa[3,4]pyrrolo[1,2-c]imidazole-3(2H)-thione;
(6R)-6-(2,3,5,6-tetrafluorophenyl)tetrahydro-1H-pyrrolo[1,2-c]imidazole-3 (2H)-thione;
(S)-6-(2,3,6-trifluorophenyl)-2,5,6,7-tetrahydro-3H-pyrrolo[,2-c]imidazole-3-thione;
(R)-6-(2,3,6-trifluorophenyl)-2,5,6,7-tetrahydro-3H-pyrrolo[2-c]imidazole-3-thione;
(R)-2-methyl-6-(2,3,5,6-tetrafluorophenyl)-2,5,6,7-tetrahydro-3H-pyrrolo[1,2-c]imidazole-3-thione;
(5aS,6aR)-5a-(3-bromo-2,6-difluorophenyl)-5,5a,6,6a-tetrahydrocyclopropa[3,4]pyrrolo[1,2-c]imidazole-3(2H)-thione;
(5aS,6aR)-5a-(5-chloro-2-fluorophenyl)-2-methyl-5,5a,6,6a-tetrahydrocyclopropa[3,4]pyrrolo[1,2-c]imidazole-3 (2H)-thione;

(S)-6-(3-bromo-2,6-difluorophenyl)-2,5,6,7-tetrahydro-3H-pyrrolo[,2-c]imidazole-3-thione;
(R)-6-(3-bromo-2,6-difluorophenyl)-2,5,6,7-tetrahydro-3H-pyrrolo[1,2-c]imidazole-3-thione;
(5aS,6aR)-5a-(3-bromo-2,6-difluorophenyl)-5,5a,6,6a-tetrahydrocyclopropa[3,4]pyrrolo[2,1-c][1,2,4]triazole-3(2H)-thione; and
(5aS,6aR)-5a-(5-bromo-2-fluorophenyl)-5,5a,6,6a-tetrahydrocyclopropa[3,4]pyrrolo[2,1-c][1,2,4]triazole-3(2H)-thione.

C. Compositions

The compounds of the invention intended for pharmaceutical use may be administered alone or in combination with one or more other compounds of the invention or in combination with one or more other drugs (or as any combination thereof). Generally, they will be administered as a formulation in association with one or more pharmaceutically acceptable excipients. Accordingly, the present invention is also directed to a pharmaceutical composition comprising (i) a therapeutically effective amount of a compound of formula I, as defined above, or a pharmaceutically acceptable salt or solvate thereof; and (ii) a pharmaceutically acceptable excipient.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

D. Methods of Use

This invention is also directed to compounds of formula I, as defined above, or a pharmaceutically acceptable salt or solvate thereof, for use in therapy, in particular for the treatment of conditions ameliorated by inhibition of DβH within the CNS.

This invention is also directed to the use of compounds of formula I, as defined above, or a pharmaceutically acceptable salt or solvate thereof, in the manufacture of a medicament for treatment of conditions ameliorated by inhibition of DβH within the CNS.

This invention is also directed to a method for treating conditions ameliorated by inhibition of dopamine-beta-hydroxylase within the CNS comprising administering a therapeutically effective amount of a compound of formula I, as defined in claim 1, or a pharmaceutically acceptable salt or solvate thereof, to a patient in need thereof.

Conditions ameliorated by inhibition of DβH within the CNS can include, but are not limited to: cocaine addiction, alcohol addiction, adjunct opioid addiction, cognition decline in FTD, cognition decline in MCI, cognition decline in AD, ADHD, PTSD and unipolar depression.

E. General Synthetic Methodology

The methods used for the synthesis of the compounds of the invention are illustrated by the schemes below. The starting materials and reagents used in preparing these compounds are available from commercial suppliers or can be prepared by methods obvious to those skilled in the art. To make the schemes easier to read, the option to incorporate deuterium at certain positions is not shown. Specifically, deuterated products can be produced using specifically deuterated starting materials, including, but not limited to, those used in Examples 1-121.

Compounds of formula I2 can generally be synthesised by the methods outlined in Scheme 1.

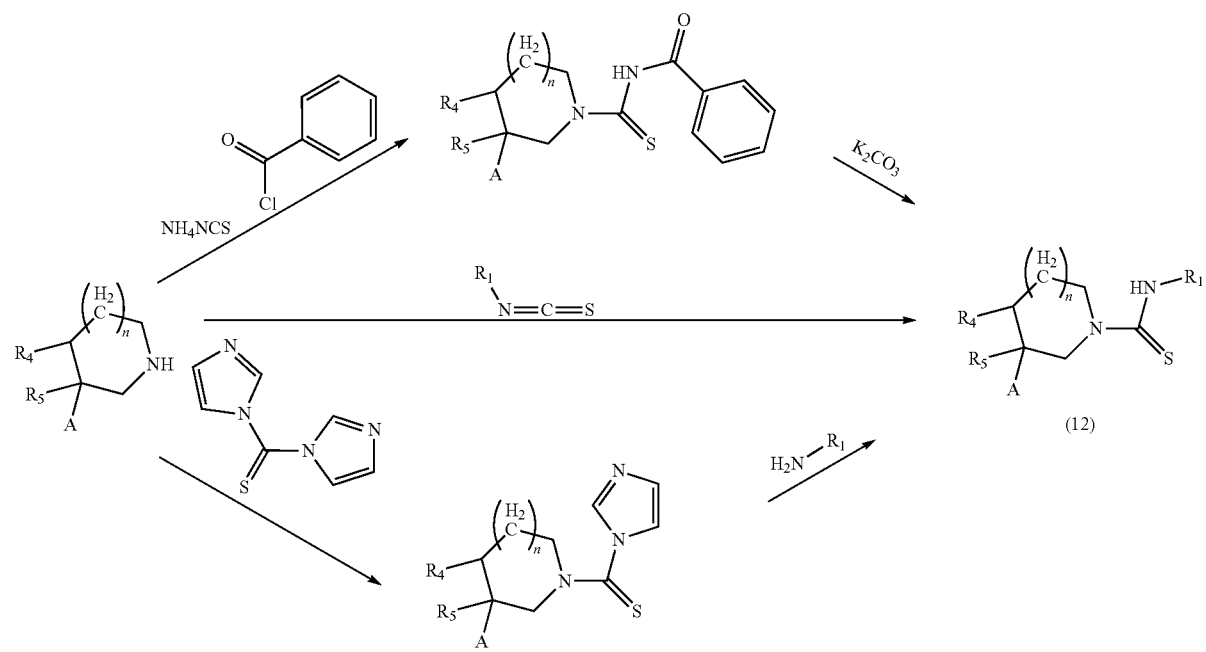

Scheme 1

Compounds of formula I4 can generally be synthesised by the method outlined in Scheme 2:

Scheme 2

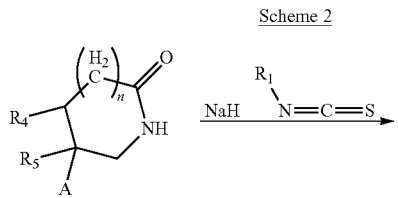

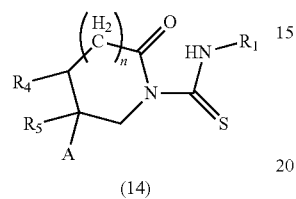

(14)

Compounds of formula Ia, where X=CH$_2$ can generally be synthesised by the method outlined in Scheme 3:

Scheme 3

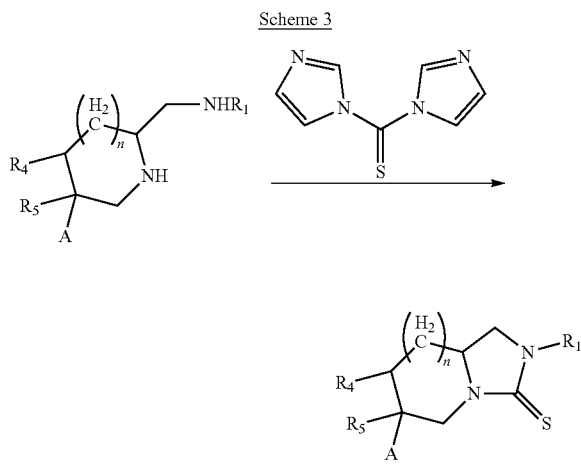

Compounds of formula Ia, where X=CR$_4$ can generally be synthesised by the method outlined in Scheme 4:

Scheme 4

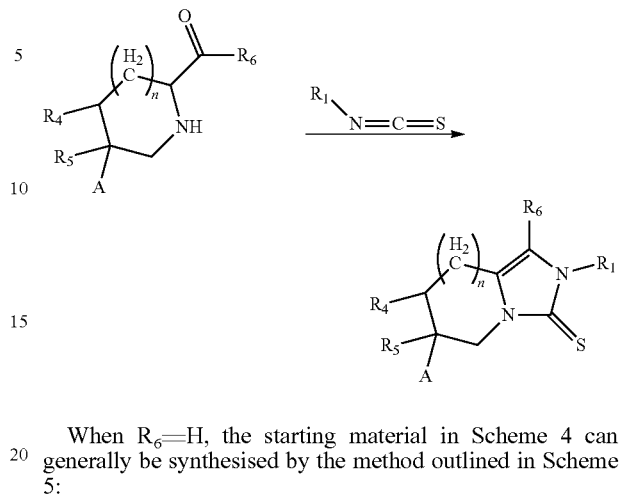

When R$_6$=H, the starting material in Scheme 4 can generally be synthesised by the method outlined in Scheme 5:

Scheme 5

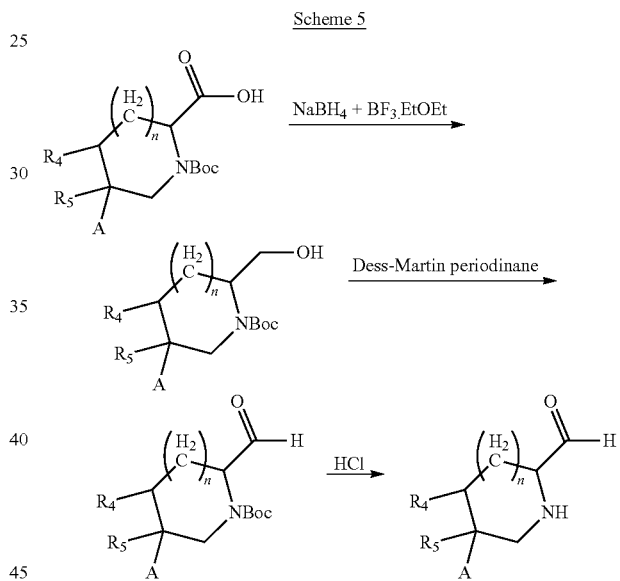

The starting material for Scheme 5, when n=0, can generally be synthesised by the method outlined in Scheme 6 as either enriched enantiomers or racemates:

Scheme 6

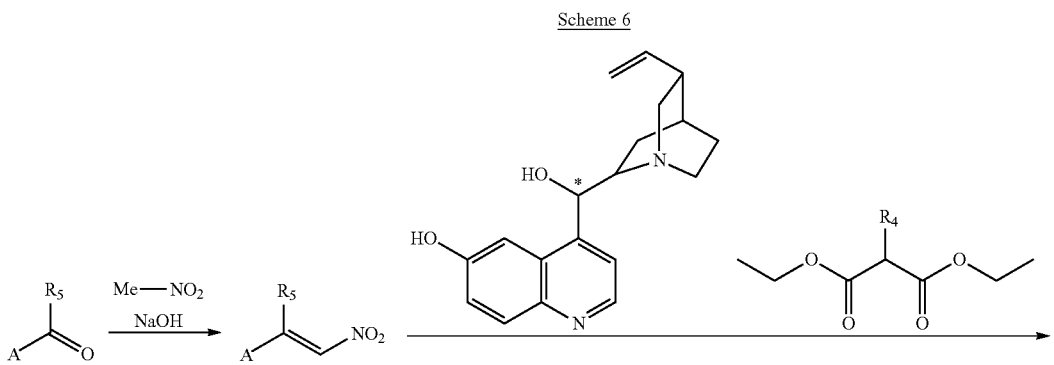

-continued

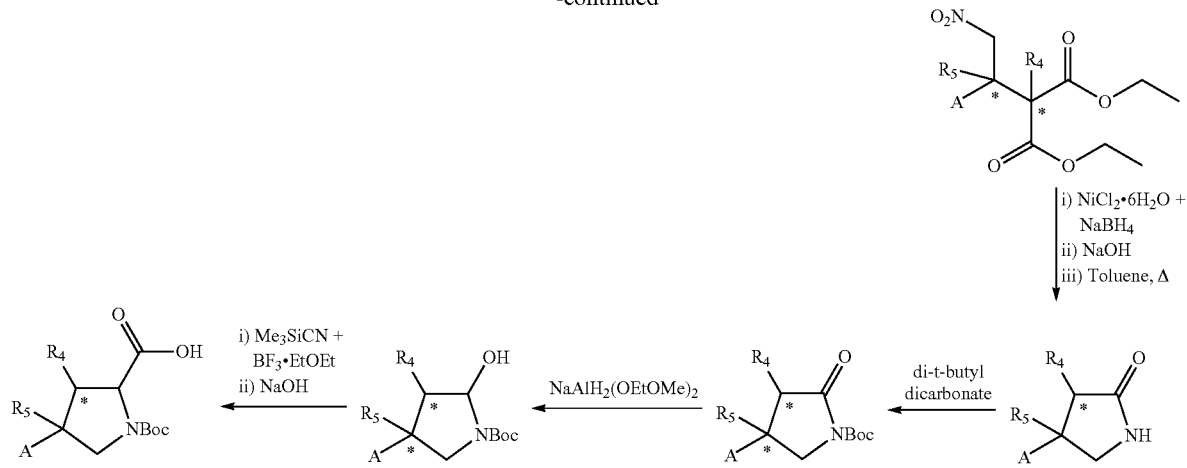

When R$_6$=H and R$_4$ and R$_5$ combine to form a cyclopropyl group, the starting material in Scheme 4 can generally be synthesised by the method outlined in Scheme 7:

Scheme 7

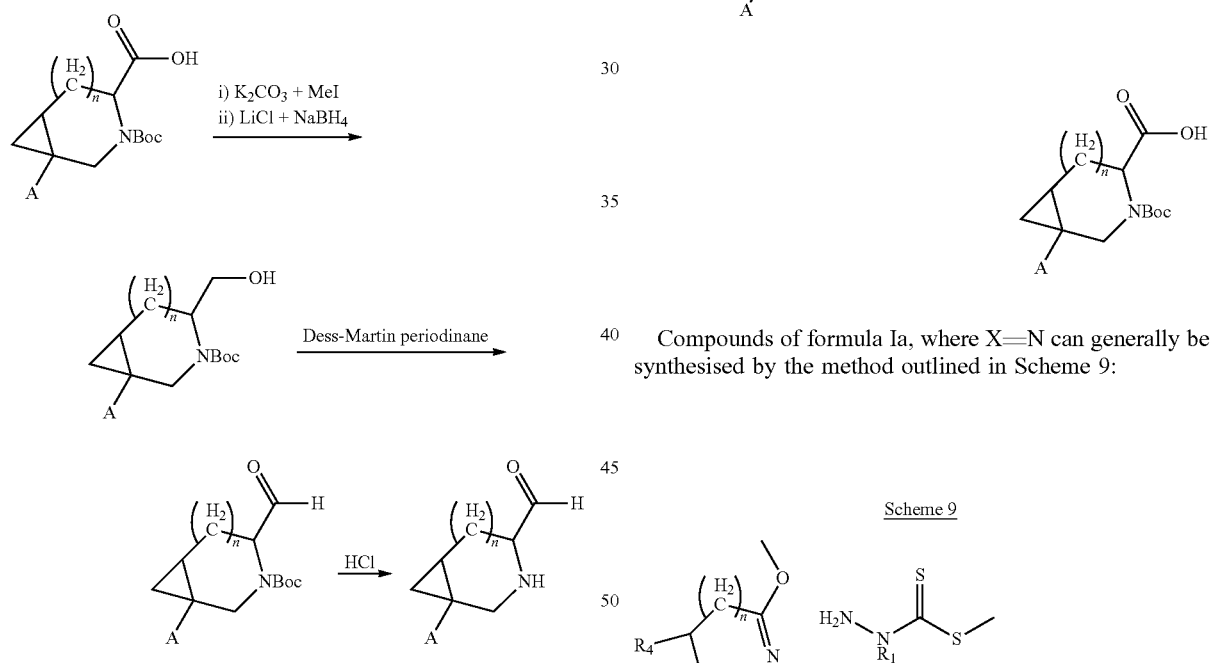

The starting material for Scheme 7 can generally be synthesised by the method outlined in Scheme 8:

Scheme 8

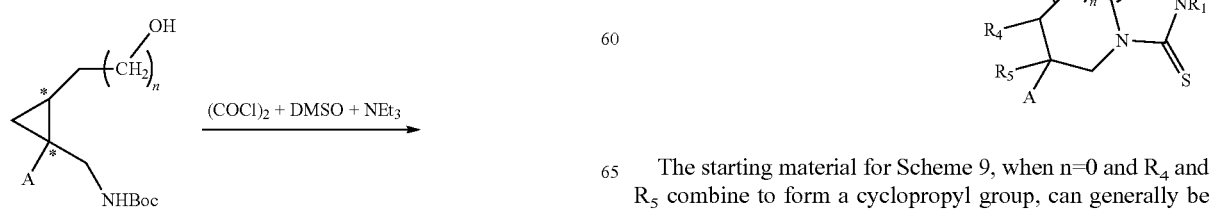

Compounds of formula Ia, where X=N can generally be synthesised by the method outlined in Scheme 9:

Scheme 9

The starting material for Scheme 9, when n=0 and R$_4$ and R$_5$ combine to form a cyclopropyl group, can generally be synthesised by the method outlined in Scheme 10:

Scheme 10

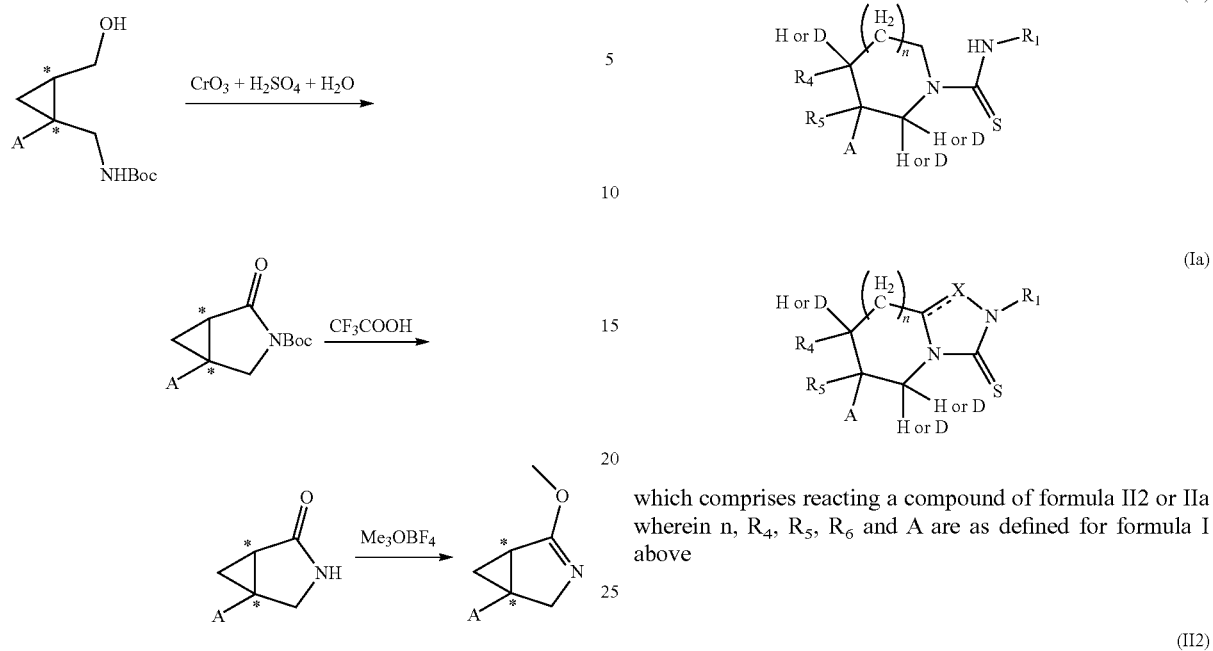

In turn, the starting material for Schemes 8 and 10 can generally be synthesised by the method outlined in Scheme 11 as either enriched enantiomers or racemates and including specific deuteration:

Scheme 11

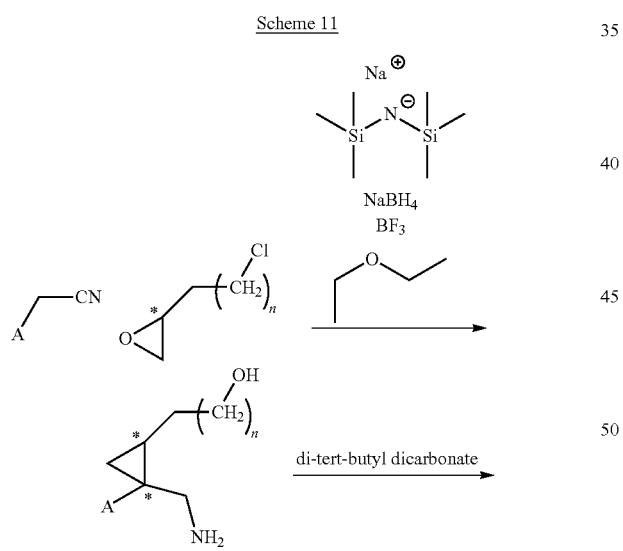

In accordance with this synthetic methodology, the invention provides a process for the preparation of compounds of formulae I2 or Ia wherein ------ is a double bond and X is $CR_6$ which comprises reacting a compound of formula II2 or IIa wherein n, $R_4$, $R_5$, $R_6$ and A are as defined for formula I above with a compound of formula $R^1$—N=C=S.

Compounds of formula II2 and IIa wherein n, $R_4$, $R_5$, $R_6$ and A are as defined for formula I above are thus useful intermediates representing further embodiments of the present invention.

F. Examples

All compounds and intermediates were characterised by NMR. The spectra were recorded on a Bruker Avance III 600 MHz spectrometer with solvent used as internal standard. $^{13}C$ spectra were recorded at 150 MHz and $^1H$ spectra were recorded at 600 MHz. Data are reported in the following order: approximate chemical shift (ppm), number of protons, multiplicity (br, broad; d, doublet; m, multiplet; s, singlet; t, triplet) and coupling constant (Hz).

Room temperature in the following protocols means the temperature ranging from 20° C. to 25° C.

Example 1: 3-Phenylpyrrolidine-1-carbothioamide

Step 1: N-(3-phenylpyrrolidine-1-carbonothioyl)benzamide

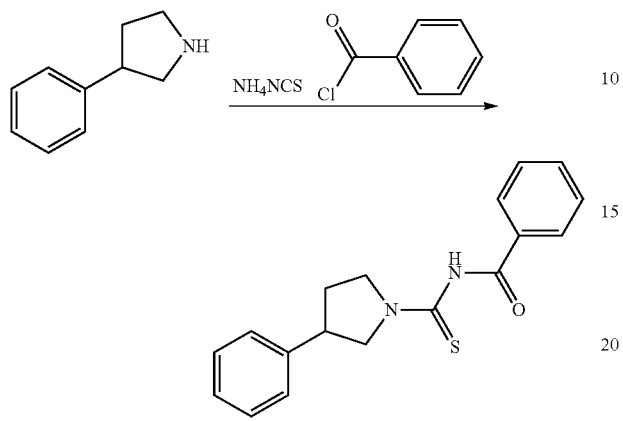

To a solution of ammonium thiocyanate (62 mg, 0.815 mmol) in acetone (2 mL) was added benzoyl chloride (0.087 mL, 0.747 mmol) at room temperature with stirring. After being stirred for 10 min. the resulting precipitate was filtered off and 3-phenylpyrrolidine (CAS #936-44-7) (100 mg, 0.679 mmol) was added to the filtrate in portions. The reaction mixture was stirred at ambient temperature for 20 h, and then evaporated to dryness. Chromatography (petroleum ether-ethyl acetate, 4:1) gave N-(3-phenylpyrrolidine-1-carbonothioyl)benzamide as an off-white powder (0.067 g, 32% yield).

Step 2: 3-phenylpyrrolidine-1-carbothioamide

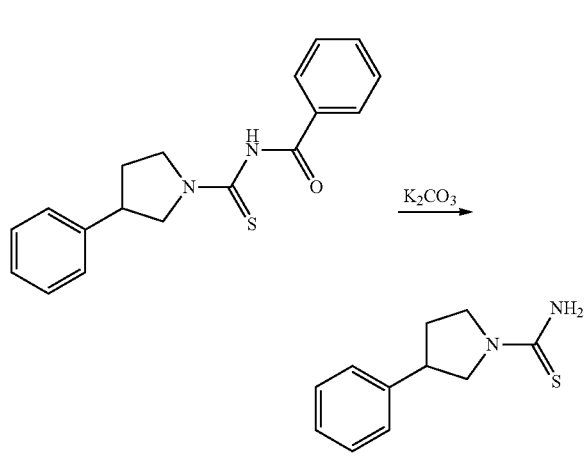

To a solution of N-(3-phenylpyrrolidine-1-carbonothioyl) benzamide (0.06 g, 0.193 mmol) in methanol (2 mL) was added 20% aq. sodium hydroxide (0.317 mL, 1.933 mmol) and the mixture was refluxed for 6 h. Thereupon, the reaction was diluted with water (4 mL) and then the organics were removed under vacuum to give the product as an oil that solidified on standing in the cold (5° C.). The crystals were collected, washed with water and dried to give 3-phenylpyrrolidine-1-carbothioamide as an off-white powder (0.018 g, 45% yield).

$^1$H NMR (DMSO-d6): 7.33 (2H, t, J=7.3 Hz), 7.29 (2H, d, J=7.2 Hz), 7.24 (1H, t, J=7.2 Hz), 7.19 (2H, br s), 4.12 (0.5H, m), 3.90 (0.5H, m), 3.78 (0.5H, m), 3.44-3.61 (2H, m), 3.26 (0.5H, m), 2.34 (0.5H, s br), 2.20 (0.5H, s br), 2.11 (0.5H, m), 1.97 (0.5H, m).
$^{13}$C NMR (DMSO-d6): 178.5, 141.2, 141.1, 128.5, 127.1, 126.8, 126.7, 57.5, 53.9, 51.3, 47.5, 44, 42.4, 33.0, 31.9.

Example 2: 3-(thiophen-2-yl)pyrrolidine-1-carbothioamide

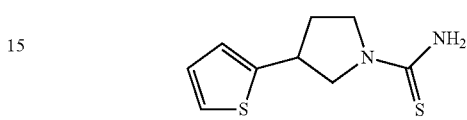

3-(Thiophen-2-yl)pyrrolidine (CAS #125067-53-0) was converted to 3-(thiophen-2-yl)pyrrolidine-1-carbothioamide by a similar procedure as described for Example 1 and the product was isolated as an off-white powder.
$^1$H NMR (DMSO-d6): 7.39 (1H, d, J=4.4 Hz), 7.19 (2H, br, s), 6.98 (1H, dd, J=5.0, 3.5 Hz), 6.96 (1H, d, J=2.9 Hz), 4.10 (0.5H, br s), 3.86 (0.5H, br s), 3.80 (1H, br s), 3.66 (0.5H, br s), 3.53 (1.5H, m), 3.38 (0.5H, m), 3.29 (0.5H, br s), 2.39 (0.5H, m), 2.26 (0.5H, br s), 2.09 (0.5H, br s), 1.95 (0.5H, br s).
$^{13}$C NMR (DMSO-d6): 178.5, 144.7, 127, 124.1, 124.1, 124, 58.1, 54.6, 51, 47.2, 39.2, 37.9, 34.1, 33.0.

Example 3: 3-(4-Fluorophenyl)pyrrolidine-1-carbothioamide

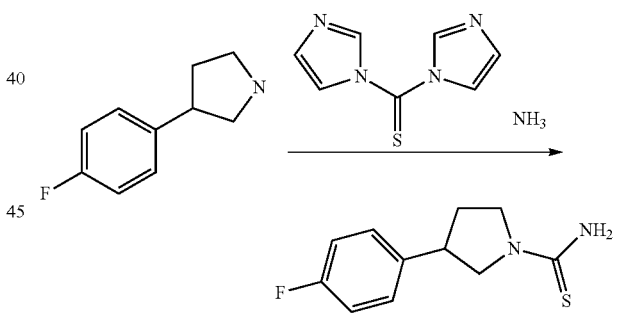

To a solution of 1,1'-thiocarbonyldiimidazole (0.570 g, 3.20 mmol) in tetrahydrofuran (6 mL) was added a solution of 3-(4-fluorophenyl)pyrrolidine (CAS #144620-11-1) (0.48 g, 2.91 mmol) in tetrahydrofuran (6.00 mL). The mixture was then stirred for 1 h at room temperature and for an additional 2 h at 55-60° C. Thereupon, tetrahydrofuran was removed under vacuum and the residue was dissolved in methanol (12 mL). The thus obtained solution was treated with 25% aq. ammonia (3.26 mL, 43.6 mmol) and then the mixture was stirred at room temperature for 5 days. The reaction was diluted with 1M HCl, the resulting precipitate was collected, washed with a mixture of methanol-water (1:1) and dried under vacuum at 50° C. to give 3-(4-fluorophenyl)pyrrolidine-1-carbothioamide as a white powder (0.22 g, 34% yield).
$^1$H NMR (DMSO-d6): 7.33 (2H, m), 7.15 (2H, m), 6.70-7.60 (2H, br s), 4.11 (0.5H, m), 3.90 (0.5H, m), 3.77

(0.5H, m), 3.52 (1.5H, m), 3.40 (1.5H, m), 3.23 (0.5H, m), 2.33 (0.5H, br s), 2.18 (0.5H, br s), 2.09 (0.5H, m), 1.96 (0.5H, m).

$^{13}$C NMR (DMSO-d6): 178.4, 161.8, 160.2, 137.2, 129, 129, 115.3, 115.1, 57.5, 54, 51.3, 47.4, 43.3, 41.7, 33.1, 31.9.

Example 4: 3-phenylpiperidine-1-carbothioamide

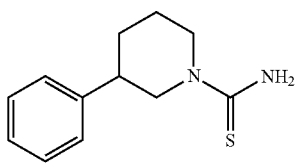 [SMILES: NC(=S)N1CCCC(c2ccccc2)C1]

3-Phenylpiperidine (CAS #3973-62-4) was converted to 3-phenylpiperidine-1-carbothioamide by a similar procedure as described for Example 3 and the product was isolated as a white powder. $^1$H NMR (DMSO-d6): 7.38 (2H, br s), 7.32 (2H, t, J=7.8 Hz), 7.29 (2H, d, J=7.8 Hz), 7.23 (1H, mt, J=7.1 Hz), 4.59 (2H, m), 2.96 (2H, m), 2.64 (1H, m), 1.90 (1H, m), 1.70 (2H, m), 1.50 (1H, m).

$^{13}$C NMR (DMSO-d6): 180.5, 143.3, 128.4, 127.1, 126.5, 53.7, 47.6, 42.0, 31.3, 25.0,

Example 5:
3-(2,4-difluorophenyl)pyrrolidine-1-carbothioamide

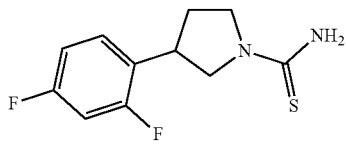 [SMILES: NC(=S)N1CCC(c2ccc(F)cc2F)C1]

3-(2,4-Difluorophenyl)pyrrolidine (CAS #1092108-80-9) was converted to 3-(2,4-difluorophenyl)pyrrolidine-1-carbothioamide by a similar procedure as described for Example 3 and the product was isolated as a beige powder.

$^1$H NMR (DMSO-d6): 7.39 (1H, m), 7.19 (1H, ddd, J=11.0, 9.2, 2.6 Hz), 7.09 (2H, br s), 7.07 (1H, ddt, J=1.0, 2.6, 8.5 Hz), 3.34-4.24 (5H, m), 2.28 (1H, br s), 2.09 (1H, br s).

$^{13}$C NMR (DMSO-d6): 178.6, 178.5, 162, 161.9, 161.2, 160.4, 160.3, 159.6, 129.4, 129.2, 129, 129, 124.9, 124.1, 115.3, 115.1, 111.7, 111.5, 104.1, 103.9, 103.8, 56.1, 52.5, 50.9, 37.1, 35.5, 31.6, 30.4.

Example 6:
(S)-3-phenylpyrrolidine-1-carbothioamide

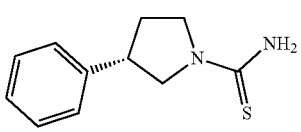 [SMILES: NC(=S)N1CC[C@@H](c2ccccc2)C1]

(S)-3-phenylpyrrolidine (CAS #62624-46-8) was converted to (S)-3-phenylpyrrolidine-1-carbothioamide by a similar procedure as described for Example 3 and the product was isolated as a beige powder.

$^1$H NMR (DMSO-d6): 7.33 (2H, t, J=7.2 Hz), 7.29 (2H, d, J=7.4 Hz), 7.24 (1H, t, J=7.1 Hz), 7.21 (2H, br s), 4.12 (0.5H, m), 3.90 (0.5H, m), 3.78 (0.5H, m), 3.44-3.61 (2H, m), 3.26 (0.5H, m), 2.34 (0.5H, s br), 2.20 (0.5H, s br), 2.11 (0.5H, m), 1.97 (0.5H, m).

$^{13}$C NMR (DMSO-d6): 178.4, 141.2, 141.1, 128.5, 127.1, 126.7, 126.7, 57.5, 53.9, 51.3, 47.5, 44, 42.4, 33.0, 31.9.

Example 7:
3-methyl-3-phenylpyrrolidine-1-carbothioamide

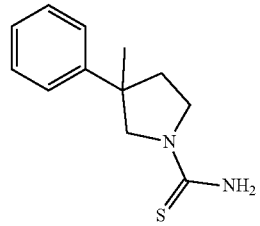

3-Methyl-3-phenylpyrrolidine (CAS #56606-73-6) was converted to 3-methyl-3-phenylpyrrolidine-1-carbothioamide by a similar procedure as described for Example 3 and the product was isolated as a white solid.

$^1$H NMR (DMSO-d6): 6.80-7.60 (7H, m), 3.89 and 3.82 (1H, 2 br d, J=11.4 Hz), 3.68 (1H, m), 3.60 and 3.54 (1H, 2 br d, J=10.8 Hz), 3.45 (0.5H, m), 2.27 (0.5H, m), 2.21 (0.5H, m), 2.10 (1H, m).

$^{13}$C NMR (DMSO-d6): 178.9, 178.6, 146.8, 146.6, 128.4, 126.3, 126.2, 125.7, 125.5, 62.3, 58.9, 50.1, 46.4, 46.2, 44.5, 37.7, 36.2, 27.5, 27.1.

Example 8: 1-phenyl-3-azabicyclo[3.1.0]hexane-3-carbothioamide

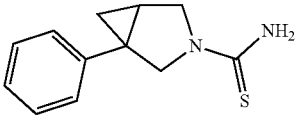 [SMILES: NC(=S)N1CC2CC2(c2ccccc2)C1]

1-phenyl-3-azabicyclo[3.1.0]hexane (CAS #67644-21-7) was converted to 1-phenyl-3-azabicyclo[3.1.0]hexane-3-carbothioamide by a similar procedure as described for Example 3 and the product was isolated as a white powder.

$^1$H NMR (DMSO-d6): 6.8-7.9 (2H, br s), 7.31 (2H, t, J=7.6 Hz), 7.31 (3H, m), 4.39 (0.5H, br s), 4.09 (0.5H, br s), 3.95 (0.5H, br s), 3.47-3.80 (2.5H, m), 1.90-2.21 (1H, m), 1.10 (1H, br dd, J=7.6, 5.0 Hz), 0.72 (1H, t, J=4.6 Hz).

$^{13}$C NMR (DMSO-d6): 179.9, 140.9, 128.4, 126.4, 126.2, 57.3, 54, 53.5, 50.2, 31.8, 30.2, 24.5, 23.6, 19.5.

Example 9:
3-cyclohexylpyrrolidine-1-carbothioamide

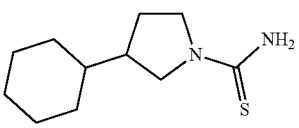 [SMILES: NC(=S)N1CCC(C2CCCCC2)C1]

3-cyclohexylpyrrolidine (CAS #78813-85-1) was converted to 3-cyclohexylpyrrolidine-1-carbothioamide by a similar procedure as described for Example 3 and the product was isolated as a white powder.

¹H NMR (DMSO-d6): 7.08 (2H, br s), 3.87 (0.5H, br t, J=9 Hz), 3.81 (0.5H, br t, J=9.7 Hz), 3.51 (0.5H, br t, J=8.5 Hz), 3.43 (0.5H, m), 3.32 (0.5H, m), 3.18 (0.5H, m), 3.03 (0.5H, t, J=10.8 Hz), 2.86 (0.5H, J=10 Hz), 2.07 (0.5H, m), 1.94 (1H, m), 1.82 (0.5H, m), 1.57-1.77 (5.5H, m), 1.42 (0.5H, m), 1.17 (4.0H, m), 0.94 (2H, m).

¹³C NMR (DMSO-d6): 178.2, 55.6, 51.9, 51.5, 47.7, 45.4, 43.6, 41.1, 40.8, 31.5, 31.4, 30.8, 30.0, 28.9, 25.6, 25.5.

Example 10: 3-(5-methylthiophen-2-yl)pyrrolidine-1-carbothioamide

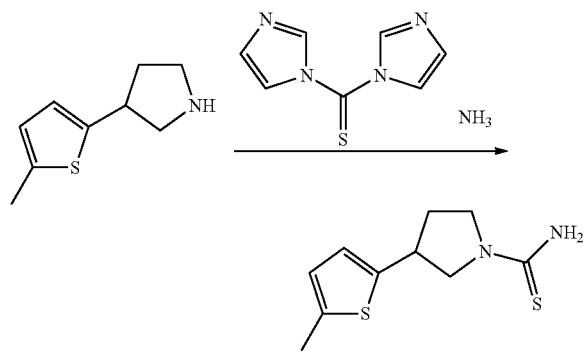

To a stirred solution of 1,1'-thiocarbonyldiimidazole (0.469 g, 2.63 mmol) in dry tetrahydrofuran (9 mL) was added a solution of 3-(5-methylthiophen-2-yl)pyrrolidine (CAS #1260863-70-4) (0.44 g, 2.63 mmol) in dry tetrahydrofuran (9 mL). The reaction was stirred for 1 h at room temperature and for an additional 2 h at 55-60° C. After being cooled to room temperature, the organics were evaporated to dryness under vacuum and the residue was treated with 2 M ethanolic ammonia solution (7.89 mL, 15.78 mmol). The reaction was stirred for 16 h in a sealed vial at 70° C. The mixture was then cooled again and quenched water (2 mL). The resulting crystals were collected, washed with a mixture of ethanol-water (1:1) and dried under vacuum at 50° C. to give 3-(5-methylthiophen-2-yl)pyrrolidine-1-carbothioamide as a white powder (0.3 g, 1.325 mmol, 50.4% yield).

¹H NMR (DMSO-d6): 6.84 (2H, br d, J=3.5 Hz), 6.71 (1H, d, J=3.2 Hz), 6.63 (1H, m), 4.04 (0.5H, br s), 3.83 (0.5H, br s), 3.72 (1H, m), 3.50 (2H, m), 3.35 (0.5H, m), 3.25 (0.5H, m), 2.39 (3H, m), 2.30 (0.5H, m), 2.22 (0.5H, br s), 2.04 (0.5H, br s), 1.90 (0.5H, br s).

¹³C NMR (DMSO-d6): 178.6, 178.5, 142.3, 142.3, 137.3, 137.2, 125.0, 123.8, 58.0, 54.4, 51.0, 47.1, 39.4, 38.0, 34.0, 32.9, 15.0,

Example 11: (R)-3-phenylpyrrolidine-1-carbothioamide

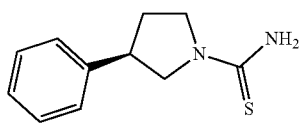 [SMILES: NC(=S)N1CC[C@H](c2ccccc2)C1]

(R)-3-phenylpyrrolidine (CAS #61586-46-7) was converted to (R)-3-phenylpyrrolidine-1-carbothioamide by a similar procedure as described for Example 10 and the product was isolated as a white powder ¹H NMR (DMSO-d6): 7.33 (2H, t, J=7.2 Hz), 7.29 (2H, d, J=7.4 Hz), 7.24 (1H, t, J=7.1 Hz), 7.21 (2H, br s), 4.12 (0.5H, m), 3.90 (0.5H, m), 3.78 (0.5H, m), 3.44-3.61 (2H, m), 3.26 (0.5H, m), 2.34 (0.5H, s br), 2.20 (0.5H, s br), 2.11 (0.5H, m), 1.97 (0.5H, m).

¹³C NMR (DMSO-d6): 178.5, 141.2, 141.1, 128.5, 127.1, 126.8, 126.7, 57.5, 53.9, 51.3, 47.5, 44, 42.4, 33, 31.9.

Example 12: 3-(3,5-Difluorophenyl)pyrrolidine-1-carbothioamide

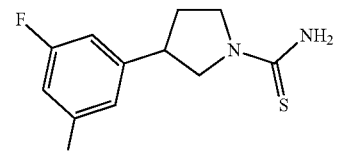

3-(3,5-Difluorophenyl)pyrrolidine (CAS #1092108-82-1) was converted to 3-(3,5-Difluorophenyl)pyrrolidine-1-carbothioamide by a similar procedure as described for Example 10 and the product was isolated as a white powder.

¹H NMR (DMSO-d6): 7.21 (2H, br s), 7.09 (3H, m), 4.12 (0.5H, br m), 3.89 (0.5H, br m), 3.79 (0.5H, br m), 3.45 (3H, br m), 3.27 (0.5H, m), 2.34 (0.5H, br m), 2.20 (0.5H, br m), 2.14 (0.5H, br m), 1.99 (0.5H, br m).

¹³C NMR (DMSO-d6): 178.5, 163.3, 163.2, 161.7, 161.6, 145.9, 110.6, 110.6, 110.5, 110.4, 102.4, 102.2, 102, 57, 53.4, 51.2, 47.3, 43.6, 42.1, 32.6, 31.4.

Example 13: 3-o-tolylpyrrolidine-1-carbothioamide

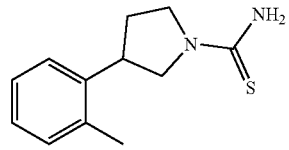

3-(o-Tolyl)pyrrolidine (CAS #954220-67-8) was converted to 3-o-tolylpyrrolidine-1-carbothioamide by a similar procedure as described for Example 10 and the product was isolated as a white powder ¹H NMR (DMSO-d6): 6.87-7.43 (6H, m), 4.02 (0.5H, m), 3.85 (0.5H, m), 3.75 (0.5H, m), 3.67 (0.5H, m), 3.51-3.62 (1.5H, m), 3.47 (0.5H, m), 3.40 (0.5H, m), 3.23 (0.5H, m), 2.32 (3H, s), 2.30 (0.5H, m), 2.14 (0.5H, m), 2.07 (0.5H, m), 1.98 (0.5H, m).

¹³C NMR (DMSO-d6): 178.4, 139.5, 139.2, 135.9, 130.3, 126.5, 126.4, 126.2, 125.2, 125.1, 56.8, 53.2, 51, 47.1, 40.1, 38.5, 32.3, 30.9, 19.3.

Example 14: 3-m-tolylpyrrolidine-1-carbothioamide

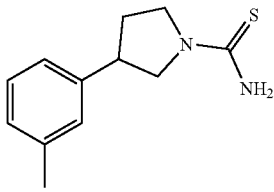

3-(m-Tolyl)pyrrolidine (CAS #954220-64-5) was converted to 3-m-tolylpyrrolidine-1-carbothioamide by a similar procedure as described for Example 10 and the product was isolated as an off-white solid.

$^1$H NMR (DMSO-d6): 6.56-7.60 (2H, br s), 7.21 (1H, t, J=7.5 Hz), 7.11 (1H, br s), 7.07 (1H, br d, J=6.3 Hz), 7.05 (1H, br d, J=7.5 Hz), 4.11 (0.5H, m), 3.90 (0.5H, m), 3.77 (0.5H, m), 3.52 (1H, m), 3.44 (1H, m), 3.35 (1H, m), 3.24 (0.5H, m), 2.32 (0.5H, m), 2.28 (3H, s), 2.18 (0.5H, m), 2.08 (0.5H, m), 1.96 (0.5H, m).

$^{13}$C NMR (DMSO-d6): 178.4, 178.4, 141.1, 141, 137.6, 128.4, 127.8, 127.4, 127.3, 124.1, 57.5, 53.9, 51.4, 47.5, 44, 42.3, 33.0, 31.8, 21.1.

Example 15: 3-(thiophen-3-yl)pyrrolidine-1-carbothioamide

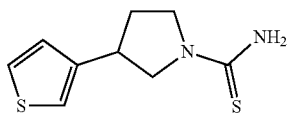 [SMILES: NC(=S)N1CCC(c2ccsc2)C1]

3-(Thiophen-3-yl)pyrrolidine (CAS #1231907-58-6) was converted to 3-(thiophen-3-yl)pyrrolidine-1-carbothioamide by a similar procedure as described for Example 10 and the product was isolated as a white powder.

$^1$H NMR (DMSO-d6): 7.51 (1H, m), 7.28 (1H, m), 7.18 (2H, br s), 7.09 (1H, m), 4.08 (0.5H, br s), 3.85 (0.5H, br s), 3.74 (0.5H, m), 3.39-3.65 (2.5H, m), 3.32 (0.5H, m), 3.25 (0.5H, m), 2.34 (0.5H, br s), 2.18 (0.5H, br s), 2.09 (0.5H, m), 1.95 (0.5H, m).

$^{13}$C NMR (DMSO-d6): 178.5, 178.4, 142.2, 127.2, 127.1, 126.5, 126.4, 120.7, 120.5, 57.2, 53.7, 51.2, 47.3, 39.8, 38.2, 32.9, 31.8.

Example 16: 3-(furan-3-yl)pyrrolidine-1-carbothioamide

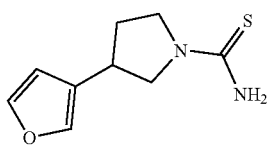 [SMILES: NC(=S)N1CCC(c2ccoc2)C1]

3-(Furan-3-yl)pyrrolidine (CAS #1260650-66-5) was converted to 3-(furan-3-yl)pyrrolidine-1-carbothioamide by a similar procedure as described for Example 10 and the product was isolated as a dark beige solid.

$^1$H NMR (DMSO-d6): 7.61 (1H, s), 7.54 (1H, s), 7.12 (2H, m), 6.49 (1H, dd, J=1.8, 0.7 Hz), 4.01 (0.5H, m), 3.81 (0.5H, m), 3.67 (0.5H, m), 3.31-3.57 (2.5H, m), 3.24 (0.5H, br s), 3.19 (0.5H, m), 2.27 (0.5H, br s), 2.12 (0.5H, br s), 1.99 (0.5H, m), 1.87 (0.5H, m).

$^{13}$C NMR (DMSO-d6): 178.5, 178.4, 143.5, 143.5, 138.9, 125.2, 110, 109.9, 57, 53.4, 51.1, 47.3, 35.1, 33.6, 32.5, 31.5.

Example 17: 3-(furan-2-yl)pyrrolidine-1-carbothioamide

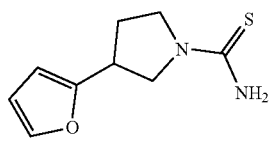 [SMILES: NC(=S)N1CCC(c2ccco2)C1]

3-(Furan-2-yl)pyrrolidine (CAS #1082926-03-1) was converted to 3-(furan-2-yl)pyrrolidine-1-carbothioamide by a similar procedure as described for Example 10 and the product was isolated as a white solid.

$^1$H NMR (DMSO-d6): 7.57 (1H, s), 7.28 (2H, br s), 6.38 (1H, m), 6.21 (1H, d, J=3.1 Hz), 3.97 (0.5H, br s), 3.77 (0.5H, br s), 3.69 (0.5H, br s), 3.52-3.66 (1.5H, m), 3.30-3.51 (2H, m), 2.31 (0.5H, br s), 2.16 (0.5H, m), 2.13 (0.5H, m), 1.99 (0.5H, br s).

$^{13}$C NMR (DMSO-d6): 178.6, 155.0, 154.8, 142.0, 110.4, 105.2, 105.0, 55.4, 51.8, 50.8, 47.0, 37.7, 36.1, 30.8, 29.6.

Example 18: 3-(2,5-difluorophenyl)pyrrolidine-1-carbothioamide

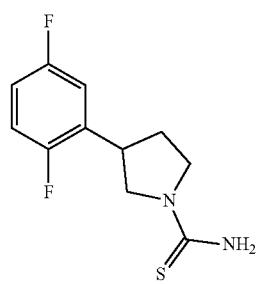 [SMILES: NC(=S)N1CCC(c2cc(F)ccc2F)C1]

3-(2,5-Difluorophenyl)pyrrolidine (CAS #1203797-48-1) was converted to 3-(2,5-difluorophenyl)pyrrolidine-1-carbothioamide by a similar procedure as described for Example 10 and the product was isolated as a white solid.

$^1$H NMR (DMSO-d6): 6.82-7.61 (5H, m), 4.09 (0.5H, m), 3.90 (0.5H, m), 3.76 (0.5H, m), 3.71 (0.5H, m), 3.46-3.64 (1H, m), 3.38 (1H, m), 2.33 (0.5H, m), 2.18 (1H, m), 2.03 (0.5H, m).

$^{13}$C NMR (DMSO-d6): 178.5, 159.1, 157.6, 157.4, 155.7, 129.9, 117.0, 116.8, 114.9, 56.0, 52.4, 51.0, 47.0, 37.4, 35.9, 31.4, 30.3.

Example 19: 3-(2,4,5-trifluorophenyl)pyrrolidine-1-carbothioamide

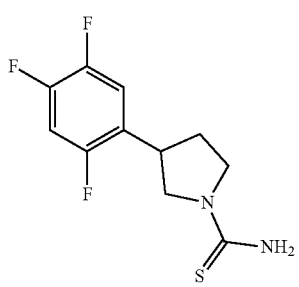 [SMILES: NC(=S)N1CCC(c2cc(F)c(F)cc2F)C1]

3-(2,4,5-Trifluorophenyl)pyrrolidine (CAS #1260814-64-9) was converted to 3-(2,4,5-trifluorophenyl)pyrrolidine-1-carbothioamide by a similar procedure as described for Example 10 and the product was isolated as a white solid.

$^1$H NMR (DMSO-d6): 7.55 (2H, m), 7.24 (2H, br s), 4.09 (0.5H, m), 3.90 (0.5H, m), 3.76 (0.5H, m), 3.69 (0.5H, m), 3.52 (2H, m), 3.37 (0.5H, m), 3.29 (0.5H, m), 2.31 (0.5H, m), 2.17 (1H, m), 2.03 (0.5H, m).

$^{13}$C NMR (DMSO-d6): 178.5, 156.4, 154.8, 148.8, 147, 145.4, 125.1, 124.9, 116.5, 116.4, 116.3, 106.2, 106.0, 106.0, 105.8, 56.0, 52.5, 51.0, 47.0, 36.9, 35.4, 31.5, 30.4.

Example 20: 3-(3,4-difluorophenyl)pyrrolidine-1-carbothioamide

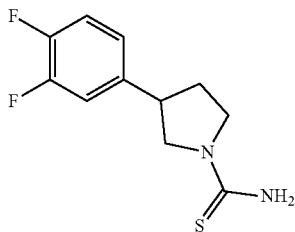 [SMILES: NC(=S)N1CCC(c2ccc(F)c(F)c2)C1]

3-(3,4-Difluorophenyl)pyrrolidine (CAS #848822-98-0) was converted to 3-(3,4-difluorophenyl)pyrrolidine-1-carbothioamide by a similar procedure as described for Example 10 and the product was isolated as a light orange solid.

$^1$H NMR (DMSO-d6): 7.41 (2H, br m), 7.16 (1H, br s), 6.59-7.86 (2H, m), 4.12 (0.5H, m), 3.90 (0.5H, m), 3.78 (0.5H, m), 3.51 (1.5H, m), 3.42 (1.5H, m 1H, s), 3.24 (0.5H, m), 2.32 (0.5H, m), 2.18 (0.5H, m), 2.11 (0.5H, m), 1.98 (0.5H, m).

$^{13}$C NMR (DMSO-d6): 178.4, 150.2, 150.2, 149.1, 149.0, 148.6, 148.5, 147.5, 147.4, 139.0, 138.9, 124.0, 117.4, 117.3, 116.3, 116.2, 57.3, 53.8, 51.3, 47.4, 43.3, 41.7, 32.8, 31.7.

Example 21: (S)-3-(2,4,6-trifluorophenyl)pyrrolidine-1-carbothioamide

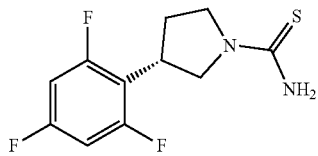 [SMILES: NC(=S)N1CC[C@@H](c2c(F)cc(F)cc2F)C1]

(S)-3-(2,4,6-Trifluorophenyl)pyrrolidine (CAS #1335508-11-6) was converted to (S)-3-(2,4,6-trifluorophenyl)pyrrolidine-1-carbothioamide by a similar procedure as described for Example 10 and the product was isolated as a white solid.

$^1$H NMR (DMSO-d6): 7.22 (2H, m), 6.50-8.0 (2H, m br), 4.03 (0.5H, br m), 3.96 (0.5H, br s), 3.81 (0.5H, br m), 3.68 (1H, br m), 3.51-3.58 (1.5H, m), 3.42 (0.5H, br m), 3.38 (0.5H, br s), 2.28 (1H, m), 2.13 (1H, br s).

$^{13}$C NMR (DMSO-d6): 178.6, 162.1, 162, 160.5, 160.4, 112.2, 101.4, 101.2, 101.0, 54.6, 51.2, 50.8, 47.5, 33.7, 32.4, 30.8, 29.7.

Example 22: 3-(2,3,4-trifluorophenyl)pyrrolidine-1-carbothioamide

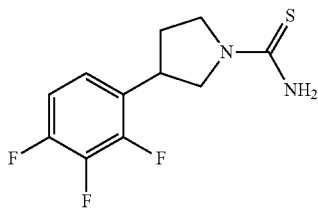 [SMILES: NC(=S)N1CCC(c2ccc(F)c(F)c2F)C1]

3-(2,3,4-Trifluorophenyl)pyrrolidine (CAS #1260884-52-3) was converted to 3-(2,3,4-trifluorophenyl)pyrrolidine-1-carbothioamide by a similar procedure as described for Example 10 and the product was isolated as an off-white solid.

$^1$H NMR (DMSO-d6): 6.15-8.25 (2H, s br), 7.33 (1H, br s), 7.21 (1H, br s), 4.09 (0.5H, br s), 3.88 (0.5H, br s), 3.76 (1H, m), 3.56 (1.5H, m), 3.50 (0.5H, br s), 3.30-3.50 (1H, m), 2.37 (0.5H, m), 2.18 (1H, br s), 2.03 (0.5H, br s).

$^{13}$C NMR (DMSO-d6): 178.6, 178.5, 149.9, 149.7, 148.3, 148.1, 139.8, 138.2, 126.1, 122.4, 112.7, 55.9, 52.4, 50.9, 47.0, 37.0, 35.5, 31.6, 30.4.

Example 23: 3-(2,3,5,6-Tetrafluorophenyl)pyrrolidine-1-carbothioamide

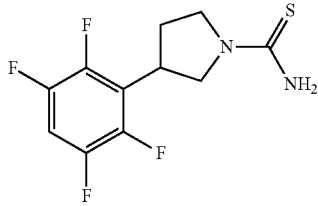 [SMILES: NC(=S)N1CCC(c2c(F)c(F)cc(F)c2F)C1]

3-(2,3,5,6-Tetrafluorophenyl)pyrrolidine (CAS #1260865-90-4) was converted to 3-(2,3,5,6-Tetrafluorophenyl)pyrrolidine-1-carbothioamide by a similar procedure as described for Example 10 and the product was isolated as an off-white powder.

$^1$H NMR (DMSO-d6): 7.84 (1H, br s), 7.26 (2H, br s), 4.10 (0.5H, m), 3.95 (1H, m), 3.78 (1H, m), 3.47 (2H, m), 3.41 (0.5H, m), 2.0-2.40 (2H, m).

$^{13}$C NMR (DMSO-d6): 178.6, 146.5, 146.4, 146.3, 145.5, 144.8, 144.8, 144.7, 143.9, 143.8, 119.4, 105.6, 105.4, 54.3, 51.1, 50.6, 47.4, 34.7, 33.3, 30.7, 29.6.

Example 24: 3-(2,3,5-trifluorophenyl)pyrrolidine-1-carbothioamide

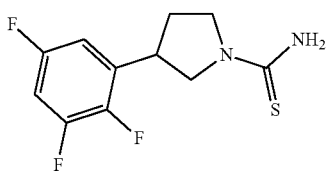 [SMILES: NC(=S)N1CCC(c2cc(F)cc(F)c2F)C1]

3-(2,3,5-Trifluorophenyl)pyrrolidine (CAS #1260885-09-3) was converted to 3-(2,3,5-trifluorophenyl)pyrrolidine-1-carbothioamide by a similar procedure as described for Example 10 and the product was isolated as a white powder.

$^1$H NMR (DMSO-d6): 7.45 (1H, br s), 7.25 (2H, br s), 7.13 (1H, m), 4.10 (0.5H, m), 3.90 (0.5H, m), 3.78 (1H, m), 3.63 (0.5H, m), 3.53 (1.5H, m), 3.41 (0.5H, m), 3.35 (0.5H, m), 2.35 (0.5H, m), 2.19 (1H, m), 2.04 (0.5H, m).

$^{13}$C NMR (DMSO-d6): 178.5, 158.2, 158.1, 156.6, 156.5, 150.5, 150.4, 150.3, 148.9, 148.8, 148.7, 145.8, 144.2, 131.5, 110.1, 104.3, 55.8, 52.3, 50.9, 47, 37.3, 35.8, 31.5, 30.3.

Example 25: (S)-3-(3,5-difluorophenyl)pyrrolidine-1-carbothioamide

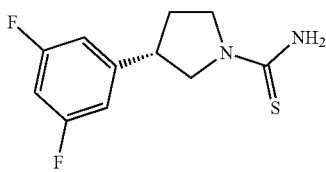 [SMILES: NC(=S)N1CC[C@@H](c2cc(F)cc(F)c2)C1]

(S)-3-(3,5-difluorophenyl)pyrrolidine (CAS #1336142-75-6) was converted to (S)-3-(3,5-difluorophenyl)pyrrolidine-1-carbothioamide by a similar procedure as described for Example 10 and the product was isolated as a white powder.

$^1$H NMR (DMSO-d6): 7.21 (2H, br s), 7.07 (3H, m), 4.12 (0.5H, m), 3.89 (0.5H, m), 3.78 (0.5H, m), 3.35-3.63 (3H, m), 3.27 (0.5H, m), 2.34 (0.5H, m), 2.20 (0.5H, m), 2.14 (0.5H, m), 1.99 (0.5H, m).

$^{13}$C NMR (DMSO-d6): 178.5, 163.3, 163.2, 161.7, 161.6, 146, 145.8, 110.6, 110.6, 110.5, 110.4, 102.3, 102.2, 102.0, 57, 53.4, 51.2, 47.3, 43.7, 42.1, 32.6, 31.4.

Example 26: (R)-3-(3,5-difluorophenyl)pyrrolidine-1-carbothioamide

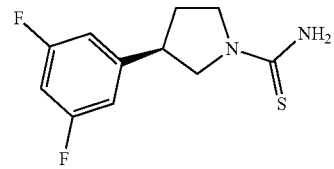 [SMILES: NC(=S)N1CC[C@H](c2cc(F)cc(F)c2)C1]

(R)-3-(3,5-difluorophenyl)pyrrolidine (CAS #1334824-24-6) was converted to (R)-3-(3,5-difluorophenyl)pyrrolidine-1-carbothioamide by a similar procedure as described for Example 10 and the product was isolated as a white powder.

$^1$H NMR (DMSO-d6): 7.21 (2H, br s), 7.07 (3H, m), 4.12 (0.5H, m), 3.89 (0.5H, m), 3.78 (0.5H, m), 3.35-3.63 (3H, m), 3.27 (0.5H, m), 2.34 (0.5H, m), 2.20 (0.5H, m), 2.14 (0.5H, m), 1.99 (0.5H, m).

$^{13}$C NMR (DMSO-d6): 178.5, 163.3, 163.2, 161.7, 161.6, 146, 145.8, 110.6, 110.5, 110.4, 102.4, 102.2, 102.0, 57.0, 53.4, 51.2, 47.3, 43.7, 42.1, 32.6, 31.4.

Example 27: (1S,5S)-1-(thiophen-2-yl)-3-azabicyclo[3.1.0]hexane-3-carbothioamide

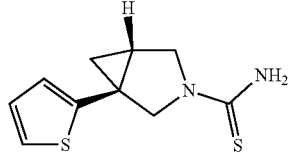 [SMILES: NC(=S)N1C[C@H]2C[C@@]2(c2cccs2)C1]

(1S,5S)-1-(thiophen-2-yl)-3-azabicyclo[3.1.0]hexane (CAS #1046141-90-5) was converted to (1S,5S)-1-(thiophen-2-yl)-3-azabicyclo[3.1.0]hexane-3-carbothioamide by a similar procedure as described for Example 10 and the product was isolated as a beige semi-solid.

$^1$H NMR (CDCl$_3$): 7.14 (1H, br d, J=4.4 Hz), 6.93 (1H, dd, J=5.1, 3.5 Hz), 6.89 (1H, br), 5.81 (2H, br s), 4.56 (0.5H, m), 4.29 (0.5H, m), 4.02 (0.5H, m), 3.94 (0.5H, m), 3.85 (0.5H, m), 3.73 (1H, m), 3.60 (0.5H, br s), 1.97 (0.5H, br s), 1.92 (0.5H, br s), 1.39 (1H, m), 0.96 (1H, m).

$^{13}$C NMR (CDCl$_3$): 180.2, 144.1, 143.8, 127, 124.2, 123.8, 123.6, 123.5, 58.9, 55.0, 54.8, 50.5, 28.6, 27.5, 27.2, 26.3, 20.1.

Example 28: (1R,5R)-1-(thiophen-2-yl)-3-azabicyclo[3.1.0]hexane-3-carbothioamide

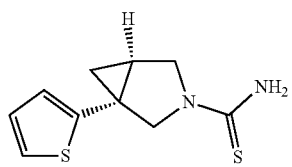 [SMILES: NC(=S)N1C[C@@H]2C[C@]2(c2cccs2)C1]

(1R,5R)-1-(thiophen-2-yl)-3-azabicyclo[3.1.0]hexane (CAS #1046141-89-2) was converted to (1R,5R)-1-(thiophen-2-yl)-3-azabicyclo[3.1.0]hexane-3-carbothioamide by a similar procedure as described for Example 10 and the product was isolated as a beige solid.

$^1$H NMR (DMSO-d6): 7.14 (1H, br d, J=4.4 Hz), 6.93 (1H, dd, J=5.1, 3.5 Hz), 6.89 (1H, br), 5.75 (2H, br s), 4.57 (0.5H, m), 4.30 (0.5H, m), 4.03 (0.5H, m), 3.95 (0.5H, m), 3.85 (0.5H, m), 3.73 (1H, m), 3.59 (0.5H, br s), 1.98 (0.5H, br s), 1.93 (0.5H, br s), 1.39 (1H, m), 0.96 (1H, m).

$^{13}$C NMR (DMSO-d6): 180.3, 144.1, 143.8, 127, 124.2, 123.8, 123.6, 123.5, 58.9, 55.0, 54.8, 50.5, 28.6, 27.5, 27.3, 26.3, 20.1.

Example 29: 3-(perfluorophenyl)pyrrolidine-1-carbothioamide

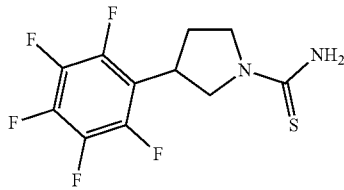 [SMILES: NC(=S)N1CCC(c2c(F)c(F)c(F)c(F)c2F)C1]

3-(Perfluorophenyl)pyrrolidine (CAS #1260650-30-3) was converted to 3-(perfluorophenyl)pyrrolidine-1-carbothioamide by a similar procedure as described for Example 10 and the product was isolated as a white powder.

$^1$H NMR (DMSO-d6): 7.27 (2H, br s), 4.09 (0.5H, br s), 3.94 (1H, br s), 3.77 (1H, br s), 3.58 (1.5H, br s), 3.46 (0.5H, br s), 3.40 (0.5H, br s), 2.37 (0.5H, br s), 2.29 (0.5H, br s), 2.23 (0.5H, br s), 2.13 (0.5H, br s).

$^{13}$C NMR (DMSO-d6): 178.6, 145.9, 144.3, 54.3, 51.1, 50.6, 47.3, 34.2, 32.8, 30.7, 29.7.

Example 30: (1S,5R)-1-(3,5-Difluorophenyl)-N-methyl-3-azabicyclo[3.1.0]hexane-3-carbothioamide

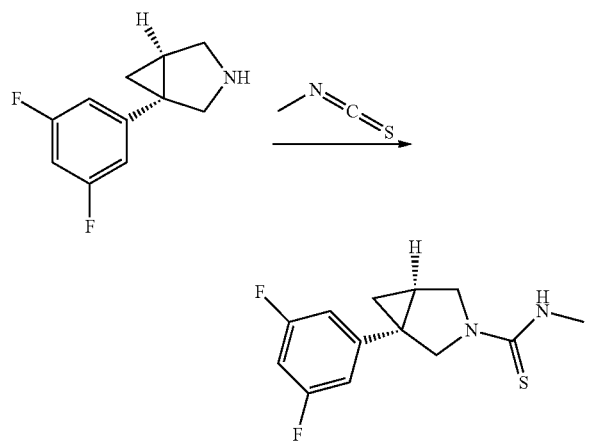

A solution of (1S,5R)-1-(3,5-difluorophenyl)-3-azabicyclo[3.1.0]hexane (Feng Xu et al.: *Org. Lett.* 8(17), 3885-3888, 2006) (0.215 g, 1.1 mmol) and methyl isothiocyanate (0.088 g, 1.210 mmol) in acetonitrile (5 mL) was stirred at room temperature for 4 h and then concentrated under reduced pressure. The residue was chromatographed (ethyl acetate-petroleum ether) to give (1S,5R)-1-(3,5-difluorophenyl)-N-methyl-3-azabicyclo[3.1.0]hexane-3-carbothioamide as a yellowish solid (0.148 g, 50% yield).

$^1$H NMR (CDCl$_3$): 6.60-6.71 (3H, m), 5.51 (1H, br s), 4.29 (1H, br s), 3.96 (1H, m), 3.81 (1H, br d, J=8.9 Hz), 3.75 (1H, d, J=7.5 Hz), 3.13 (3H, d, J=4.5 Hz), 2.02 (1H, dt, J=8.4, 4.4 Hz), 1.21 (1H, dd, J=5.4, 8.3), 0.94 (1H, t, J=4.9 Hz).

$^{13}$C NMR (CDCl$_3$): 181, 163.9, 163.8, 162.3, 162.2, 144.4, 144.4, 109.6, 109.5, 109.4, 109.4, 102.2, 102.1, 101.9, 55.5, 51.6, 32.4, 31.1, 24.7, 20.4.

Example 31: N-methyl-3-phenylpyrrolidine-1-carbothioamide

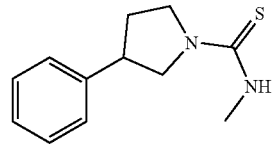

3-Phenylpyrrolidine (CAS #936-44-7) was converted to N-methyl-3-phenylpyrrolidine-1-carbothioamide by a similar procedure as described for Example 30 and the product was isolated as a white solid.

$^1$H NMR (CDCl$_3$): 7.34 (2H, t, J=7.8 Hz), 7.27 (1H, m), 7.23 (2H, d, J=7.9 Hz), 5.32 (1H, br s), 3.68-4.46 (2H, m), 3.62 (1H, br s), 3.49 (1H, br s), 3.17 (3H, d, J=4.55 Hz), 2.40 (1H, br s), 2.07-2.20 (1H, m).

$^{13}$C NMR (CDCl$_3$): 179.8, 140.4, 128.7, 127.1, 126.9, 55.6, 49.2, 43.7, 32.7, 32.4.

Example 32: 3-(3,5-difluorophenyl)-N-methylpyrrolidine-1-carbothioamide

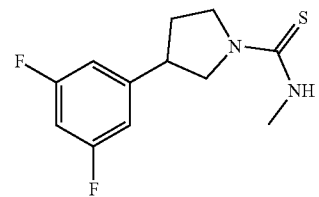 [SMILES: CNC(=S)N1CCC(c2cc(F)cc(F)c2)C1]

3-(3,5-Difluorophenyl)pyrrolidine (CAS #1092108-82-1) was converted to 3-(3,5-difluorophenyl)-N-methylpyrrolidine-1-carbothioamide by a similar procedure as described for Example 30 and the product was isolated as a white solid.

$^1$H NMR (DMSO-d6): 7.31 (1H, br q, J=4.0 Hz), 7.11 (1H, tt, J=2.3, 9.3 Hz), 7.07 (2H, m), 3.98 (1H, br s), 3.73 (1H, br m), 3.48 (2H, br m), 3.39 (1H, m), 2.89 (3H, d, J=4.3 Hz), 2.28 (1H, br m), 2.07 (1H, br m).

$^{13}$C NMR (DMSO-d6): 179.4, 163.8, 163.7, 162.2, 162.1, 146.5, 146.5, 146.4, 111, 110.9, 102.8, 102.6, 102.5, 56.2, 50.3, 43.1, 32.4, 32.1.

Example 33: N-methyl-3-(2,3,5,6-tetrafluorophenyl) pyrrolidine-1-carbothioamide

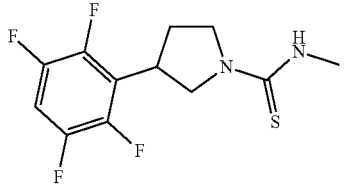 [SMILES: CNC(=S)N1CCC(c2c(F)c(F)cc(F)c2F)C1]

3-(2,3,5,6-Tetrafluorophenyl)pyrrolidine (CAS #1260865-90-4) was converted to N-methyl-3-(2,3,5,6-tetrafluorophenyl)pyrrolidine-1-carbothioamide by a similar procedure as described for Example 30 and the product was isolated as a white powder.

$^1$H NMR (DMSO-d6): 7.83 (1H, m), 7.36 (1H, br q, J=3.7 Hz), 3.99 (1H, br s), 3.83 (1H, m), 3.77 (1H, br s), 3.60 (1H, m), 3.48 (1H, m), 2.89 (3H, d, J=4.1 Hz), 2.31 (1H, br s), 2.25 (1H, br m).

$^{13}$C NMR (DMSO-d6): 179.1, 146.5, 146.4, 146.3, 145.5, 145.4, 144.9, 144.8, 144.7, 143.9, 143.8, 119.5, 119.4, 119.3, 105.7, 105.5, 105.3, 52.8, 48.4, 33.6, 32.0, 30.0.

Example 34: 1-(3,5-difluorophenyl)-3-azabicyclo[3.1.0]hexane-3-carbothioamide

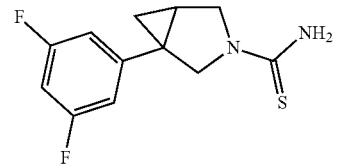 [SMILES: NC(=S)N1CC2CC2(c2cc(F)cc(F)c2)C1]

1-(3,5-Difluorophenyl)-3-azabicyclo[3.1.0]hexane (Feng Xu et al.: Org. Lett. 8(17), 3885-3888, 2006) was converted to 1-(3,5-difluorophenyl)-3-azabicyclo[3.1.0]hexane-3-carbothioamide by a similar procedure as described for Example 10 and the product was isolated as a white powder.

$^1$H NMR (DMSO-d6): 7.30 (2H, br s), 7.07 (1H, br t, J=9.2 Hz), 6.94 (2H, br s), 4.39 (0.5H, br s), 4.07 (0.5H, br s), 3.92 (0.5H, br s), 3.58-3.80 (2H, m), 3.53 (0.5H, br s), 2.21 (0.5H, br s), 2.12 (0.5H, br s), 1.20 (1H, br s), 0.78 (1H, br s).

$^{13}$C NMR (DMSO-d6): 179.9, 163.4, 163.3, 161.7, 161.6, 145.9, 145.9, 145.8, 109.8, 109.7, 109.5, 109.4, 101.8, 101.6, 101.5, 56.5, 53.7, 52.8, 49.9, 31.7, 30.1, 25.4, 24.7, 20.4, 20.0.

Example 35: (1R,5S)-1-(3,5-difluorophenyl)-3-azabicyclo[3.1.0]hexane-3-carbothioamide

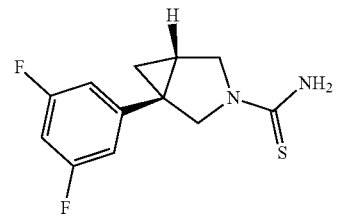 [SMILES: NC(=S)N1C[C@H]2C[C@@]2(c2cc(F)cc(F)c2)C1]

(1R,5S)-1-(3,5-difluorophenyl)-3-azabicyclo[3.1.0]hexane (Feng Xu et al.: Org. Lett. 8(17), 3885-3888, 2006) was converted to (1R,5S)-1-(3,5-difluorophenyl)-3-azabicyclo[3.1.0]hexane-3-carbothioamide by a similar procedure as described for Example 10 and the product was isolated as a white powder.

$^1$H NMR (DMSO-d6): 7.30 (2H, br s), 7.07 (1H, br t, J=9.2 Hz), 6.94 (2H, br s), 4.39 (0.5H, br s), 4.07 (0.5H, br s), 3.92 (0.5H, br s), 3.58-3.80 (2H, m), 3.53 (0.5H, br s), 2.21 (0.5H, br s), 2.12 (0.5H, br s), 1.20 (1H, br s), 0.78 (1H, br s).

$^{13}$C NMR (DMSO-d6): 179.9, 163.4, 163.3, 161.7, 161.6, 145.9, 145.9, 145.8, 109.7, 109.5, 101.8, 101.6, 101.4, 56.5, 53.7, 52.7, 50.0, 31.7, 30.2, 25.4, 24.7, 20.4, 20.0.

Example 36: (1S,5R)-1-(3,5-difluorophenyl)-3-azabicyclo[3.1.0]hexane-3-carbothioamide

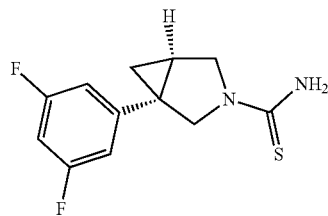 [SMILES: NC(=S)N1C[C@@H]2C[C@]2(c2cc(F)cc(F)c2)C1]

(1S,5R)-1-(3,5-difluorophenyl)-3-azabicyclo[3.1.0]hexane (Feng Xu et al.: Org. Lett. 8(17), 3885-3888, 2006) was converted to (1S,5R)-1-(3,5-difluorophenyl)-3-azabicyclo[3.1.0]hexane-3-carbothioamide by a similar procedure as described for Example 10 and the product was isolated as a white powder.

$^1$H NMR (DMSO-d6): 7.30 (2H, br s), 7.07 (1H, br t, J=9.2 Hz), 6.94 (2H, br s), 4.39 (0.5H, br s), 4.07 (0.5H, br s), 3.92 (0.5H, br s), 3.58-3.80 (2H, m), 3.53 (0.5H, br s), 2.21 (0.5H, br s), 2.12 (0.5H, br s), 1.20 (1H, br s), 0.78 (1H, br s).

$^{13}$C NMR (DMSO-d6): 179.9, 163.4, 163.3, 161.7, 161.6, 145.9, 145.9, 109.7, 109.5, 101.8, 101.6, 101.4, 56.5, 53.7, 52.8, 50, 31.7, 30.2, 25.5, 24.7, 20.4, 20.0,

Example 37: 1-(2,4-difluorophenyl)-3-azabicyclo[3.1.0]hexane-3-carbothioamide

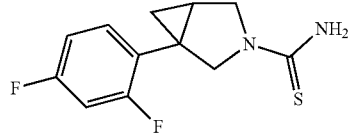 [SMILES: NC(=S)N1CC2CC2(c2ccc(F)cc2F)C1]

1-(2,4-Difluorophenyl)-3-azabicyclo[3.1.0]hexane (Feng Xu et al.: Org. Lett. 8(17), 3885-3888, 2006) was converted to 1-(2,4-difluorophenyl)-3-azabicyclo[3.1.0]hexane-3-carbothioamide by a similar procedure as described for Example 10 and the product was isolated as a white powder.

$^1$H NMR (DMSO-d6): 7.42 (1H, m), 7.24 (1H, br t, J=9.3 Hz), 7.05 (1H, br t, J=7.5 Hz), 6.80-7.60 (2H, br s), 4.30 (0.5H, m), 4.09 (0.5H, m), 3.87 (0.5H, m), 3.71 (0.5H, m), 3.66 (0.5H, m), 3.58 (0.5H, m), 3.48 (0.5H, m), 3.35 (0.5H, m), 2.09 (0.5H, m), 1.93 (0.5H, m), 1.10 (1H, br s), 0.70 (1H, t, J=4.7 Hz).

¹³C NMR (DMSO-d6): 179.8, 162.7, 162.6, 162.3, 162.2, 161, 160.9, 160.7, 160.6, 131.9, 123.5, 111.5, 111.3, 104.2, 104.0, 103.9, 57.9, 54.1, 53.9, 50.0, 27.6, 26.2, 22.8, 21.8, 16.8, 16.7.

Example 38: 1-(2,5-difluorophenyl)-3-azabicyclo[3.1.0]hexane-3-carbothioamide

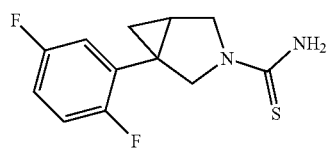 [SMILES: NC(=S)N1CC2CC2(c2cc(F)ccc2F)C1]

1-(2,5-Difluorophenyl)-3-azabicyclo[3.1.0]hexane (Feng Xu et al.: *Org. Lett.* 8(17), 3885-3888, 2006) was converted to 1-(2,5-difluorophenyl)-3-azabicyclo[3.1.0]hexane-3-carbothioamide by a similar procedure as described for Example 10 and the product was isolated as a white powder.

¹H NMR (DMSO-d6): 7.20-7.28 (2H, m), 7.16 (1H, m), 6.60-8.00 (2H, br s), 4.33 (0.5H, br m), 4.09 (0.5H, br m), 3.90 (0.5H, br m), 3.71 (0.5H, br m), 3.65 (0.5H, br m), 3.46-3.61 (1H, m), 3.40 (0.5H, br m), 2.18 (0.5H, br m), 2.03 (0.5H, br m), 1.14 (1H, br s), 0.73 (1H, t, J=4.8 Hz).

¹³C NMR (DMSO-d6): 179.8, 158.8, 157.2, 129.2, 117, 117, 116.9, 116.8, 115.4, 115.3, 57.5, 53.8, 49.9, 28.2, 26.7, 23, 22.1, 17.4, 17.1.

Example 39: (1S,5R)-1-(3,5-Difluorophenyl)-N-propyl-3-azabicyclo[3.1.0]hexane-3-carbothioamide

Step 1: ((1S,5R)-1-(3,5-difluorophenyl)-3-azabicyclo[3.1.0]hexan-3-yl)(1H-imidazol-1-yl)methanethione

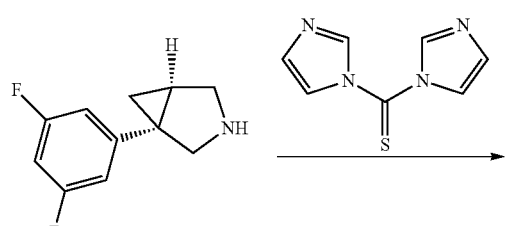

To a solution of 1,1'-thiocarbonyldiimidazole (0.329 g, 1.844 mmol) in dry tetrahydrofuran (6 mL) was added a solution of (1S,5R)-1-(3,5-difluorophenyl)-3-azabicyclo[3.1.0]hexane (Feng Xu et al.: Org. Lett. 8(17), 3885-3888, 2006) (0.36 g, 1.844 mmol) in dry tetrahydrofuran (6 mL). The solution was stirred at room temperature for 1 h and then at 50-55° C. for 2 h. After being cooled to room temperature, the solution was concentrated under reduced pressure. The residue was chromatographed (ethyl acetate-petroleum ether) to give ((1S,5R)-1-(3,5-difluorophenyl)-3-azabicyclo[3.1.0]hexan-3-yl)(1H-imidazol-1-yl)methanethione (0.31 g, 55% yield).

Step 2: (1S,5R)-1-(3,5-Difluorophenyl)-N-propyl-3-azabicyclo[3.1.0]hexane-3-carbothioamide

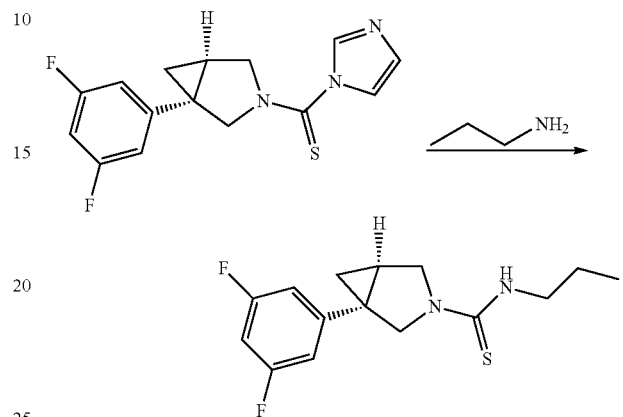

To a solution of ((1S,5R)-1-(3,5-difluorophenyl)-3-azabicyclo[3.1.0]hexan-3-yl)(1H-imidazol-1-yl)methanethione (0.15 g, 0.491 mmol) in dry tetrahydrofuran (3 mL) was added propan-1-amine (0.081 mL, 0.982 mmol) and the mixture was stirred at 65° C. for 16 h. The solvents were evaporated off and then the residue was chromatographed (petroleum ether-ethyl acetate) to give (1S,5R)-1-(3,5-difluorophenyl)-N-propyl-3-azabicyclo[3.1.0]hexane-3-carbothioamide as a yellowish viscous oil (0.093 g, 64% yield).

¹H NMR (CDCl₃): 6.65-6.74 (3H, m), 5.30 (1H, t, J=4.7 Hz), 4.29 (1H, br m), 3.96 (1H, br m), 3.82 (1H, br d, J=8.9 Hz), 3.76 (1H, br d, J=7.0 Hz), 3.60 (2H, m), 2.03 (1H, dt, J=4.3, 8.3 Hz), 1.65 (2H, m), 1.23 (1H, d m, J=5.3 Hz), 0.97 (3H, t, J=7.5 Hz), 0.97 (1H, m).

¹³C NMR (CDCl₃): 180.2, 164, 163.9, 162.3, 162.2, 144.5, 144.4, 144.4, 109.7, 109.6, 109.5, 109.5, 102.3, 102.1, 102.0, 55.4, 51.5, 47.4, 31.1, 24.7, 22.5, 20.3, 11.4.

Example 40: 1-(2,5-difluorophenyl)-N-(2-mercaptoethyl)-3-azabicyclo[3.1.0]hexane-3-carbothioamide

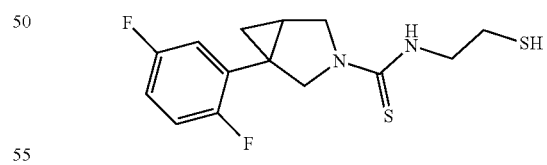

1-(2,5-Difluorophenyl)-3-azabicyclo[3.1.0]hexane (Feng Xu et al.: *Org. Lett.* 8(17), 3885-3888, 2006) was converted to 1-(2,5-difluorophenyl)-N-(2-mercaptoethyl)-3-azabicyclo[3.1.0]hexane-3-carbothioamide by a similar procedure as described for Example 39 and the product was isolated as a colourless oil.

¹H NMR (DMSO-d6): 7.56 (1H, t br, J=4.5 Hz), 7.24 (2H, m), 7.16 (1H, m), 4.17 (1H, s br), 3.91 (1H, s br), 3.67 (1H, m), 3.56 (2H, m), 3.50 (1H, br s), 2.63 (2H, q, J=7.1 Hz), 2.39 (1H, m), 2.14 (1H, br s), 1.13 (1H, dd, J=8.0, 5.1 Hz), 0.76 (1H, t, J=4.8 Hz).

¹³C NMR (DMSO-d6): 179.3, 158.8, 158.7, 157.2, 157.1, 129.3, 129.3, 129.2, 129.2, 117.0, 117.0, 117.0, 116.9, 116.9, 116.8, 115.5, 115.4, 115.3, 115.2, 53.6, 49.6, 47.8, 47, 27.1, 22.8, 22.2, 17.6.

Example 41: (1S,5R)-1-(3,5-difluorophenyl)-N-methyl-4-oxo-3-azabicyclo[3.1.0]hexane-3-carbothioamide

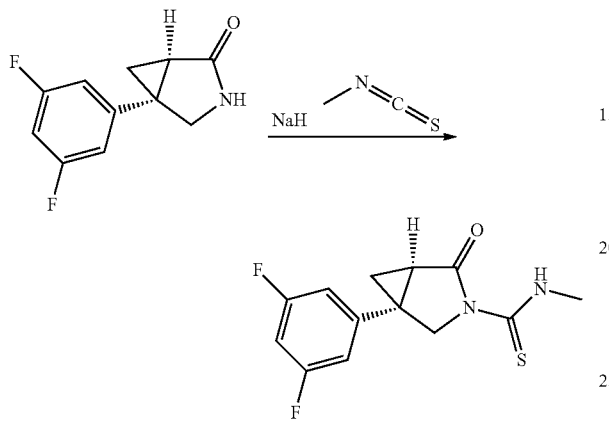

To a solution of (1R,5S)-5-(3,5-difluorophenyl)-3-azabicyclo[3.1.0]hexan-2-one (Example 60, step 2) (0.628 g, 3 mmol) in dry tetrahydrofuran (15 mL) was added sodium hydride (60% in mineral oil) (0.180 g, 4.5 mmol) at 0-5° C. in portions. The mixture was stirred for 30 min at room temperature, and methyl isothiocyanate (0.329 g, 4.5 mmol) was then added at −78° C. The mixture was allowed to reach room temperature over 3 h, then carefully quenched with aq. ammonium chloride solution, and extracted with a mixture of ethyl acetate-petroleum ether (2:1). The organic phase was dried over MgSO₄ and evaporated to dryness. The residue was triturated with petroleum ether, then filtered, washed with petroleum ether, and dried under vacuum. Chromatography (ethyl acetate-petroleum ether; 1: 4) afforded (1S,5R)-1-(3,5-difluorophenyl)-N-methyl-4-oxo-3-azabicyclo[3.1.0]hexane-3-carbothioamide as a white powder (0.036 g, 4% yield).

¹H NMR (DMSO-d6): 10.37 (1H, br s), 7.18 (2H, m), 7.15 (1H, tt, J=2.3, 9.3 Hz), 4.50 (1H, dd, J=11.4, 1.7 Hz), 4.16 (1H, d, J=11.3 Hz), 3.02 (3H, d, J=2.8 Hz), 2.76 (1H, ddd, J=1.7, 3.5, 9.1 Hz), 1.68 (1H, dd, J=9.1, 4.8 Hz), 1.43 (1H, dd, J=4.8, 3.6 Hz).

¹³C NMR (DMSO-d6): 180.5, 174.4, 163.3, 163.2, 161.7, 161.6, 143.3, 143.3, 143.2, 111.0, 111.0, 110.9, 110.8, 102.9, 102.7, 102.6, 56.1, 32.1, 30.1, 26.8, 26.7, 26.7, 20.7.

Example 42: 4-(3,5-difluorophenyl)-N-methyl-2-oxopyrrolidine-1-carbothioamide

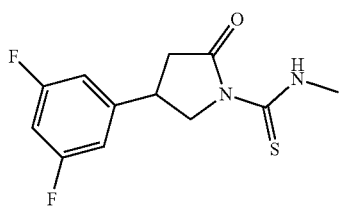 [SMILES: CNC(=S)N1CC(c2cc(F)cc(F)c2)CC1=O]

4-(3,5-Difluorophenyl)pyrrolidin-2-one (CAS #1604786-89-1) was converted to 4-(3,5-difluorophenyl)-N-methyl-2-oxopyrrolidine-1-carbothioamide by a similar procedure as described for Example 41 and the product was isolated as a beige powder.

¹H NMR (DMSO-d6): 10.51 (1H, br q, J=4.5 Hz), 7.10-7.20 (3H, m), 4.54 (1H, dd, J=10.7, 8.2 Hz), 3.85 (1H, dd, J=10.8, 9.0 Hz), 3.68 (1H, quin, J=9.0 Hz), 3.05 (3H, d, J=4.5 Hz), 2.95-3.05 (2H, m).

¹³C NMR (DMSO-d6): 180.1, 174.7, 163.3, 163.3, 161.7, 161.6, 145.5, 145.4, 145.3, 110.8, 110.7, 110.6, 110.6, 102.7, 102.5, 102.4, 56.7, 40.3, 35.1, 32.2.

Example 43: 1-(3,5-Difluorophenyl)-N-methyl-4-oxo-3-azabicyclo[3.1.0]hexane-3-carbothioamide

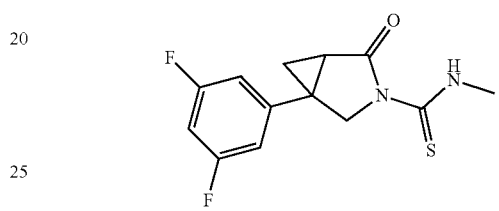

5-(3,5-Difluorophenyl)-3-azabicyclo[3.1.0]hexan-2-one was converted to 1-(3,5-Difluorophenyl)-N-methyl-4-oxo-3-azabicyclo[3.1.0]hexane-3-carbothioamide by a similar procedure as described for Example 41 and the product was isolated as a beige powder.

¹H NMR (DMSO-d6): 10.37 (1H, q, J=4.5 Hz), 7.18 (2H, m), 7.15 (1H, tt, J=2.3, 9.3 Hz), 4.50 (1H, dd, J=11.4, 1.7 Hz), 4.16 (1H, d, J=11.3 Hz), 3.02 (3H, d, J=4.5 Hz), 2.76 (1H, ddd, J=1.7, 3.5, 9.1 Hz), 1.68 (1H, dd, J=9.1, 4.8 Hz), 1.43 (1H, dd, J=4.8, 3.6 Hz).

¹³C NMR (DMSO-d6): 180.5, 174.4, 163.3, 163.2, 161.7, 161.6, 143.3, 143.3, 143.2, 111.0, 111.0, 110.9, 110.8, 102.9, 102.7, 102.5, 56.1, 32.1, 30.1, 26.7, 26.7, 20.7.

Example 44: 6-Phenyltetrahydro-1H-pyrrolo[1,2-c]imidazole-3(2H)-thione

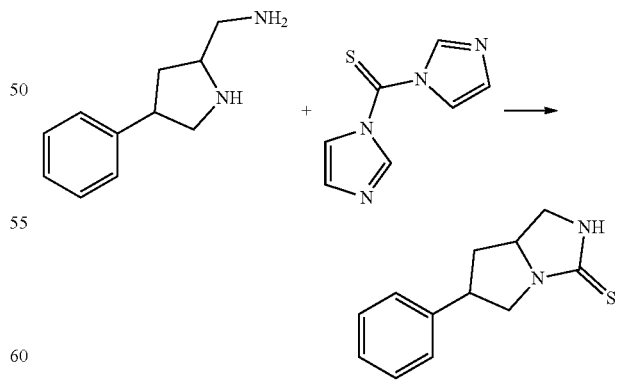

A solution of 1,1'-thiocarbonyldiimidazole (0.159 g, 0.894 mmol) in dichloromethane (2 mL) was added dropwise to a solution of (4-phenylpyrrolidin-2-yl)methanamine (CAS #82256-70-0) (0.150 g, 0.851 mmol) in dichloromethane (2 mL) at room temperature. The thus obtained orange solution was allowed to stir at room temperature for 1 h, diluted with dichloromethane, and then washed with water. The organic layer was dried over MgSO₄ and evaporated under vacuum to give the crude product as an orange oil. Chromatography (dichloromethane-methanol) followed by trituration (petroleum ether-ethyl acetate) afforded 6-phenyltetrahydro-1H-pyrrolo[1,2-c]imidazole-3(2H)-thione as a beige solid (0.076 g, 41% yield).

¹H NMR (DMSO-d6): 8.61 (1H, s), 7.31 (2H, t, J=7.5 Hz), 7.25 (2H, d, J=8.6 Hz), 7.22 (1H, t m, J=7.2 Hz), 4.17 (1H, m, J=10.1, 4.5 Hz), 3.74 (1H, dd, J=7.3, 10.3 Hz), 3.67 (1H, t, J=9.8 Hz), 3.60 (1H, t, J=9.3 Hz), 3.55 (1H, m), 3.44 (1H, dd, J=3.7, 10.4 Hz), 2.26 (1H, m), 1.50 (1H, q, J=11.3 Hz).

¹³C NMR (DMSO-d6): 186.3, 142.6, 128.6, 127.1, 126.5, 63.1, 54.2, 46.2, 45, 39.2.

Example 45: 1-(3,5-Difluorophenyl)-3-azabicyclo[3.1.0]hexane-3-carbothiohydrazide Step 1:
N-(3-phenylpyrrolidine-1-carbonothioyl)benzamide

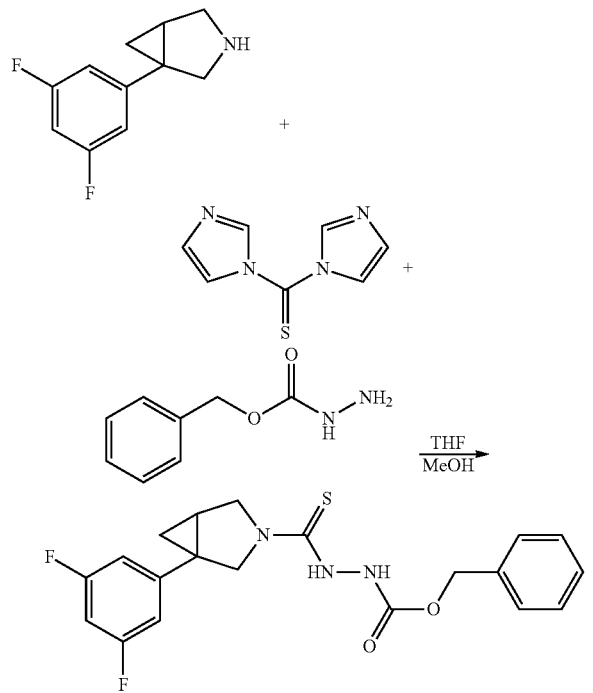

To a solution of 1,1'-thiocarbonyldiimidazole (201 mg, 1.127 mmol) in anhydrous tetrahydrofuran (2.6 mL) was added dropwise a solution of 1-(3,5-difluorophenyl)-3-azabicyclo[3.1.0]hexane (Feng Xu et al.: *Org. Lett.* 8(17), 3885-3888, 2006) (200 mg, 1.025 mmol) in anhydrous tetrahydrofuran (2.6 mL) at room temperature. The reaction was stirred at room temperature for 1 h, then heated at 55° C. for 2 h. Thereupon, the solvent was evaporated off and the resulting yellow oil was dissolved in methanol (2.5 mL) followed by addition of benzyl carbazate (341 mg, 2.049 mmol) in one portion. The reaction was heated at reflux temperature for 24 h, the solvent was then evaporated off and the residue was dissolved in dichloromethane, washed with water, dried over MgSO₄, filtered and evaporated to dryness. The thus obtained yellow oil was purified by chromatography (dichloromethane-methanol) to give benzyl 2-(1-(3,5-difluorophenyl)-3-azabicyclo[3.1.0]hexane-3-carbonothioyl)hydrazinecarboxylate as a yellow oil (0.27 g, 0.67 mmol, 65% yield).

Step 2:
N-(3-phenylpyrrolidine-1-carbonothioyl)benzamide

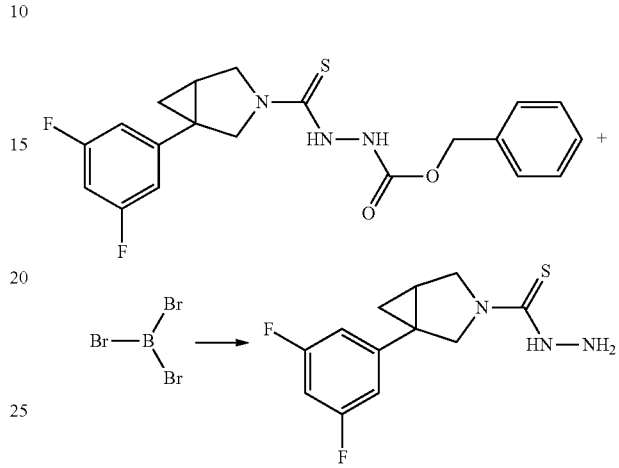

To a stirred solution of benzyl 2-(1-(3,5-difluorophenyl)-3-azabicyclo[3.1.0]hexane-3-carbonothioyl)hydrazinecarboxylate (270 mg, 0.67 mmol) in dichloromethane (5 mL) was added dropwise boron tribromide (0.19 mL, 2.008 mmol) at −78° C. under nitrogen. The solution was stirred in the cold for 5 min, then was allowed to warm up to room temperature naturally and stirred for 1.5 h. The mixture was then cooled again to 0-5° C. followed by quenching with water. The resulting emulsion then was extracted with a mixture of 30% 2-propanol in dichloromethane, the organic phase was washed with water, dried over MgSO₄, filtered and evaporated to dryness. The thus obtained yellow oil was purified by chromatography (dichloromethane-methanol), Recrystallization from 2-propanol afforded 1-(3,5-difluorophenyl)-3-azabicyclo[3.1.0]hexane-3-carbothiohydrazide as a pink solid (0.015 g, 8% yield).

¹H NMR (DMSO-d6): 8.80 (1H, s), 7.08 (1H, tt, J=9.4, 2.4 Hz), 6.95 (2H, m), 4.64 (2H, br s), 4.17 (1H, br d, J=10.9 Hz), 3.89 (1H, br d, J=11.0 Hz), 3.68 (1H, d, J=10.9 Hz), 3.59 (1H, br dd, J=10.9, 4.2 Hz), 2.18 (1H, dt, J=8.3, 4.2 Hz), 1.19 (1H, dd, J=8.0, 5.1 Hz), 0.77 (1H, t, J=4.8 Hz).

¹³C NMR (DMSO-d6): 180.7, 163.4, 163.3, 161.8, 161.7, 146, 145.9, 145.8, 109.7, 109.7, 109.6, 109.5, 101.8, 101.7, 101.5, 54.4, 51.7, 30.4, 24.6, 20.3.

Example 46: 1-(3,5-Difluorophenyl)-N,N-dimethyl-3-azabicyclo[3.1.0]hexane-3-carbothioamide

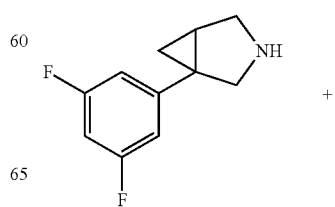

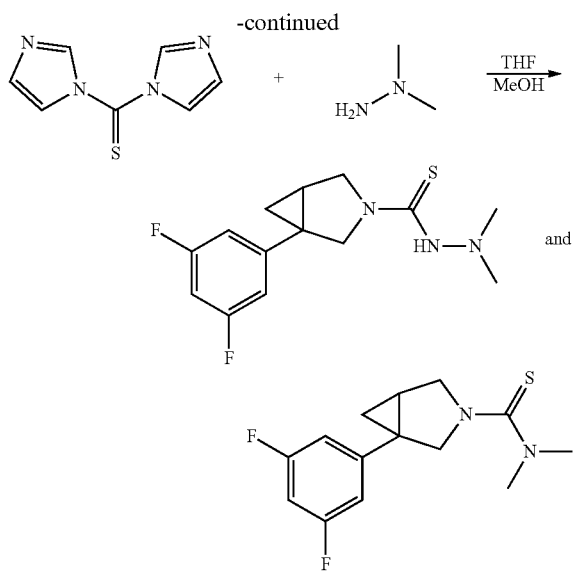

To a solution of 1,1'-thiocarbonyldiimidazole (201 mg, 1.127 mmol) in anhydrous tetrahydrofuran (2.6 mL) was added dropwise a solution of 1-(3,5-difluorophenyl)-3-azabicyclo[3.1.0]hexane (Feng Xu et al.: *Org. Lett.* 8(17), 3885-3888, 2006) (200 mg, 1.025 mmol) in anhydrous tetrahydrofuran (2.6 mL) at room temperature. The solution was stirred at room temperature for 1 h, then was heated at 55° C. for 2 h. The solvent was evaporated off under vacuum and the oily residue was dissolved in methanol (4.1 mL), followed by addition of 1,1-dimethylhydrazine (0.13 mL 1.690 mmol). The mixture was then heated to reflux and stirred for 24 h, and then cooled to room temperature, whereupon the solvent was evaporated off. The yellow oily residue was dissolved in dichloromethane, washed with water, dried over MgSO$_4$, filtered and evaporated to dryness. Chromatography (petroleum ether-ethyl acetate) afforded 1-(3,5-difluorophenyl)-N,N-dimethyl-3-azabicyclo[3.1.0] hexane-3-carbothioamide as a light yellow oil (0.124 g, 26% yield).

$^1$H NMR (CDCl$_3$): 6.70 (2H, m), 6.67 (1H, tt, J=2.3, 8.9 Hz), 4.59 (1H, d, J=11.0 Hz), 4.16 (1H, d, J=11.0 Hz), 3.72 (1H, dd, J=3.6, 10.9 Hz), 3.71 (1H, dd, J=1.2, 10.9 Hz), 3.13 (6H, m), 1.84 (1H, m), 1.07 (1H, m), 0.98 (1H, m).

$^{13}$C NMR (CDCl$_3$): 191.7, 163.9, 163.8, 162.3, 162.2, 144.8, 109.7, 109.7, 109.6, 109.6, 102.1, 101.9, 101.7, 57.2, 54.4, 43.2, 30.0, 24.3, 17.4.

Example 47: N-(cyanomethyl)-1-(2,5-difluorophenyl)-3-azabicyclo[3.1.0]hexane-3-carbothioamide

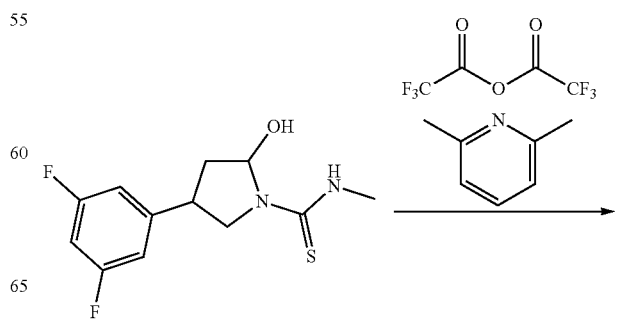

1-(2,5-Difluorophenyl)-3-azabicyclo[3.1.0]hexane (Feng Xu et al.: *Org. Lett.* 8(17), 3885-3888, 2006) was converted to N-(cyanomethyl)-1-(2,5-difluorophenyl)-3-azabicyclo [3.1.0]hexane-3-carbothioamide by a similar procedure as described for Example 30 and the product was isolated as a brownish red solid.

$^1$H NMR (DMSO-d6): 7.99 (1H, br s), 7.25 (2H, m), 7.17 (1H, m), 4.45 (2H, br d, J=5.1 Hz), 3.44-4.40 (4H, br m), 2.19 (1H, br s), 1.16 (1H, m), 0.80 (1H, m).

$^{13}$C NMR (DMSO-d6): 179.7, 158.8, 158.7, 157.2, 157.1, 129.1, 129.1, 129.0, 129.0, 129.0, 129.0, 117.6, 117.1, 117.0, 117.0, 116.9, 116.8, 116.8, 115.5, 115.5, 115.4, 115.3, 58.3, 54.5, 53.6, 49.9, 33.2, 28.1, 26.4, 23, 21.6, 17.8.

Example 48: 3-(3,5-Difluorophenyl)-N-methyl-2,3-dihydro-1H-pyrrole-1-carbothioamide Step 1: 4-(3,5-difluorophenyl)-2-hydroxy-N-methylpyrrolidine-1-carbothioamide

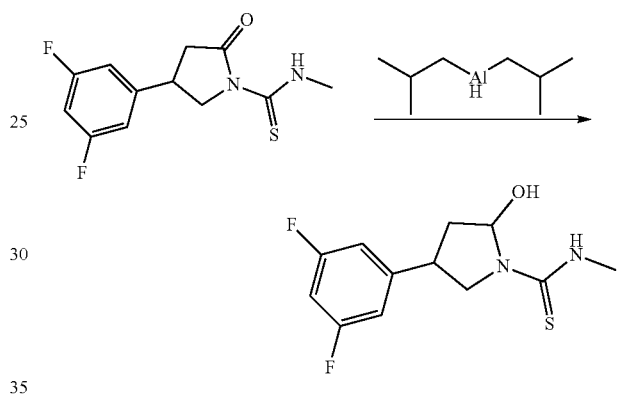

To a solution of 4-(3,5-difluorophenyl)-N-methyl-2-oxopyrrolidine-1-carbothioamide (Example 42) (0.270 g, 1 mmol) in dry toluene (5 mL) was added dropwise 1 M diisobutylaluminum hydride (2.70 mL, 2.70 mmol) in toluene at 0-5° C. and the reaction was stirred for 1 h in the cold. Thereupon, the mixture was quenched with ice-water, stirred for 1 h in the cold, diluted with ethyl acetate (20 mL) and then filtered through a celite plug. The organic phase was dried over MgSO$_4$ and evaporated to dryness. Purification by chromatography (petroleum ether-ethyl acetate) afforded 4-(3,5-difluorophenyl)-2-hydroxy-N-methylpyrrolidine-1-carbothioamide as a white powder (0.14 g, 51% yield).

Step 2: 3-(3,5-Difluorophenyl)-N-methyl-2,3-dihydro-1H-pyrrole-1-carbothioamide

-continued

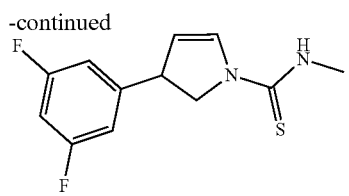

To a solution of 4-(3,5-difluorophenyl)-2-hydroxy-N-methylpyrrolidine-1-carbothioamide (0.2 g, 0.734 mmol) in dry toluene (5 mL) was added 2,6-lutidine (0.428 mL, 3.67 mmol) followed by addition of 2,2,2-trifluoroacetic anhydride (0.23 mL, 1.76 mmol) at −10° C. under nitrogen. The reaction was allowed to warm up to room temperature and stirred for 20 h. Thereupon, the mixture was quenched with water (10 mL) and stirred for 30 min. The organic phase was evaporated to dryness, the residue was then dissolved in ethanol (15 mL) and treated with 5 M sodium hydroxide (0.3 mL, 1.469 mmol) at room temperature for 1 h. Thereupon, the mixture was evaporated to dryness and the residue was partitioned between dichloromethane and water.

The organic phase was dried over MgSO$_4$, evaporated to dryness under vacuum and chromatographed (petroleum ether-ethyl acetate) to give 3-(3,5-difluorophenyl)-N-methyl-2,3-dihydro-1H-pyrrole-1-carbothioamide as a white powder (0.063 g, 33% yield).

$^1$H NMR (DMSO-d6): 7.80 (1H, br s), 7.41 (1H, br d, J=2.3 Hz), 7.11 (1H, m), 6.93 (2H, m), 5.37 (1H, dd, J=4.1, 2.6 Hz), 4.37 (1H, m), 4.23 (1H, t, J=11.2 Hz), 3.70 (1H, dd, J=11.6, 5.7 Hz), 2.91 (3H, d, J=4.3 Hz).

$^{13}$C NMR (DMSO-d6): 176.6, 163.5, 163.4, 161.8, 161.8, 148.5, 148.4, 148.3, 133.4, 112.2, 110.4, 110.2, 102.6, 102.4, 102.2, 55.9, 46.6, 31.9.

Example 49: 6-phenyl-6,7-dihydro-2H-pyrrolo[1,2-c]imidazole-3(5H)-thione

Step 1: 2-phenylpent-4-enenitrile

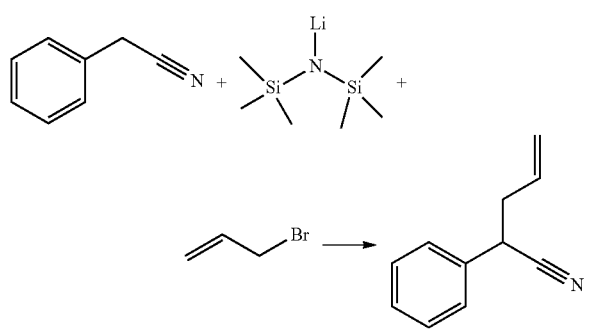

To a stirred solution of 2-phenylacetonitrile (3.15 mL, 27.3 mmol) in tetrahydrofuran (136 mL) was added lithium hexamethyldisilazane (30 mL, 30.0 mmol) dropwise at −78° C. The resulting yellow solution was allowed to stir in the cold for 30 min, whereupon 3-bromoprop-1-ene (2.3 mL, 27.2 mmol) was added dropwise and the mixture was stirred at room temperature. The solvent was then removed under vacuum and the product was purified by chromatography (petroleumether-ethyl acetate; 1:0, 9:1, then 6:1) and isolated as a yellow oil. (Yield: 2.62 g, 63%).

Step 2: 2-phenylpent-4-en-1-amine

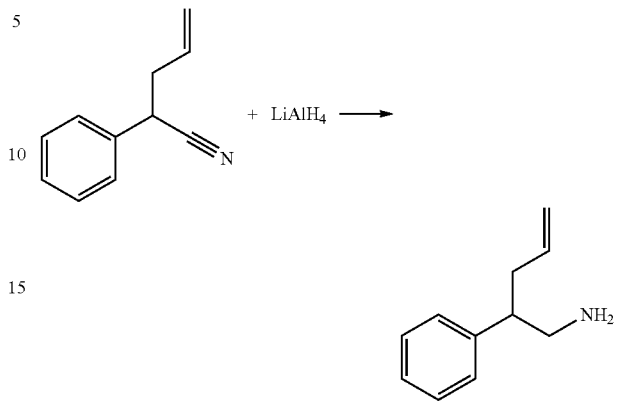

To a stirred solution of 2-phenylpent-4-enenitrile (2.82 g, 17.94 mmol) in dry tetrahydrofuran (60 mL) was added lithium aluminum hydride (1.362 g, 35.9 mmol) portionwise at 0° C. The thus obtained pink suspension was allowed to stir at room temperature for 5 min and then at 60° C. overnight. Thereupon, water (1.5 mL) was added followed by slow addition of a mixture of 50% sodium hydroxide (1.5 mL) and water (3 mL) at 0° C. The organic layer was diluted with a mixture of dichloromethane-2-propanol (7:3), dried over MgSO$_4$ and filtered through a celite plug. The filtrate was evaporated to dryness under vacuum to give a clear oil. The product was purified by chromatography (dichloromethane-methanol) and isolated as a dark yellow oil. (Yield: 1.13 g, 39%).

Step 3: 4-methyl-N-(2-phenylpent-4-en-1-yl)benzenesulfonamide

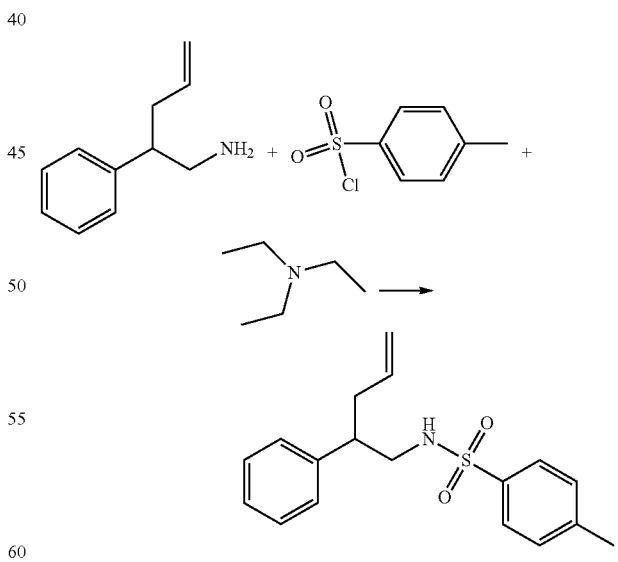

To a stirred solution of 2-phenylpent-4-en-1-amine (1.13 g, 7.01 mmol) and triethylamine (1.074 mL, 7.71 mmol) in dichloromethane (35 mL) was added tosyl chloride (1.336 g, 7.01 mmol) portionwise at room temperature. The resulting yellow solution was allowed to stir at room temperature overnight. The reaction was then diluted with dichloromethane and quenched with water. The organic layer was separated, dried over MgSO₄ and evaporated to dryness under vacuum to give a yellow oil. The product was purified by chromatography (petroleum ether-ethyl acetate 1:0, 9:1, 6:1, then 4:1) and isolated as a yellow oil. (Yield: 1.03 g, 44%).

Step 4: (4-phenyl-1-tosylpyrrolidin-2-yl)methanol

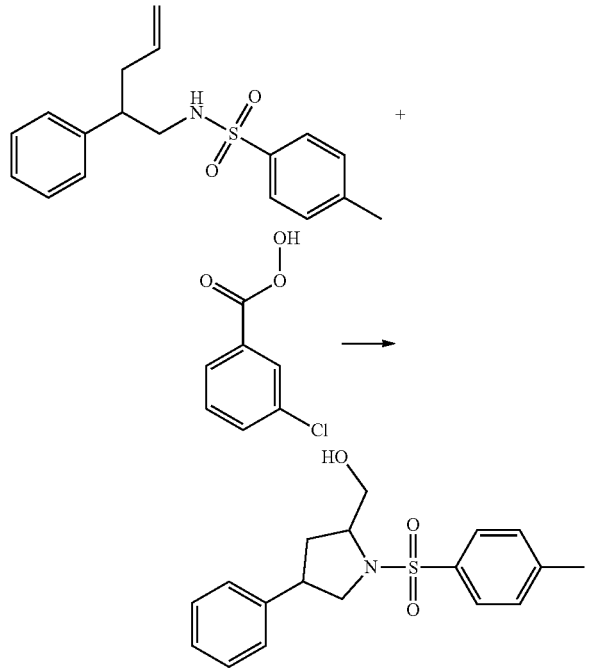

3-Chlorobenzoperoxoic acid (0.676 g, 3.92 mmol) was added portionwise to a stirred solution of 4-methyl-N-(2-phenylpent-4-enyl)benzenesulfonamide (1.03 g, 3.27 mmol) in dichloromethane (16 mL) at 0° C. The reaction mixture was allowed to warm up to room temperature and stirred for 2 days. Thereupon, water was added, the organic layer was diluted with dichloromethane, separated, dried over MgSO₄ and evaporated to dryness under reduced pressure. The product was purified by chromatography (petroleum ether-ethyl acetate; 1:1) and isolated as a clear oil. (Yield: 0.215 g, 20%).

Step 5: (4-phenylpyrrolidin-2-yl)methanol

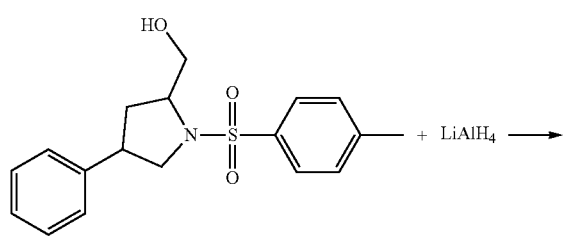

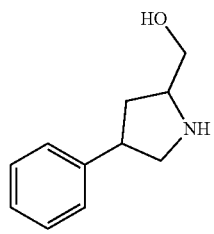

Lithium aluminium hydride (0.223 g, 5.88 mmol) was added portionwise to a stirred solution of (4-phenyl-1-tosylpyrrolidin-2-yl)methanol (0.487 g, 1.469 mmol) in dry terahydrofuran (7 mL) at 0° C. under nitrogen. The thus obtained grey suspension was allowed to stir at room temperature overnight, whereupon the reaction was quenched with water (0.3 mL) followed by dropwise addition of a mixture of 50% NaOH (0.3 mL) and water (0.6 mL). The mixture was then dried over MgSO₄ and filtered through a celite plug. The filtrate was evaporated to dryness under vacuum to give a semisolid on trituration with ethyl acetate. The solid was suspended in ethyl acetate, filtered off and the filtrate was evaporated to dryness to leave a clear oil. (Yield: 0.318 g, 122% (intermediate not purified prior to next step)).

Step 6: tert-butyl 2-(hydroxymethyl)-4-phenylpyrrolidine-1-carboxylate

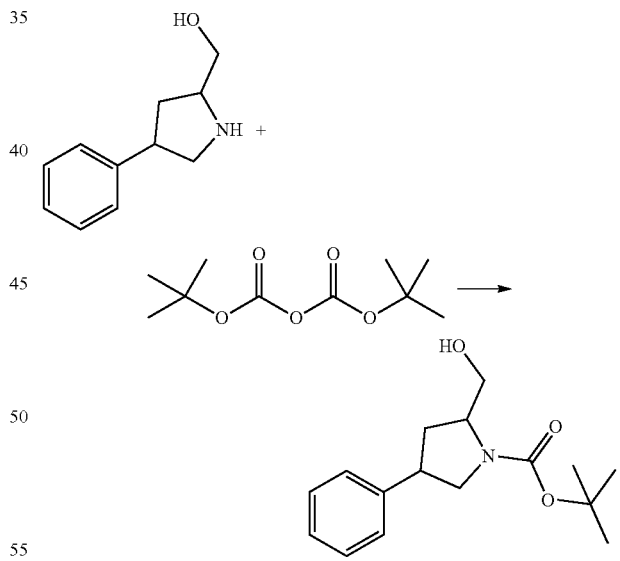

To a stirred solution of (4-phenylpyrrolidin-2-yl)methanol (0.260 g, 1.467 mmol) in ethanol (3 mL) was added di-tert-butyl dicarbonate (0.352 g, 1.614 mmol) at 0° C. The resulting yellow solution was allowed to stir at room temperature overnight. The solvent was then evaporated to dryness under vacuum and the thus obtained mixture was separated by chromatography (petroleum ether-ethyl acetate (1:0, 3:1, 2:1, then 1:1). The product was isolated as a clear oil. (Yield: 0.298 g, 73%).

Step 7: tert-butyl 2-formyl-4-phenylpyrrolidine-1-carboxylate

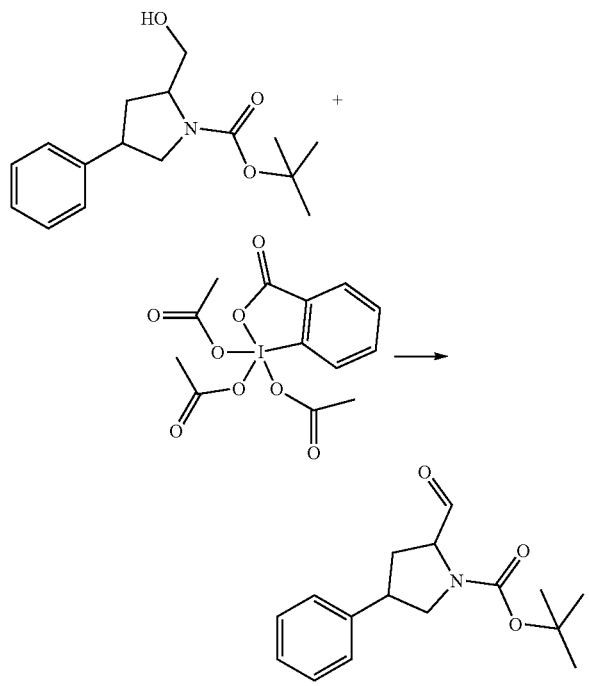

Dess-Martin periodinane (3-oxo-1λ⁵-benzo[d][1,2]iodaoxole-1,1,1(3H)-triyl triacetate) (0.443 g, 1.046 mmol) was added in one portion to a stirred solution of tert-butyl 2-(hydroxymethyl)-4-phenylpyrrolidine-1-carboxylate (0.290 g, 1.046 mmol) in dichloromethane (13 mL) at room temperature and the reaction was then stirred for 3 h. Thereupon, the solvent was evaporated off and the resulting residue was azeotroped with toluene. The product was purified by chromatography (petroleum ether-ethyl acetate; 1:0, 4:1, 3:1, 2:1, 1:1) and isolated as a clear oil. (Yield: 0.234 g, 81%).

Step 8: 4-phenylpyrrolidine-2-carbaldehyde hydrochloride

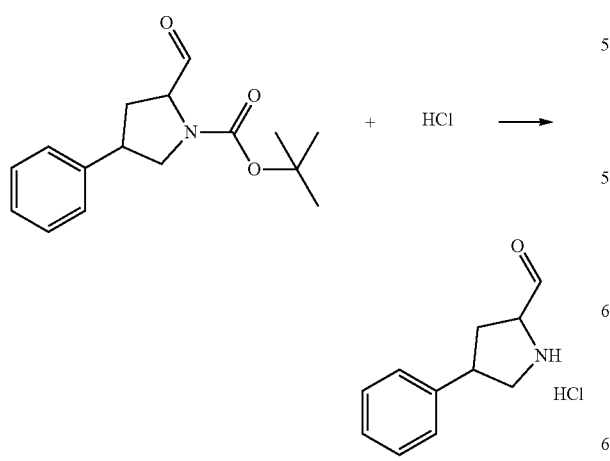

A 2 M solution of HCl (3.34 mL, 6.68 mmol) in diethyl ether was added to tert-butyl 2-formyl-4-phenylpyrrolidine-1-carboxylate (0.230 g, 0.835 mmol) at room temperature and the thus obtained yellow mixture was allowed to stir at room temperature for 3 h. The solvent was then evaporated off under vacuum to leave a yellow oil. (Yield: 0.177 g, 100%).

Step 9: 6-phenyl-6,7-dihydro-2H-pyrrolo[1,2-c]imidazole-3(5H)-thione

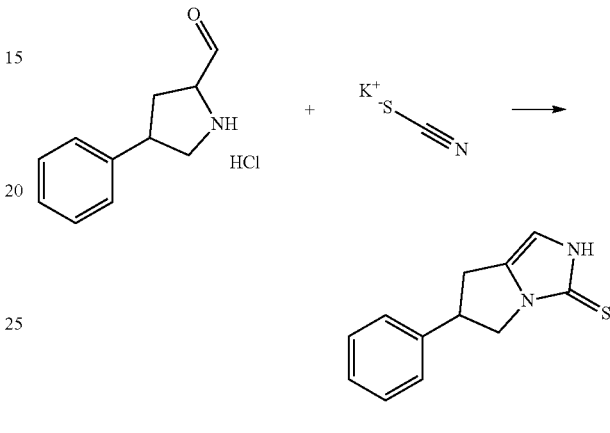

To a stirred solution of 4-phenylpyrrolidine-2-carbaldehyde hydrochloride (0.177 g, 0.836 mmol) in dimethylformamide (3.5 mL) was added potassium thiocyanate (0.163 g, 1.672 mmol) and the thus obtained yellow solution was allowed to stir at 100° C. for 1 h and 45 min to give a brown solution. The reaction mixture was allowed to cool to room temperature, and then diluted with water (3 mL) and diethyl ether, respectively. The aqueous layer was extracted with ethyl acetate (3 times) and the combined organic layers were washed with water (twice), dried over MgSO₄ and evaporated to dryness under vacuum to give a brown solid. Recrystallization from isopropanol afforded a beige solid. (Yield: 24 mg, 12%).

¹H NMR (DMSO-d6): 11.78 (1H, br s), 7.15-7.45 (5H, m), 6.63 (1H, s), 4.17 (1H, dd, J=11.2, 8.1 Hz), 4.08 (1H, quin, J=8.1 Hz), 3.67 (1H, dd, J=11.2, 8.1 Hz), 3.24 (1H, ddd, J=15.0, 7.9, 0.7 Hz), 2.86 (1H, ddd, J=15.4, 8.5, 1.5 Hz).

¹³C NMR (DMSO-d6): 155.9, 141.3, 132.7, 128.7, 127.2, 127.0, 106.7, 50.4, 47.0, 31.2.

Example 50: 6-(3,5-difluorophenyl)-6,7-dihydro-2H-pyrrolo[1,2-c]imidazole-3(5H)-thione

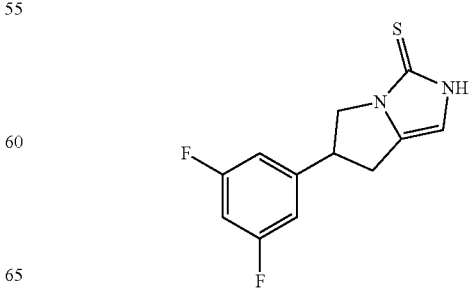

2-(3,5-difluorophenyl)acetonitrile was converted to 6-(3,5-difluorophenyl)-6,7-dihydro-2H-pyrrolo[1,2-c]imidazole-3(5H)-thione by a similar procedure as described for Example 49 and the product was isolated as a dark beige solid.

¹H NMR (DMSO-d6): 11.81 (1H, br s), 7.11-7.18 (3H, m), 6.64 (1H, m), 4.19 (1H, dd, J=11.2, 7.9 Hz), 4.12 (1H, quin, J=8.3 Hz), 3.70 (1H, dd, J=11.2, 8.5 Hz), 3.23 (1H, ddd, J=15.3, 7.9, 0.9 Hz), 2.90 (1H, ddd, J=15.3, 8.9, 1.6 Hz).

¹³C NMR (DMSO-d6): 163.3, 163.2, 161.7, 161.6, 156.0, 145.5, 145.4, 145.4, 132.3, 110.8, 110.8, 110.7, 110.7, 106.8, 102.7, 102.5, 102.3, 49.9, 46.6, 30.8.

Example 51: 6-(2,4-Difluorophenyl)-6,7-dihydro-2H-pyrrolo[1,2-c]imidazole-3(5H)-thione Step 1: (E)-N-(2-(2,4-difluorophenyl)-3-(dimethylamino)allylidene)-N-methylmethanaminium hexafluorophosphate(V)

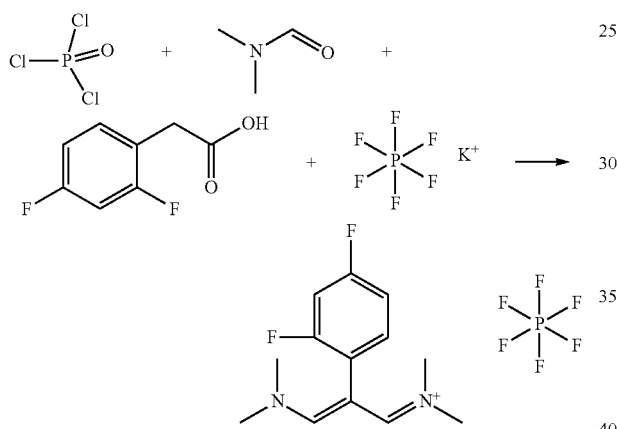

Phosphoryl trichloride (8.12 mL, 87 mmol) was added dropwise to N,N-dimethylformamide (8.32 mL, 107 mmol) at 0° C. to give a clear viscous solution. The mixture was allowed to warm up to room temperature and stirred for 1 h before adding a solution of 2-(2,4-difluorophenyl)acetic acid (5 g, 29.0 mmol) in N,N-dimethylformamide (15 mL). The resulting yellow solution was allowed to stir at 70° C. overnight. The thus obtained brown reaction mixture was cooled to room temperature and slowly poured onto a mixture of ice-water (60 mL) and a solution of potassium hexafluorophosphate(V) (8.02 g, 43.6 mmol) in water (20 mL). The resulting yellow precipitate was filtered off, washed with cold water and dried under vacuum. (Yield: 10 g, 85%).

Step 2: ethyl 4-(2,4-difluorophenyl)-1H-pyrrole-2-carboxylate

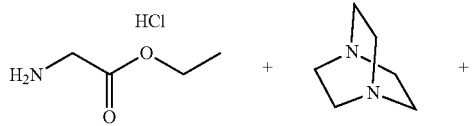

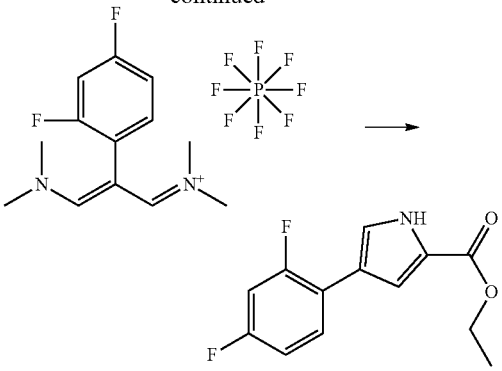

To a stirred solution of ethyl 2-aminoacetate hydrochloride (5.45 g, 39.0 mmol) and (E)-N-(2-(2,4-difluorophenyl)-3-(dimethylamino)allylidene)-N-methylmethanaminium hexafluorophosphate(V) (10 g, 26.0 mmol) in N,N-dimethylformamide (240 mL) was added 1,4-diazabicyclo[2.2.2]octane (7.30 g, 65.1 mmol) at room temperature and the thus obtained yellow suspension was allowed to stir at 100° C. overnight. The mixture was then poured onto ice-water (ca. 400 mL) and allowed to stir at room temperature for 1 h. The resulting precipitate was filtered off, washed with water to give the product as a brown solid. (Yield: 4.5 g, 65%).

Step 3: 1-tert-butyl 2-ethyl 4-(2,4-difluorophenyl)-1H-pyrrole-1,2-dicarboxylate

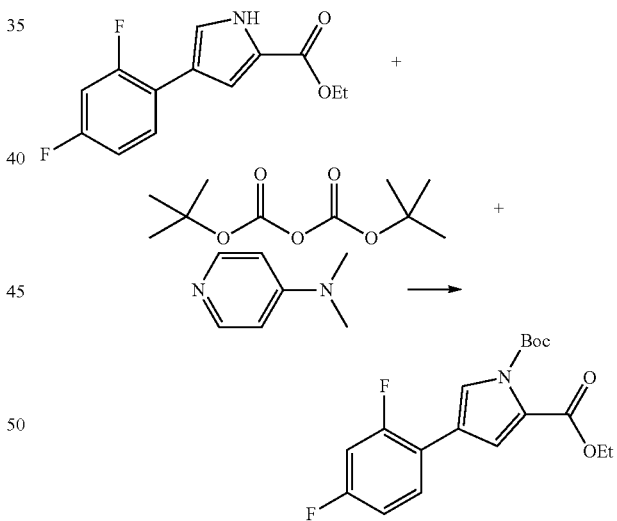

To a stirred solution of ethyl 4-(2,4-difluorophenyl)-1H-pyrrole-2-carboxylate (4.5 g, 17.91 mmol) and di-tert-butyl dicarbonate (4.30 g, 19.70 mmol) in acetonitrile (90 mL) was added N,N-dimethylpyridin-4-amine (0.219 g, 1.791 mmol) at room temperature. The resulting clear solution was allowed to stir at room temperature overnight. Thereupon, the reaction mixture was quenched with water, the organic layer was diluted with dichloro methane, separated, dried over MgSO₄ and evaporated to dryness under vacuum to give a brown oil. The product was purified by chromatography (petroleum ether-ethyl acetate; 1:0, 8:1, then 6:1) and isolated as a yellow oil. (Yield: 5.46 g, 82%).

Step 4: 1-tert-butyl 2-ethyl 4-(2,4-difluorophenyl)pyrrolidine-1,2-dicarboxylate

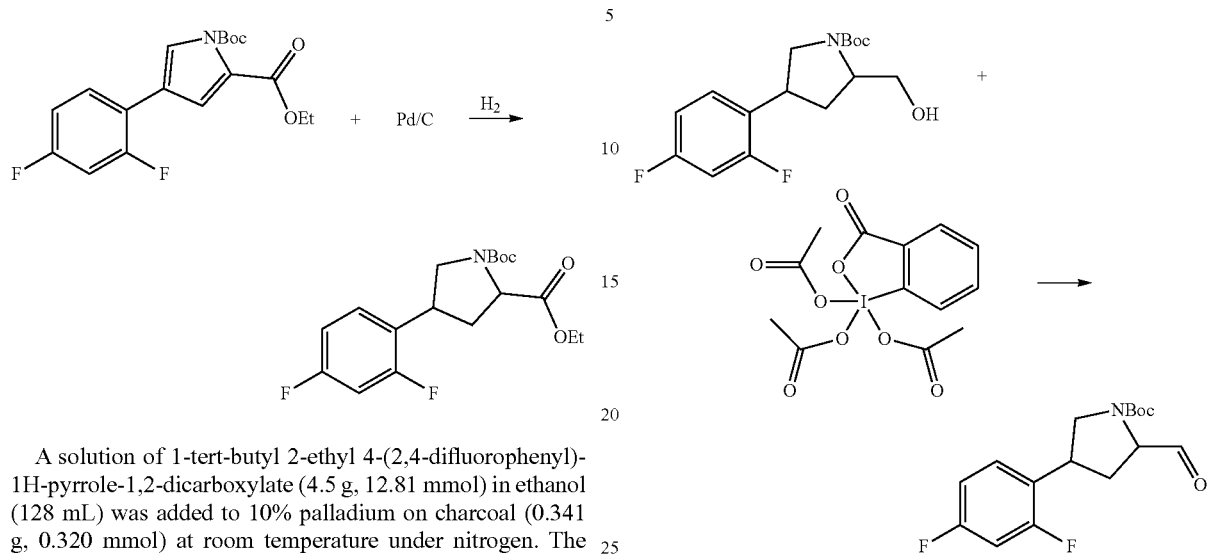

A solution of 1-tert-butyl 2-ethyl 4-(2,4-difluorophenyl)-1H-pyrrole-1,2-dicarboxylate (4.5 g, 12.81 mmol) in ethanol (128 mL) was added to 10% palladium on charcoal (0.341 g, 0.320 mmol) at room temperature under nitrogen. The mixture was allowed to stir at 60° C. under 10 bar of hydrogen for 3 h. Thereupon, the mixture was cooled to room temperature, purged with argon, filtered through a celite plug and washed with dichloromethane. The filtrate was evaporated to dryness under vacuum to give a clear oil. (Yield: 5.38 g, 93%).

Step 5: (3-(2,4-difluorophenyl)pyrrolidin-2-yl)methanol

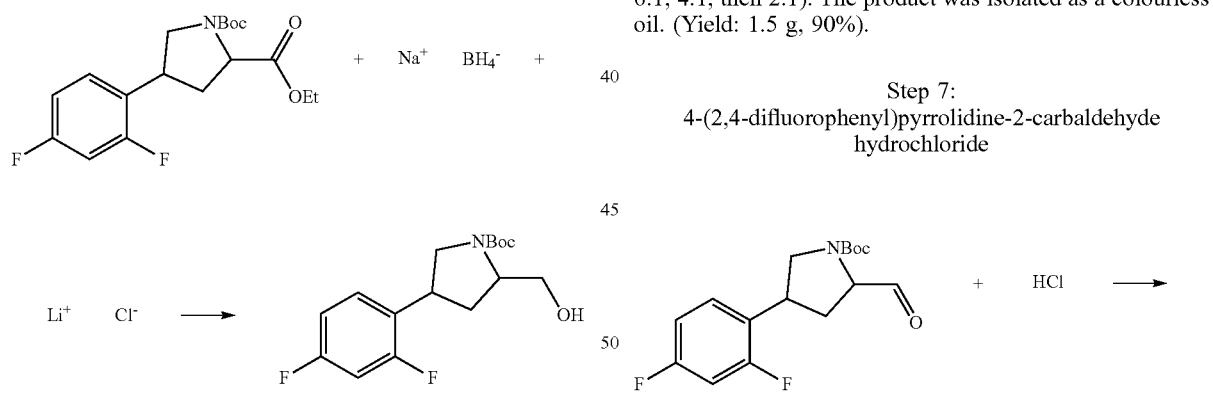

To a stirred solution of 1-tert-butyl 2-ethyl 4-(2,4-difluorophenyl)pyrrolidine-1,2-dicarboxylate (5.38 g, 15.14 mmol) and lithium chloride (2.246 g, 53.0 mmol) in a mixture of methanol (38 mL) and tetrahydrofuran (38 mL) was added sodium borohydride (2.005 g, 53.0 mmol) at 0° C. The thus obtained white suspension was allowed to stir at room temperature overnight. Thereupon, a second crop of lithium chloride (1 g) and sodium borohydride (1 g) was added and the mixture was allowed to stir for additional 48 h. Water was then added, whereupon the organic layer was diluted with dichloromethane, separated, dried over MgSO$_4$ and evaporated to dryness under vacuum. The product was purified by chromatography (petroleum ether-ethyl acetate) and then isolated as a yellow oil. (Yield: 1.96 g, 41%).

Step 6: tert-butyl 4-(2,4-difluorophenyl)-2-formylpyrrolidine-1-carboxylate

To a stirred solution of tert-butyl 4-(2,4-difluorophenyl)-2-(hydroxymethyl)pyrrolidine-1-carboxylate (1.96 g, 6.26 mmol) in dichloromethane (78 mL) was added Dess-Martin periodinane (3-oxo-1$\lambda^5$-benzo[d][1,2]iodaoxole-1,1,1(3H)-triyl triacetate) (2.65 g, 6.26 mmol) at room temperature. The thus obtained pale pink suspension was allowed to stir at room temperature for 4 h. The solvent was then evaporated off under vacuum and the product was purified by chromatography (petroleum ether-ethyl acetate; 1:0, 8:1, 6:1, 4:1, then 2:1). The product was isolated as a colourless oil. (Yield: 1.5 g, 90%).

Step 7: 4-(2,4-difluorophenyl)pyrrolidine-2-carbaldehyde hydrochloride

A 2 M solution of HCl (19.27 mL, 38.5 mmol) in diethyl ether was added to tert-butyl 4-(2,4-difluorophenyl)-2-formylpyrrolidine-1-carboxylate (1.5 g, 4.82 mmol) at room temperature and the yellow solution was allowed to stir at room temperature for 4 h. The solvent was then evaporated off under vacuum to give the product as a yellow oil. (Yield: 1.19 g, 100%).

Step 8: 6-(2,4-difluorophenyl)-6,7-dihydro-2H-pyrrolo[1,2-c]imidazole-3(5H)-thione

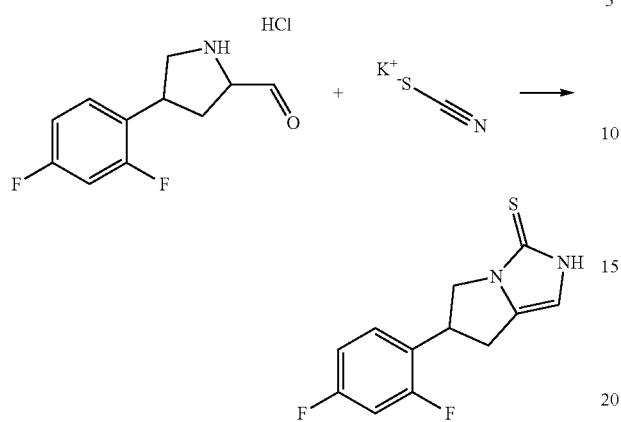

To a stirred solution of 4-(2,4-difluorophenyl)pyrrolidine-2-carbaldehyde hydrochloride (1.19 g, 4.80 mmol) in N,N-dimethylformamide (24 mL) was added potassium thiocyanate (0.934 g, 9.61 mmol) at room temperature, whereupon the resulting brown solution was allowed to stir at 100° C. for 90 min. Thereupon, water was added and the organic layer was diluted with diethyl ether containing few drops of ethyl acetate. The organic layer was separated and the aqueous layer was extracted again. The combined organic layers were washed with water (three times), dried over MgSO$_4$ and evaporated to dryness under vacuum to give a brown semisolid. Recrystallisation from ethanol afforded the product as a beige solid. (Yield: 0.08 g, 6%).

$^1$H NMR (DMSO-d6): 11.83 (1H, br s), 7.45 (1H, td, J=8.7, 6.7 Hz), 7.28 (1H, ddd, J=2.7, 9.4, 11.5 Hz), 7.09 (1H, dt, J=2.6, 8.6 Hz), 6.64 (1H, s), 4.24 (1H, quin, J=8.0 Hz), 4.15 (1H, dd, J=11.1, 8.1 Hz), 3.72 (1H, dd, J=11.3, 7.8 Hz), 3.24 (1H, dd, J=8.2, 15.2 Hz), 2.90 (1H, ddd, J=15.5, 8.3, 1.5 Hz).

$^{13}$C NMR (DMSO-d6): 162.3, 162.2, 161.1, 161, 160.6, 160.5, 159.5, 159.4, 156, 132.2, 129.9, 129.8, 129.8, 129.8, 124.3, 124.3, 124.2, 124.2, 111.8, 111.8, 111.7, 111.7, 106.9, 104.3, 104.2, 104.0, 49.3, 40.1, 30.1.

Example 52: 6-(2,5-difluorophenyl)-6,7-dihydro-2H-pyrrolo[1,2-c]imidazole-3(5H)-thione

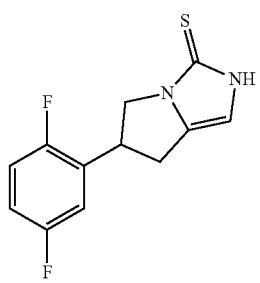 [SMILES: Fc1ccc(F)c(C2Cc3c[nH]c(=S)n3C2)c1]

2-(2,5-Difluorophenyl)acetic acid was converted to 6-(2,5-difluorophenyl)-6,7-dihydro-2H-pyrrolo[1,2-c]imidazole-3(5H)-thione by a similar procedure as described for Example 51 and the product was isolated as a beige solid.

$^1$H NMR (DMSO-d6): 11.83 (1H, br s), 7.30 (2H, m), 7.19 (1H, m), 6.65 (1H, s), 4.27 (1H, quin, J=8.1 Hz), 4.16 (1H, dd, J=11.2, 8.2 Hz), 3.75 (1H, dd, J=8.1, 11.2 Hz), 3.24 (1H, dd, J=15.5, 8.0 Hz), 2.94 (1H, br dd, J=15.3, 8.4 Hz).

$^{13}$C NMR (DMSO-d6): 159, 157.5, 157.2, 156, 155.6, 132.1, 129.8, 129.7, 129.7, 129.6, 117.2, 117.1, 117.0, 117.0, 115.5, 115.5, 115.4, 115.4, 115.4, 115.3, 115.3, 115.2, 106.9, 49.1, 40.5, 29.9.

Example 53: 5a-(3,5-difluorophenyl)-5,5a,6,6a-tetrahydrocyclopropa[3,4]pyrrolo[1,2-c]imidazole-3(2H)-thione

Step 1: (2-(aminomethyl)-2-(3,5-difluorophenyl)cyclopropyl)methanol

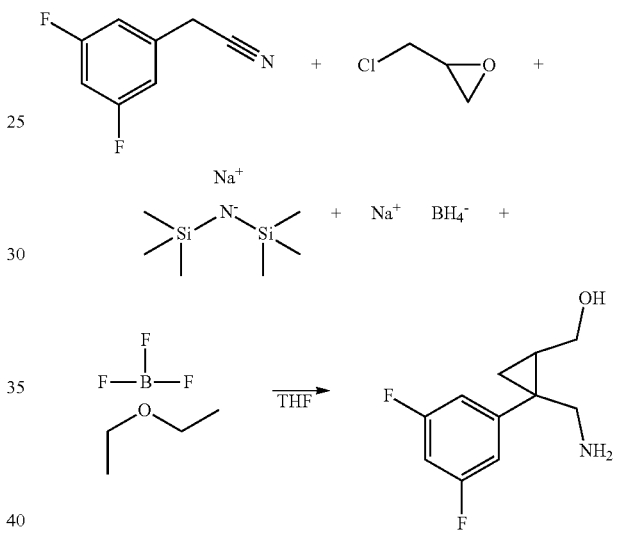

To a stirred solution of 3,5-difluorophenylacetonitrile (3 g, 19.59 mmol) in dry terahydrofuran (30 mL), was added 2-(chloromethyl)oxirane (1.839 mL, 23.51 mmol) at room temperature, under nitrogen, The reaction was then cooled to 0° C. and 2 M sodium bis(trimethylsilyl)amide in terahydrofuran (17.14 mL, 34.3 mmol) was added, dropwise at 0-5° C. Thereupon, the thus obtained red mixture was allowed to warm up to room temperature and stirred for 3 h. The reaction was diluted with dry terahydrofuran (30 mL), cooled to 0° C., whereupon sodium borohydride (2.96 g, 78 mmol) was added, followed by dropwise addition of boron trifluoride diethyl etherate (9.93 mL, 78 mmol). The mixture was allowed to warm up to room temperature and stirred overnight. The resulting pale yellow suspension was cooled to 0° C. and carefully quenched with 2 M HCl (58.8 mL, 118 mmol). The terahydrofuran was then evaporated off and the aqueous phase was washed with diethyl ether. The pH of the aqueous phase was set to pH=10 by adding 3 M sodium hydroxide and then extracted with dichloromethane. The organic phase was dried over MgSO$_4$, filtered and evaporated to dryness under vacuum to leave a yellow oil. (Yield: 3.01 g, 65%).

Step 2: tert-butyl (1-(3,5-difluorophenyl)-2-(hydroxymethyl)cyclopropyl)methylcarbamate

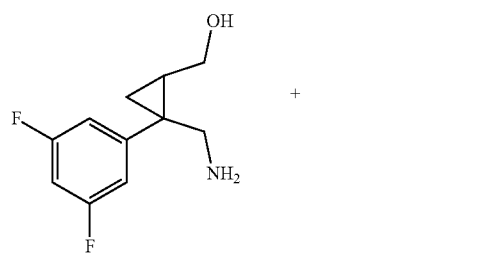

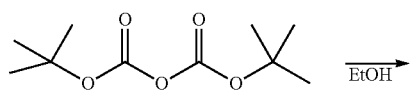

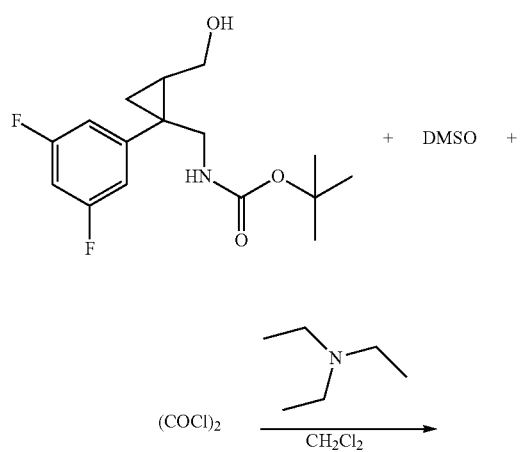

To an ice-cold solution of (2-(aminomethyl)-2-(3,5-difluorophenyl)cyclopropyl)methanol (3 g, 14.07 mmol) in ethanol (32 mL) was added di-tert-butyl dicarbonate (3.38 g, 15.48 mmol). The solution was stirred at room temperature for 4 h and then the solvent was evaporated off under vacuum. The resulting yellow oil was purified by chromatography (dichloromethane-methanol). The product was isolated as a pale yellow oil. (Yield: 3.9 g, 88%).

Step 3: tert-butyl 1-(3,5-difluorophenyl)-4-hydroxy-3-azabicyclo[3.1.0]hexane-3-carboxylate

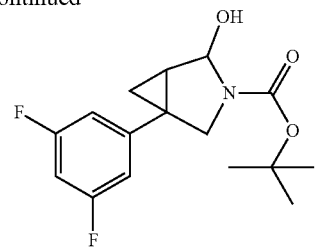

To a stirred solution of oxalyl dichloride (1.194 mL, 13.69 mmol) in dry dichloromethane (33 mL), was added dropwise a solution of dimethylsulfoxide (1.945 mL, 27.4 mmol) in dry dichloromethane (6 mL) at −78° C. The reaction mixture was stirred in the cold for 5 min, and then a solution of tert-butyl (1-(3,5-difluorophenyl)-2-(hydroxymethyl)cyclopropyl)methylcarbamate (3.9 g, 12.45 mmol) in dry dichloromethane (12 mL) was added dropwise. The mixture was stirred at −78° C. for 45 min and then triethylamine (8.67 mL, 62.2 mmol) was added. The reaction was allowed to warm up gradually to room temperature and stirred at room temperature for 2 h. Thereupon, the mixture was washed three times with water, dried over MgSO₄, filtered and evaporated to dryness to give a yellow oil. (Yield: 3.96 g, 82%).

Step 4: tert-butyl 4-cyano-1-(3,5-difluorophenyl)-3-azabicyclo[3.1.0]hexane-3-carboxylate

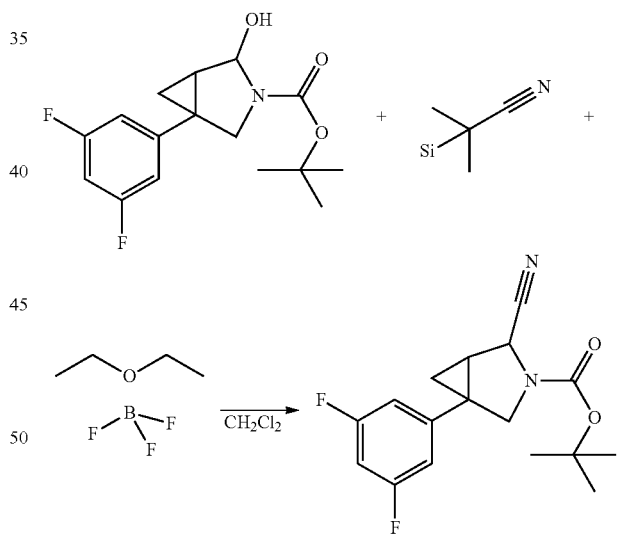

To a stirred solution of tert-butyl 1-(3,5-difluorophenyl)-4-hydroxy-3-azabicyclo[3.1.0]hexane-3-carboxylate (3.9 g, 12.53 mmol) in dry dichloromethane (260 mL) was added trimethylsilanecarbonitrile (4.46 mL, 33.4 mmol) at room temperature under nitrogen. The solution was then cooled to −78° C. and boron trifluoride etherate (4.62 mL, 36.7 mmol) was added dropwise. The reaction mixture was stirred in the cold for 4 h. and then saturated solution of sodium bicarbonate was added and the mixture was allowed to warm up to room temperature.

The organic phase was separated and aqueous phase was extracted with dichloromethane. The combined organic phases were dried over MgSO₄, filtered and evaporated to dryness to leave a pinkish oil. (Yield: 3.88 g, 77%).

Step 5: 3-(tert-butoxycarbonyl)-5-(3,5-difluorophenyl)-3-azabicyclo[3.1.0]hexane-2-carboxylic acid

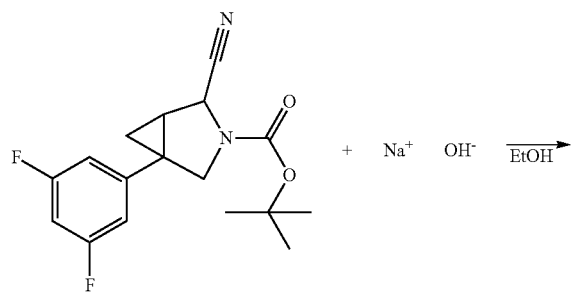

To a stirred solution of tert-butyl 4-cyano-1-(3,5-difluorophenyl)-3-azabicyclo[3.1.0]hexane-3-carboxylate (3.6 g, 11.24 mmol) in ethanol (36 mL), was added a solution of 3 M sodium hydroxide (18.73 mL, 56.2 mmol) at room temperature. The solution was heated at 80° C. for 3 h. and then was cooled to room temperature. Thereupon, ethanol was evaporated off and the aqueous phase was acidified with 2 M HCl solution and then extracted with ethyl acetate. The organic phase was dried over MgSO₄, filtered and evaporated to dryness to leave a yellow solid. (Yield: 2.95 g, 66%).

Step 6: tert-butyl 3-tert-butyl 2-methyl 5-(3,5-difluorophenyl)-3-azabicyclo[3.1.0]hexane-2,3-dicarboxylate

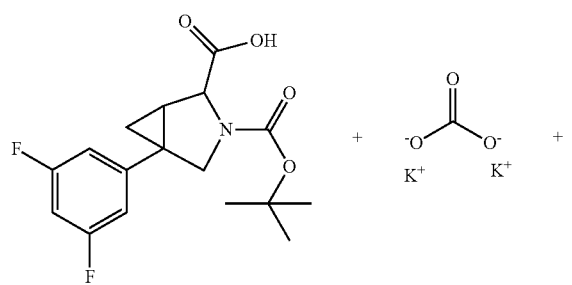

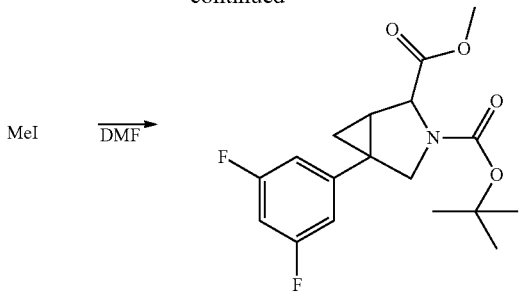

To a stirred solution of 3-(tert-butoxycarbonyl)-5-(3,5-difluorophenyl)-3-azabicyclo[3.1.0]hexane-2-carboxylic acid (1.8 g, 5.30 mmol) in N,N-dimethylforamide (18 mL) was added potassium carbonate (2.133 g, 15.44 mmol) followed by addition of methyl iodide (1.658 mL, 26.5 mmol). The reaction was stirred at room temperature for 6 h, water was then added and the mixture was extracted with ethyl acetate. The organic phase was dried over MgSO₄, filtered and evaporated to dryness. The thus obtained yellow oil was purified by chromatography (petroleum ether-ethyl acetate). The product was isolated as a pale yellow oil. (Yield: 1.36 g, 69%).

Step 7: tert-butyl 1-(3,5-difluorophenyl)-4-(hydroxymethyl)-3-azabicyclo[3.1.0]hexane-3-carboxylate

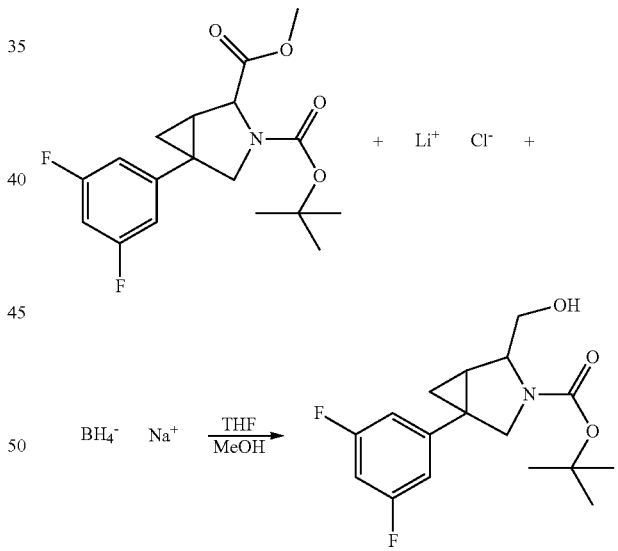

To a stirred solution of 3-tert-butyl 2-methyl 5-(3,5-difluorophenyl)-3-azabicyclo[3.1.0]hexane-2,3-dicarboxylate (1.35 g, 3.82 mmol) in a mixture of methanol (10 mL) and dry tetrahydrofuran (10 mL), was added lithium chloride (0.274 mL, 13.37 mmol) at 0° C. followed by addition of sodium borohydride (0.506 g, 13.37 mmol). The resulting white suspension was allowed to warm up to room temperature and stirred overnight. Water was then added and the mixture was extracted with dichloromethane. The organic phase was dried over MgSO₄, filtered and evaporated to dryness to leave the product as a pale yellow oil. (Yield: 1.23 g, 94%).

Step 8: tert-butyl 1-(3,5-difluorophenyl)-4-formyl-3-azabicyclo[3.1.0]hexane-3-carboxylate

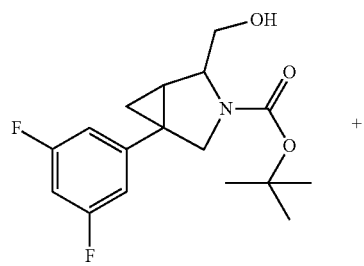

+

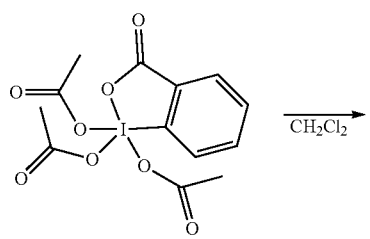

$\xrightarrow{CH_2Cl_2}$

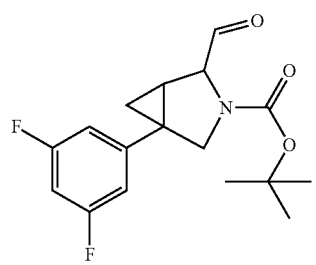

To a stirred solution of tert-butyl 1-(3,5-difluorophenyl)-4-(hydroxymethyl)-3-azabicyclo[3.1.0]hexane-3-carboxylate (1.23 g, 3.78 mmol) in dichloromethane (45 mL) was added, Dess-Martin periodinane (3-oxo-1-benzo[d][1,2]iodaoxole-1,1,1(3H)-triyl triacetate) (1.603 g, 3.78 mmol) at room temperature and the reaction was stirred for 24 h. The mixture was then evaporated to small volume and separated by chromatography (petroleum ether-ethyl acetate). The product was isolated as a pale yellow oil. (Yield: 0.96 g, 79%).

Step 9: 5-(3,5-difluorophenyl)-3-azabicyclo[3.1.0]hexane-2-carbaldehyde hydrochloride

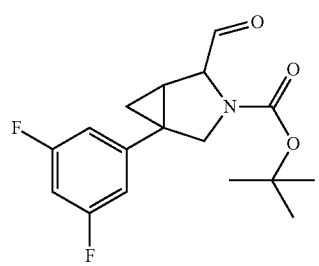 + HCl →

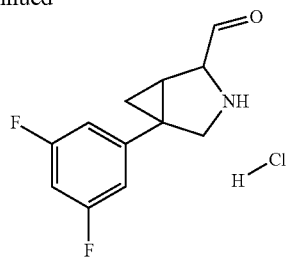

2 M HCl in diethyl ether (10.64 mL, 21.28 mmol) was added to tert-butyl 1-(3,5-difluorophenyl)-4-formyl-3-azabicyclo[3.1.0]hexane-3-carboxylate (0.86 g, 2.66 mmol) to give a colourless solution. The solution was stirred at room temperature for 3 h, whereupon the solvent was evaporated off and the residues was azeotroped with toluene to leave the product as a yellow oil. (Yield: 0.690 g, 90%).

Step 10: 5a-(3,5-difluorophenyl)-5,5a,6,6a-tetrahydrocyclopropa[3,4]pyrrolo[1,2-c]imidazole-3(2H)-thione To a stirred solution of 5-(3,5-difluorophenyl)-3-azabicyclo[3.1.0]hexane-2-carbaldehyde hydrochloride (690 mg, 2.66 mmol) in N,N-dimethylformamide (13 mL) was added potassium thiocyanate (516 mg, 5.31 mmol), at room temperature, The solution was then heated at 100° C. for 90 min. Thereupon, the mixture was cooled to room temperature, water was added and then extracted with diethyl ether. The organic phase was washed with water, dried over MgSO$_4$, filtered and evaporated to dryness to leave a brown oil. Chromatography (dichloromethane-methanol) followed by recrystallization from 2-propanol afforded the product as a beige solid. (Yield: 0.068 g, 8%).

$^1$H NMR (DMSO-d6): 11.75 (1H, br s), 7.12 (3H, m), 6.67 (1H, s), 4.22 (1H, d, J=12.2 Hz), 4.05 (1H, d, J=12.2 Hz), 3.00 (1H, dd, J=8.3, 4.3 Hz), 1.67 (1H, dd, J=8.4, 5.3 Hz), 1.19 (1H, t, J=4.8 Hz).

$^{13}$C NMR (DMSO-d6): 163.4, 163.3, 161.8, 161.7, 156.8, 144.8, 144.8, 144.7, 134.5, 110.1, 110.1, 110.0, 109.9, 105.9, 102.3, 102.1, 101.9, 50.6, 36.4, 25.3, 23.0.

Example 54: (5aS,6aR)-5a-(3,5-difluorophenyl)-5,5a,6,6a-tetrahydrocyclopropa[3,4]pyrrolo[1,2-c]imidazole-3(2H)-thione

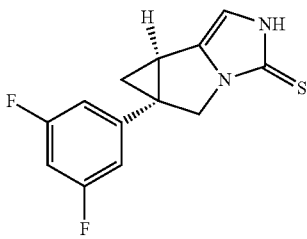 [SMILES: Fc1cc(F)cc([C@]23C[C@H]2c2c[nH]c(=S)n2C3)c1]

3,5-Difluorophenylacetonitrile and (R)-2-(chloromethyl) oxirane was converted to (5aS,6aR)-5a-(3,5-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

¹H NMR (DMSO-d6): 11.75 (1H, br s), 7.12 (3H, m), 6.67 (1H, s), 4.22 (1H, d, J=12.2 Hz), 4.05 (1H, d, J=12.2 Hz), 3.00 (1H, dd, J=8.3, 4.3 Hz), 1.67 (1H, dd, J=8.4, 5.3 Hz), 1.19 (1H, t, J=4.8 Hz).

¹³C NMR (DMSO-d6): 163.4, 163.3, 161.8, 161.7, 156.8, 144.9, 144.8, 144.7, 134.5, 110.1, 110.1, 110, 109.9, 105.9, 102.3, 102.1, 101.9, 50.6, 36.4, 25.3, 23.0.

Example 55: 5a-(2,5-difluorophenyl)-5,5a,6,6a-tetrahydrocyclopropa[3,4]pyrrolo[1,2-c]imidazole-3(2H)-thione

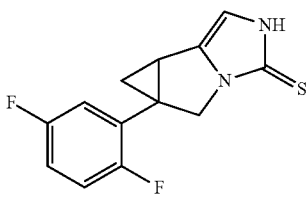 [SMILES: Fc1ccc(F)c(C23CC2c2c[nH]c(=S)n2C3)c1]

2,5-Difluorophenylacetonitrile and 2-(chloromethyl)oxirane was converted to 5a-(2,5-difluorophenyl)-5,5a,6,6a-tetrahydrocyclopropa[34]pyrrolo[1,2-c]imidazole-3(2H)-thione by a similar procedure as described for Example 53 and the product was isolated as a beige solid.

¹H NMR (DMSO-d6): 11.77 (1H, br s), 7.30 (2H, m), 7.21 (1H, m), 6.69 (1H, s), 4.11 (1H, d, J=12.4 Hz), 3.83 (1H, d, J=12.2 Hz), 2.89 (1H, dd, J=8.3, 4.2 Hz), 1.66 (1H, dd, J=8.4, 5.3 Hz), 1.18 (1H, m).

¹³C NMR (DMSO-d6): 158.8, 158.7, 157.2, 157.1, 156.6, 134.5, 128.6, 128.6, 128.5, 128.4, 117.2, 117.1, 117.0, 117.0, 117.0, 116.8, 116.8, 115.9, 115.8, 115.7, 106.2, 51.4, 51.4, 32.7, 22.3, 21.0.

Example 56: (5aS,6aR)-5a-(2,5-difluorophenyl)-5,5a,6,6a-tetrahydrocyclopropa[3,4]pyrrolo[1,2-c]imidazole-3(2H)-thione

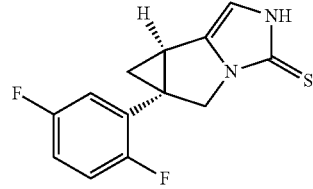 [SMILES: Fc1ccc(F)c([C@]23C[C@H]2c2c[nH]c(=S)n2C3)c1]

2,5-Difluorophenylacetonitrile and (R)-2-(chloromethyl) oxirane was converted to (5aS,6aR)-5a-(2,5-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

¹H NMR (DMSO-d6): 11.77 (1H, br s), 7.30 (2H, m), 7.21 (1H, m), 6.69 (1H, d, J=2 Hz), 4.11 (1H, d, J=12.4 Hz), 3.83 (1H, d, J=12.2 Hz), 2.89 (1H, dd, J=8.3, 4.2 Hz), 1.66 (1H, dd, J=8.4, 5.3 Hz), 1.18 (1H, m).

¹³C NMR (DMSO-d6): 158.8, 158.7, 157.2, 157.2, 157.1, 157.1, 156.7, 134.5, 128.6, 128.5, 128.5, 128.4, 117.2, 117.1, 117.0, 117.0, 116.9, 116.8, 116.8, 115.9, 115.9, 115.8, 115.7, 106.1.

Example 57: (5aR,6aS)-5a-(2,5-difluorophenyl)-5,5a,6,6a-tetrahydrocyclopropa[3,4]pyrrolo[1,2-c]imidazole-3(2H)-thione

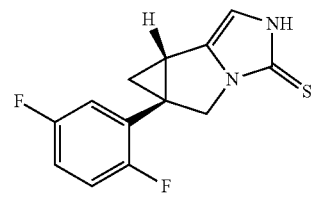 [SMILES: Fc1ccc(F)c([C@@]23C[C@@H]2c2c[nH]c(=S)n2C3)c1]

2,5-Difluorophenylacetonitrile and (S)-2-(chloromethyl) oxirane was converted to (5aR,6aS)-5a-(2,5-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

¹H NMR (DMSO-d6): 11.77 (1H, br s), 7.30 (2H, m), 7.21 (1H, m), 6.69 (1H, s), 4.11 (1H, d, J=12.4 Hz), 3.83 (1H, d, J=12.2 Hz), 2.89 (1H, dd, J=8.3, 4.2 Hz), 1.66 (1H, dd, J=8.4, 5.3 Hz), 1.18 (1H, m).

¹³C NMR (DMSO-d6): 158.8, 158.7, 158.7, 157.2, 157.1, 156.6, 134.5, 128.6, 128.6, 128.5, 128.4, 117.2, 117.1, 117.0, 117.0, 117.0, 116.8, 116.8, 115.9, 115.9, 115.8, 115.7, 106.2, 51.4, 51.4, 32.7, 22.3, 21.0.

Example 58: (R)-6-(3,5-difluorophenyl)-6,7-di-hydro-2H-pyrrolo[1,2-c]imidazole-3(5H)-thione Step 1: (E)-1,3-difluoro-5-(2-nitrovinyl)benzene

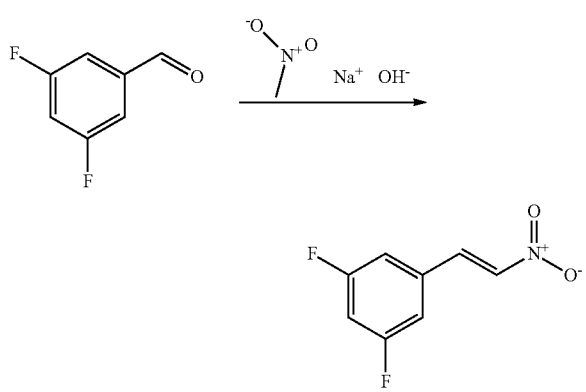

To a solution of methanol (72 mL), water (36 mL), and 2.5 M sodium hydroxide (32.4 mL, 81 mmol) was added a solution of 3,5-difluorobenzaldehyde (10 g, 70.4 mmol) and nitromethane (4.36 mL, 81 mmol) in methanol (12.00 mL) dropwise over 30 min at 5° C., while the internal temperature was maintained between 5 and 10° C. with external cooling. The reaction was then agitated in the cold for an additional 0.5 h, and then a solution of cc. HCl (11.73 mL, 141 mmol) in water (36 mL) was added in one portion at 0-10° C. with stirring. The resulting crystals were collected, washed with water and dried to give the product as a light yellow powder. (Yield: 7.0 g, 54%).

Step 2: (R)-diethyl 2-(1-(3,5-difluorophenyl)-2-nitroethyl)malonate

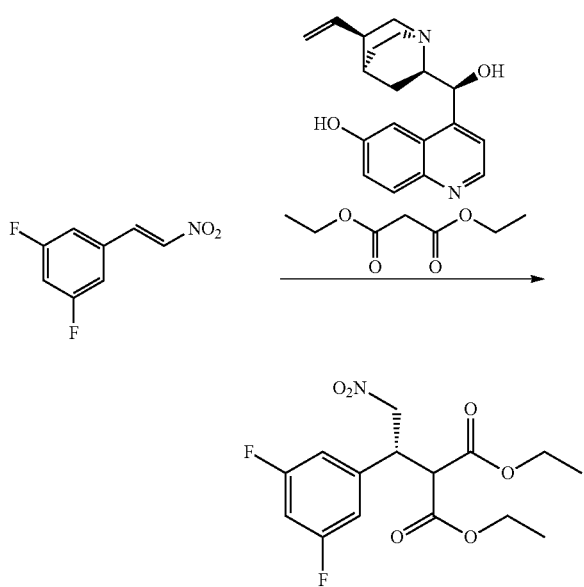

To a stirred solution of (E)-1,3-difluoro-5-(2-nitrovinyl)benzene (7.4 g, 40.0 mmol) in dry tetrahydrofuran (75 mL) was added 4-((S)-hydroxy((1S,2R,4S,5R)-5-vinylquinuclidin-2-yl)methyl)quinolin-6-ol (CAS #70877-75-7) (0.620 g, 1.999 mmol) at room temperature with stirring followed by addition of diethyl malonate (8.65 mL, 56.7 mmol). The mixture was cooled to −5 to −7° C. under inert atmosphere and stirred for 20 h in the cold. Thereupon, the mixture was evaporated to dryness under vacuum and the residue was taken up in dichloromethane (100 mL), washed with 1 M HCl, brine, dried over MgSO$_4$ and filtered on a silica pad. The filtrate was concentrated to 20 mL, and the residue was crystallized on dilution with petroleum ether (ca. 50 mL). The mixture was further diluted with petroleum ether (120 mL), and aged at 5-10° C. The resulting solid was collected, washed with petroleum ether, and dried to give the product as an off-white powder. (Yield: 9.1 g, 70%).

Step 3: (4R)-ethyl 4-(3,5-difluorophenyl)-2-oxopyrrolidine-3-carboxylate

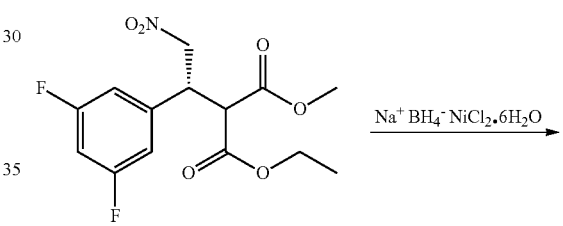

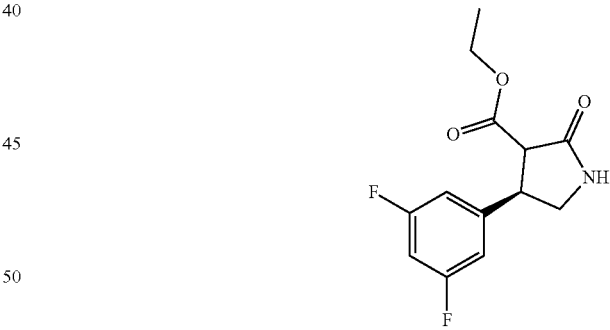

To a suspension of (R)-diethyl 2-(1-(3,5-difluorophenyl)-2-nitroethyl)malonate (9 g, 26.1 mmol) in methanol (150 mL) was added nickel(II) chloride hexahydrate (6.20 g, 26.1 mmol) followed by addition of sodium borohydride (7.89 g, 209 mmol) in portions with ice cooling. The mixture was stirred for 6 h at room temperature, then quenched with ammonium chloride solution (250 mL), diluted with dichloromethane (150 mL), acidified with 6 M HCl to pH=2, and stirred for 16 h. Thereupon, the mixture was extracted with dichloromethane, the organic phase was dried over MgSO$_4$ and evaporated to dryness to give the product as a beige powder. (Yield: 6.87 g, 98%).

Step 4: (4R)-4-(3,5-difluorophenyl)-2-oxopyrrolidine-3-carboxylic acid

Step 5: (R)-4-(3,5-difluorophenyl)pyrrolidin-2-one

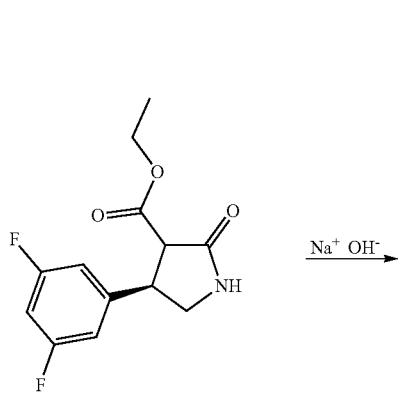

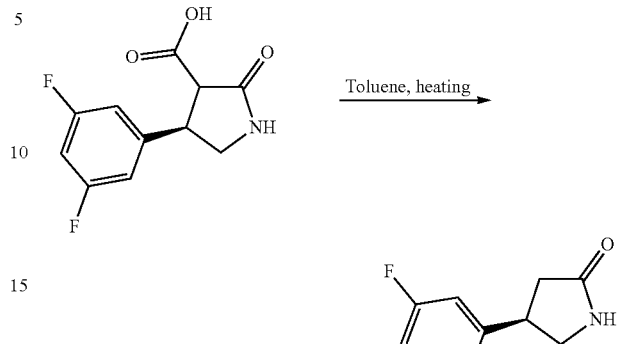

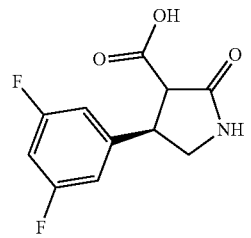

A solution of (4R)-4-(3,5-difluorophenyl)-2-oxopyrrolidine-3-carboxylic acid (5.2 g, 21.56 mmol) in toluene (300 mL) was stirred under reflux for 3 h, whereupon the mixture was evaporated to dryness, Crystallization from petroleum ether afforded beige powder. Yield: 4.06 g, 96%.

Step 6: (R)-tert-butyl 4-(3,5-difluorophenyl)-2-oxopyrrolidine-1-carboxylate

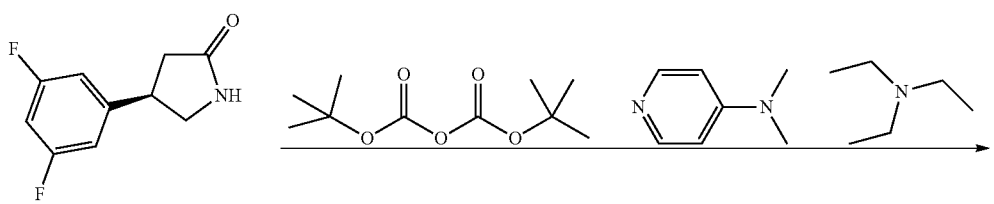

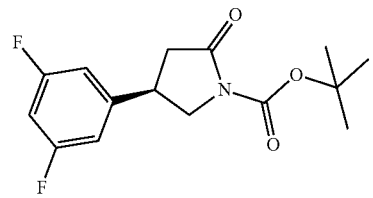

To a stirred solution of (4R)-ethyl 4-(3,5-difluorophenyl)-2-oxopyrrolidine-3-carboxylate (6.85 g, 25.4 mmol) in ethanol (100 mL) was added 1 M sodium hydroxide (30.5 mL, 30.5 mmol). The resulting suspension was stirred for 1 h, the organics were then removed under vacuum, and the residue was dissolved in water (250 mL). The product was crystallized on acidification with 6 M HCl. The resulting crystals were collected, washed with cold water and dried under vacuum at 50° C. to give the product as a beige powder. Yield: 5.2 g, 21, 85%.

To a stirred solution of (R)-4-(3,5-difluorophenyl)pyrrolidin-2-one (4.05 g, 20.54 mmol) in dry dichloromethane (15 mL) was added at room temperature di-tert-butyl dicarbonate (6.72 g, 30.8 mmol) followed by addition of N,N-dimethylpyridin-4-amine (2.509 g, 20.54 mmol) and triethyl amine (2.86 mL, 20.54 mmol). The mixture was then stirred at room temperature for 3 h, and then concentrated under vacuum. Chromatography (petroleum ether-ethyl acetate; 4:1) gave an oil which was crystallized from petroleum ether (60 mL), The product was isolated as a white powder. Yield: 6.24 g, 88%.

Step 7: (4R)-tert-butyl 4-(3,5-difluorophenyl)-2-hydroxypyrrolidine-1-carboxylate

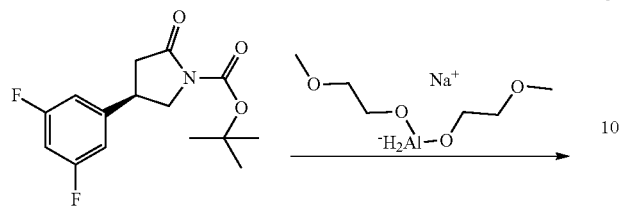

To a stirred solution of (R)-tert-butyl 4-(3,5-difluorophenyl)-2-oxopyrrolidine-1-carboxylate (2 g, 6.73 mmol) in dry diethyl ether (30 mL) was added dropwise 65% RED-Al (bis(2-methoxyethoxy)aluminum(III) sodium hydride) (1.212 mL, 4.04 mmol) in toluene at 0-5° C. under nitrogen and the mixture was stirred for 30 min. in the cold. Thereupon, the mixture was quenched with sodium bicarbonate solution and stirred for 30 min. The organic phase was dried over MgSO₄, and evaporated to dryness to give the product as colourless oil. (Yield: 2.07 g, 93%).

Step 8: (4R)-tert-butyl 2-cyano-4-(3,5-difluorophenyl)pyrrolidine-1-carboxylate

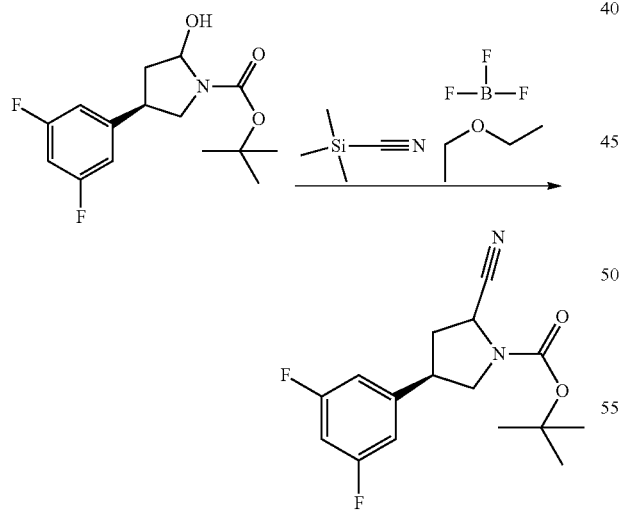

To a stirred solution of (4R)-tert-butyl 4-(3,5-difluorophenyl)-2-hydroxypyrrolidine-1-carboxylate (2 g, 6.68 mmol) in dry dichloromethane (50 mL) was added trimethylsilanecarbonitrile (1.792 mL, 13.36 mmol) followed by addition of boron trifluoride diethyl etherate (1.863 mL, 14.70 mmol) at −70° C. The mixture was stirred for 4 h in the cold, quenched with sodium bicarbonate solution, and then allowed to warm up with stirring to room temperature. The organic phase was dried over MgSO₄, filtered and evaporated to dryness under vacuum. Chromatography (petroleum ether-ethyl acetate; 9:1) afforded the compound as a colourless oil. (Yield: 1.36 g, 66%).

Step 9: (4R)-1-(tert-butoxycarbonyl)-4-(3,5-difluorophenyl)pyrrolidine-2-carboxylic acid

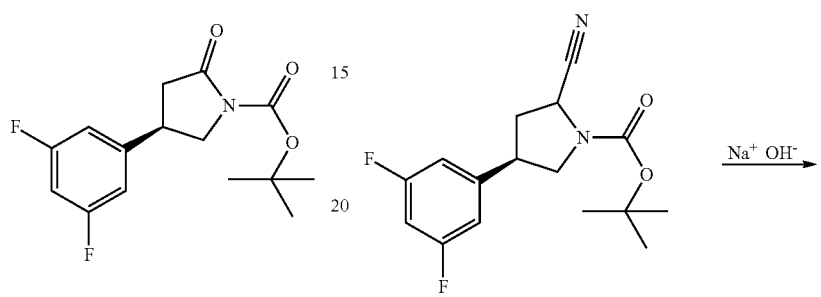

To a stirred solution of (4R)-tert-butyl 2-cyano-4-(3,5-difluorophenyl)pyrrolidine-1-carboxylate (1.35 g, 4.38 mmol) in ethanol (15 mL) was added 3 M sodium hydroxide (7.30 mL, 21.89 mmol) and the solution was gently refluxed (oil bath at 80° C.) for 3 h. Thereupon, ethanol was removed under vacuum and the residue was diluted with water (10 mL), and then acidified with 2 M HCl to pH=2 at 10-15° C. The mixture was extracted with dichloromethane (40 mL), the insoluble materials in both phases was filtered off, whereupon the organic phase was washed with brine, dried over MgSO₄ and evaporated to dryness to give 0.89 g of yellowish oil. (Yield: 62%).

Step 10: (4R)-tert-butyl 4-(3,5-difluorophenyl)-2-(hydroxymethyl)pyrrolidine-1-carboxylate

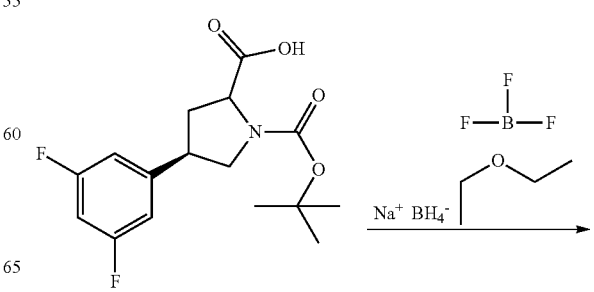

85

-continued

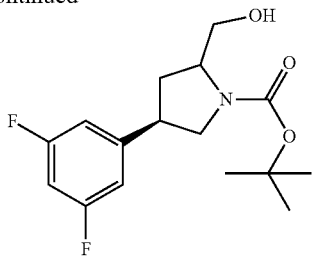

To a stirred solution of (4R)-1-(tert-butoxycarbonyl)-4-(3,5-difluorophenyl)pyrrolidine-2-carboxylic acid (0.45 g, 1.375 mmol) in isopropyl acetate (2 mL) was added sodium borohydride (0.083 g, 2.200 mmol) at 0-5° C. followed by addition of boron trifluoride diethyl etherate (0.348 mL, 2.75 mmol. The mixture was stirred for 2 h in the cold, then quenched with 0.5 M sodium hydroxide (9.90 mL, 4.95 mmol), and allowed to stir at room temperature for 30 min. The organic phase was separated, dried over MgSO₄, evaporated to dryness to leave an oil. Purification by chromatography (petroleum ether-EtOAc; 4:1, then 2:1). The product was isolated as a yellowish oil. (Yield: 0.29 g, 67%).

Step 11: (4R)-tert-butyl 4-(3,5-difluorophenyl)-2-formylpyrrolidine-1-carboxylate

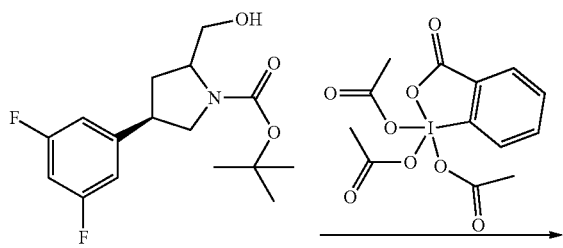

To a stirred solution of (4R)-tert-butyl 4-(3,5-difluorophenyl)-2-(hydroxymethyl)pyrrolidine-1-carboxylate (0.28 g, 0.894 mmol) in dry dichloromethane (8 mL) was added Dess-Martin periodinane (3-oxo-1λ⁵-benzo[d][1,2]iodaoxole-1,1,1(3H)-triyl triacetate) (0.379 g, 0.894 mmol) in one portion to give a clear solution. Thereupon, the mixture was stirred at room temperature for 3 h, concentrated to approximately one third and subjected to chromatography (petroleum ether-ethyl acetate 9:1, then 4:1). The product was isolated as yellowish oil. (Yield: 0.25 g, 90%).

86

Step 12: (R)-6-(3,5-difluorophenyl)-6,7-dihydro-2H-pyrrolo[1,2-c]imidazole-3(5H)-thione

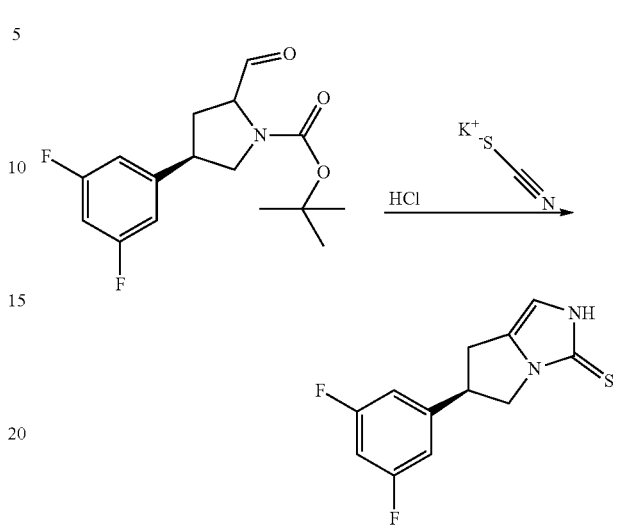

A solution of (4R)-tert-butyl 4-(3,5-difluorophenyl)-2-formylpyrrolidine-1-carboxylate (0.24 g, 0.771 mmol) in 2 M HCl (3.08 mL, 6.17 mmol) in diethyl ether was stirred at room temperature for 16 h. whereupon diethyl ether was evaporated off under reduced pressure, and the residue dissolved in a mixture of ethanol (5 mL) and water (5 mL). Thereupon, potassium thiocyanate (0.082 g, 0.848 mmol) was added followed by addition of cc. HCl (0.032 mL, 0.385 mmol) and the solution was stirred under reflux for 5 h. The mixture was then cooled in ice-water bath, the resulting solid was collected by filtration, washed with water, isopropanol and petroleum ether, and then dried at 50° C. under vacuum to give the product as a beige powder. (Yield: 0.12 g, 62%).
¹H NMR (DMSO-d6): 11.81 (1H, br s), 7.15 (3H, m), 6.65 (1H, s), 4.20 (1H, dd, J=11.0, 8.1 Hz), 4.13 (1H, quin, J=8.3 Hz), 3.72 (1H, dd, J=11.2, 8.5 Hz), 3.24 (1H, ddd, J=15.3, 7.9, 0.9 Hz), 2.92 (1H, ddd, J=15.3, 9.0, 1.8 Hz).
¹³C NMR (DMSO-d6): 163.3, 163.2, 161.7, 161.6, 156, 145.5, 145.5, 145.4, 132.3, 110.8, 110.8, 110.7, 110.7, 106.9, 102.7, 102.5, 102.3, 49.9, 46.6, 30.8.

Example 59: (S)-6-(3,5-difluorophenyl)-6,7-dihydro-2H-pyrrolo[1,2-c]imidazole-3(5H)-thione (E)-1,3-Difluoro-5-(2-nitrovinyl)benzene (using 4-((R)-hydroxy((1S,2S,4S,5R)-5-vinylquinuclidin-2-yl)methyl)quinolin-6-ol as catalyst (CAS #524-63-0)) was converted to (S)-6-(3,5-difluorophenyl)-6,7-dihydro-2H-pyrrolo[1,2-c]imidazole-3(5H)-thione by a similar procedure as described for Example 58 and the product was isolated as a dark beige powder ¹H NMR (DMSO-d6): 11.81 (1H, br s), 7.15 (3H, m), 6.65 (1H, s), 4.20 (1H, dd, J=11.0, 8.1 Hz), 4.13 (1H, quin, J=8.3 Hz), 3.72 (1H, dd, J=11.2, 8.5 Hz), 3.24 (1H, ddd, J=15.3, 7.9, 0.9 Hz), 2.92 (1H, ddd, J=15.3, 9.0, 1.8 Hz).

¹³C NMR (DMSO-d6): 163.3, 163.2, 161.7, 161.6, 156, 145.5, 145.5, 145.4, 132.3, 110.9, 110.8, 110.7, 110.7, 106.9, 102.7, 102.5, 102.4, 49.9, 46.6, 30.8.

Example 60: (5aS,6aR)-5a-(3,5-difluorophenyl)-5,5a,6,6a-tetrahydrocyclopropa[3,4]pyrrolo[2,1-c][1,2,4]triazole-3(2H)-thione Step 1: (1S,5R)-tert-butyl 1-(3,5-difluorophenyl)-4-oxo-3-azabicyclo[3.1.0]hexane-3-carboxylate

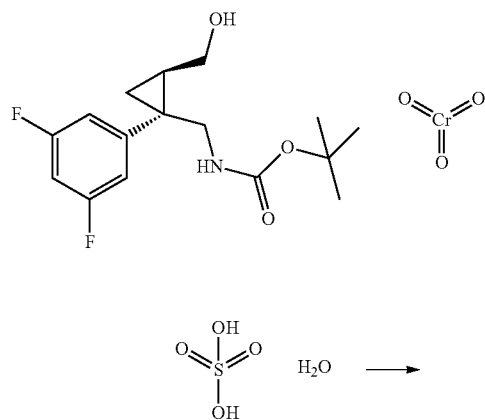

To an ice-cooled stirred solution of chromium (VI) oxide (2.137 g, 21.37 mmol) in water (3.77 mL) was added dropwise sulfuric acid (1.125 mL, 21.10 mmol). Thereupon, the obtained orange solution was added dropwise to an ice-cooled solution of tert-butyl ((((1S,2R)-1-(3,5-difluorophenyl)-2-(hydroxymethyl)cyclopropyl)methyl)carbamate (2.85 g, 9.10 mmol) in acetone (57 mL) (prepared according to step 1-3 of Example 53 from 2-(3,5-difluorophenyl)acetonitrile and (R)-2-(chloromethyl)oxirane). The reaction was stirred in the cold for 1 h, and then 25 mL of isopropanol was added, followed by addition of water. The thus obtained dark aqueous phase was extracted with dichloromethane, whereupon the organic phase was washed with water and evaporated to dryness to give the product as a semi-solid mass. Trituration with disopropyl ether afforded the product as a white powder. (Yield: 1.813 g, 64%).

Step 2: (1R,5S)-5-(3,5-difluorophenyl)-3-azabicyclo[3.1.0]hexan-2-one

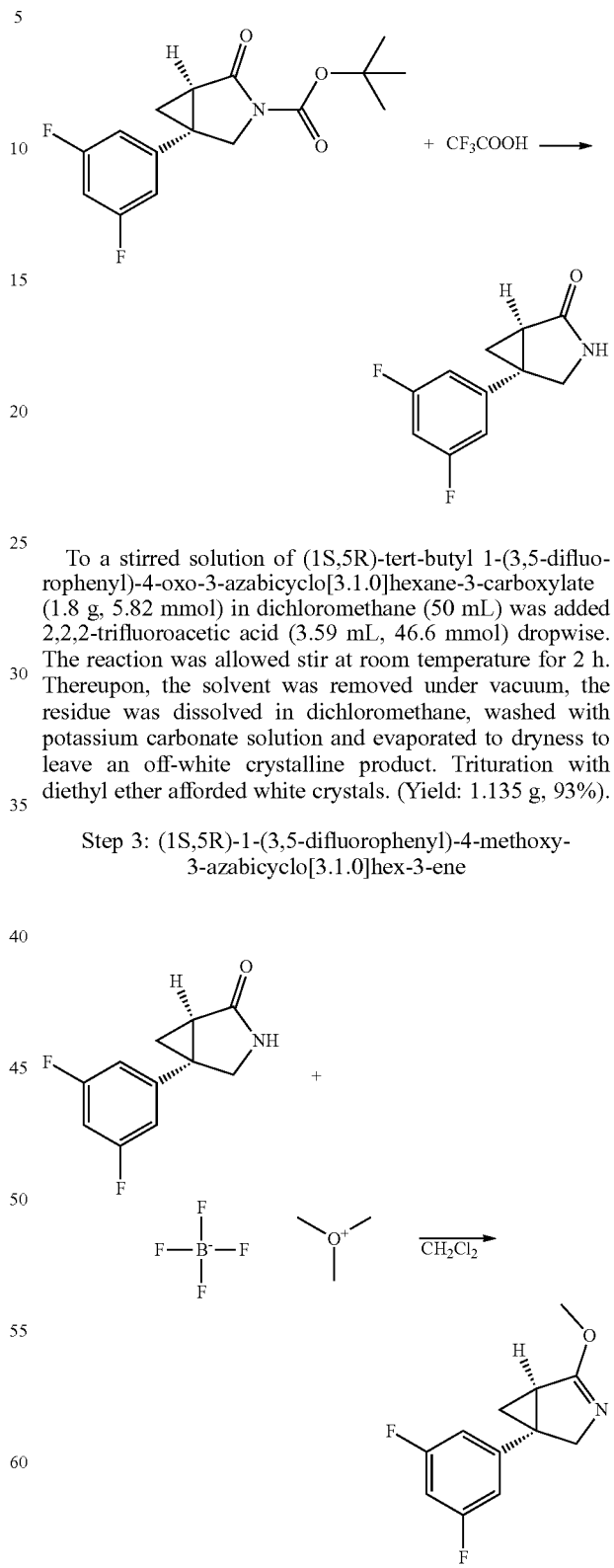

To a stirred solution of (1S,5R)-tert-butyl 1-(3,5-difluorophenyl)-4-oxo-3-azabicyclo[3.1.0]hexane-3-carboxylate (1.8 g, 5.82 mmol) in dichloromethane (50 mL) was added 2,2,2-trifluoroacetic acid (3.59 mL, 46.6 mmol) dropwise. The reaction was allowed stir at room temperature for 2 h. Thereupon, the solvent was removed under vacuum, the residue was dissolved in dichloromethane, washed with potassium carbonate solution and evaporated to dryness to leave an off-white crystalline product. Trituration with diethyl ether afforded white crystals. (Yield: 1.135 g, 93%).

Step 3: (1S,5R)-1-(3,5-difluorophenyl)-4-methoxy-3-azabicyclo[3.1.0]hex-3-ene

To a stirred solution of (1R,5S)-5-(3,5-difluorophenyl)-3-azabicyclo[3.1.0]hexan-2-one (1.0 g, 4.78 mmol) in dry Step 4: methyl 2-((1R,5S)-5-(3,5-difluorophenyl)-3-azabicyclo[3.1.0]hex-2-en-2-yl)hydrazinecarbodithioate

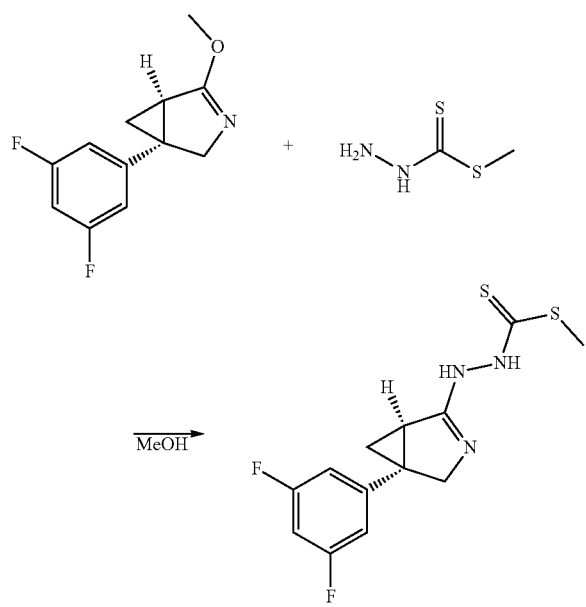

To a stirred solution of (1S,5R)-1-(3,5-difluorophenyl)-4-methoxy-3-azabicyclo[3.1.0]hex-3-ene (1.07 g, 4.79 mmol) in methanol (10 mL) was added methyl hydrazinecarbodithioate (0.586 g, 4.79 mmol) in portions. The solution was stirred at room temperature for 1 h, and then evaporated to dryness to leave a colourless foam. (Yield: 1.5 g, 90%).

Step 5: methyl (5aS,6aR)-5a-(3,5-difluorophenyl)-5,5a,6,6a-tetrahydrocyclopropa[3,4]pyrrolo[2,1-c][1,2,4]triazole-3(2H)-thione

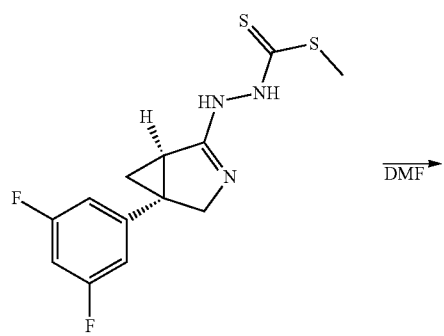

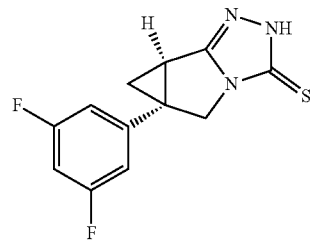

A stirred solution of methyl 2-((1R,5S)-5-(3,5-difluorophenyl)-3-azabicyclo[3.1.0]hex-2-en-2-yl)hydrazinecarbodithioate (1.5 g, 4.79 mmol) in N,N-dimethylformamide (25 mL) was heated at reflux under inert atmosphere for 1 h. The mixture was then cooled to room temperature, poured onto ice and stirred for 30 min. The resulting precipitate was filtered off, the filter cake was washed with water and dissolved in ethyl acetate. The organic phase was washed with water again, dried over MgSO$_4$, filtered and evaporated to dryness. Chromatography (dichloromethane-methanol; 98:2) followed by trituration with a mixture of petroleum ether-diethyl ether afforded the product as an off-white solid. (Yield: 0.104 g, 7%).

$^1$H NMR (DMSO-d6): 13.19 (1H, br s), 7.20 (2H, m), 7.15 (1H, tt, J=2.3, 9.3 Hz), 4.25 (1H, dd, J=11.9, 0.7 Hz), 4.09 (1H, d, J=11.9 Hz), 3.13 (1H, ddd, J=0.8, 4.4, 8.7 Hz), 1.80 (1H, dd, J=8.7, 5.6 Hz), 1.47 (1H, dd, J=5.6, 4.3 Hz).

$^{13}$C NMR (DMSO-d6): 163.7, 163.3, 163.2, 161.7, 161.6, 157.9, 143.6, 143.6, 143.5, 110.6, 110.6, 110.5, 110.4, 102.7, 102.5, 102.4, 49.1, 36.9, 23.0, 21.0.

Example 61: (S)-6-(2,3,5,6-tetrafluorophenyl)-6,7-dihydro-2H-pyrrolo[1,2-c]imidazole-3(5H)-thione

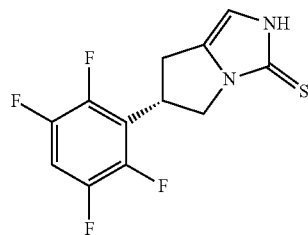 [SMILES: Fc1cc(F)c(F)c([C@@H]2Cc3c[nH]c(=S)n3C2)c1F]

(E)-1,2,4,5-tetrafluoro-5-(2-nitrovinyl)benzene (using 4-((R)-hydroxy((1S,2S,4S,5R)-5-vinylquinuclidin-2-yl)methyl)quinolin-6-ol as catalyst (CAS #524-63-0)) was converted to (S)-6-(2,3,5,6-tetrafluorophenyl)-6,7-dihydro-2H-pyrrolo[1,2-c]imidazole-3(5H)-thione by a similar procedure as described for Example 59 and the product was isolated as a dark beige powder.

$^1$H NMR (DMSO-d6): 11.86 (1H, br s), 7.86 (1H, m), 6.64 (1H, s), 4.54 (1H, quin, J=8.5 Hz), 4.20 (1H, dd, J=11.6, 9.2 Hz), 3.79 (1H, dd, J=11.7, 7.6 Hz), 3.33 (1H, m), 2.97 (1H, dd, J=16.0, 7.6 Hz).

$^{13}$C NMR (DMSO-d6): 155.9, 146.3, 145.3, 144.7, 143.6, 132.0, 120.5, 120.4, 120.3, 106.7, 105.9, 105.7, 105.6, 48.4, 35.8, 29.4.

Example 62: (R)-6-(2,3,5,6-tetrafluorophenyl)-6,7-dihydro-2H-pyrrolo[1,2-c]imidazole-3(5H)-thione

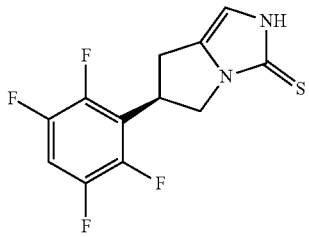 [SMILES: Fc1cc(F)c(F)c([C@H]2Cc3c[nH]c(=S)n3C2)c1F]

(E)-1,2,4,5-terafluoro-5-(2-nitrovinyl)benzene (using 4-((S)-hydroxy((1S,2R,4S,5R)-5-vinylquinuclidin-2-yl)methyl)quinolin-6-ol as catalyst (CAS #70877-75-7)) was converted to (R)-6-(2,3,5,6-tetrafluorophenyl)-6,7-dihydro-2H-pyrrolo[1,2-c]imidazole-3(5H)-thione by a similar procedure as described for Example 58 and the product was isolated as a beige powder.

$^1$H NMR (DMSO-d6): 11.86 (1H, br s), 7.85 (1H, tt, J=10.4, 7.6 Hz), 6.64 (1H, m), 4.54 (1H, m), 4.20 (1H, dd, J=11.7, 9.2 Hz), 3.79 (1H, dd, J=11.7, 7.6 Hz), 3.33 (1H, m), 2.97 (1H, ddd, J=1.2, 8.0, 16 Hz).

$^{13}$C NMR (DMSO-d6): 155.9, 146.4, 146.3, 146.3, 145.3, 145.2, 144.8, 144.7, 144.6, 143.7, 143.6, 132, 120.5, 106.7, 105.9, 105.7, 105.6, 48.4, 35.8, 29.4.

Example 63: (5aS,6aR)-5a-(2,3,5-trifluorophenyl)-5,5a,6,6a-tetrahydrocyclopropa[3,4]pyrrolo[1,2-c]imidazole-3 (2H)-thione

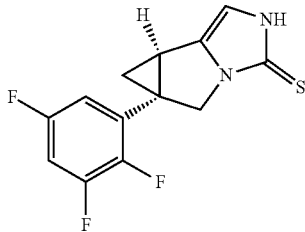 [SMILES: Fc1cc(F)c(F)c([C@]23C[C@H]2c2c[nH]c(=S)n2C3)c1]

2,3,5-Trifluorophenylacetonitrile and (R)-2-(chloromethyl)oxirane was converted to (5aS,6aR)-5a-(2,3,5-trifluorophenyl)-5,5a,6,6a-tetrahydrocyclopropa[3,4]pyrrolo[1,2-c]imidazole-3 (2H)-thione by a similar procedure as described for Example 53 and the product was isolated as a beige solid.

$^1$H NMR (DMSO-d6): 11.78 (1H, br s), 7.50 (1H, m), 7.19 (1H, m), 6.70 (1H, d, J=2.1 Hz), 4.12 (1H, d, J=12.0 Hz), 3.88 (1H, d, J=12.0 Hz), 2.95 (1H, dd, J=8.5, 4.3 Hz), 1.67 (1H, dd, J=8.4, 5.5 Hz), 1.22 (1H, m).

$^{13}$C NMR (DMSO-d6): 157.8, 157.8, 156.7, 156.2, 156.2, 150.5, 150.4, 150.3, 148.9, 148.8, 148.7, 147.3, 147.2, 147.2, 147.2, 145.7, 145.6, 145.6, 145.5, 134.3, 130.2, 130.1, 130.0, 112.3, 112.2, 106.3, 105.3, 105.2, 105.1, 105.0, 51.2, 51.2, 32.6, 32.5, 22.5, 21.1.

Example 64: (5aS,6aR)-5a-(2,6-difluorophenyl)-5,5a,6,6a-tetrahydrocyclopropa[3,4]pyrrolo[1,2-c]imidazole-3(2H)-thione

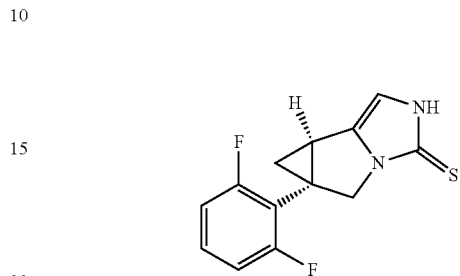

2,6-Difluorophenylacetonitrile and (R)-2-(chloromethyl)oxirane was converted to (5aS,6aR)-5a-(2,6-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

$^1$H NMR (DMSO-d6): 11.78 (1H, br s), 7.43 (1H, m), 7.13 (2H, m), 6.70 (1H, s), 4.05 (1H, d, J=12.2 Hz), 3.70 (1H, d, J=12.2 Hz), 2.71 (1H, dd, J=8.3, 4.3 Hz), 1.65 (1H, dd, J=8.2, 5.6 Hz), 1.28 (1H, t, J=4.9 Hz).

$^{13}$C NMR (DMSO-d6): 162.7, 162.6, 161, 161, 156.6, 134.6, 130.5, 130.4, 130.3, 115.2, 115.1, 115.0, 112, 112.0, 111.8, 111.8, 106.4, 51.6, 26.4, 21.7, 21.4.

Example 65: (5aR,6aS)-5a-(2,6-difluorophenyl)-5,5a,6,6a-tetrahydrocyclopropa[3,4]pyrrolo[1,2-c]imidazole-3(2H)-thione

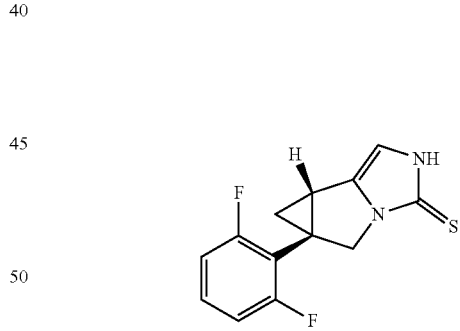

2,6-Difluorophenylacetonitrile and (S)-2-(chloromethyl)oxirane was converted to (5aR,6aS)-5a-(2,6-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

$^1$H NMR (DMSO-d6): 11.78 (1H, br s), 7.43 (1H, m), 7.13 (2H, m), 6.70 (1H, s), 4.05 (1H, d, J=12.2 Hz), 3.70 (1H, d, J=12.2 Hz), 2.71 (1H, dd, J=8.3, 4.3 Hz), 1.65 (1H, dd, J=8.2, 5.6 Hz), 1.28 (1H, t, J=4.9 Hz).

$^{13}$C NMR (DMSO-d6): 162.7, 162.6, 161, 161, 156.6, 134.6, 130.5, 130.4, 130.3, 115.2, 115.1, 115, 112, 112, 111.9, 111.8, 106.4, 51.6, 26.4, 21.7, 21.4.

Example 66: (5aS,6aR)-5a-(2,3-difluorophenyl)-5,5a,6,6a-tetrahydrocyclopropa[3,4]pyrrolo[1,2-c]imidazole-3(2H)-thione

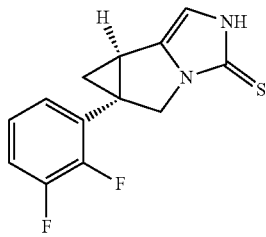 [SMILES: Fc1cccc([C@]23C[C@H]2c2c[nH]c(=S)n2C3)c1F]

2,3-Difluorophenylacetonitrile and (R)-2-(chloromethyl)oxirane was converted to (5aS,6aR)-5a-(2,3-difluorophenyl)-5,5a,6,6a-tetrahydrocyclopropa[3,4]pyrrolo[1,2-c]imidazole-3(2H)-thione by a similar procedure as described for Example 53 and the product was isolated as a light yellow solid.

$^1$H NMR (DMSO-d6): 11.77 (1H, br s), 7.39 (1H, m), 7.23 (1H, m), 7.20 (1H, m), 6.70 (1H, d, J=2.2 Hz), 4.12 (1H, d, J=12.2 Hz), 3.85 (1H, d, J=12.2 Hz), 2.87 (1H, dd, J=8.4, 4.3 Hz), 1.65 (1H, dd, J=8.4, 5.4 Hz), 1.21 (1H, t, J=4.8 Hz).

$^{13}$C NMR (DMSO-d6): 156.7, 150.7, 150.6, 150.4, 150.3, 149, 148.9, 148.7, 148.6, 134.5, 129.1, 129.1, 125.6, 124.9, 124.9, 124.9, 124.8, 116.9, 116.8, 106.2, 51.5, 51.5, 32.5, 32.5, 22.1, 20.9.

Example 67: (5aR,6aS)-5a-(2,3-difluorophenyl)-5,5a,6,6a-tetrahydrocyclopropa[3,4]pyrrolo[1,2-c]imidazole-3(2H)-thione

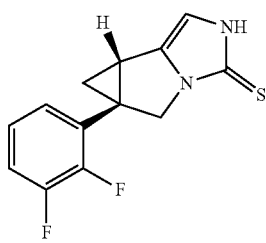 [SMILES: Fc1cccc([C@@]23C[C@@H]2c2c[nH]c(=S)n2C3)c1F]

2,3-Difluorophenylacetonitrile and (S)-2-(chloromethyl)oxirane was converted to (5aR,6aS)-5a-(2,3-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

$^1$H NMR (DMSO-d6): 11.77 (1H, br s), 7.39 (1H, m), 7.23 (1H, m), 7.20 (1H, m), 6.70 (1H, d, J=2.2 Hz), 4.12 (1H, d, J=12.2 Hz), 3.85 (1H, d, J=12.2 Hz), 2.87 (1H, dd, J=8.4, 4.3 Hz), 1.65 (1H, dd, J=8.4, 5.4 Hz), 1.21 (1H, t, J=4.8 Hz).

$^{13}$C NMR (DMSO-d6): 156.7, 150.6, 150.6, 150.4, 150.3, 149, 148.9, 148.7, 148.6, 134.5, 129.1, 129.1, 125.6, 124.9, 124.8, 124.8, 124.8, 116.9, 116.7, 106.2, 51.5, 51.5, 32.5, 32.4, 22.1, 20.9.

Example 68: (5aS,6aR)-5a-(2,3,6-trifluorophenyl)-5,5a,6,6a-tetrahydrocyclopropa[3,4]pyrrolo[1,2-c]imidazole-3 (2H)-thione

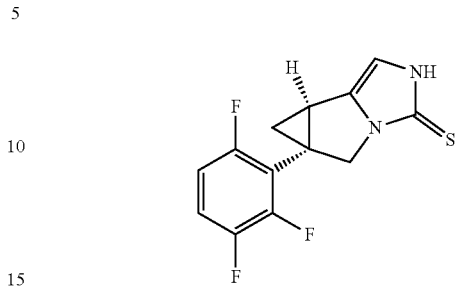

2,3,6-Trifluorophenylacetonitrile and (R)-2-(chloromethyl)oxirane was converted to (5aS,6aR)-5a-(2,3,6-trifluorophenyl)-5,5a,6,6a-tetrahydrocyclopropa[3,4]pyrrolo[1,2-c]imidazole-3 (2H)-thione by a similar procedure as described for Example 53 and the product was isolated as a light beige solid.

$^1$H NMR (DMSO-d6): 11.79 (1H, br s), 7.50 (1H, m, J=9.4, 5.0 Hz), 7.17 (1H, m), 6.71 (1H, d, J=2.2 Hz), 4.06 (1H, d, J=12.2 Hz), 3.76 (1H, d, J=12.2 Hz), 2.77 (1H, dd, J=8.3, 4.3 Hz), 1.69 (1H, dd, J=8.2, 5.6 Hz), 1.31 (1H, t, J=5.0 Hz).

$^{13}$C NMR (DMSO-d6): 158.1, 158.1, 156.6, 156.5, 156.5, 150.2, 150.2, 150.1, 150.1, 148.6, 148.5, 148.5, 148.4, 147.4, 147.3, 145.8, 145.7, 134.3, 117.2, 117.2, 117.2, 117.1, 117.1, 117.1, 117.0, 117.0, 111.7, 111.6, 111.6, 111.6, 111.5, 111.5, 111.5, 111.4, 106.5, 51.4, 26.5, 21.5, 21.3.

Example 69: (5aR,6aS)-5a-(2,3,6-trifluorophenyl)-5,5a,6,6a-tetrahydrocyclopropa[3,4]pyrrolo[1,2-c]imidazole-3 (2H)-thione

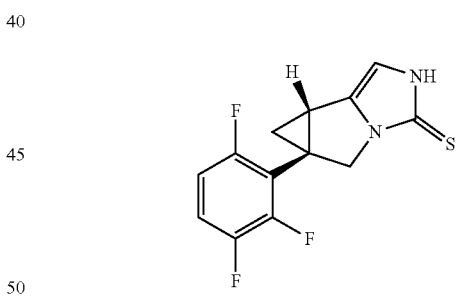

2,3,6-Trifluorophenylacetonitrile and (S)-2-(chloromethyl)oxirane was converted to (5aR,6aS)-5a-(2,3,6-trifluorophenyl)-5,5a,6,6a-tetrahydrocyclopropa[3,4]pyrrolo[1,2-c]imidazole-3 (2H)-thione by a similar procedure as described for Example 53 and the product was isolated as a beige solid.

$^1$H NMR (DMSO-d6): 11.79 (1H, br s), 7.50 (1H, m, J=9.4, 5.0 Hz), 7.17 (1H, m), 6.71 (1H, d, J=2.2 Hz), 4.06 (1H, d, J=12.2 Hz), 3.76 (1H, d, J=12.2 Hz), 2.77 (1H, dd, J=8.3, 4.3 Hz), 1.69 (1H, dd, J=8.2, 5.6 Hz), 1.31 (1H, t, J=5.0 Hz).

$^{13}$C NMR (DMSO-d6): 158.1, 156.6, 156.5, 150.2, 150.2, 150.1, 150.1, 148.6, 148.5, 148.5, 148.4, 147.3, 147.3, 145.8, 145.6, 134.3, 117.2, 117.2, 117.1, 117.1, 117.0, 117.0, 117.0, 111.6, 111.4, 106.5, 51.3, 26.5, 21.5, 21.3.

Example 70: (5aS,6aR)-5a-(2,4-difluorophenyl)-5,5a,6,6a-tetrahydrocyclopropa[3,4]pyrrolo[1,2-c]imidazole-3(2H)-thione

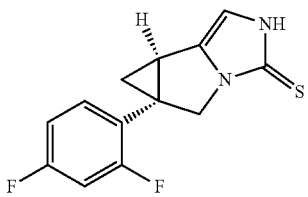 [SMILES: Fc1ccc([C@]23C[C@H]2c2c[nH]c(=S)n2C3)c(F)c1]

2,4-Difluorophenylacetonitrile and (R)-2-(chloromethyl)oxirane was converted to (5aS,6aR)-5a-(2,4-difluorophenyl)-5,5a,6,6a-tetrahydrocyclopropa[3,4]pyrrolo[1,2-c]imidazole-3 (2H)-thione by a similar procedure as described for Example 53 and the product was isolated as a beige solid.

$^1$H NMR (DMSO-d6): 11.76 (1H, br s), 7.47 (1H, td, J=8.7, 6.6 Hz), 7.29 (1H, ddd, J=10.9, 9.2, 2.6 Hz), 7.08 (1H, tdd, J=1.0, 2.8, 8.6 Hz), 6.68 (1H, d, J=2.2 Hz), 4.08 (1H, d, J=12.0 Hz), 3.77 (1H, d, J=12.2 Hz), 2.77 (1H, dd, J=8.3, 4.2 Hz), 1.62 (1H, dd, J=8.3, 5.4 Hz), 1.15 (1H, t, J=4.8 Hz).

$^{13}$C NMR (DMSO-d6): 162.7, 162.6, 162.6, 162.6, 161.1, 161, 161, 160.9, 156.6, 134.7, 131.8, 131.8, 131.8, 131.7, 123.1, 123, 123, 122.9, 111.6, 111.5, 111.4, 111.4, 106.1, 104.4, 104.2, 104, 51.7, 32.2, 21.8, 20.7.

Example 71: (5aS,6aR)-5a-(3,4-difluorophenyl)-5,5a,6,6a-tetrahydrocyclopropa[3,4]pyrrolo[1,2-c]imidazole-3(2H)-thione

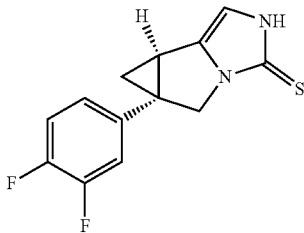 [SMILES: Fc1ccc([C@]23C[C@H]2c2c[nH]c(=S)n2C3)cc1F]

3,4-Difluorophenylacetonitrile and (R)-2-(chloromethyl)oxirane was converted to (5aS,6aR)-5a-(3,4-difluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

$^1$H NMR (DMSO-d6): 11.74 (1H, br s), 7.48 (1H, ddd, J=12.1, 7.7, 2.1 Hz), 7.39 (1H, dt, J=10.5, 8.7 Hz), 7.21 (1H, m), 6.66 (1H, s), 4.20 (1H, d, J=12.2 Hz), 3.99 (1H, d, J=12.2 Hz), 2.89 (1H, dd, J=8.3, 4.2 Hz), 1.64 (1H, dd, J=8.2, 5.3 Hz), 1.13 (1H, t, J=4.8 Hz).

$^{13}$C NMR (DMSO-d6): 156.7, 150.2, 150.1, 149.2, 149.1, 148.6, 148.5, 147.6, 147.5, 137.9, 137.9, 137.8, 137.8, 134.8, 123.9, 123.9, 123.8, 123.8, 117.5, 117.4, 116.4, 116.3, 105.9, 51.2, 36.1, 24.4.

Example 72: (5aS,6aR)-5a-(2,4,5-trifluorophenyl)-5,5a,6,6a-tetrahydrocyclopropa[3,4]pyrrolo[1,2-c]imidazole-3 (2H)-thione

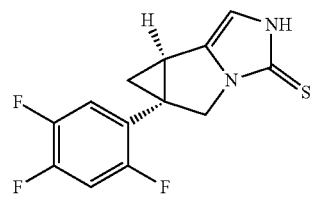 [SMILES: Fc1cc(F)c([C@]23C[C@H]2c2c[nH]c(=S)n2C3)cc1F]

2,4,5-Trifluorophenylacetonitrile and (R)-2-(chloromethyl)oxirane was converted to (5aS,6aR)-5a-(2,4,5-trifluorophenyl)-5,5a,6,6a-tetrahydrocyclopropa[3,4]pyrrolo[1,2-c]imidazole-3 (2H)-thione by a similar procedure as described for Example 53 and the product was isolated as a beige solid.

$^1$H NMR (DMSO-d6): 11.76 (1H, br s), 7.59 (2H, m), 6.69 (1H, d, J=2.1 Hz), 4.08 (1H, d, J=12.0 Hz), 3.81 (1H, d, J=12.0 Hz), 2.86 (1H, dd, J=8.3, 4.2 Hz), 1.65 (1H, dd, J=8.4, 5.4 Hz), 1.17 (1H, t, J=4.8 Hz).

$^{13}$C NMR (DMSO-d6): 157.9, 157.8, 156.6, 156.2, 156.2, 149.5, 149.4, 149.4, 147.9, 147.8, 147.7, 146.6, 146.6, 145.0, 145.0, 134.5, 123.8, 123.8, 123.8, 123.7, 118.7, 118.7, 118.6, 118.6, 106.4, 106.3, 106.2, 106.1, 51.5, 51.4, 32.2, 22.2, 21.0.

Example 73: (5aS,6aR)-5a-(3-chloro-5-fluorophenyl)-5,5a,6,6a-tetrahydrocyclopropa[3,4]pyrrolo[1,2-c]imidazole-3 (2H)-thione

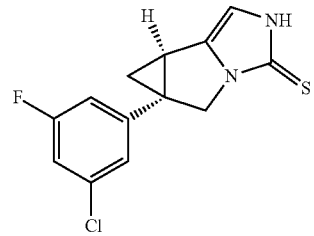 [SMILES: Fc1cc(Cl)cc([C@]23C[C@H]2c2c[nH]c(=S)n2C3)c1]

2-(3-Chloro-5-fluorophenyl)acetonitrile and (R)-2-(chloromethyl)oxirane was converted to (5aS,6aR)-5a-(3-chloro-5-fluorophenyl)-5,5a,6,6a-tetrahydrocyclopropa[3,4]pyrrolo[1,2-c]imidazole-3(2H)-thione by a similar procedure as described for Example 53 and the product was isolated as a beige solid.

$^1$H NMR (DMSO-d6): 11.74 (1H, br s), 7.31 (2H, m), 7.26 (1H, ddd, J=1.7, 2.2, 10.1 Hz), 6.67 (1H, d, J=2.2 Hz), 4.23 (1H, d, J=12.2 Hz), 4.04 (1H, d, J=12.0 Hz), 3.01 (1H, dd, J=8.4, 4.3 Hz), 1.67 (1H, dd, J=8.4, 5.3 Hz), 1.17 (1H, dd, J=4.4, 5.2 Hz).

$^{13}$C NMR (DMSO-d6): 163.1, 161.4, 156.8, 144.8, 144.7, 134.5, 134.2, 134.1, 123.1, 123.1, 114.3, 114.2, 113, 112.8, 105.9, 50.7, 36.3, 36.3, 25.1, 22.8.

Example 74: (5aS,6aR)-5a-(5-chloro-2-fluorophenyl)-5,5a,6,6a-tetrahydrocyclopropa[3,4]pyrrolo[1,2-c]imidazole-3 (2H)-thione

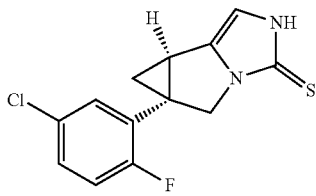

2-(5-Chloro-2-fluorophenyl)acetonitrile and (R)-2-(chloromethyl)oxirane was converted to (5aS,6aR)-5a-(5-chloro-2-fluorophenyl)-5,5a,6,6a-tetrahydrocyclopropa[3,4]pyrrolo[1,2-c]imidazole-3(2H)-thione by a similar procedure as described for Example 53 and the product was isolated as a light yellow solid.

$^1$H NMR (DMSO-d6): 11.76 (1H, br s), 7.49 (1H, dd, J=6.5, 2.7 Hz), 7.43 (1H, ddd, J=8.7, 4.3, 2.8 Hz), 7.30 (1H, dd, J=9.9, 8.9 Hz), 6.69 (1H, s), 4.10 (1H, d, J=12.0 Hz), 3.81 (1H, d, J=12.2 Hz), 2.89 (1H, dd, J=8.3, 4.2 Hz), 1.67 (1H, dd, J=8.4, 5.4 Hz), 1.17 (1H, t, J=4.8 Hz).

$^{13}$C NMR (DMSO-d6): 161.3, 159.7, 156.6, 134.6, 130.2, 130.1, 129.4, 129.3, 128.8, 128.7, 128.3, 128.3, 117.6, 117.4, 106.2, 51.5, 51.5, 32.6, 22.1, 20.9.

Example 75: (5aS,6aR)-5a-(2-chloro-5-fluorophenyl)-5,5a,6,6a-tetrahydrocyclopropa[3,4]pyrrolo[1,2-c]imidazole-3 (2H)-thione

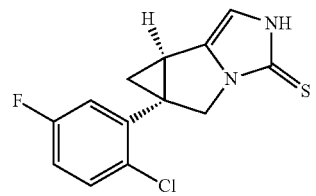 [SMILES: Fc1ccc(Cl)c([C@]23C[C@H]2c2c[nH]c(=S)n2C3)c1]

2-(2-Chloro-5-fluorophenyl)acetonitrile and (R)-2-(chloromethyl)oxirane was converted to (5aS,6aR)-5a-(2-chloro-5-fluorophenyl)-5,5a,6,6a-tetrahydrocyclopropa[3,4]pyrrolo[1,2-c]imidazole-3(2H)-thione by a similar procedure as described for Example 53 and the product was isolated as a light yellow solid.

$^1$H NMR (DMSO-d6): 11.76 (1H, br s), 7.56 (1H, dd, J=8.8, 5.1 Hz), 7.39 (1H, dd, J=9.2, 3.1 Hz), 7.24 (1H, td, J=8.5, 3.1 Hz), 6.69 (1H, d, J=2.2 Hz), 4.08 (1H, d, J=12.2 Hz), 3.76 (1H, d, J=12.0 Hz), 2.77 (1H, dd, J=8.4, 4.3 Hz), 1.69 (1H, dd, J=8.4, 5.4 Hz), 1.20 (1H, dd, J=5.3, 4.4 Hz).

$^{13}$C NMR (DMSO-d6): 161.5, 159.9, 156.5, 139.2, 139.1, 134.9, 131.2, 131.2, 130.4, 130.4, 118.9, 118.8, 116.6, 116.4, 106.2, 51.2, 36.4, 22.1, 21.8.

Example 76: (5aS,6aR)-5a-(3,5-difluorophenyl)-2-methyl-5,5a,6,6a-tetrahydrocyclopropa[3,4]pyrrolo[1,2-c]imidazole-3 (2H)-thione Step 1: (5aS,6aR)-5a-(3,5-difluorophenyl)-1-hydroxy-2-methylhexahydrocyclopropa[3,4]pyrrolo[1,2-c]imidazole-3(2H)-thione

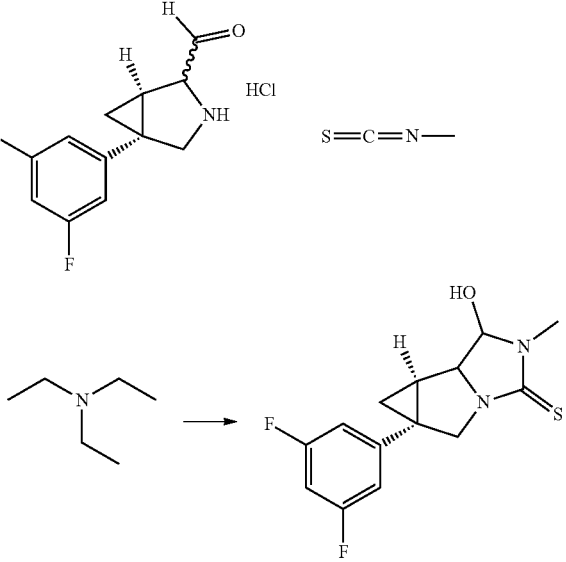

To a solution of (1R,5S)-5-(3,5-difluorophenyl)-3-azabicyclo[3.1.0]hexane-2-carbaldehyde hydrochloride (analogous to Example 53 step 10) (0.460 g, 1,771 mmol) in dichloromethane (4.4 mL) was added isothiocyanatomethane (0,155 g, 2,126 mmol) and triethylamine (0.299 mL, 2,126 mmol). The reaction mixture was stirred at room temperature for 24 h. Thereupon, the mixture was quenched with water and extracted with dichloromethane. The organic phase was dried over MgSO$_4$, filtered and evaporated to dryness. Chromatography (ethyl acetate-petroleum ether; 1:6) afforded the product as a brown solid. (Yield: 0.129 g, 29%).

Step 2: (5aS,6aR)-5a-(3,5-difluorophenyl)-2-methyl-5,5a,6,6a-tetrahydrocyclopropa[3,4]pyrrolo[1,2-c]imidazole-3(2H)-thione

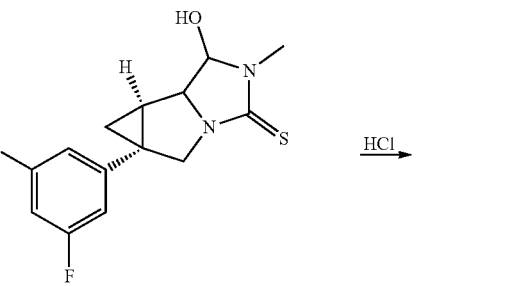

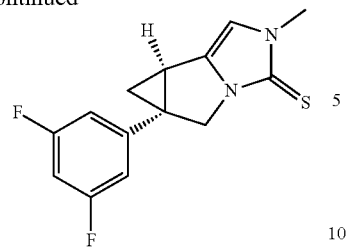

To a stirred solution of (5aS,6aR)-5a-(3,5-difluorophenyl)-1-hydroxy-2-methylhexahydrocyclopropa[3,4]pyrrolo[1,2-c]imidazole-3(2H)-thione) (0,095 g, 0,321 mmol) in a mixture of ethanol (0.801 mL) and water (0.801 mL) was added 6 M HCl (0.107 mL, 0,641 mmol). The reaction mixture was heated at reflux for 2 h. Thereupon, the mixture was cooled down to room temperature, and ethanol was removed under vacuum. The residue was extracted with dichloromethane, whereupon the organic phase was dried over $MgSO_4$, filtrated, concentrated under reduced pressure to give a brown solid which was purified by chromatography (ethyl acetate-petroleum ether; 1:1). The product was isolated as brown solid. (Yield: 0.067 g, 54%).

$^1$H NMR ($CDCl_3$): 6.78 (2H, m), 6.74 (1H, m), 6.44 (1H, s), 4.31 (1H, d, J=12.2 Hz), 4.20 (1H, d, J=12.3 Hz), 3.57 (3H, s), 2.62 (1H, dd, J=8.3, 4.0 Hz), 1.69 (1H, dd, J=8.2, 5.6 Hz), 1.18 (1H, dd, J=5.4, 4.3 Hz).

$^{13}$C NMR ($CDCl_3$): 164.1, 164, 162.4, 162.3, 158, 143.3, 143.2, 143.1, 133.3, 110.3, 110.2, 110.1, 110.1, 109.7, 103.1, 103, 102.8, 52.7, 36.2, 34.8, 24.2, 23.2.

Example 77: (5aS,6aR)-2-cyclopropyl-5a-(3,5-difluorophenyl)-5,5a,6,6a-tetrahydrocyclopropa[3,4]pyrrolo[1,2-c]imidazole-3 (2H)-thione

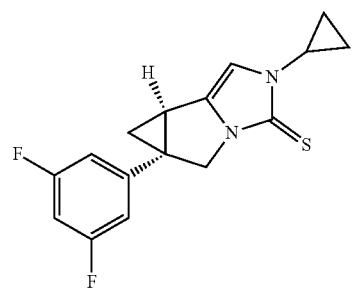 [SMILES: Fc1cc(F)cc([C@]23C[C@H]2c2cn(C4CC4)c(=S)n2C3)c1]

(1R,5S)-5-(3,5-Difluorophenyl)-3-azabicyclo[3.1.0]hexane-2-carbaldehyde hydrochloride was converted to (5aS,6aR)-2-cyclopropyl-5a-(3,5-difluorophenyl)-5,5a,6,6a-tetrahydrocyclopropa[3,4]pyrrolo[1,2-c]imidazole-3 (2H)-thione by a similar procedure as described for Example 76 and the product was isolated as a brown solid.

$^1$H NMR (DMSO-d6): 7.12 (3H, m), 6.79 (1H, s), 4.25 (1H, d, J=12.2 Hz), 4.08 (1H, d, J=12.2 Hz), 3.37 (1H, m), 3.00 (1H, dd, J=8.4, 4.3 Hz), 1.68 (1H, dd, J=8.4, 5.3 Hz), 1.20 (1H, t, J=4.8 Hz), 0.93 (2H, m), 0.86 (2H, m).

$^{13}$C NMR (DMSO-d6): 163.4, 163.3, 161.7, 161.7, 158.7, 144.7, 144.6, 144.6, 132.8, 110.2, 110.2, 110.1, 110.0, 107.6, 102.3, 102.2, 102.0, 51.4, 35.8, 35.8, 29.5, 25.1, 23.0, 6.4, 6.4.

Example 78: (5aS,6aR)-5a-(2,5-difluorophenyl)-1-methyl-5,5a,6,6a-tetrahydrocyclopropa[3,4]pyrrolo[1,2-c]imidazole-3 (2H)-thione

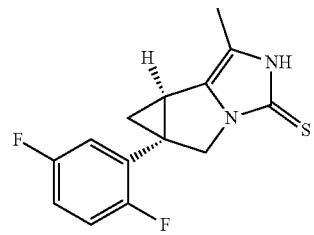 [SMILES: Cc1[nH]c(=S)n2c1[C@@H]1C[C@]1(c1cc(F)ccc1F)C2]

Compound was prepared in an analogous manner to Example 80 from (5S)-3-(tert-butoxycarbonyl)-5-(2,5-difluorophenyl)-3-azabicyclo[3.1.0]hexane-2-carboxylic acid and methylmagnesium iodide and isolated as a yellow solid.

$^1$H NMR (DMSO-d6): 11.66 (1H, br s), 7.28 (2H, m), 7.20 (1H, m), 4.06 (1H, d, J=12.0 Hz), 3.78 (1H, d, J=12.0 Hz), 2.86 (1H, dd, J=8.2, 4.3 Hz), 2.09 (1H, m), 2.04 (3H, s), 1.63 (1H, dd, J=8.1, 5.4 Hz), 1.13 (1H, t, J=4.8 Hz).

$^{13}$C NMR (DMSO-d6): 158.8, 158.7, 157.2, 157.1, 155.7, 130.3, 128.8, 128.8, 128.8, 128.7, 128.6, 117.2, 117.1, 117.0, 116.9, 116.8, 115.9, 115.8, 115.7, 115.7, 114.8, 51.5, 32.5, 22.4, 20.3, 9.4.

Example 79: (5aS,6aR)-5a-(3,5-difluorophenyl)-1-methyl-5,5a,6,6a-tetrahydrocyclopropa[3,4]pyrrolo[1,2-c]imidazole-3 (2H)-thione

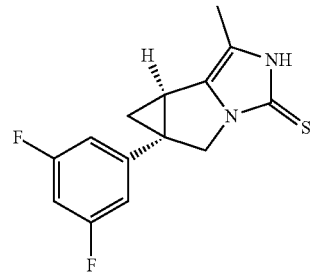 [SMILES: Cc1[nH]c(=S)n2c1[C@@H]1C[C@]1(c1cc(F)cc(F)c1)C2]

Compound was prepared in an analogous manner to Example 80 from (5S)-3-(tert-butoxycarbonyl)-5-(3,5-difluorophenyl)-3-azabicyclo[3.1.0]hexane-2-carboxylic acid and methylmagnesium iodide and isolated as a yellow solid.

$^1$H NMR (DMSO-d6): 1.63 (1H, br s), 7.10 (3H, m), 4.17 (1H, d, J=12.0 Hz), 4.00 (1H, d, J=12.2 Hz), 2.97 (1H, dd, J=8.3, 4.3 Hz), 2.03 (3H, s), 1.65 (1H, dd, J=8.2, 5.1 Hz), 1.15 (1H, m).

$^{13}$C NMR (DMSO-d6): 163.4, 163.3, 161.8, 161.7, 156, 145, 130.2, 114.5, 110, 110, 109.9, 109.9, 102.1, 50.7, 36.1, 25.4, 22.4, 9.4.

Example 80: (S)-1-butyl-6-(3,5-difluorophenyl)-6,7-dihydro-2H-pyrrolo[1,2-c]imidazole-3(5H)-thione

Step 1: (4S)-tert-butyl 4-(3,5-difluorophenyl)-2-(methoxy(methyl)carbamoyl)pyrrolidine-1-carboxylate

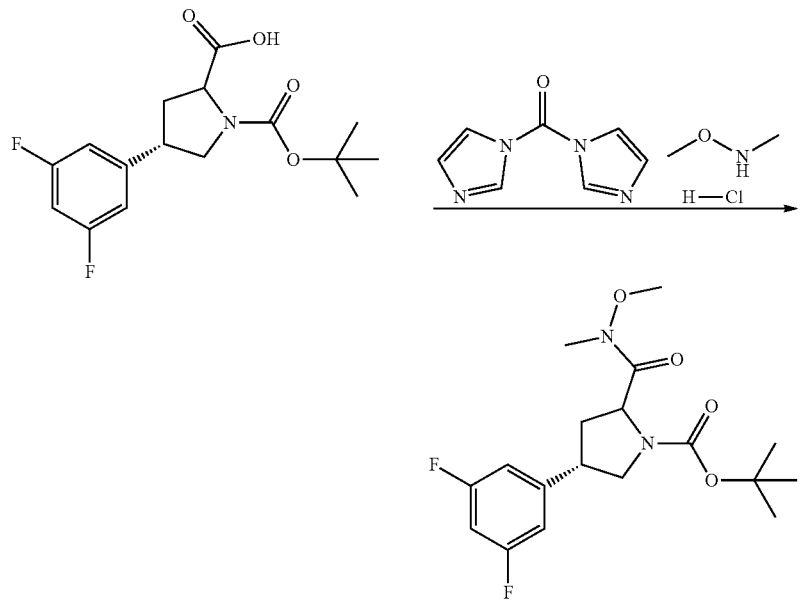

To a solution of (4S)-1-(tert-butoxycarbonyl)-4-(3,5-difluorophenyl)pyrrolidine-2-carboxylic acid (analogous to Example 58 step 9) (0.982 g, 3 mmol) in dry dichloromethane (10 mL) was added di(1H-imidazol-1-yl)methanone (0.584 g, 3.60 mmol) in portions at room temperature and the mixture was stirred for 30 min. Thereupon, N,O-dimethylhydroxylamine hydrochloride (0.351 g, 3.60 mmol) was added and the stirring was continued at room temperature for 40 h.

The reaction was then washed with water, the organic phase was dried over $MgSO_4$ and concentrated under vacuum. Chromatography (petroleum ether-ethyl acetate; 2:1) afforded the product as an off-white solid. (Yield: 0.92 g, 83%).

Step 2: tert-butyl (4S)-4-(3,5-difluorophenyl)-2-pentanoylpyrrolidine-1-carboxylate

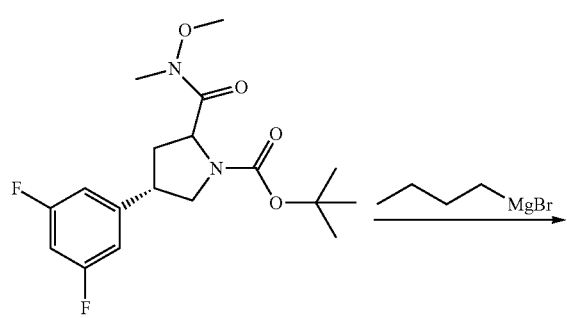

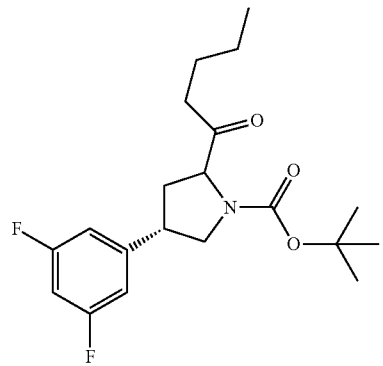

To a solution of (4S)-tert-butyl 4-(3,5-difluorophenyl)-2-(methoxy(methyl)carbamoyl)pyrrolidine-1-carboxylate (0.40 g, 1.08 mmol) in dry tetrahydrofuran (2 mL) was added 2 M butylmagnesium bromide (1.62 mL, 3.24 mmol) at 0-5° C. under nitrogen. The mixture was allowed to warm up to room temperature and stirred for 3 h. Thereupon, the mixture was poured onto 1 M HCl and then extracted with diethyl ether. The organic phase was washed with brine, dried over $MgSO_4$, and evaporated to dryness. Chromatography (petroleum ether-ethyl acetate; 9:1) afforded the product as a colourless oil. (Yield: 0.2 g, 50%).

Step 3: (S)-1-benzyl-6-(3,5-difluorophenyl)-6,7-dihydro-2H-pyrrolo[1,2-c]imidazole-3(5H)-thione

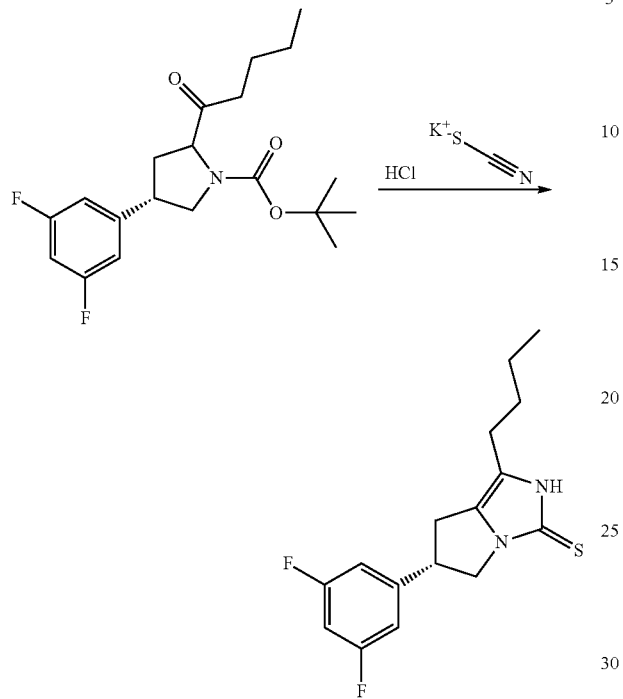

A mixture of (4S)-tert-butyl 4-(3,5-difluorophenyl)-2-pentanoylpyrrolidine-1-carboxylate (0.19 g, 0.517 mmol) and 4 M HCl (2.59 mL, 10.34 mmol) in dioxane was stirred at room temperature overnight. The mixture was then cooled to room temperature and evaporated to dryness. The thus obtained oily residue was dissolved in a mixture of ethanol (2 mL) and water (2 mL), followed by addition of potassium thiocyanate (0.055 g, 0.569 mmol) and 6 M HCl (0.043 mL, 0.259 mmol). The mixture was stirred under reflux for 1 h, then stirred at room temperature for 30 min. The obtained solid was collected by filtration, washed with a mixture of ethanol water (1:1) and dried under vacuum at 50° C. to give the product as a light beige powder. (Yield: 0.12 g, 75%).

$^1$H NMR (DMSO-d6): 11.71 (1H, s), 7.13 (3H, m), 4.14 (1H, dd, J=11.2, 7.9 Hz), 4.07 (1H, quin, J=8.1 Hz), 3.67 (1H, dd, J=11.1, 8.3 Hz), 3.20 (1H, dd, J=15.0, 7.8 Hz), 2.84 (1H, dd, J=15.1, 8.8 Hz), 2.35 (2H, t, J=7.5 Hz), 1.50 (2H, m), 1.26 (2H, m), 0.86 (3H, t, J=7.4 Hz).

$^{13}$C NMR (DMSO-d6): 163.3, 163.2, 161.7, 161.6, 155.1, 145.8, 145.7, 145.6, 127.6, 120, 110.8, 110.7, 110.6, 110.6, 102.6, 102.5, 102.3, 49.9, 46.5, 30.4, 29.8, 23.6, 21.5, 13.6.

Example 81: 6-cyclohexyl-6,7-dihydro-2H-pyrrolo[1,2-c]imidazole-3(5H)-thione

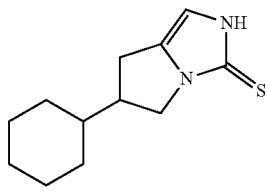 [SMILES: S=c1[nH]cc2n1CC(C1CCCCC1)C2]

Compound was prepared in an analogous manner to Example 58 from diethyl 2-(1-cyclohexyl-2-nitroethyl)malonate (Liu, Jin-ming; Wang, Xin; Ge, Ze-mei; Sun, Qi; Cheng, Tie-ming; Li, Run-tao Tetrahedron (2011), 67(3), 636-640) and isolated as a beige powder.

$^1$H NMR (DMSO-d6): 11.68 (1H, br s), 6.52 (1H, s), 3.84 (1H, dd, J=11.3, 7.9 Hz), 3.33 (1H, dd, J=9.0, 11.5 Hz), 2.86 (1H, ddd, J=0.8, 7.8, 15.1 Hz), 2.57 (1H, m), 2.47 (1H, m), 1.65 (5H, m), 1.43 (1H, m), 1.18 (3H, m), 0.96 (2H, m).

$^{13}$C NMR (DMSO-d6): 155.6, 133.2, 106.3, 48.4, 47.8, 41, 30.7, 30.4, 27.5, 25.9, 25.5.

Example 82: (S)-6-(2,3,5-trifluorophenyl)-2,5,6,7-tetrahydro-3H-pyrrolo[1,2-c]imidazole-3-thione

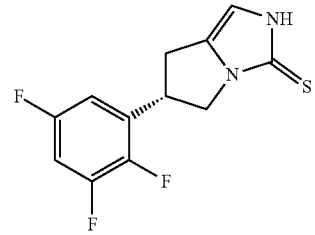 [SMILES: Fc1cc(F)c(F)c([C@@H]2Cc3c[nH]c(=S)n3C2)c1]

Compound was prepared in an analogous manner to Example 59 from (E)-1,2,5-trifluoro-3-(2-nitrovinyl)benzene using 4-((R)-hydroxy((1S,2S,4S,5R)-5-vinylquinuclidin-2-yl)methyl)quinolin-6-ol as catalyst CAS #524-63-0) and isolated as a beige powder.

$^1$H NMR (DMSO-D6): 11.84 (1H, br s), 7.48 (1H, m), 7.21 (1H, m), 6.65 (1H, m), 4.33 (1H, quin, J=8.2 Hz), 4.17 (1H, dd, J=11.3, 8.1 Hz), 3.77 (1H, dd, J=11.4, 8.1 Hz), 3.26 (1H, ddd, J=15.4, 8.2, 0.9 Hz), 2.94 (1H, ddd, J=15.4, 8.5, 1.5 Hz).

$^{13}$C NMR (DMSO-d6): 158.1, 158.1, 158.0, 158.0, 156.5, 156.5, 156.4, 156.4, 156.1, 150.6, 150.5, 150.4, 148.9, 148.8, 148.7, 145.7, 145.7, 145.6, 145.6, 144.1, 144.1, 144.0, 144.0, 131.9, 131.5, 131.4, 131.4, 131.3, 110.7, 110.5, 107.0, 104.9, 104.7, 104.7, 104.5, 49.0, 40.3, 30.0.

Example 83: (R)-6-(2,3,5-trifluorophenyl)-2,5,6,7-tetrahydro-3H-pyrrolo[1,2-c]imidazole-3-thione

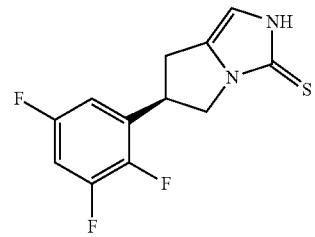 [SMILES: Fc1cc(F)c(F)c([C@H]2Cc3c[nH]c(=S)n3C2)c1]

Compound was prepared in an analogous manner to Example 58 from (E)-1,2,5-trifluoro-3-(2-nitrovinyl)benzene using 4-((S)-hydroxy((1S,2R,4S,5R)-5-vinylquinuclidin-2-yl)methyl)quinolin-6-ol as catalyst (CAS #70877-75-7) and isolated as a beige powder.

$^1$H NMR (DMSO-d6): 11.84 (1H, br s), 7.48 (1H, m), 7.21 (1H, m), 6.65 (1H, m), 4.33 (1H, quin, J=8.2 Hz), 4.17

(1H, dd, J=11.3, 8.1 Hz), 3.77 (1H, dd, J=11.4, 8.1 Hz), 3.26 (1H, ddd, J=15.4, 8.2, 0.9 Hz), 2.94 (1H, ddd, J=15.4, 8.5, 1.5 Hz).

$^{13}$C NMR (DMSO-d6): 158.1, 158.1, 158.0, 158.0, 156.5, 156.5, 156.4, 156.4, 156.1, 150.6, 150.5, 150.4, 148.9, 148.8, 148.7, 145.7, 145.7, 145.6, 145.6, 144.1, 144.1, 144.0, 144.0, 131.9, 131.5, 131.4, 131.4, 131.3, 110.7, 110.5, 107.0, 104.9, 104.7, 104.7, 104.5, 49.1, 40.3, 30.0.

Example 84: (S)-6-(2,6-difluorophenyl)-2,5,6,7-tetrahydro-3H-pyrrolo[1,2-c]imidazole-3-thione

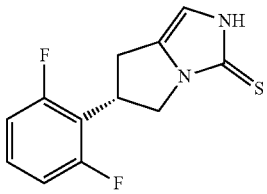 [SMILES: Fc1cccc(F)c1[C@@H]1Cc2c[nH]c(=S)n2C1]

Compound was prepared in an analogous manner to Example 59 from (E)-1,3-difluoro-2-(2-nitrovinyl)benzene using 4-((R)-hydroxy((1S,2S,4S,5R)-5-vinylquinuclidin-2-yl)methyl)quinolin-6-ol as catalyst (CAS #524-63-0) and isolated as a greenish powder.

$^1$H NMR (DMSO-d6): 11.84 (1H, br s), 7.41 (1H, m), 7.13 (2H, m), 6.63 (1H, m), 4.47 (1H, quin, J=8.7 Hz), 4.17 (1H, dd, J=10.8, 9.8 Hz), 3.73 (1H, dd, J=11.4, 8.2 Hz), 3.29 (1H, dd, J=15.8, 9.3 Hz), 2.92 (1H, dd, J=15.8, 8.4 Hz).

$^{13}$C NMR (DMSO-d6): 161.6, 161.6, 160.0, 159.9, 155.9, 132.3, 129.8, 129.7, 129.7, 116.7, 116.6, 116.4, 112.3, 112.2, 112.1, 112.1, 106.6, 48.6, 35.3, 29.6.

Example 85: (S)-6-(3-chloro-2,6-difluorophenyl)-2,5,6,7-tetrahydro-3H-pyrrolo[1,2-c]imidazole-3-thione

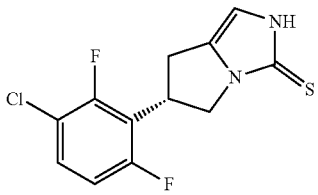 [SMILES: Fc1ccc(Cl)c(F)c1[C@@H]1Cc2c[nH]c(=S)n2C1]

Compound was prepared in an analogous manner to Example 59 from (E)-1-chloro-2,4-difluoro-3-(2-nitrovinyl)benzene using 4-((R)-hydroxy((1 S,2S,4S,5R)-5-vinylquinuclidin-2-yl)methyl)quinolin-6-ol as catalyst (CAS #524-63-0) and isolated as a white powder.

$^1$H NMR (DMSO-d6): 11.85 (1H, br s), 7.61 (1H, td, J=8.7, 5.6 Hz), 7.22 (1H, dt, J=1.6, 9.6 Hz), 6.63 (1H, s), 4.50 (1H, quin, J=8.5 Hz), 4.18 (1H, dd, J=11.5, 9.3 Hz), 3.75 (1H, dd, J=11.7, 7.7 Hz), 3.31 (1H, dd, J=9.4, 16 Hz), 2.93 (1H, dd, J=15.8, 7.8 Hz).

$^{13}$C NMR (DMSO-d6): 160.2, 160.1, 158.5, 158.5, 156.6, 156.5, 155.8, 155, 154.9, 132.3, 129.7, 129.7, 118.9, 118.8, 118.7, 116.1, 116.1, 116, 113.3, 113.3, 113.1, 113.1, 106.6, 48.5, 35.7, 29.5.

Example 86: (R)-6-(3-chloro-2,6-difluorophenyl)-2,5,6,7-tetrahydro-3H-pyrrolo[1,2-c]imidazole-3-thione

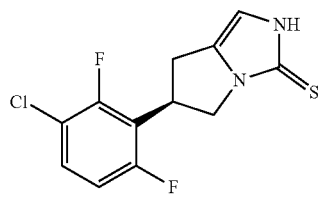 [SMILES: Fc1ccc(Cl)c(F)c1[C@H]1Cc2c[nH]c(=S)n2C1]

Compound was prepared in an analogous manner to Example 58 from (E)-1-chloro-2,4-difluoro-3-(2-nitrovinyl)benzene using 4-((S)-hydroxy((1S,2R,4S,5R)-5-vinylquinuclidin-2-yl)methyl)quinolin-6-ol as catalyst (CAS #70877-75-7) and isolated as a white powder.

$^1$H NMR (DMSO-d6): 11.85 (1H, br s), 7.61 (1H, td, J=8.7, 5.6 Hz), 7.22 (1H, dt, J=1.6, 9.6 Hz), 6.63 (1H, s), 4.50 (1H, quin, J=8.5 Hz), 4.18 (1H, dd, J=11.5, 9.3 Hz), 3.75 (1H, dd, J=11.7, 7.7 Hz), 3.31 (1H, dd, J=9.4, 16 Hz), 2.93 (1H, dd, J=15.8, 7.8 Hz).

$^{13}$C NMR (DMSO-d6): 160.2, 160.1, 158.5, 158.5, 156.6, 156.5, 155.8, 155, 154.9, 132.2, 129.7, 129.6, 118.9, 118.8, 118.7, 116.1, 116.1, 116, 115.9, 113.3, 113.2, 113.1, 113.1, 106.6, 48.5, 35.7, 29.5.

Example 87: (R)-6-(2,6-difluorophenyl)-2,5,6,7-tetrahydro-3H-pyrrolo[1,2-c]imidazole-3-thione

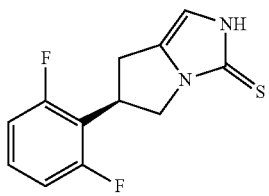 [SMILES: Fc1cccc(F)c1[C@H]1Cc2c[nH]c(=S)n2C1]

Compound was prepared in an analogous manner to Example 58 from (E)-1,3-difluoro-2-(2-nitrovinyl)benzene using 4-((S)-hydroxy((1S,2R,4S,5R)-5-vinylquinuclidin-2-yl)methyl)quinolin-6-ol as catalyst (CAS #70877-75-7) and isolated as a white powder.

$^1$H NMR (DMSO-d6): 11.84 (1H, br s), 7.41 (1H, m), 7.13 (2H, t, J=8.1 Hz), 6.63 (1H, s), 4.47 (1H, quin, J=8.7 Hz), 4.17 (1H, m), 3.73 (1H, dd, J=11.4, 8.2 Hz), 3.29 (1H, dd, J=15.7, 9.2 Hz), 2.92 (1H, br dd, J=15.7, 8.4 Hz).

$^{13}$C NMR (DMSO-d6): 161.6, 161.6, 160.0, 159.9, 155.8, 132.3, 129.8, 129.7, 116.7, 116.6, 116.4, 112.3, 112.2, 112.1, 112.1, 106.6, 48.6, 35.3, 29.6.

Example 88: (5aS,6aR)-5a-(3-chloro-2,6-difluorophenyl)-5,5a,6,6a-tetrahydrocyclopropa[3,4]pyrrolo[2,1-c][1,2,4]triazole-3(2H)-thione

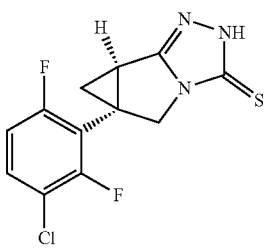 [SMILES: Fc1ccc(Cl)c(F)c1[C@]12C[C@H]1c1n[nH]c(=S)n1C2]

Compound was prepared in an analogous manner to Example 60 from tert-butyl ((((1S,2R)-1-(3-chloro-2,6-difluorophenyl)-2-(hydroxymethyl)cyclopropyl)methyl)carbamate and isolated as a pink solid.

$^1$H NMR (DMSO-d6): 13.30 (1H, s), 7.67 (1H, td, J=8.7, 5.6 Hz), 7.24 (1H, td, J=9.1, 1.4 Hz), 4.12 (1H, d, J=12.6 Hz), 3.86 (1H, d, J=12.2 Hz), 2.95 (1H, dd, J=8.9, 4.2 Hz), 1.81 (1H, dd, J=8.8, 5.9 Hz), 1.68 (1H, m).

$^{13}$C NMR (DMSO-d6): 163.6, 161.2, 161.1, 159.5, 159.5, 157.8, 157.7, 157.5, 156.1, 156.0, 130.8, 130.7, 116.1, 116.0, 115.9, 115.8, 115.8, 115.7, 113.0, 113.0, 112.9, 112.8, 49.5, 27.3, 20.1, 19.6.

Example 89: (5aS,6aR)-5a-(2-chloro-6-fluorophenyl)-5,5a,6,6a-tetrahydrocyclopropa[3,4]pyrrolo[1,2-c]imidazole-3 (2H)-thione

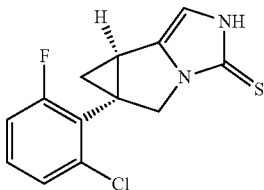 [SMILES: Fc1cccc(Cl)c1[C@]12C[C@H]1c1c[nH]c(=S)n1C2]

Compound was prepared in an analogous manner to Example 53 from 2-(2-chloro-6-fluorophenyl)acetonitrile and (R)-2-(chloromethyl)oxirane and isolated as a beige solid.

$^1$H NMR (DMSO-d6): 11.78 (1H, br s), 7.42 (1H, m), 7.38 (1H, m), 7.27 (1H, ddd, J=9.7, 8.3, 1.2 Hz), 6.72 (1H, d, J=2.2 Hz), 4.04 (1H, br d, J=12.0 Hz), 3.67 (1H, d, J=12.0 Hz), 2.73 (1H, m), 1.67 (1H, br s), 1.34 (1H, t, J=5.1 Hz).

$^{13}$C NMR (DMSO-d6): 162.7, 161.1, 156.5, 136.4, 134.7, 130.7, 130.6, 125.7, 125.7, 124.8, 124.7, 115.1, 114.9, 106.4, 51, 29.9, 22.8, 22.7, 22.7.

Example 90: (5aS,6aR)-5a-(3-chloro-2,6-difluorophenyl)-5,5a,6,6a-tetrahydrocyclopropa[3,4]pyrrolo[1,2-c]imidazole-3 (2H)-thione

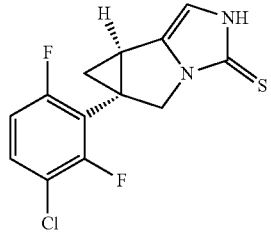

Compound was prepared in an analogous manner to Example 53 from 2-(3-chloro-2,6-difluorophenyl)acetonitrile and (R)-2-(chloromethyl)oxirane and isolated as an orange solid.

$^1$H NMR (DMSO-d6): 11.80 (1H, br s), 7.64 (1H, m), 7.22 (1H, t, J=8.8 Hz), 6.72 (1H, d, J=2.1 Hz), 4.06 (1H, d, J=12.2 Hz), 3.76 (1H, d, J=12.2 Hz), 2.77 (1H, dd, J=8.3, 4.3 Hz), 1.69 (1H, dd, J=8.1, 5.6 Hz), 1.31 (1H, t, J=5.0 Hz).

$^{13}$C NMR (DMSO-d6): 161.3, 161.2, 159.6, 159.6, 157.8, 157.8, 156.6, 156.2, 156.1, 134.3, 130.3, 130.3, 117.1, 117.0, 116.8, 115.8, 115.7, 115.6, 115.6, 112.9, 112.9, 112.8, 112.8, 106.5, 51.4, 26.7, 21.6, 21.5.

Example 91: (5aS,6aR)-5a-(5-chloro-2-fluorophenyl)-5,5a,6,6a-tetrahydrocyclopropa[3,4]pyrrolo[1,2-c]imidazole-3(2H)-thione-5,5-d$_2$

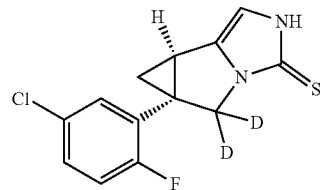 [SMILES: [2H]C1([2H])n2c(c[nH]c2=S)[C@@H]2C[C@@]21c1cc(Cl)ccc1F]

Compound was prepared from 2-(5-chloro-2-fluorophenyl)acetonitrile and (R)-2-(chloromethyl)oxirane using NaBD$_4$ as reducing agent (Example 53 step 1) and isolated as an off-white solid.

$^1$H NMR (DMSO-d6): 11.76 (1H, br s), 7.49 (1H, dd, J=6.5, 2.6 Hz), 7.43 (1H, ddd, J=8.6, 4.3, 2.8 Hz), 7.30 (1H, t, J=9.4 Hz), 6.68 (1H, s), 2.88 (1H, dd, J=8.3, 4.2 Hz), 1.67 (1H, dd, J=8.3, 5.4 Hz), 1.17 (1H, t, J=4.8 Hz).

$^{13}$C NMR (DMSO-d6): 161.3, 159.7, 156.6, 134.6, 130.1, 130.1, 129.3, 129.3, 128.8, 128.7, 128.3, 128.3, 117.5, 117.4, 106.1, 50.9, 32.4, 22.1, 20.8.

Example 92: (5aS,6aR)-5a-(3-chloro-2-fluorophenyl)-5,5a,6,6a-tetrahydrocyclopropa[3,4]pyrrolo[1,2-c]imidazole-3 (2H)-thione

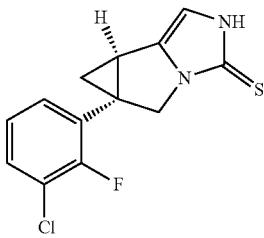 [SMILES: Fc1c(Cl)cccc1[C@]12C[C@H]1c1c[nH]c(=S)n1C2]

Compound was prepared in an analogous manner to Example 53 from 2-(3-chloro-2-fluorophenyl)acetonitrile and (R)-2-(chloromethyl)oxirane and isolated as a beige solid.

$^1$H NMR (DMSO-d6): 11.77 (1H, br s), 7.54 (1H, m), 7.39 (1H, m), 7.21 (1H, t, J=7.8 Hz), 6.69 (1H, d, J=2.2 Hz), 4.11 (1H, d, J=12.0 Hz), 3.83 (1H, d, J=12.2 Hz), 2.86 (1H, dd, J=8.4, 4.3 Hz), 1.65 (1H, dd, J=8.4, 5.3 Hz), 1.20 (1H, t, J=4.8 Hz).

$^{13}$C NMR (DMSO-d6): 157.8, 156.7, 156.2, 134.5, 129.9, 129.4, 129.4, 128.6, 128.5, 125.4, 125.4, 119.9, 119.8, 106.2, 51.6, 51.5, 32.8, 22.1, 20.9.

Example 93: (5aS,6aR)-5a-(5-bromo-2-fluorophenyl)-5,5a,6,6a-tetrahydrocyclopropa[3,4]pyrrolo[1,2-c]imidazole-3 (2H)-thione

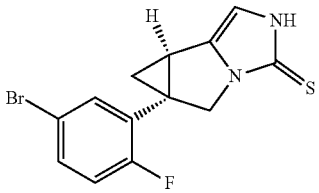

Compound was prepared in an analogous manner to Example 53 from 2-(5-bromo-2-fluorophenyl)acetonitrile and (R)-2-(chloromethyl)oxirane and isolated as a beige solid.

$^1$H NMR (DMSO-d6): 11.76 (1H, br s), 7.61 (1H, dd, J=6.7, 2.5 Hz), 7.55 (1H, ddd, J=8.7, 4.5, 2.6 Hz), 7.24 (1H, dd, J=10.1, 8.8 Hz), 6.68 (1H, d, J=2.2 Hz), 4.09 (1H, d, J=12.0 Hz), 3.80 (1H, d, J=12.0 Hz), 2.88 (1H, dd, J=8.4, 4.3 Hz), 1.67 (1H, dd, J=8.4, 5.4 Hz), 1.16 (1H, t, J=4.8 Hz).

$^{13}$C NMR (DMSO-d6): 161.8, 160.2, 156.6, 134.6, 133.0, 133.0, 132.4, 129.2, 129.1, 118.0, 117.8, 116.2, 116.2, 106.2, 51.5, 51.5, 32.6, 22.1, 20.9.

Example 94: (5aS,6aR)-5a-(3-bromo-5-fluorophenyl)-5,5a,6,6a-tetrahydrocyclopropa[3,4]pyrrolo[1,2-c]imidazole-3 (2H)-thione

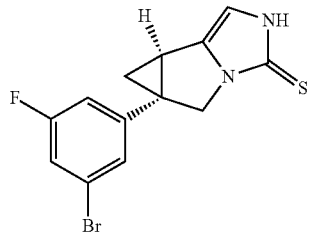

Compound was prepared in an analogous manner to Example 53 from 2-(3-bromo-5-fluorophenyl)acetonitrile and (R)-2-(chloromethyl)oxirane and isolated as a dark yellow solid.

$^1$H NMR (DMSO-d6): 11.74 (1H, br s), 7.43 (1H, s), 7.43 (1H, m), 7.29 (1H, dt, J=10.0, 1.9 Hz), 6.66 (1H, d, J=2.2 Hz), 4.23 (1H, d, J=12.0 Hz), 4.02 (1H, d, J=12.2 Hz), 3.01 (1H, dd, J=8.4, 4.3 Hz), 1.67 (1H, dd, J=8.3, 5.4 Hz), 1.16 (1H, t, J=4.8 Hz).

$^{13}$C NMR (DMSO-d6): 163.0, 161.4, 156.8, 145.0, 145.0, 134.6, 126.0, 125.9, 122.2, 122.1, 117.1, 117.0, 113.4, 113.3, 105.9, 50.8, 36.3, 36.3, 25.1, 22.8.

Example 95: (S)-6-(3,5-difluorophenyl)-1-methyl-2,5,6,7-tetrahydro-3H-pyrrolo[1,2-c]imidazole-3-thione Step 1: ((4S)-tert-butyl 2-(cyano(hydroxy)methyl)-4-(3,5-difluorophenyl)pyrrolidine-1-carboxylate

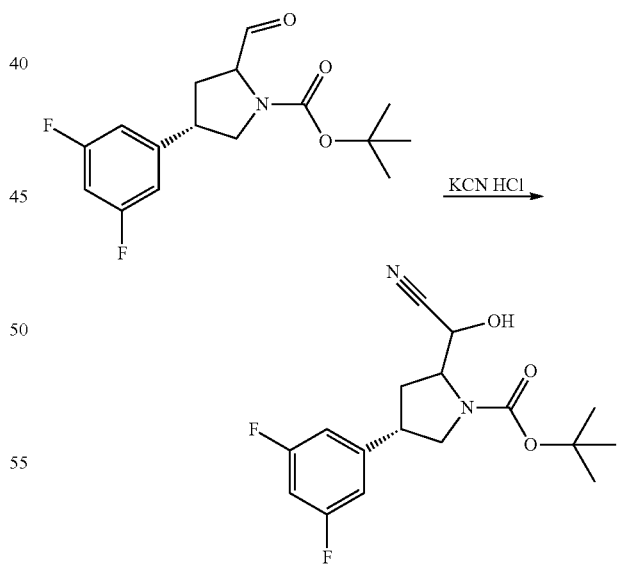

To a stirred solution of (4S)-tert-butyl 4-(3,5-difluorophenyl)-2-formylpyrrolidine-1-carboxylate (1.2 g, 3.85 mmol) in a mixture of tetrahydrofuran (10 mL) and water (5 mL) was added potassium cyanide (0.301 g, 4.63 mmol) followed by addition of cc HCl (0.319 mL, 3.85 mmol).

The mixture was stirred for 8 h, then extracted with dichloromethane. The organic phase was washed with brine, dried over MgSO₄ and evaporated to dryness to give (4S)-tert-butyl 2-(cyano(hydroxy)methyl)-4-(3,5-difluorophenyl)pyrrolidine-1-carboxylate as a yellowish oil. (Yield: 1.44 g, 99%).

Step 2: (4S)-tert-butyl 4-(3,5-difluorophenyl)-2-(2-ethoxy-1-hydroxy-2-oxoethyl)pyrrolidine-1-carboxylate

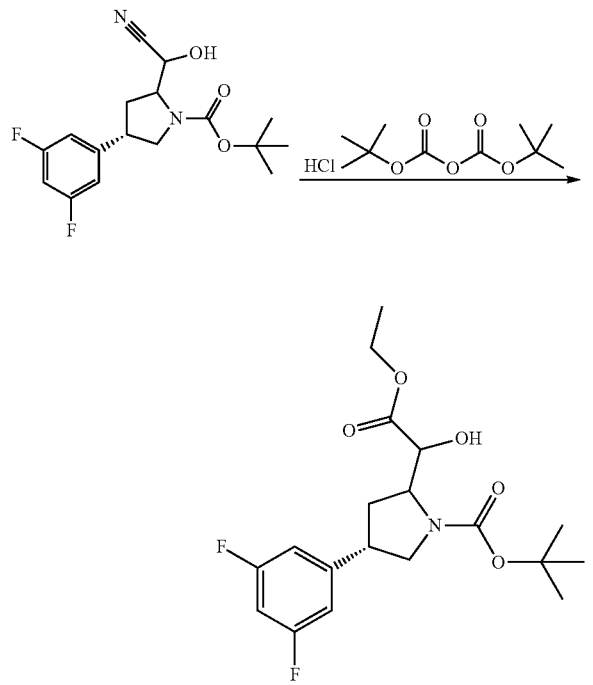

A mixture of (4S)-tert-butyl 2-(cyano(hydroxy)methyl)-4-(3,5-difluorophenyl)pyrrolidine-1-carboxylate (1.43 g, 3.80 mmol) and 2 M HCl (28.5 mL, 57.1 mmol) was stirred under reflux for 16 h. After cooling to room temperature the mixture was filtered through a celite plug to remove insoluble coloured precipitate and then the filtrate was evaporated to dryness under vacuum. The residue was azeotroped twice with dry ethanol and the residue was taken up in abs. ethanol (20 mL). The thus obtained solution was treated with 4 M HCl (9.51 mL, 38.0 mmol) in dioxane and stirred under reflux for 2 h. The mixture was evaporated to dryness, and then azeotroped with abs. ethanol. The resulting semisolid was taken up in abs. ethanol (30 mL), neutralized by addition of triethylamine to pH=6-7, then a second crop of triethylamine (0.530 mL, 3.80 mmol) was added followed by addition of di-tert-butyl dicarbonate (0.830 g, 3.80 mmol). The reaction was allowed to stir at room temperature for 2 h, and then evaporated to dryness at 40° C. The residue was partitioned between dichloromethane and water, the organic phase was dried over MgSO₄ and concentrated under reduced pressure. Chromatography (petroleum ether-ethyl acetate; 9:1, then 4:1) gave the product as a yellow oil. (Yield: 1.16 g, 79%).

Step 3: (4S)-tert-butyl 4-(3,5-difluorophenyl)-2-(2-ethoxy-2-oxoacetyl)pyrrolidine-1-carboxylate

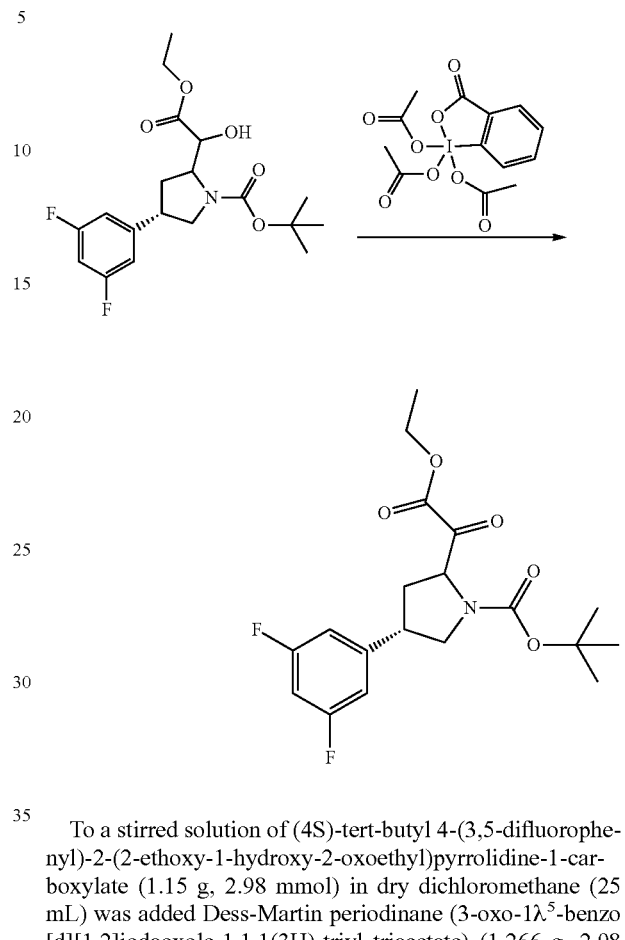

To a stirred solution of (4S)-tert-butyl 4-(3,5-difluorophenyl)-2-(2-ethoxy-1-hydroxy-2-oxoethyl)pyrrolidine-1-carboxylate (1.15 g, 2.98 mmol) in dry dichloromethane (25 mL) was added Dess-Martin periodinane (3-oxo-1$\lambda^5$-benzo[d][1,2]iodaoxole-1,1,1(3H)-triyl triacetate) (1.266 g, 2.98 mmol) at room temperature in one portion and the mixture was stirred for 2 h. The reaction mixture was concentrated under vacuum, whereupon the reside was purified by chromatography (petroleum ether-ethyl acetate; 4:1). The product was isolated as a yellowish oil. (1.08 g, 94% yield).

Step 4: ethyl 2-((4S)-4-(3,5-difluorophenyl)pyrrolidin-2-yl)-2-oxoacetate hydrochloride

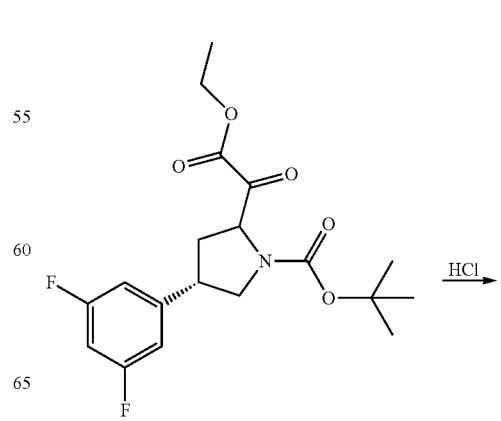

-continued

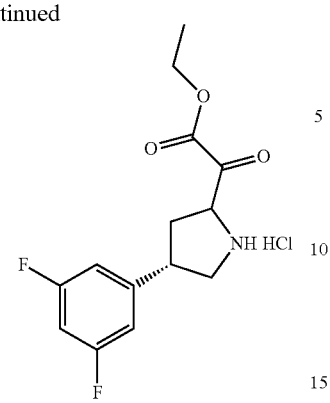

To a stirred solution of (4S)-tert-butyl 4-(3,5-difluorophenyl)-2-(2-ethoxy-2-oxoacetyl)pyrrolidine-1-carboxylate (0.4 g, 1.043 mmol) in 4 M HCl (5.22 mL, 20.87 mmol) in dioxane was stirred at room temperature for 4 h. The reaction mixture was diluted with a mixture of diethyl ether (20 mL) and petroleum ether (5 mL) and stirred for 30 min, Thereupon, the resulting precipitate was collected, washed with diethyl ether, petroleum ether and dried under vacuum at 50° C. to give ethyl 2-((4S)-4-(3,5-difluorophenyl)pyrrolidin-2-yl)-2-oxoacetate hydrochloride as a white powder. (Yield: 0.34 g, 92%).

Step 5: (S)-ethyl 6-(3,5-difluorophenyl)-3-thioxo-3,5,6,7-tetrahydro-2H-pyrrolo[1,2-c]imidazole-1-carboxylate

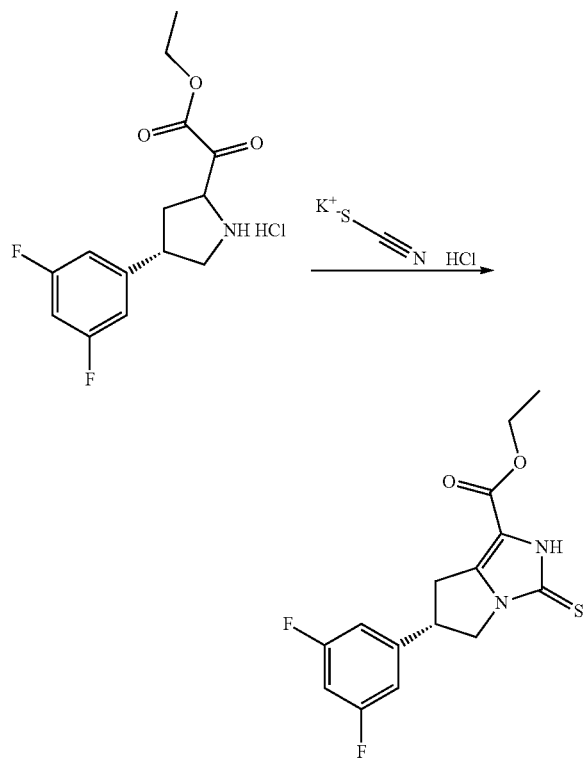

A solution of ethyl 2-((4S)-4-(3,5-difluorophenyl)pyrrolidin-2-yl)-2-oxoacetate hydrochloride (0.33 g, 1.032 mmol), 6 M HCl (0.086 mL, 0.516 mmol) and potassium thiocyanate (0.110 g, 1.135 mmol) in a mixture of ethanol (5 mL) and water (5 mL) was stirred under reflux for 30 min. The reaction was then cooled to room temperature, and the resulting solid was collected, washed with a mixture of ethanol and water (1:1), and dried under vacuum at 50° C. to give (S)-ethyl 6-(3,5-difluorophenyl)-3-thioxo-3,5,6,7-tetrahydro-2H-pyrrolo[1,2-c]imidazole-1-carboxylate as a white solid. (Yield: 0.28 g, 84%).

Step 6: S)-6-(3,5-difluorophenyl)-1-methyl-6,7-dihydro-2H-pyrrolo[1,2-c]imidazole-3(5H)-thione

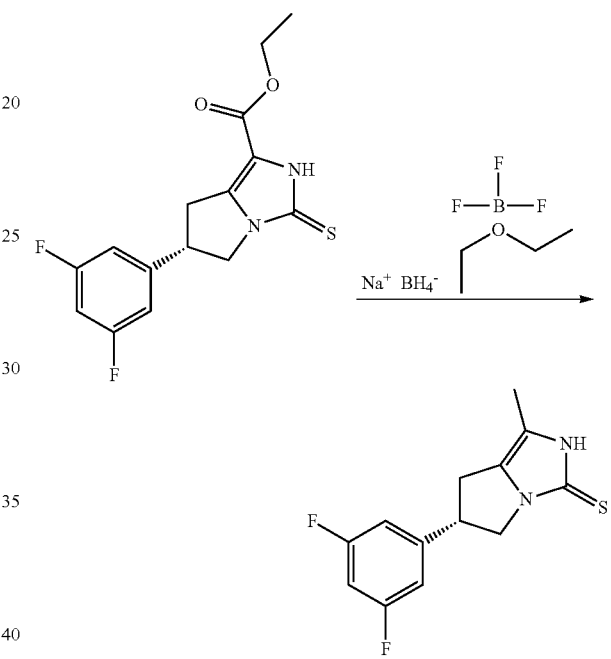

To a solution of (S)-ethyl 6-(3,5-difluorophenyl)-3-thioxo-3,5,6,7-tetrahydro-2H-pyrrolo[1,2-c]imidazole-1-carboxylate (0.1 g, 0.308 mmol) in dry tetrahydrofuran (2 mL) was added sodium borohydride (0.058 g, 1.542 mmol) followed by addition of boron trifluoride etherate (0.195 mL, 1.542 mmol) with ice-water bath cooling. The mixture was allowed to warm up to room temperature and stirred for 16 h. Thereupon, the mixture was cooled again to 0-5° C., and quenched with 2 M HCl (1.233 ml, 2.467 mmol). The organic solvents were removed under vacuum, and then the residue extracted with ethyl acetate. The organic phase was dried over MgSO$_4$, filtered and evaporated to dryness. Chromatography (petroleum ether-ethyl acetate; 1:1 gave (S)-6-(3,5-difluorophenyl)-1-methyl-6,7-dihydro-2H-pyrrolo[1,2-c]imidazole-3(5H)-thione as a white powder (0.021 g, 0.079 mmol, 25.6% yield).

$^1$H NMR (DMSO-d6): 11.69 (1H, br s), 7.13 (3H, m), 5.76 (1H, s), 4.15 (1H, dd, J=11.2, 7.9 Hz), 4.07 (1H, quin, J=7.8 Hz), 3.66 (1H, dd, J=11.2, 8.4 Hz), 3.18 (1H, m), 2.82 (1H, ddd, J=15.0, 8.9, 1.3 Hz), 1.98 (3H, s).

$^{13}$C NMR (DMSO-d6): 163.3, 163.2, 161.7, 161.6, 155.1, 145.7, 145.7, 145.6, 127.8, 115.4, 110.8, 110.7, 110.6, 110.6, 102.6, 102.5, 102.3, 50.0, 46.5, 30.0, 9.4.

Example 96: (R)-1-methyl-6-(2,3,5,6-tetrafluorophenyl)-2,5,6,7-tetrahydro-3H-pyrrolo[1,2-c]imidazole-3-thione

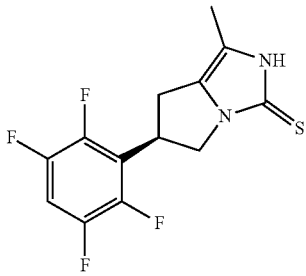 [SMILES: Cc1[nH]c(=S)n2c1C[C@H](c1c(F)c(F)cc(F)c1F)C2]

Compound was prepared in an analogous manner to Example 80 from (4R)-1-(tert-butoxycarbonyl)-4-(2,3,5,6-tetrafluorophenyl)pyrrolidine-2-carboxylic acid and methylmagnesium iodide and isolated as an off-white powder.

$^1$H NMR (DMSO-d6): 11.74 (1H, br s), 7.85 (1H, m), 4.49 (1H, quin, J=8.5 Hz), 4.42 (1H, m), 4.15 (1H, dd, J=11.6, 9.2 Hz), 3.76 (1H, dd, J=11.7, 7.8 Hz), 3.27 (1H, dd, J=15.6, 9.2 Hz), 2.89 (1H, dd, J=15.4, 7.9 Hz), 1.97 (3H, s).

$^{13}$C NMR (DMSO-d6): 155.0, 146.4, 146.3, 146.3, 145.3, 145.2, 144.8, 144.7, 144.6, 143.7, 143.6, 127.5, 120.5, 120.4, 120.3, 115.3, 105.9, 105.7, 105.6, 48.4, 35.9, 28.6, 9.3.

Example 97: (S)-1-methyl-6-(2,3,5,6-tetrafluorophenyl)-2,5,6,7-tetrahydro-3H-pyrrolo[1,2-c]imidazole-3-thione

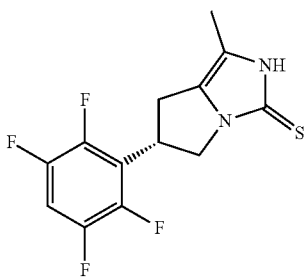 [SMILES: Cc1[nH]c(=S)n2c1C[C@@H](c1c(F)c(F)cc(F)c1F)C2]

Compound was prepared in an analogous manner to Example 80 from (4S)-1-(tert-butoxycarbonyl)-4-(2,3,5,6-tetrafluorophenyl)pyrrolidine-2-carboxylic acid and methylmagnesium iodide and isolated as a light beige powder.

$^1$H NMR (DMSO-d6): 11.74 (1H, br s), 7.85 (1H, m), 4.49 (1H, quin, J=8.5 Hz), 4.15 (1H, dd, J=11.6, 9.2 Hz), 3.76 (1H, dd, J=11.7, 7.8 Hz), 3.27 (1H, dd, J=15.6, 9.2 Hz), 2.89 (1H, dd, J=15.4, 7.9 Hz), 1.97 (3H, s).

$^{13}$C NMR (DMSO-d6): 155, 146.4, 146.3, 146.3, 145.3, 145.2, 144.8, 144.7, 144.6, 143.7, 143.6, 127.5, 120.5, 120.4, 120.3, 115.3, 105.9, 105.7, 105.6, 48.7, 48.4, 35.9, 28.6, 9.3.

Example 98: (S)-6-(2,6-difluorophenyl)-1-methyl-2,5,6,7-tetrahydro-3H-pyrrolo[1,2-c]imidazole-3-thione

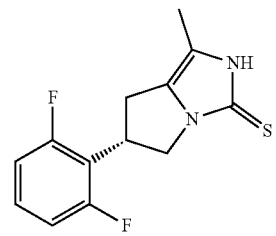 [SMILES: Cc1[nH]c(=S)n2c1C[C@@H](c1c(F)cccc1F)C2]

Compound was prepared in an analogous manner to Example 80 from (4S)-1-(tert-butoxycarbonyl)-4-(2,6-difluorophenyl)pyrrolidine-2-carboxylic acid and methylmagnesium iodide and isolated as a light beige powder.

$^1$H NMR (DMSO-d6): 11.72 (1H, br s), 7.40 (1H, m), 7.13 (2H, m), 4.41 (1H, quin, J=8.7 Hz), 4.12 (1H, br t, J=10.1 Hz), 3.70 (1H, dd, J=8.8, 10.8 Hz), 3.21 (1H, br dd, J=15.3, 9.2 Hz), 2.84 (1H, br dd, J=15.2, 8.6 Hz), 1.97 (3H, s).

$^{13}$C NMR (DMSO-d6): 161.6, 161.6, 160.0, 159.9, 155.0, 129.8, 129.7, 129.7, 127.8, 116.6, 116.5, 116.4, 115.2, 112.3, 112.2, 112.1, 112.1, 48.6, 35.4, 28.8, 9.3.

Example 99: (5aS,6aR)-5a-(5-chloro-2-fluorophenyl)-1-methyl-5,5a,6,6a-tetrahydrocyclopropa[3,4]pyrrolo[1,2-c]imidazole-3 (2H)-thione

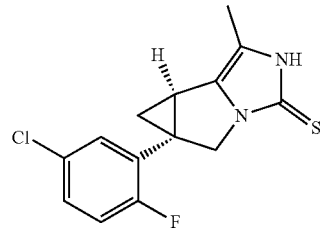 [SMILES: Cc1[nH]c(=S)n2c1[C@@H]1C[C@]1(c1cc(Cl)ccc1F)C2]

Compound was prepared in an analogous manner to Example 80 from tert-butyl (1S,5R)-1-(5-chloro-2-fluorophenyl)-4-(methoxy(methyl)carbamoyl)-3-azabicyclo[3.1.0]hexane-3-carboxylate and methylmagnesium iodide. The product was isolated as a beige solid.

$^1$H NMR (DMSO-d6): 11.65 (1H, br s), 7.47 (1H, dd, J=6.5, 2.6 Hz), 7.42 (1H, ddd, J=8.8, 4.4, 2.7 Hz), 7.29 (1H, dd, J=10.0, 8.9 Hz), 4.06 (1H, d, J=11.7 Hz), 3.77 (1H, d, J=12.0 Hz), 2.87 (1H, dd, J=8.2, 4.3 Hz), 2.04 (3H, m), 1.64 (1H, dd, J=8.1, 5.4 Hz), 1.12 (1H, t, J=4.8 Hz).

$^{13}$C NMR (DMSO-d6): 161.3, 159.7, 155.7, 130.3, 130.1, 130.1, 129.3, 129.3, 129.0, 128.9, 128.3, 128.3, 117.6, 117.4, 114.8, 51.5, 51.5, 32.3, 22.3, 20.2, 9.4.

Example 100: (5aS,6aR)-5a-(5-chloro-2-fluorophenyl)-1-(methyl-d₃)-5,5a,6,6a-tetrahydrocyclopropa[3,4]pyrrolo[1,2-c]imidazole-3 (2H)-thione

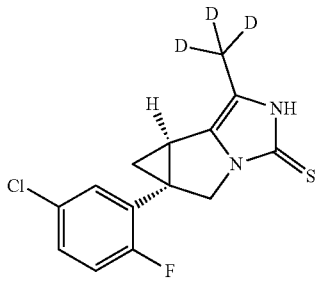 [SMILES: [2H]C([2H])([2H])c1[nH]c(=S)n2c1[C@@H]1C[C@]1(c1cc(Cl)ccc1F)C2]

Compound was prepared in an analogous manner to Example 80 from tert-butyl (1S,5R)-1-(5-chloro-2-fluorophenyl)-4-(methoxy(methyl)carbamoyl)-3-azabicyclo[3.1.0]hexane-3-carboxylate and methyl-d₃-magnesium iodide. The product was isolated as a light orange solid.

¹H NMR (DMSO-d6): 11.65 (1H, s), 7.47 (1H, dd, J=6.6, 2.8 Hz), 7.42 (1H, ddd, J=8.8, 4.4, 2.7 Hz), 7.29 (1H, m), 4.06 (1H, d, J=11.9 Hz), 3.77 (1H, d, J=12.0 Hz), 2.87 (1H, dd, J=8.3, 4.3 Hz), 1.64 (1H, dd, J=8.3, 5.4 Hz), 1.12 (1H, t, J=4.8 Hz).

¹³C NMR (DMSO-d6): 161.3, 159.7, 155.7, 155.6, 130.3, 130.1, 130.1, 129.3, 129.3, 129.0, 128.9, 128.3, 128.3, 117.6, 117.4, 114.7, 114.6, 51.5, 51.5, 32.3, 22.3, 20.2.

Example 101: (5aS,6aR)-5a-(5-chloro-2-fluorophenyl)-2-(methyl-d₃)-5,5a,6,6a-tetrahydrocyclopropa[3,4]pyrrolo[1,2-c]imidazole-3 (2H)-thione

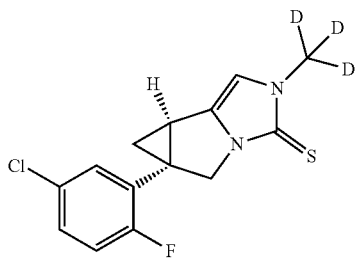 [SMILES: [2H]C([2H])([2H])n1cc2n(c1=S)C[C@@]1(c3cc(Cl)ccc3F)C[C@@H]21]

Compound was prepared in an analogous manner to Example 76 from (1R,5S)-5-(5-chloro-2-fluorophenyl)-3-azabicyclo[3.1.0]hexane-2-carbaldehyde hydrochloride and isothiocyanatomethane-d₃ and isolated as a yellow oil.

¹H NMR (DMSO-d6): 7.50 (1H, dd, J=6.5, 2.5 Hz), 7.43 (1H, m), 7.30 (1H, t, J=9.5 Hz), 6.93 (1H, s), 4.13 (1H, br d, J=12.0 Hz), 3.84 (1H, d, J=12.0 Hz), 2.92 (1H, dd, J=8.2, 4.1 Hz), 1.69 (1H, dd, J=8.3, 5.5 Hz), 1.17 (1H, t, J=4.8 Hz).

¹³C NMR (DMSO-d6): 161.3, 159.7, 157.2, 132.9, 130.2, 130.2, 129.4, 129.4, 128.7, 128.6, 128.3, 128.3, 117.6, 117.4, 110.4, 52.3, 52.3, 32, 22.1, 20.9.

Example 102: 5a-(5-chloro-2-fluorophenyl)-5,5a,6,6a-tetrahydrocyclopropa[3,4]pyrrolo[1,2-c]imidazole-3(2H)-thione-6,6,6a-d₃

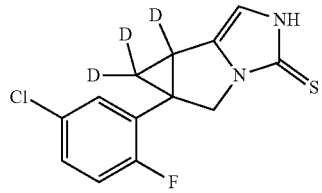 [SMILES: [2H]C1([2H])C2([2H])c3c[nH]c(=S)n3CC12c1cc(Cl)ccc1F]

Compound was prepared in an analogous manner to Example 53 from 2-(5-chloro-2-fluorophenyl)acetonitrile and 2-(chloromethyl-d₂)oxirane-2,3,3-d₃ and isolated as a beige solid.

¹H NMR (DMSO-d6): 11.76 (1H, br s), 7.49 (1H, dd, J=6.5, 2.7 Hz), 7.43 (1H, ddd, J=8.8, 4.4, 2.8 Hz), 7.30 (1H, dd, J=10.0, 8.8 Hz), 6.68 (1H, d, J=2.3 Hz), 4.10 (1H, dd, J=12.0, 1.8 Hz), 3.81 (1H, d, J=12.0 Hz).

¹³C NMR (DMSO-d6): 161.3, 159.7, 156.6, 134.5, 130.2, 130.2, 129.4, 129.3, 128.8, 128.7, 128.3, 128.3, 117.6, 117.4, 106.2, 51.5, 51.4, 32.4, 21.6, 21.4, 21.2, 20.6, 20.5, 20.3.

Example 103: (5aR,6aS)-5a-(3-chloro-2,6-difluorophenyl)-5,5a,6,6a-tetrahydrocyclopropa[3,4]pyrrolo[1,2-c]imidazole-3 (2H)-thione

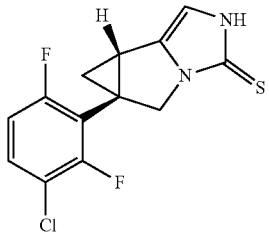

Compound was prepared in an analogous manner to Example 53 from 2-(3-chloro-2,6-difluorophenyl)acetonitrile and (S)-2-(chloromethyl)oxirane and isolated as a beige solid.

¹H NMR (DMSO-d6): 11.79 (1H, br s), 7.64 (1H, m), 7.21 (1H, t, J=8.7 Hz), 6.71 (1H, d, J=2.2 Hz), 4.05 (1H, d, J=12.2 Hz), 3.76 (1H, d, J=12.3 Hz), 2.76 (1H, dd, J=8.4, 4.4 Hz), 1.69 (1H, dd, J=8.2, 5.6 Hz), 1.30 (1H, t, J=5.0 Hz).

¹³C NMR (DMSO-d6): 161.3, 161.2, 159.6, 159.6, 157.8, 157.8, 156.6, 156.2, 156.1, 134.3, 130.3, 130.3, 117.1, 117.0, 116.8, 115.8, 115.7, 115.7, 115.6, 113.0, 112.9, 112.8, 106.5, 51.4, 26.7, 21.6, 21.5.

Example 104: (R)-6-(3-chloro-2,6-difluorophenyl)-1-methyl-2,5,6,7-tetrahydro-3H-pyrrolo[1,2-c]imidazole-3-thione

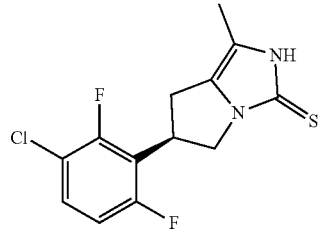 [SMILES: Cc1[nH]c(=S)n2c1C[C@H](c1c(F)ccc(Cl)c1F)C2]

Compound was prepared in an analogous manner to Example 80 from (4S)-1-(tert-butoxycarbonyl)-4-(3-chloro-2,6-difluorophenyl)pyrrolidine-2-carboxylic acid and methylmagnesium iodide and isolated as an off-white powder.

¹H NMR (DMSO-d6): 11.73 (1H, br s), 7.61 (1H, td, J=8.8, 5.6 Hz), 7.21 (1H, t, J=9.5 Hz), 4.44 (1H, quin, J=8.6 Hz), 4.13 (1H, dd, J=11.4, 9.2 Hz), 3.72 (1H, dd, J=11.6, 7.9 Hz), 3.23 (1H, m), 2.84 (1H, dd, J=15.5, 8.1 Hz), 1.97 (3H, s).

¹³C NMR (DMSO-d6): 160.2, 160.1, 158.5, 158.5, 156.6, 156.5, 155, 154.9, 154.9, 129.7, 129.7, 127.7, 118.9, 118.7, 118.6, 116.1, 116.1, 116.0, 116.0, 115.2, 113.3, 113.3, 113.1, 113.1, 48.5, 35.8, 28.7, 9.4.

Example 105: (S)-6-(3-chloro-2,6-difluorophenyl)-1-methyl-2,5,6,7-tetrahydro-3H-pyrrolo[1,2-c]imidazole-3-thione

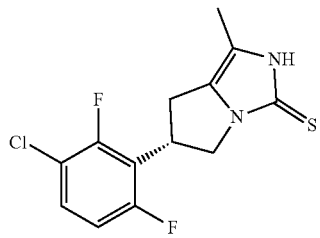 [SMILES: Cc1[nH]c(=S)n2c1C[C@@H](c1c(F)ccc(Cl)c1F)C2]

Compound was prepared in an analogous manner to Example 80 from (4R)-1-(tert-butoxycarbonyl)-4-(3-chloro-2,6-difluorophenyl)pyrrolidine-2-carboxylic acid and methylmagnesium iodide and isolated as a light beige powder.

¹H NMR (DMSO-d6): 11.73 (1H, br s), 7.61 (1H, td, J=8.8, 5.6 Hz), 7.21 (1H, t, J=9.5 Hz), 4.44 (1H, quin, J=8.6 Hz), 4.13 (1H, dd, J=11.4, 9.2 Hz), 3.72 (1H, dd, J=11.6, 7.9 Hz), 3.23 (1H, m), 2.84 (1H, dd, J=15.5, 8.1 Hz), 1.97 (3H, s).

¹³C NMR (DMSO-d6): 160.2, 160.1, 158.5, 158.5, 156.6, 156.5, 154.9, 154.9, 129.7, 129.6, 127.7, 118.9, 118.7, 118.6, 116.1, 116.1, 116.0, 115.9, 115.2, 113.3, 113.3, 113.1, 113.1, 48.5, 35.7, 28.7, 9.4.

Example 106: (5aS,6aS)-5a-(3,5-difluorophenyl)-2,5,5a,6,6a,7-hexahydro-3H-cyclopropa[d]imidazo[1,5-a]pyridine-3-thione Step 1: ((1R,2S)-2-(((tert-butoxycarbonyl)amino)methyl)-2-(3,5-difluorophenyl)cyclopropyl)methyl 4-methylbenzenesulfonate

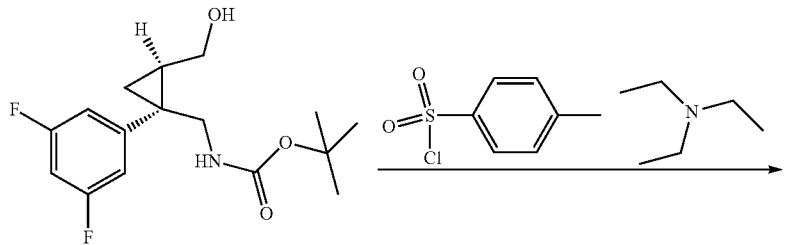

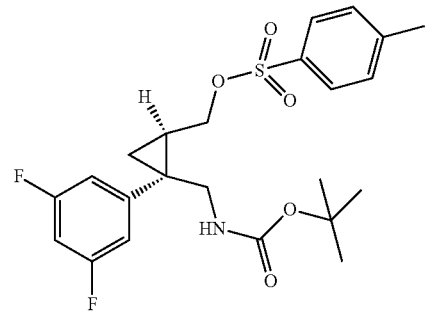

To a stirred solution of tert-butyl ((1S,2R)-1-(3,5-difluorophenyl)-2-(hydroxymethyl)cyclopropyl)methylcarbamate (1.0 g, 3.19 mmol) (prepared according to Example 53 from 2-(3,5-difluorophenyl)acetonitrile and (R)-2-(chloromethyl)oxirane)) in dry dichloromethane (10 mL) was added triethylamine (0.89 mL, 6.38 mmol) followed by addition of N,N-dimethylpyridin-4-amine (0.039 g, 0.319 mmol) and tosyl chloride (0.730 g, 3.83 mmol) at 0-5° C. under nitrogen. The mixture was stirred for 2 h in ice and then allowed to warm up naturally to room temperature over 30 min. Thereupon, the mixture was washed with sodium bicarbonate solution, 10% citric acid, then dried over MgSO$_4$ and finally evaporated to give the crude product as a light brown oil (1.37 g, 73% yield).

Step 2: tert-butyl (((1S,2S)-2-(cyanomethyl)-1-(3,5-difluorophenyl)cyclopropyl)methyl)carbamate

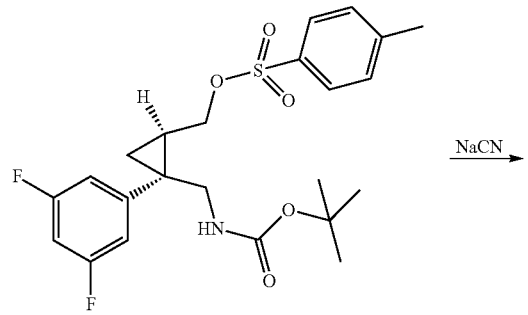

To a solution of sodium cyanide (0.204 g, 4.16 mmol) in dimethyl sulfoxide (12 mL) was added ((1R,2S)-2-((tert-butoxycarbonylamino)methyl)-2-(3,5-difluorophenyl)cyclopropyl)methyl 4-methylbenzenesulfonate (1.35 g, 2.310 mmol) and the mixture was stirred at room temperature for 4 h. The reaction was then diluted with water (30 mL) followed by extraction with diethyl ether. The organic phase was washed with brine, dried over MgSO$_4$ and evaporated to dryness.

The resulting oil was crystallised from petroleum ether, filtered and dried under vacuum to give tert-butyl (((1S,2S)-2-(cyanomethyl)-1-(3,5-difluorophenyl)cyclopropyl)methylcarbamate as a light beige powder (0.57 g, 77% yield).

Step 3: tert-butyl (((1S,2S)-2-(2-amino-2-oxoethyl)-1-(3,5-difluorophenyl)cyclopropyl)methyl)carbamate

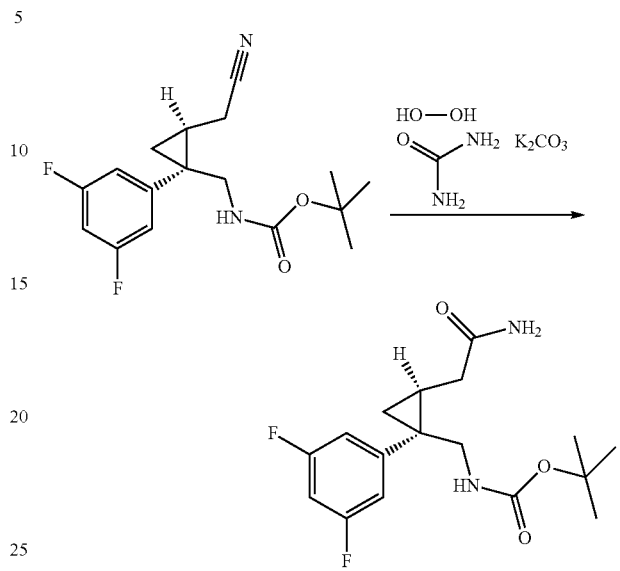

To a solution of tert-butyl ((1S,2S)-2-(cyanomethyl)-1-(3,5-difluorophenyl)cyclopropyl)methylcarbamate (1.69 g, 5.24 mmol) in a mixture of acetone (30 mL) and water (10 mL) was added urea hydrogen peroxide addition complex (2.466 g, 26.2 mmol) followed by addition of potassium carbonate (0.145 g, 1.049 mmol) and the mixture was stirred at room temperature for 20 h. Acetone was then removed under vacuum and the residue was partitioned between water and a mixture of ethyl acetate and petroleum ether (1:1). The organic phase was dried over MgSO$_4$ and evaporated to dryness to give the title product as a colourless oil (1.98 g, 100% yield).

Step 4: (1S,6S)-1-(3,5-difluorophenyl)-3-azabicyclo[4.1.0]heptan-4-one

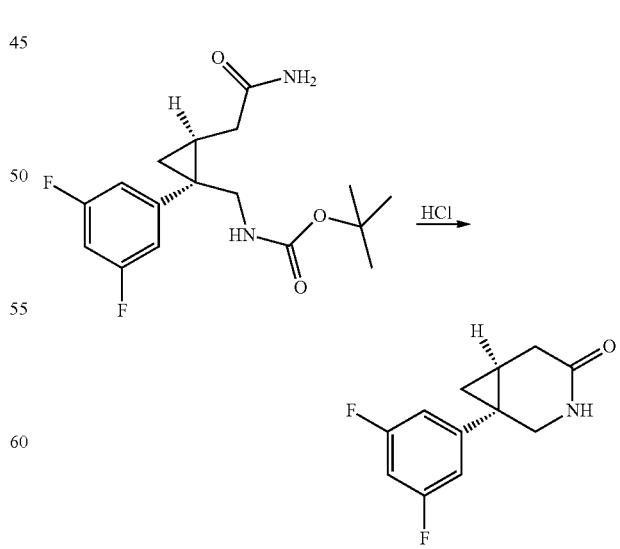

tert-Butyl ((1 S,2S)-2-(2-amino-2-oxoethyl)-1-(3,5-difluorophenyl)cyclopropyl)methylcarbamate (1.78 g, 5.23 mmol) was stirred under reflux with 2 M HCl (39 mL, 78 mmol) for 2 h. Thereupon, the mixture was evaporated to dryness and then azeotroped with abs. ethanol. The oily residue was dissolved in abs. ethanol (80 mL) followed by addition of 4 M HCl (13.0 mL, 52.1 mmol) in dioxane. The thus obtained solution was stirred under reflux for 30 min and evaporated to dryness. The residue was taken up in methanol (20 mL), and then pH was adjusted to 9-10 by addition of 25% sodium methoxide in methanol. The mixture was stirred overnight at 50-55° C. Methanol was then removed under vacuum, and the residue crystallized form water. The resulting solid was collected, washed with water and dried to give (1S,6S)-1-(3,5-difluorophenyl)-3-azabicyclo[4.1.0]heptan-4-one as a beige powder (0.9 g, 77% yield).

Step 5: tert-butyl (1S,6S)-1-(3,5-difluorophenyl)-4-oxo-3-azabicyclo[4.1.0]heptane-3-carboxylate

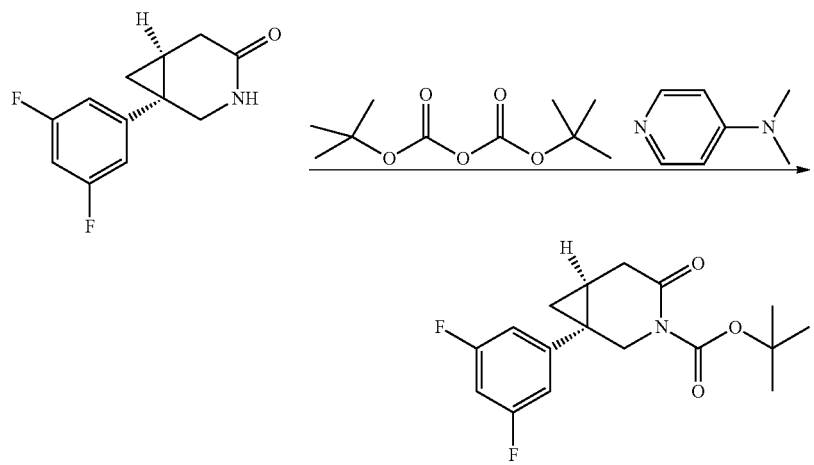

To a solution of (1S,6S)-1-(3,5-difluorophenyl)-3-azabicyclo[4.1.0]heptan-4-one (0.88 g, 3.94 mmol) and N,N-dimethylpyridin-4-amine (0.482 g, 3.94 mmol) in dry dichloromethane (3 mL) was added di-tert-butyl dicarbonate (1.291 g, 5.91 mmol) at room temperature in portions. The mixture was stirred for 4 h at room temperature, then diluted with dichloromethane to 50 mL and finally washed with 10% citric acid (25 mL). The organic phase was dried over MgSO₄, filtered on a silica pad, and then the filtrate evaporated to dryness to give (1S,6S)-tert-butyl 1-(3,5-difluorophenyl)-4-oxo-3-azabicyclo[4.1.0]heptane-3-carboxylate as a light beige powder (1.18 g, 93% yield).

Step 6: tert-butyl (1S,6S)-1-(3,5-difluorophenyl)-4-hydroxy-3-azabicyclo[4.1.0]heptane-3-carboxylate

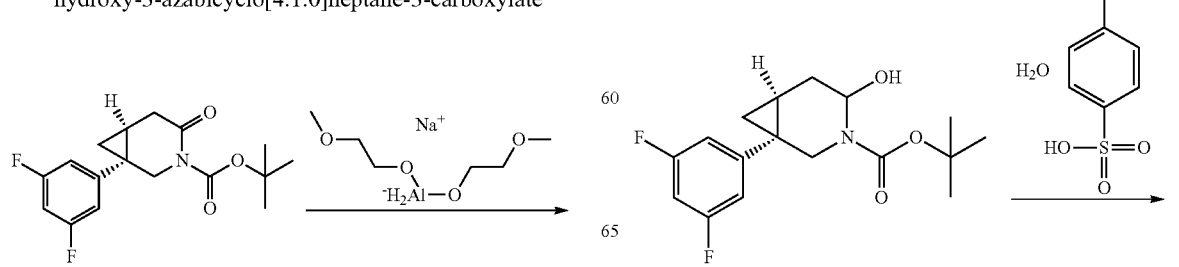

-continued

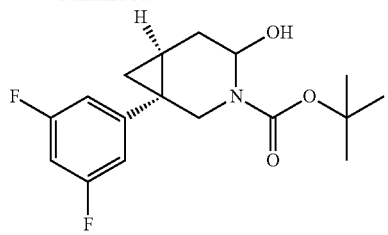

To a solution of (1S,6S)-tert-butyl 1-(3,5-difluorophenyl)-4-oxo-3-azabicyclo[4.1.0]heptane-3-carboxylate (1.17 g, 3.62 mmol) in a mixture of dry diethyl ether (18 mL) and tetrahydrofuran (6 mL) was added dropwise 65% RED-Al (bis(2-methoxyethoxy)aluminum(III) sodium hydride) (2.17 mL, 7.24 mmol) in toluene at 0-5° C. and the mixture was stirred for 30 min. under nitrogen. The mixture was then quenched with a cold solution of saturated sodium bicarbonate and allowed to stir at ambient for 30 min. The organic phase was separated, and the aqueous phase was extracted with diethyl ether. The combined organic phases were dried over MgSO₄ and evaporated to dryness to give (1S,6S)-tert-butyl 1-(3,5-difluorophenyl)-4-hydroxy-3-azabicyclo[4.1.0] heptane-3-carboxylate as a yellowish oil. (1.15 g, 98% yield).

Step 7 tert-butyl (1S,6S)-1-(3,5-difluorophenyl)-4-methoxy-3-azabicyclo[4.1.0]heptane-3-carboxylate

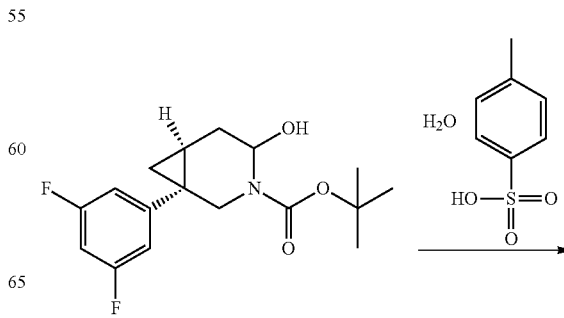

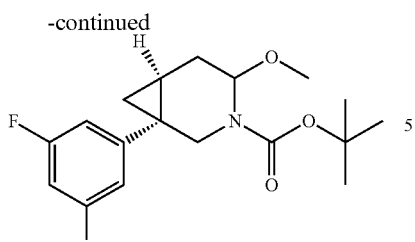

To a solution of (1S,6S)-tert-butyl 1-(3,5-difluorophenyl)-4-hydroxy-3-azabicyclo[4.1.0]heptane-3-carboxylate (1.14 g, 3.50 mmol) in methanol (35 mL) was added 4-methylbenzenesulfonic acid hydrate (0.067 g, 0.350 mmol) at room temperature and the solution was stirred for 24 h. Thereupon, the mixture was neutralized with 1 M sodium hydroxide (0.35 mL, 0.350 mmol) and evaporated to dryness. The residue was taken up in a mixture of petroleum ether and ethyl acetate (4:1), then chromatographed in a mixture of petroleum ether-ethyl acetate (9:1), to give (1S,6S)-tert-butyl 1-(3,5-difluorophenyl)-4-methoxy-3-azabicyclo[4.1.0]heptane-3-carboxylate as a colourless oil (0.71 g, 60% yield).

Step 8 tert-butyl (1S,6S)-4-cyano-1-(3,5-difluorophenyl)-3-azabicyclo[4.1.0]heptane-3-carboxylate

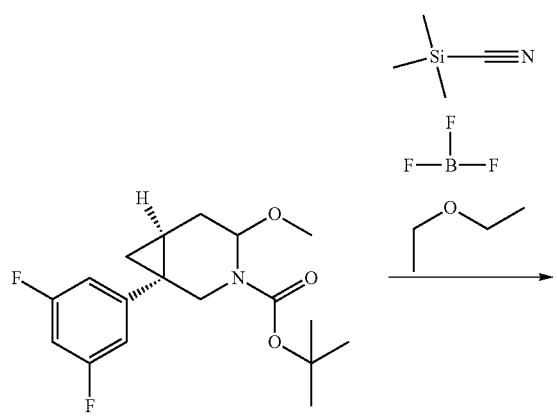

To a solution of (1S,6S)-tert-butyl 1-(3,5-difluorophenyl)-4-methoxy-3-azabicyclo[4.1.0]heptane-3-carboxylate (0.71 g, 2.092 mmol) in dry dichloromethane (15 mL) was added trimethylsilanecarbonitrile (0.561 mL, 4.18 mmol) followed by addition of boron trifluoride etherate (0.58 mL, 4.60 mmol) at −70° C. The mixture was stirred for 4 h in the cold, and then quenched with aqueous sodium bicarbonate and allowed to warm up to room temperature. The organic phase was dried over MgSO$_4$ and evaporated to dryness. Chromatography petroleum ether-ethyl acetate; 9:1) afforded the product as a colourless oil (0.095 g, 13%).

Step 9 tert-butyl (1S,6S)-4-carbamoyl-1-(3,5-difluorophenyl)-3-azabicyclo[4.1.0]heptane-3-carboxylate

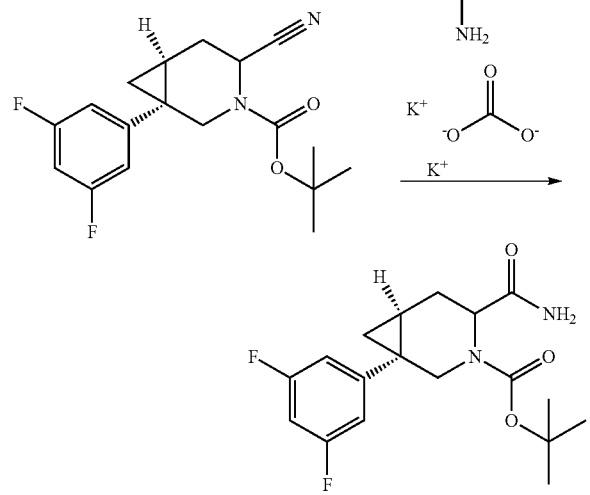

To a solution of (1S,6S)-tert-butyl 4-cyano-1-(3,5-difluorophenyl)-3-azabicyclo[4.1.0]heptane-3-carboxylate (0.09 g, 0.269 mmol) in a mixture of acetone (1.5 mL) and water (0.5 mL) was added urea hydrogen peroxide addition complex (0.127 g, 1.346 mmol) followed by addition of potassium carbonate (0.0074 mg, 0.054 mmol) and the solution was stirred at room temperature for 16 h. Acetone was then removed under vacuum, the oily residue was diluted with water (2 mL) and then extracted with a mixture of petroleum ether-ethyl acetate (1:1). The organic phase was dried over MgSO$_4$ and evaporated to dryness to give (1S,6S)-tert-butyl 4-carbamoyl-1-(3,5-difluorophenyl)-3-azabicyclo[4.1.0]heptane-3-carboxylate (0.09 g, 95% yield).

Step 10 (1S,6S)-3-(tert-butoxycarbonyl)-1-(3,5-difluorophenyl)-3-azabicyclo[4.1.0]heptane-4-carboxylic acid

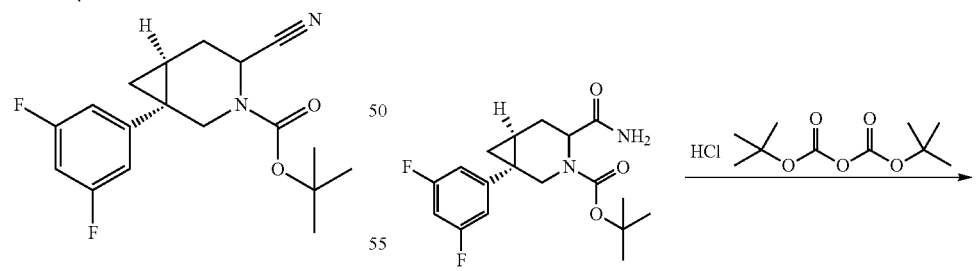

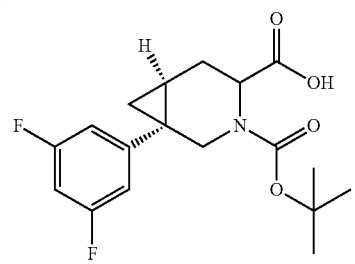

A suspension of (1S,6S)-tert-butyl 4-carbamoyl-1-(3,5-difluorophenyl)-3-azabicyclo[4.1.0]heptane-3-carboxylate (0.09 g, 0.255 mmol) in 2 M HCl (1.92 mL, 3.83 mmol) was stirred under reflux for 3 h. The reaction mixture was concentrated under vacuum, the residue was dissolved in water and then the pH was adjusted to 7 by adding 1 M sodium hydroxide (0.511 mL, 0.511 mmol). The solution was concentrated to 2 mL, followed by addition of methanol (2 mL) and di-tert-butyl dicarbonate (0.123 g, 0.562 mmol). The mixture was stirred for 45 min, whereupon a second crop of di-tert-butyl dicarbonate (0.347 g, 1.592 mmol) was added and the reaction was stirred for 1 h. Thereupon, methanol was removed under vacuum, the residue was diluted with water (10 mL) and washed with petroleum ether. The aqueous phase was acidified to pH=2 by adding 2 M HCl, and then extracted with dichloromethane. The organic phase was dried over MgSO₄, filtered and evaporated to dryness to give the product as an off-white powder (0.07 g, 78% yield).

Step 11 tert-butyl (1S,6S)-1-(3,5-difluorophenyl)-4-(hydroxymethyl)-3-azabicyclo[4.1.0]heptane-3-carboxylate

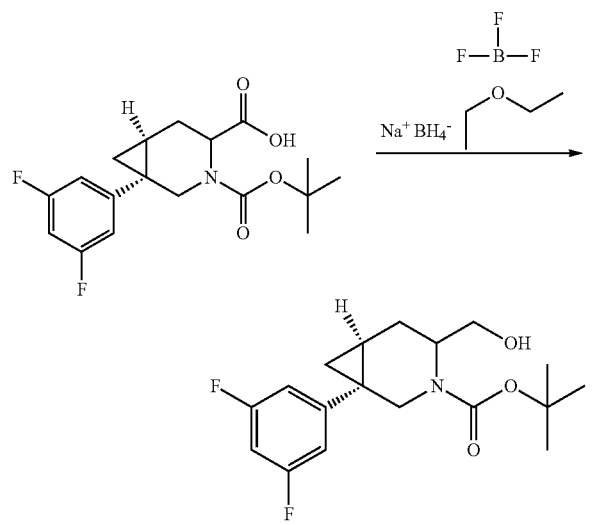

To a solution of (1S,6S)-3-(tert-butoxycarbonyl)-1-(3,5-difluorophenyl)-3-azabicyclo[4.1.0]heptane-4-carboxylic acid (0.07 g, 0.198 mmol) in isopropyl acetate (1.5 mL) was added sodium borohydride (0.018 g, 0.475 mmol) at 0-5° C. followed by addition of boron trifluoride etherate (0.075 mL, 0.594 mmol). The mixture was stirred in the cold for 2 h, then a second crop of sodium borohydride (0.018 g, 0.475 mmol) and boron trifluoride etherate (0.075 mL, 0.594 mmol) was added. After being stirred for 30 min. in the cold the reaction mixture was quenched with 1 M sodium hydroxide (1.070 mL, 1.070 mmol) and stirred at room temperature for 30 min. The organic phase was separated, dried over MgSO₄ and evaporated to dryness to give (1S,6S)-tert-butyl 1-(3,5-difluorophenyl)-4-(hydroxymethyl)-3-azabicyclo[4.1.0]heptane-3-carboxylate as a white powder (0.066 g, 98% yield).

Step 12 tert-butyl (1S,6S)-1-(3,5-difluorophenyl)-4-formyl-3-azabicyclo[4.1.0]heptane-3-carboxylate

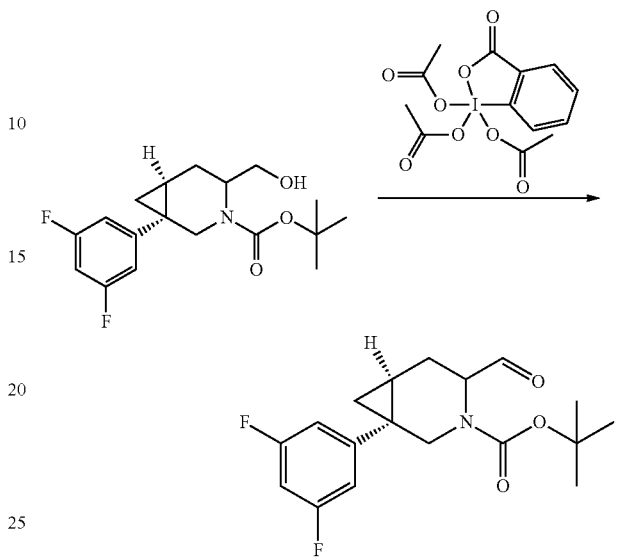

To a solution of (1S,6S)-tert-butyl 1-(3,5-difluorophenyl)-4-(hydroxymethyl)-3-azabicyclo[4.1.0]heptane-3-carboxylate (0.066 g, 0.194 mmol) in dry dichloromethane (2 mL) was added Dess-Martin periodinane (3-oxo-1λ⁵-benzo[d][1,2]iodaoxole-1,1,1(3H)-triyl triacetate) (0.082 g, 0.194 mmol) in one portion to give a clear solution. The mixture was stirred for 2 h at room temperature, and then concentrated under vacuum. Chromatography (petroleum ether-ethyl acetate; 9:1, then 4:1) gave (1S,6S)-tert-butyl 1-(3,5-difluorophenyl)-4-formyl-3-azabicyclo[4.1.0]heptane-3-carboxylate as a yellowish oil (0.054 g, 82% yield).

Step 13 (5aS,6aS)-5a-(3,5-difluorophenyl)-2,5,5a,6,6a,7-hexahydro-3H-cyclopropa[d]imidazo[1,5-a]pyridine-3-thione

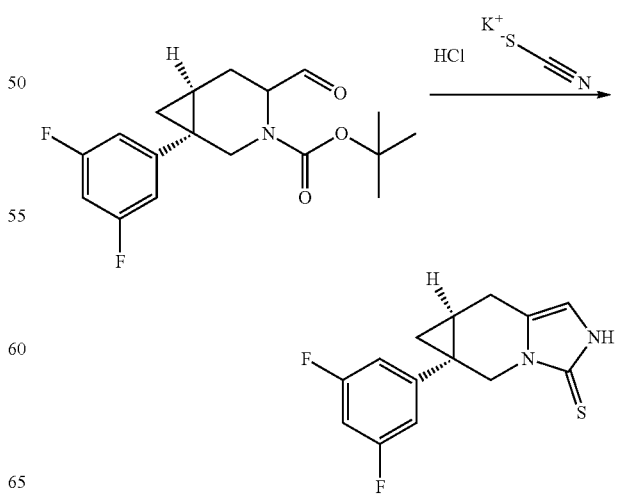

A solution of (1S,6S)-tert-butyl 1-(3,5-difluorophenyl)-4-formyl-3-azabicyclo[4.1.0]heptane-3-carboxylate (0.054 g, 0.160 mmol) in 4 M HCl (0.6 mL, 2.401 mmol) in dioxane was stirred at room temperature for 2 h. The mixture was then diluted with petroleum ether (10 mL) and stirred for 1 h. The resulting oily precipitate was dissolved in a mixture of ethanol (1 mL) and water (1 mL), and potassium thiocyanate (0.017 g, 0.176 mmol) was then added followed by addition of 6 M HCl (0.013 mL, 0.080 mmol) and the solution was stirred under reflux for 1 h. The product crystallized on cooling to room temperature. The mixture was then stirred at room temperature for 30 min, the crystals were collected and washed with a mixture of ethanol-water (1:1) to give (5aS,6aS)-5a-(3,5-difluorophenyl)-5a,6,6a,7-tetrahydro-2H-cyclopropa[d]imidazo[1,5-a]pyridine-3(5H)-thione as alight beige powder (0.023 g, 0.083 mmol, 52% yield).

$^1$H NMR (DMSO-d6): 12.06 (1H, br s), 7.15 (3H, m), 6.71 (1H, t, J=1.8 Hz), 4.61 (1H, d, J=13.1 Hz), 3.92 (1H, d, J=13.1 Hz), 3.11 (1H, ddd, J=2.0, 3.3, 15.9 Hz), 2.99 (1H, dd, J=2.2, 15.9 Hz), 1.68 (1H, m), 1.05 (1H, dd, J=8.9, 5.8 Hz), 0.52 (1H, t, J=5.7 Hz).

$^{13}$C NMR (DMSO-d6): 163.4, 163.3, 161.7, 161.7, 159.4, 147.2, 147.2, 147.1, 123.9, 110.9, 110.9, 110.8, 110.7, 110.1, 102.4, 102.3, 102.1, 44.3, 23.5, 20.5, 18.6, 11.6.

Example 107: (6R,7S)-7-methyl-6-(2,3,5,6-tetrafluorophenyl)-2,5,6,7-tetrahydro-3H-pyrrolo[1,2-c]imidazole-3-thione

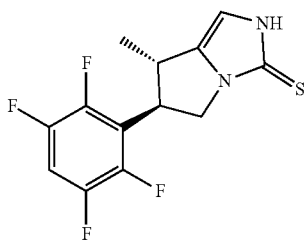 [SMILES: C[C@@H]1c2c[nH]c(=S)n2C[C@H]1c1c(F)c(F)cc(F)c1F]

Compound was prepared in an analogous manner to Example 58 from (E)-1,2,4,5-tetrafluoro-2-(2-nitrovinyl)benzene and diethyl 2-methylmalonate using 4-((S)-hydroxy((1S,2R,4S,5R)-5-vinylquinuclidin-2-yl)methyl)quinolin-6-ol as catalyst CAS #70877-75-7). The title compound was isolated as an off-white powder.

$^1$H NMR (DMSO-d6): 11.87 (1H, br s), 7.89 (1H, m), 6.70 (1H, t, J=2.0 Hz), 4.20 (1H, dd, J=), 4.04 (1H, q, J=9.1 Hz), 3.84 (1H, dd, J=11.2, 9.4 Hz), 3.40 (1H, m), 1.23 (3H, d, J=6.6 Hz).

$^{13}$C NMR (DMSO-d6): 156.0, 146.5, 146.4, 146.3, 145.6, 145.5, 144.8, 144.8, 144.7, 144.0, 143.8, 136.7, 118.4, 118.3, 118.2, 106.7, 106.2, 106.1, 105.9, 47.5, 44.6, 37.6, 17.1.

Example 108: (6R,7R)-7-methyl-6-(2,3,5,6-tetrafluorophenyl)-2,5,6,7-tetrahydro-3H-pyrrolo[1,2-c]imidazole-3-thione

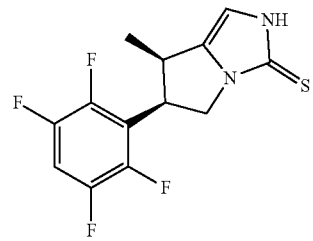 [SMILES: C[C@H]1c2c[nH]c(=S)n2C[C@H]1c1c(F)c(F)cc(F)c1F]

Compound was prepared in an analogous manner to Example 58 from (E)-1,2,4,5-tetrafluoro-2-(2-nitrovinyl)benzene and diethyl 2-methylmalonate using 4-((S)-hydroxy((1S,2R,4S,5R)-5-vinylquinuclidin-2-yl)methyl)quinolin-6-ol as catalyst CAS #70877-75-7). The title compound was isolated as a light beige powder.

$^1$H NMR (DMSO-d6): 11.77 (1H, br s), 7.86 (1H, m), 6.63 (1H, m), 4.56 (1H, td, J=8.5, 4.4 Hz), 4.19 (1H, dd, J=12.3, 8.3 Hz), 4.04 (1H, dd, J=12.3, 4.4 Hz), 3.74 (1H, quin, J=7.2 Hz), 0.87 (3H, d, J=7.0 Hz).

$^{13}$C NMR (DMSO-d6): 155.8, 146.4, 146.3, 146.2, 145.5, 145.4, 144.8, 144.7, 144.6, 143.8, 143.7, 137.2, 118.7, 118.5, 118.4, 106.2, 106.0, 105.9, 105.7, 47.7, 41.7, 34.3, 14.2.

Example 109: (5aS,6aR)-5a-(3,5-dichlorophenyl)-5,5a,6,6a-tetrahydrocyclopropa[3,4]pyrrolo[1,2-c]imidazole-3 (2H)-thione

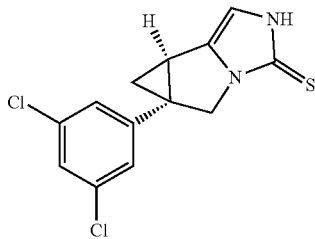 [SMILES: S=c1[nH]cc2n1C[C@@]1(c3cc(Cl)cc(Cl)c3)C[C@@H]21]

Compound was prepared in an analogous manner to Example 53 from 2-(3,5-dichlorophenyl)acetonitrile and (R)-2-(chloromethyl)oxirane and isolated as a yellow solid.

$^1$H NMR (DMSO-d6): 11.74 (1H, br s), 7.49 (1H, t, J=1.8 Hz), 7.44 (2H, d, J=1.8 Hz), 6.67 (1H, s), 4.24 (1H, d, J=12.2 Hz), 4.02 (1H, d, J=12.0 Hz), 3.03 (1H, dd, J=8.4, 4.3 Hz), 1.68 (1H, dd, J=8.4, 5.3 Hz), 1.16 (1H, t, J=4.8 Hz).

$^{13}$C NMR (DMSO-d6): 156.8, 144.4, 134.6, 134.2, 126.4, 105.9, 50.8, 36.3, 24.9, 22.6.

Example 110: (5aR,6aS)-5a-(5-chloro-2-fluorophenyl)-5,5a,6,6a-tetrahydrocyclopropa[3,4]pyrrolo[1,2-c]imidazole-3 (2H)-thione

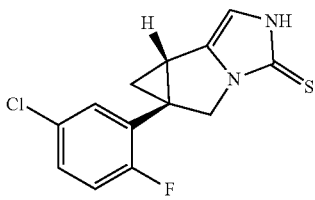 [SMILES: Fc1ccc(Cl)cc1[C@@]12C[C@@H]1c1c[nH]c(=S)n1C2]

Compound was prepared in an analogous manner to Example 53 from 2-(5-chloro-2-fluorophenyl)acetonitrile and (S)-2-(chloromethyl)oxirane and isolated as a beige solid.

$^1$H NMR (DMSO-d6): 11.76 (1H, br s), 7.49 (1H, dd, J=6.5, 2.7 Hz), 7.43 (1H, ddd, J=8.8, 4.4, 2.7 Hz), 7.30 (1H, dd, J=10.0, 8.8 Hz), 6.69 (1H, d, J=2.3 Hz), 4.10 (1H, d, J=12.0 Hz), 3.81 (1H, d, J=12.2 Hz), 2.89 (1H, dd, J=8.3, 4.2 Hz), 1.67 (1H, dd, J=8.4, 5.4 Hz), 1.17 (1H, t, J=4.7 Hz).

$^{13}$C NMR (DMSO-d6): 161.3, 159.7, 156.6, 134.6, 130.2, 130.1, 129.4, 129.3, 128.8, 128.7, 128.3, 128.3, 117.6, 117.4, 106.2, 51.5, 51.5, 32.6, 22.1, 20.9.

Example 111: (6R)-6-(2,3,5,6-tetrafluorophenyl)tetrahydro-1H-pyrrolo[1,2-c]imidazole-3(2H)-thione

Step 1: tert-butyl (4R)-2-((1,3-dioxoisoindolin-2-yl)methyl)-4-(2,3,5,6-tetrafluorophenyl)pyrrolidine-1-carboxylate

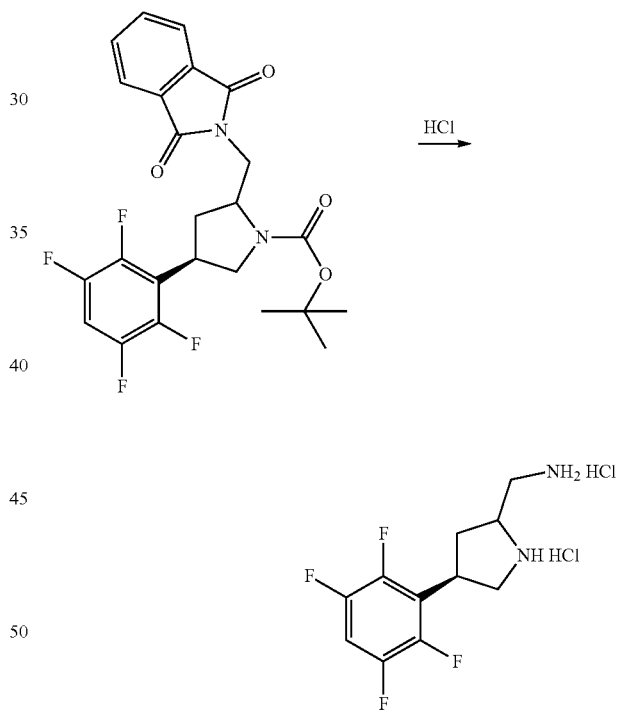

To a stirred solution of (4R)-tert-butyl 2-(hydroxymethyl)-4-(2,3,5,6-tetrafluorophenyl)pyrrolidine-1-carboxylate (analogous to Example 58 step 10) (0.49 g, 1.262 mmol), phtalimide (0.312 g, 2.121 mmol) and triphenylphosphine (0.546 g, 2.083 mmol) in tetrahydrofuran (10 mL) was added dropwise under nitrogen at 0-5° C. with stirring diethyl (E)-diazene-1,2-dicarboxylate (0.32 mL, 2.02 mmol). The mixture was allowed to warm up naturally to room temperature and stirred for 64 h. The mixture was then evaporated to dryness under vacuum and the residue was purified by chromatography (petroleum ether-ethyl acetate; 9:1, then 4:1) to give (4R)-tert-butyl 2-((1,3-dioxoisoindolin-2-yl)methyl)-4-(2,3,5,6-tetrafluorophenyl)pyrrolidine-1-carboxylate as a foam (0.502 g, 83% yield),

Step 2: ((4R)-4-(2,3,5,6-tetrafluorophenyl)pyrrolidin-2-yl)methanamine dihydrochloride

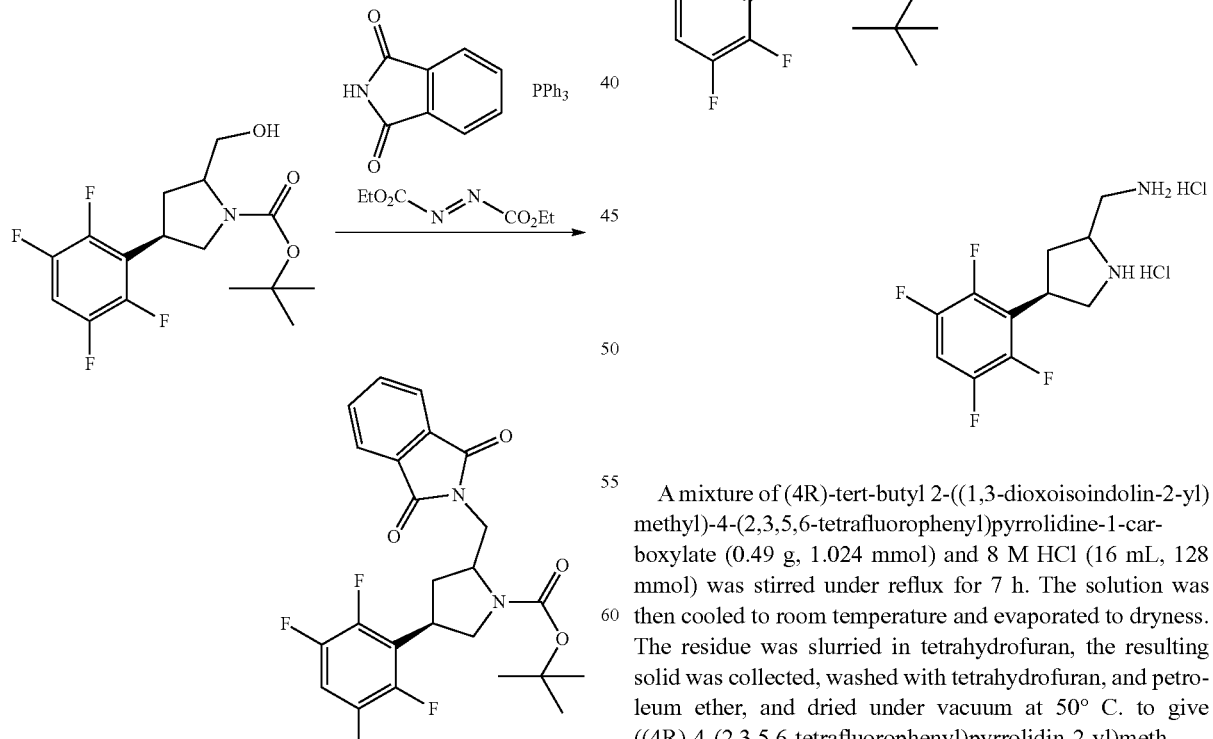

A mixture of (4R)-tert-butyl 2-((1,3-dioxoisoindolin-2-yl)methyl)-4-(2,3,5,6-tetrafluorophenyl)pyrrolidine-1-carboxylate (0.49 g, 1.024 mmol) and 8 M HCl (16 mL, 128 mmol) was stirred under reflux for 7 h. The solution was then cooled to room temperature and evaporated to dryness. The residue was slurried in tetrahydrofuran, the resulting solid was collected, washed with tetrahydrofuran, and petroleum ether, and dried under vacuum at 50° C. to give ((4R)-4-(2,3,5,6-tetrafluorophenyl)pyrrolidin-2-yl)methanamine dihydrochloride as a white powder (0.265 g, 81% yield).

Step 3: (6R)-6-(2,3,5,6-tetrafluorophenyl)hexahydro-3H-pyrrolo[1,2-c]imidazole-3-thione

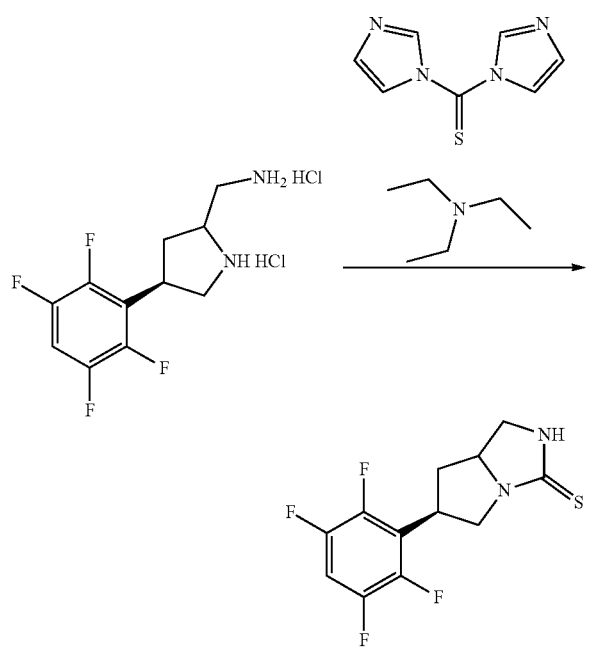

To a mixture of ((4R)-4-(2,3,5,6-tetrafluorophenyl)pyrrolidin-2-yl)methanamine dihydrochloride (0.24 g, 0.747 mmol) and triethylamine (0.229 mL, 1.644 mmol) in dry tetrahydrofuran (7.5 mL) was added in portions with stirring di(1H-imidazol-1-yl)methanethione (0.133 g, 0.747 mmol) and the mixture was stirred at room temperature for 30 min. Tetrahydrofuran was then removed under vacuum, the residue was suspended in 1 M HCl (20 mL) with sonication. The thus obtained solid was collected, washed with water and dried under vacuum at 50° C. The crude product was filtered through a short silica pad in a mixture of ethyl acetate-dichloromethane to give (6R)-6-(2,3,5,6-tetrafluorophenyl) tetrahydro-1H-pyrrolo[1,2-c]imidazole-3(2H)-thione as a white powder (0.12 g, 55% yield).

$^1$H NMR (DMSO-d6): 8.87 (0.7H, s), 8.62 (0.3H, s), 7.80 (1H, m), 4.44 (0.7H, dd, J=11.9, 8.5 Hz), 4.29 (0.7H, qd, J=8.2, 2.9 Hz), 4.21 (0.3H, m), 3.93 (0.6H, m), 3.71 (1H, m), 3.55 (1H, m), 3.45 (0.3H, dd, J=10.5, 3.7 Hz), 3.39 (0.7H, m), 3.12 (0.7H, dd, J=11.7, 8.9 Hz), 2.18 (1H, m), 2.06 (0.7H, m), 1.73 (0.3H, m).

$^{13}$C NMR (DMSO-d6): 186.5, 186.3, 146.4, 146.3, 146.2, 145.2, 145.1, 144.8, 144.7, 144.6, 143.6, 143.5, 121.5, 121.4, 121.3, 120.9, 120.8, 120.7, 105.4, 105.3, 105.2, 105.2, 105.1, 105.0, 62.7, 60.8, 52.2, 51.1, 47.4, 36.6, 35.9, 34.2, 31.7.

Example 112: (S)-6-(2,3,6-trifluorophenyl)-2,5,6,7-tetrahydro-3H-pyrrolo[1,2-c]imidazole-3-thione

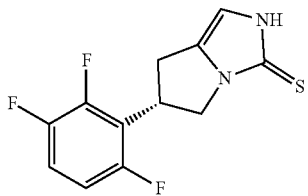 [SMILES: Fc1ccc(F)c([C@@H]2Cc3c[nH]c(=S)n3C2)c1F]

Compound was prepared in an analogous manner to Example 59 from (E)-2,3,6-trifluoro-5-(2-nitrovinyl)benzene using 4-((R)-hydroxy((1S,2S,4S,5R)-5-vinylquinuclidin-2-yl)methyl)quinolin-6-ol as catalyst (CAS #524-63-0) and isolated as a light khaki powder.

$^1$H NMR (DMSO-d6): 11.85 (1H, br s), 7.47 (1H, qd, J=9.5, 4.9 Hz), 7.18 (1H, tdd, J=9.6, 9.6, 3.8, 1.9 Hz), 6.63 (1H, d, J=1.9 Hz), 4.49 (1H, quin, J=8.6 Hz), 4.19 (1H, dd, J=11.3, 9.4 Hz), 3.75 (1H, dd, J=11.6, 7.8 Hz), 3.32 (1H, dd, J=15.9, 9.3 Hz), 2.94 (1H, dd, J=15.9, 7.8 Hz).

$^{13}$C NMR (DMSO-d6): 157.0, 156.9, 155.9, 155.4, 155.3, 155.3, 155.3, 149.1, 149.1, 149.0, 149.0, 147.6, 147.5, 147.5, 147.4, 147.4, 147.3, 146, 145.9, 145.9, 132.2, 119, 118.9, 118.9, 118.8, 116.5, 116.5, 116.4, 116.3, 112.0, 112.0, 112.0, 111.9, 111.8, 111.8, 111.8, 111.8, 106.6, 48.5, 35.7, 29.5.

Example 113: (R)-6-(2,3,6-trifluorophenyl)-2,5,6,7-tetrahydro-3H-pyrrolo[1,2-c]imidazole-3-thione

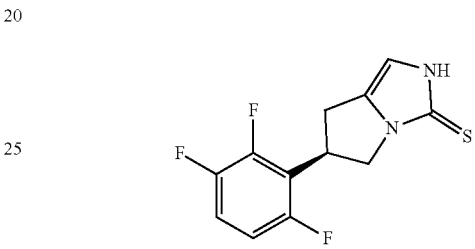

Compound was prepared in an analogous manner to Example 58 from (E)-2,3,6-trifluoro-5-(2-nitrovinyl)benzene using 4-((S)-hydroxy((1S,2R,4S,5R)-5-vinylquinuclidin-2-yl)methyl)quinolin-6-ol as catalyst (CAS #70877-75-7) and isolated as a light khaki powder.

$^1$H NMR (DMSO-d6): 11.84 (1H, br s), 7.46 (1H, qd, J=9.5, 5.1 Hz), 7.17 (1H, ddt, J=1.9, 3.9, 9.8 Hz), 6.62 (1H, d, J=2.1 Hz), 4.48 (1H, quin, J=8.6 Hz), 4.17 (1H, dd, J=11.3, 9.4 Hz), 3.74 (1H, dd, J=11.6, 7.9 Hz), 3.31 (1H, dd, J=9.6, 16 Hz), 2.93 (1H, dd, J=15.8, 7.9 Hz).

$^{13}$C NMR (DMSO-d6): 157, 157, 156.9, 156.9, 155.9, 155.4, 155.4, 155.3, 155.3, 149.1, 149.1, 149, 149, 147.6, 147.6, 147.5, 147.4, 147.4, 147.3, 146, 146, 145.9, 145.9, 132.2, 119, 118.9, 118.9, 118.8, 116.5, 116.5, 116.4, 116.3, 112, 112, 112, 112, 111.9, 111.8, 111.8, 111.8, 106.6, 48.5, 35.7, 29.5.

Example 114: (R)-2-methyl-6-(2,3,5,6-tetrafluorophenyl)-2,5,6,7-tetrahydro-3H-pyrrolo[1,2-c]imidazole-3-thione

Step 1: (4R)-4-(2,3,5,6-tetrafluorophenyl)pyrrolidine-2-carboxylic acid

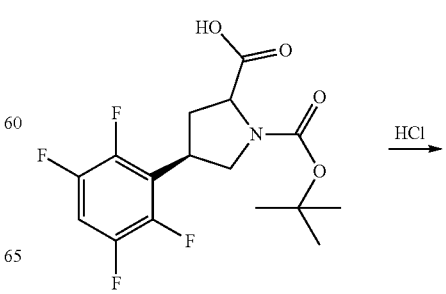

-continued

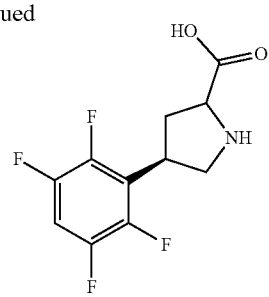

A suspension of (4R)-1-(tert-butoxycarbonyl)-4-(2,3,5,6-tetrafluorophenyl)pyrrolidine-2-carboxylic acid (0.45 g, 1.239 mmol) (analogous to Example 58 step 10) in 2 M HCl (9.29 mL, 18.58 mmol) was stirred under reflux for 2 h. Thereupon, the mixture was concentrated under vacuum, the residue was dissolved in water, and then pH was adjusted to 7 with 5 M sodium hydroxide. The resulting precipitate was collected, washed with water and dried to give (4R)-4-(2,3,5,6-tetrafluorophenyl)pyrrolidine-2-carboxylic acid as an off-white powder (0.2 g, 61% yield).

Step 2: (6R)-2-methyl-6-(2,3,5,6-tetrafluorophenyl)-3-thioxohexahydro-1H-pyrrolo[1,2-c]imidazol-1-one

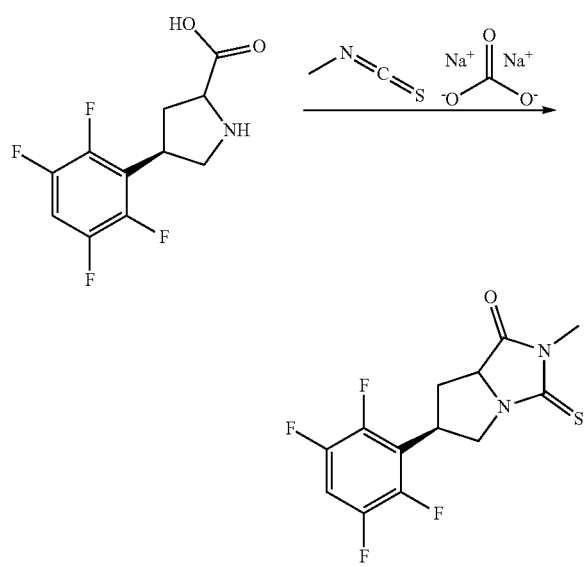

To a solution of (4R)-4-(2,3,5,6-tetrafluorophenyl)pyrrolidine-2-carboxylic acid (0.18 g, 0.684 mmol) in 0.5 M sodium carbonate (10.94 mL, 5.47 mmol) and dioxane (11 mL) was added methyl isothiocyanate (0.100 g, 1.368 mmol). The mixture was stirred for 1 h at room temperature, then heated at 50-60° C. to give clear solution. Thereupon, the reaction was allowed to cool down naturally to room temperature, and then acidified to pH=1-2 by adding cc HCl. The reaction was heated under reflux for 1 h, and then evaporate to ca. 5 mL of volume and the separated oily product crystallised on standing. Thereupon, the mixture was diluted with water (10 mL), stirred at 0-5° C. for 30 min, the resulting solid was collected, washed with water and dried under vacuum to give (6R)-2-methyl-6-(2,3,5,6-tetrafluorophenyl)-3-thioxohexahydro-1H-pyrrolo[1,2-c]imidazol-1-one as a light cream powder (0.20 g, 92% yield).

Step 3: (R)-2-methyl-6-(2,3,5,6-tetrafluorophenyl)-2,5,6,7-tetrahydro-3H-pyrrolo[1,2-c]imidazole-3-thione

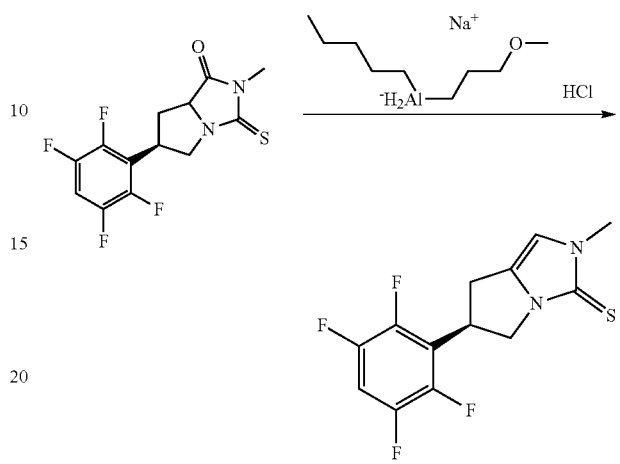

To a solution of (6R)-2-methyl-6-(2,3,5,6-tetrafluorophenyl)-3-thioxohexahydro-1H-pyrrolo[1,2-c]imidazol-1-one (0.17 g, 0.534 mmol) in dry tetrahydrofuran (3 mL) was added 65% RED-Al (bis(2-methoxyethoxy)aluminum(III) sodium hydride) (0.104 mL, 0.347 mmol) in toluene dropwise at 0-5° C. under nitrogen and the mixture was allowed to stir in the cold for 30 min. Thereupon, the mixture was quenched with cc HCl (0.445 mL, 5.34 mmol), and allowed to warm up naturally room temperature and stirred for 1 h. The solvents were then evaporated off, and the residue was taken up in ethyl acetate. The organic phase was dried over MgSO$_4$, filtered, and evaporated to dryness. Chromatography (petroleum ether-ethyl acetate; 2:1, then 1:1) afforded (R)-2-methyl-6-(2,3,5,6-tetrafluorophenyl)-6,7-dihydro-2H-pyrrolo[,2-c]imidazole-3(5H)-thione as a white powder (0.094 g, 58% yield).

$^1$H NMR (DMSO-d6): 7.86 (1H, m), 6.88 (1H, s), 4.52 (1H, quin, J=8.4 Hz), 4.23 (1H, dd, J=11.4, 9.5 Hz), 3.83 (1H, dd, J=11.7, 7.5 Hz), 3.36 (1H, dd, J=9.4, 16.1 Hz), 3.34 (3H, s), 2.99 (1H, dd, J=16.1, 7.6 Hz).

$^{13}$C NMR (DMSO-d6): 156.5, 146.4, 146.4, 146.3, 146.3, 146.2, 145.3, 145.3, 145.3, 145.3, 145.3, 145.2, 145.2, 145.2, 144.8, 144.8, 144.7, 144.7, 144.7, 144.6, 144.6, 143.7, 143.7, 143.7, 143.6, 143.6, 143.6, 130.4, 120.6, 120.5, 120.4, 110.8, 105.9, 105.7, 105.6, 49.3, 35, 34.1, 29.4.

Example 115: (5aS,6aR)-5a-(3-bromo-2,6-difluorophenyl)-5,5a,6,6a-tetrahydrocyclopropa[3,4]pyrrolo[1,2-c]imidazole-3 (2H)-thione

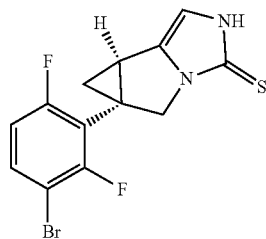 [SMILES: Fc1ccc(Br)c(F)c1[C@]12C[C@H]1c1c[nH]c(=S)n1C2]

Compound was prepared in an analogous manner to Example 53 from 2-(3-bromo-2,6-difluorophenyl)acetonitrile and (R)-2-(chloromethyl)oxirane and isolated as a white solid.

¹H NMR (DMSO-d6): 11.78 (1H, s), 7.74 (1H, td, J=8.4, 5.9 Hz), 7.16 (1H, dt, J=1, 9.2 Hz), 6.71 (1H, d, J=2.2 Hz), 4.05 (1H, d, J=12.2 Hz), 3.75 (1H, d, J=12.2 Hz), 2.75 (1H, dd, J=8.4, 4.4 Hz), 1.69 (1H, dd, J=8.3, 5.6 Hz), 1.29 (1H, t, J=4.9 Hz).

¹³C NMR (DMSO-d6): 162, 161.9, 160.3, 160.3, 158.9, 158.8, 157.2, 157.2, 156.6, 134.4, 133.1, 133.1, 117.1, 117, 116.8, 113.5, 113.5, 113.4, 113.4, 106.6, 103.8, 103.7, 103.6, 103.6, 51.4, 26.8, 21.8, 21.6.

Example 116: (5aS,6aR)-5a-(5-chloro-2-fluorophenyl)-2-methyl-5,5a,6,6a-tetrahydrocyclopropa[3,4]pyrrolo[1,2-c]imidazole-3 (2H)-thione

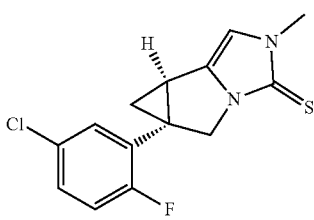 [SMILES: Cn1cc2n(c1=S)C[C@@]1(c3cc(Cl)ccc3F)C[C@@H]21]

Compound was prepared in an analogous manner to Example 114 from (1R,5S)-3-(tert-butoxycarbonyl)-5-(5-chloro-2-fluorophenyl)-3-azabicyclo[3.1.0]hexane-2-carboxylic acid and isolated as a light beige solid.

¹H NMR (DMSO-d6): 7.50 (1H, dd, J=6.5, 2.7 Hz), 7.43 (1H, ddd, J=8.8, 4.4, 2.7 Hz), 7.30 (1H, dd, J=9.9, 8.9 Hz), 6.93 (1H, s), 4.13 (1H, d, J=11.9 Hz), 3.84 (1H, d, J=12.0 Hz), 2.92 (1H, dd, J=8.4, 4.2 Hz), 1.69 (1H, dd, J=8.4, 5.4 Hz), 1.17 (1H, t, J=4.8 Hz).

¹³C NMR (DMSO-d6): 161.3, 159.7, 157.2, 132.9, 130.2, 130.2, 129.4, 129.4, 128.7, 128.6, 128.3, 128.3, 117.6, 117.4, 110.4, 52.3, 52.3, 34.1, 31.9, 22.1, 20.9.

Example 117: (S)-6-(3-bromo-2,6-difluorophenyl)-2,5,6,7-tetrahydro-3H-pyrrolo[1,2-c]imidazole-3-thione

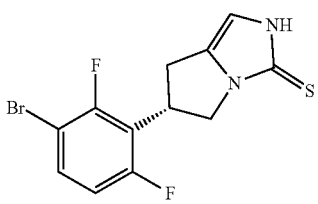 [SMILES: Fc1ccc(Br)c(F)c1[C@@H]1Cc2c[nH]c(=S)n2C1]

(E)-1-bromo-2,4-difluoro-3-(2-nitrovinyl)benzene (using 4-((R)-hydroxy((1S,2S,4S,5R)-5-vinylquinuclidin-2-yl)methyl)quinolin-6-ol as catalyst (CAS #524-63-0)) was converted to (S)-6-(3-bromo-2,6-difluorophenyl)-2,5,6,7-tetrahydro-3H-pyrrolo[1,2-c]imidazole-3-thione by a similar procedure as described for Example 59 and the product was isolated as a light khaki powder.

¹H NMR (DMSO-d6): 11.85 (1H, br s), 7.72 (1H, ddd, J=8.9, 8.1, 5.8 Hz), 7.16 (1H, t, J=9.4 Hz), 6.63 (1H, s), 4.50 (1H, quin, J=8.5 Hz), 4.17 (1H, dd, J=11.5, 9.3 Hz), 3.74 (1H, dd, J=11.7, 7.7 Hz), 3.31 (1H, dd, J=16.1, 9.5 Hz), 2.92 (1H, dd, J=15.9, 7.8 Hz).

¹³C NMR (DMSO-d6): 160.8, 160.8, 159.2, 159.1, 157.6, 157.5, 155.9, 155.9, 155.8, 132.5, 132.4, 132.3, 118.9, 118.8, 118.6, 113.8, 113.8, 113.6, 113.6, 106.6, 104.1, 104.1, 103.9, 103.9, 48.6, 35.7, 29.5.

Example 118: (R)-6-(3-bromo-2,6-difluorophenyl)-2,5,6,7-tetrahydro-3H-pyrrolo[1,2-c]imidazole-3-thione

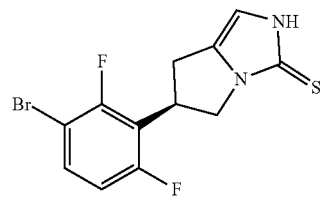 [SMILES: Fc1ccc(Br)c(F)c1[C@H]1Cc2c[nH]c(=S)n2C1]

(E)-3-bromo-2,6-difluoro-5-(2-nitrovinyl)benzene (using 4-((S)-hydroxy((1S,2R,4S,5R)-5-vinylquinuclidin-2-yl)methyl)quinolin-6-ol as catalyst (CAS #70877-75-7)) was converted to (R)-6-(3-bromo-2,6-difluorophenyl)-2,5,6,7-tetrahydro-3H-pyrrolo[1,2-c]imidazole-3-thione by a similar procedure as described for Example 58 and the product was isolated as a light beige powder.

¹H NMR (DMSO-d6): 11.85 (1H, br s), 7.72 (1H, ddd, J=8.9, 8.1, 5.8 Hz), 7.16 (1H, t, J=9.4 Hz), 6.63 (1H, s), 4.50 (1H, quin, J=8.5 Hz), 4.17 (1H, dd, J=11.5, 9.3 Hz), 3.74 (1H, dd, J=11.7, 7.7 Hz), 3.31 (1H, dd, J=16.1, 9.5 Hz), 2.92 (1H, dd, J=15.9, 7.8 Hz).

¹³C NMR (DMSO-d6): 160.8, 160.8, 159.2, 159.1, 157.6, 157.5, 155.9, 155.9, 155.8, 132.5, 132.4, 132.3, 118.9, 118.8, 118.6, 113.8, 113.8, 113.6, 113.6, 106.6, 104.1, 104.1, 103.9, 103.9, 48.6, 35.7, 29.5.

Example 119: (5aS,6aR)-5a-(3-bromo-2,6-difluorophenyl)-5,5a,6,6a-tetrahydrocyclopropa[3,4]pyrrolo[2,1-c][1,2,4]triazole-3(2H)-thione

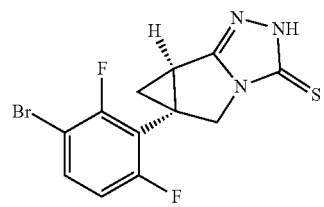 [SMILES: Fc1ccc(Br)c(F)c1[C@]12C[C@H]1c1n[nH]c(=S)n1C2]

Compound was prepared in an analogous manner to Example 60 from tert-butyl (((1S,2R)-1-(3-bromo-2,6-difluorophenyl)-2-(hydroxymethyl)cyclopropyl)methyl)carbamate and isolated as a pink solid.

¹H NMR (DMSO-d6): 13.29 (1H, s), 7.78 (1H, td, J=8.5, 5.9 Hz), 7.18 (1H, td, J=9.2, 1.3 Hz), 4.12 (1H, d, J=12.2 Hz), 3.85 (1H, d, J=12.2 Hz), 2.94 (1H, dd, J=8.8, 4.3 Hz), 1.81 (1H, dd, J=8.8, 5.9 Hz), 1.67 (1H, d, J=4.7 Hz).

¹³C NMR (DMSO-d6): 163.6, 161.8, 161.8, 160.2, 160.2, 158.8, 158.7, 157.6, 157.1, 157.1, 133.5, 133.5, 116.1, 116.0, 115.9, 113.6, 113.5, 113.4, 113.4, 103.8, 103.8, 103.6, 103.6, 49.5, 27.4, 20.1, 19.7.

Example 120: (5aS,6aR)-5a-(5-bromo-2-fluorophenyl)-5,5a,6,6a-tetrahydrocyclopropa[3,4]pyrrolo[2,1-c][1,2,4]triazole-3(2H)-thione

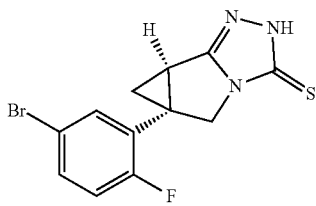 [SMILES: Fc1ccc(Br)cc1[C@]12C[C@H]1c1n[nH]c(=S)n1C2]

Compound was prepared in an analogous manner to Example 60 from tert-butyl ((((1S,2R)-1-(5-bromo-2-fluorophenyl)-2-(hydroxymethyl)cyclopropyl)methyl)carbamate and isolated as a pale brown solid.

$^1$H NMR (DMSO-d6): 7.69 (1H, dd, J=6.7, 2.5 Hz), 7.58 (1H, ddd, J=8.8, 4.5, 2.6 Hz), 7.26 (1H, dd, J=10.0, 8.8 Hz), 4.15 (1H, d, J=11.9 Hz), 3.87 (1H, d, J=11.9 Hz), 3.08 (1H, dd, J=8.9, 4.0 Hz), 1.78 (1H, dd, J=8.7, 5.6 Hz), 1.51 (1H, dd, J=4.3, 5.5 Hz).

$^{13}$C NMR (DMSO-d6): 163.6, 161.8, 160.1, 157.9, 133.2, 133.2, 132.7, 132.7, 128.3, 128.1, 118.0, 117.9, 116.2, 49.7, 33, 20.6, 19.1.

Example 121: (5aS,6aR)-5a-(3-bromo-2,6-difluorophenyl)-1-methyl-5,5a,6,6a-tetrahydrocyclopropa[3,4]pyrrolo[1,2-c]imidazole-3 (2H)-thione

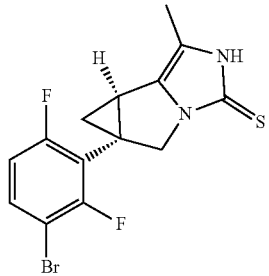 [SMILES: Cc1[nH]c(=S)n2c1[C@@H]1C[C@]1(c1c(F)ccc(Br)c1F)C2]

Compound was prepared in an analogous manner to Example 80 from 2-(5-bromo-2,6-difluorophenyl)acetonitrile and (R)-2-(chloromethyl)oxirane and isolated as a white solid.

$^1$H NMR (DMSO-d6): 11.68 (1H, br s), 7.74 (1H, td, J=8.4, 5.9 Hz), 7.15 (1H, td, J=9.2, 1.2 Hz), 4.01 (1H, d, J=12.3 Hz), 3.71 (1H, d, J=12.0 Hz), 2.72 (1H, dd, J=8.3, 4.5 Hz), 2.05 (3H, s), 1.65 (1H, dd, J=8.2, 5.6 Hz), 1.25 (1H, t, J=5.0 Hz).

$^{13}$C NMR (DMSO-d6): 161.9, 161.9, 160.3, 160.2, 158.8, 158.8, 157.2, 157.1, 155.7, 133.0, 133.0, 130.0, 117.2, 117.1, 115.1, 113.5, 113.3, 103.7, 103.7, 103.6, 51.4, 26.5, 21.8, 20.9, 9.4.

Example 122: (5aS,6aR)-5a-(5-bromo-2-fluorophenyl)-1-methyl-5,5a,6,6a-tetrahydrocyclopropa[3,4]pyrrolo[1,2-c]imidazole-3 (2H)-thione

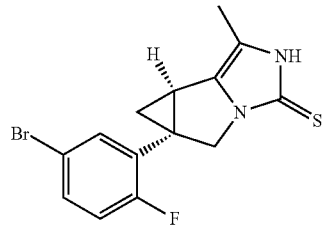 [SMILES: Cc1[nH]c(=S)n2c1[C@@H]1C[C@]1(c1cc(Br)ccc1F)C2]

Step 1: ((1R,2S)-2-(aminomethyl)-2-(5-bromo-2-fluorophenyl)cyclopropyl)methanol

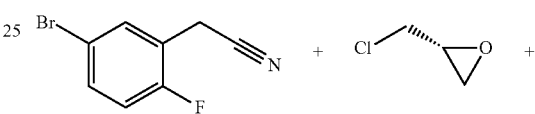

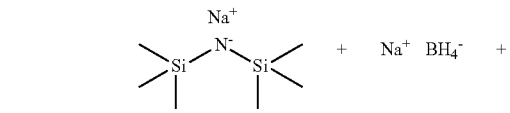

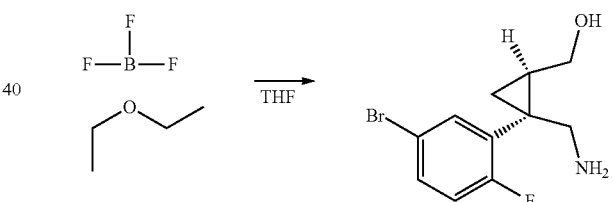

To a stirred solution of 2-(5-bromo-2-fluorophenyl)acetonitrile (10 g, 46.7 mmol) in dry tetrahydrofuran (100 mL), was added (R)-2-(chloromethyl)oxirane (4.38 mL, 56.1 mmol) at room temperature, under inert atmosphere, The reaction was then cooled to 0° C. and 2 M sodium bis(trimethylsilyl)amide in tetrahydrofuran (40.9 mL, 82 mmol) was added dropwise keeping the temperature between 0-5° C. Thereupon, the obtained red mixture was allowed to warm up to room temperature and stirred for 3 h. The reaction was diluted with dry tetrahydrofuran (100 mL), cooled to 0° C. and sodium borohydride (7.07 g, 187 mmol) was added, followed by dropwise addition of boron trifluoride etherate (23.68 mL, 187 mmol). The mixture was allowed to warm to room temperature naturally and stirred overnight. The obtained pale yellow suspension was then cooled to 0° C. and carefully quenched with 2 M HCl (140 ml, 280 mmol). The tetrahydrofuran was evaporated off under vacuum, the aqueous phase was washed with diethyl ether (discarded), then was basified to pH=10 (3 M NaOH) and extracted with dichloromethane. The organic phase was dried over MgSO$_4$, filtered and evaporated to leave a yellow oil. Yield: 11.75 g, 73%.

Step 2: tert-butyl (((1S,2R)-1-(5-bromo-2-fluorophenyl)-2-(hydroxymethyl)cyclopropyl)methyl)carbamate

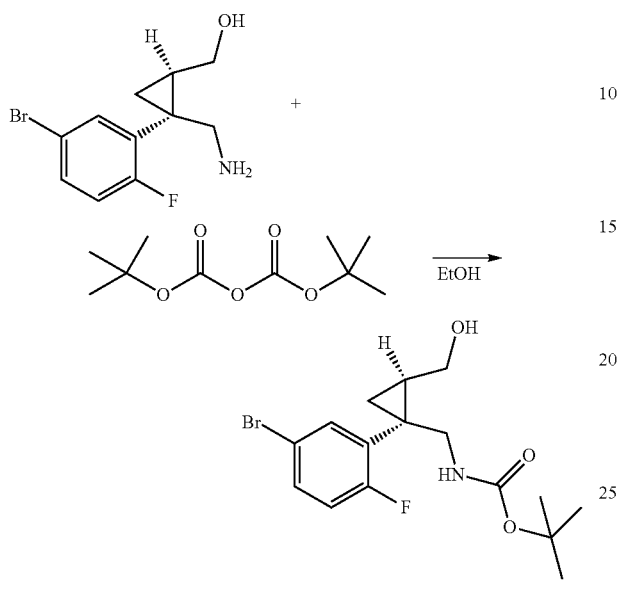

To an ice-cooled solution of (((1R,2S)-2-(aminomethyl)-2-(5-bromo-2-fluorophenyl)cyclopropyl)methanol (11.75 g, 42.9 mmol) in ethanol (145 mL), was added di-tert-butyl dicarbonate (9.35 g, 42.9 mmol). The solution was stirred at room temperature for 4 h. Then the solvent was evaporated and the residue was separated on a column. The titled compound was isolated as a yellow foam. Yield: 10.1 g, 56%.

Step 3: tert-butyl (1S,5R)-1-(5-bromo-2-fluorophenyl)-4-hydroxy-3-azabicyclo[3.1.0]hexane-3-carboxylate

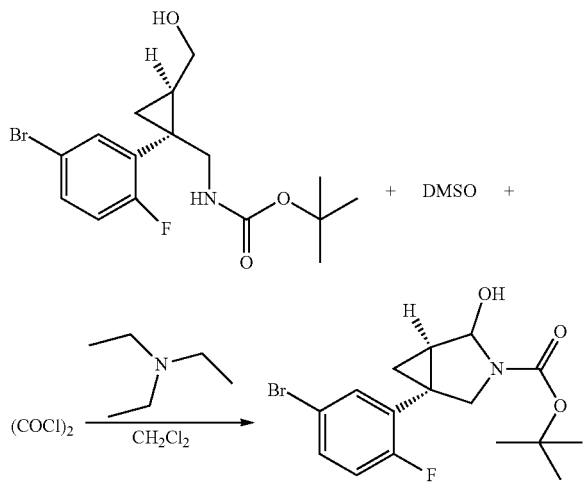

To a stirred solution of oxalyl dichloride (2.60 mL, 29.7 mmol) in dry dichloromethane (62.8 mL), was added dropwise a solution of DMSO (4.21 mL, 59.4 mmol) in dry dichloromethane (12.5 mL) at −78° C. over 30 min. The reaction mixture was stirred for 5 min in the cold, and then a solution of tert-butyl (((1S,2R)-1-(5-bromo-2-fluorophenyl)-2-(hydroxymethyl)cyclopropyl)methyl)carbamate (10.1 g, 27.0 mmol) in dry dichloromethane (25 mL) was added, dropwise over 30 min. The mixture was stirred at −78° C. for 1 h, and then triethylamine (18.8 mL, 135 mmol) was added. The reaction was allowed to warm up gradually to room temperature and stirred for 2 h. Thereupon the mixture was washed three times with water, dried over MgSO$_4$, filtered and evaporated to give a yellow oil. Yield: 10.1 g, 85%.

Step 4: tert-butyl (1S,5R)-1-(5-bromo-2-fluorophenyl)-4-cyano-3-azabicyclo[3.1.0]hexane-3-carboxylate

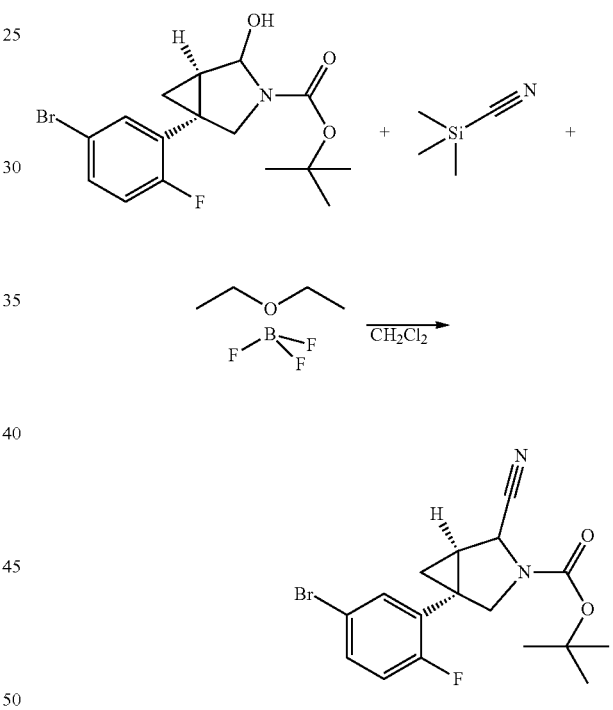

To a stirred solution of tert-butyl (1S,5R)-1-(5-bromo-2-fluorophenyl)-4-hydroxy-3-azabicyclo[3.1.0]hexane-3-carboxylate (10.1 g, 27.1 mmol) in dry dichloromethane (133 mL) was added trimethylsilanecarbonitrile (9.71 mL, 72.4 mmol) at room temperature under inert atmosphere. Then, the solution was cooled to −78° C. and boron trifluoride diethyl etherate (10.08 mL, 80.0 mmol) was added dropwise. The reaction mixture was stirred at −78° C. for 4 h., and then saturated solution of NaHCO$_3$ was added and the mixture was allowed to warm to room temperature. The organic phase was separated and aqueous phase was extracted with dichloromethane. The combined organic phases were dried over MgSO$_4$, filtered and evaporated to give 10.3 g of yellow oil. Yield: 85%.

Step 5: (1R,5S)-5-(5-bromo-2-fluorophenyl)-3-(tert-butoxycarbonyl)-3-azabicyclo[3.1.0]hexane-2-carboxylic acid

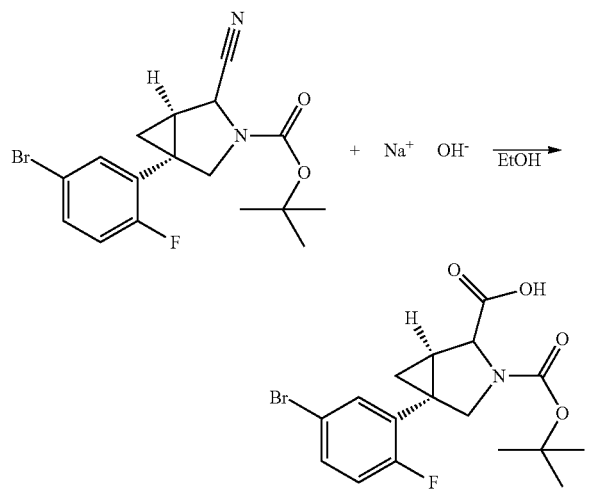

To a stirred solution of tert-butyl (1S,5R)-1-(5-bromo-2-fluorophenyl)-4-cyano-3-azabicyclo[3.1.0]hexane-3-carboxylate (10.3 g, 27.0 mmol) in ethanol (93 mL), at room temperature was added a solution of 3 M NaOH (45 mL, 135 mmol). The solution was heated at 80° C. for 3 h. Then, the reaction was cooled to room temperature, ethanol was evaporated and the aq. phase was acidified with 2N HCl solution, the resulting solid was filtered off, dissolved in a mixture of dichloromethane-isopropanol (7:3). The organic phase was dried over MgSO4, filtered and evaporated to give the titled product as a yellow semi-solid. Yield: 10.5 g, 78%.

Step 6: tert-butyl (1S,5R)-1-(5-bromo-2-fluorophenyl)-4-(methoxy(methyl)carbamoyl)-3-azabicyclo[3.1.0]hexane-3-carboxylate

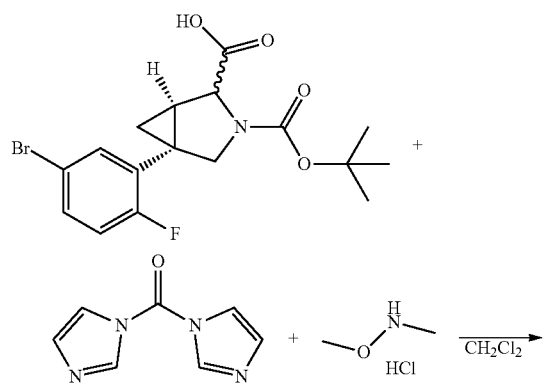

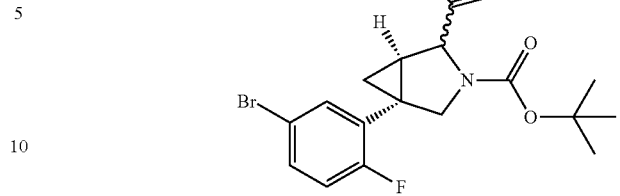

To a stirred solution of ((1R,5S)-5-(5-bromo-2-fluorophenyl)-3-(tert-butoxycarbonyl)-3-azabicyclo[3.1.0]hexane-2-carboxylic acid (2.5 g, 6.25 mmol) in anhydrous dichloromethane (36 mL) was added di(1H-imidazol-1-yl)methanone (1.215 g, 7.50 mmol) portion wise under nitrogen and the reaction stirred for 30 min. Thereupon, N,O-dimethylhydroxylamine hydrochloride (0.731 g, 7.50 mmol) was added and the mixture was stirred overnight. The reaction mixture was then diluted with dichloromethane (ca. to 60 mL) and washed with water. The organic phase was dried over MgSO4, filtered and evaporated to give the titled product as a yellow yellow oil. Yield: 1.57 g, 45%.

Step 7: tert-butyl (1S,5R)-4-acetyl-1-(5-bromo-2-fluorophenyl)-3-azabicyclo[3.1.0]hexane-3-carboxylate

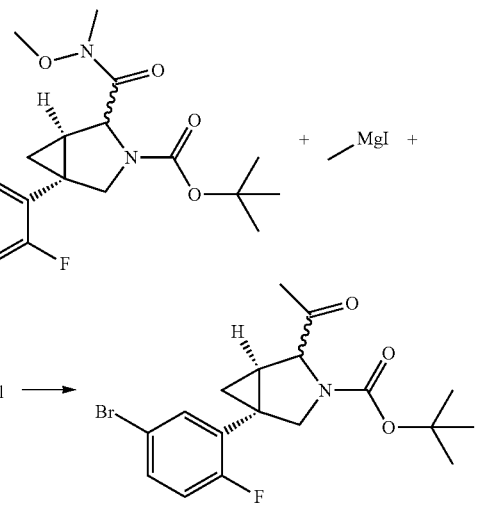

To a stirred solution of (1S,5R)-tert-butyl 1-(5-bromo-2-fluorophenyl)-4-(methoxy(methyl)carbamoyl)-3-azabicyclo[3.1.0]hexane-3-carboxylate (1.57 g, 3.54 mmol) in anhydrous tetrahydrofuran (15 mL) was added methylmagnesium iodide (3.54 ml, 10.62 mmol) dropwise at 0° C. The reaction mixture was stirred in the cold for 1 h, and then quenched by addition of 1 M HCl (14.17 ml, 14.17 mmol). The mixture was extracted with a mixture of ethyl acetate-petroleum ether (1:1). The organic phase was washed with brine, dried over MgSO4, filtered and evaporated to give 1.34 g of yellow oil. Yield: 86%.

Step 8: 1-((1R,5S)-5-(5-bromo-2-fluorophenyl)-3-azabicyclo[3.1.0]hexan-2-yl)ethan-1-one hydrochloride

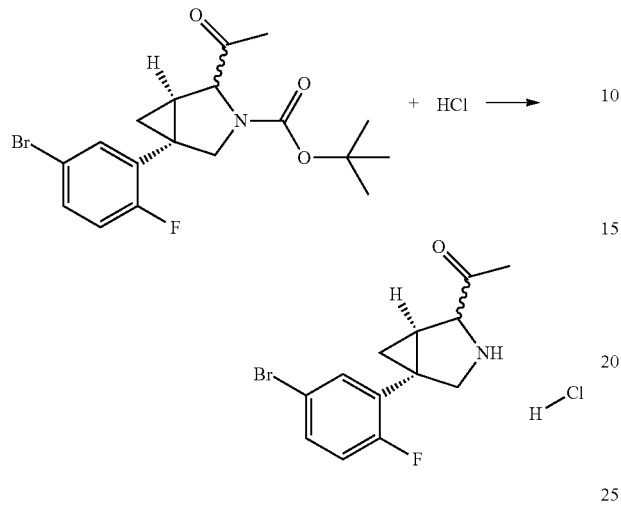

To a stirred solution of (1S,5R)-tert-butyl 4-acetyl-1-(5-bromo-2-fluorophenyl)-3-azabicyclo[3.1.0]hexane-3-carboxylate (1.33 g, 3.34 mmol) was added 4 M HCl in dioxane (6.68 mL, 26.7 mmol) and then the mixture was stirred at room temperature for 2 h. Thereupon, diethyl ether was added and the mixture was evaporated to dryness to give an orange oil. Yield: 1.2 g, 91%.

Step 9: (5aS,6aR)-5a-(5-bromo-2-fluorophenyl)-1-methyl-5,5a,6,6a-tetrahydrocyclopropa[3,4]pyrrolo[1,2-c]imidazole-3(2H)-thione

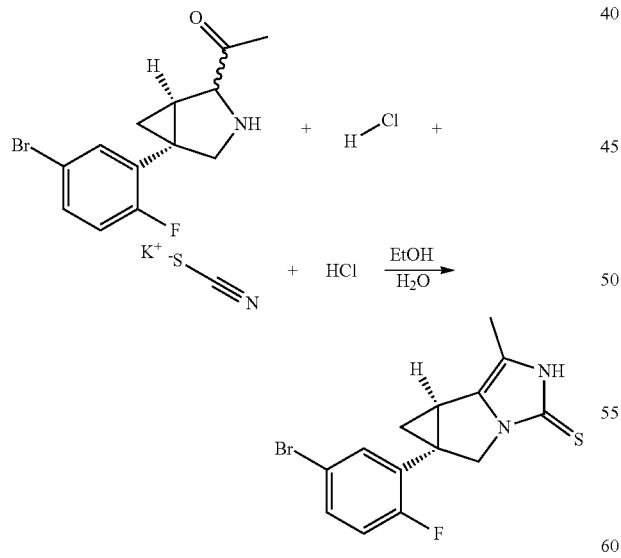

To a stirred solution of 1-((1R,5S)-5-(5-bromo-2-fluorophenyl)-3-azabicyclo[3.1.0]hexan-2-yl)ethanone hydrochloride (1.1 g, 3.29 mmol) in a mixture of ethanol (13.5 mL) and water (13.5 mL) was added potassium thiocyanate (0.351 g, 3.62 mmol) followed by addition of cc. HCl (0.135 mL, 1.644 mmol). The solution was heated at reflux for 1 h.

The reaction was cooled to room temperature, and then ethanol was removed. The aqueous phase was extracted with dichloromethane, the organic phase was dried over MgSO$_4$, filtered and evaporated. Chromatography in a mixture of dichloromethane-methanol afforded the titled compound as a beige foam. Yield: 0.9 g, 77%.

$^1$H NMR (DMSO-d6): 11.65 (1H, s), 7.59 (1H, dd, J=6.7, 2.5 Hz), 7.55 (1H, ddd, J=8.7, 4.5, 2.6 Hz), 7.24 (1H, dd, J=10.1, 8.7 Hz), 4.05 (1H, d, J=12.0 Hz), 3.76 (1H, d, J=12.0 Hz), 2.87 (1H, dd, J=8.3, 4.3 Hz), 2.04 (3H, s), 1.64 (1H, dd, J=8.2, 5.3 Hz), 1.12 (1H, t, J=4.8 Hz).

$^{13}$C NMR (DMSO-d6): 161.8, 160.2, 155.7, 132.9, 132.9, 132.3, 132.2, 130.2, 129.4, 129.3, 118, 117.8, 116.2, 116.2, 114.8, 51.5, 51.5, 32.2, 22.2, 20.2, 9.3.

Example 123: (5aS,6aR)-5a-(3-chloro-2,6-difluorophenyl)-1-methyl-5,5a,6,6a-tetrahydrocyclopropa[3,4]pyrrolo[1,2-c]imidazole-3 (2H)-thione

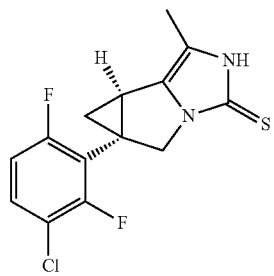 [SMILES: Cc1[nH]c(=S)n2c1[C@@H]1C[C@]1(c1c(F)ccc(Cl)c1F)C2]

Compound was prepared in an analogous manner to Example 122 from 2-(3-chloro-2,6-difluorophenyl)acetonitrile. The product was isolated as a beige solid.

$^1$H NMR (DMSO-d6): 11.68 (1H, s), 7.63 (1H, td, J=8.6, 5.8 Hz), 7.21 (1H, t, J=8.6 Hz), 4.01 (1H, d, J=12.2 Hz), 3.72 (1H, d, J=12.2 Hz), 2.73 (1H, dd, J=8.2, 4.4 Hz), 2.05 (3H, s), 1.65 (1H, dd, J=8.2, 5.6 Hz), 1.25 (1H, t, J=5.0 Hz).

$^{13}$C NMR (DMSO-d6): 161.2, 161.2, 159.6, 159.6, 157.8, 157.8, 156.2, 156.1, 155.7, 130.3, 130.2, 129.9, 117.2, 117.1, 117, 115.7, 115.7, 115.6, 115.6, 115.1, 112.9, 112.9, 112.8, 112.8, 51.4, 26.4, 21.7, 20.8, 9.4.

Example 124: (R)-6-(3-bromo-2,6-difluorophenyl)-1-methyl-2,5,6,7-tetrahydro-3H-pyrrolo[1,2-c]imidazole-3-thione

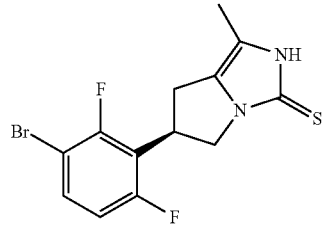 [SMILES: Cc1[nH]c(=S)n2c1C[C@H](c1c(F)ccc(Br)c1F)C2]

Compound was prepared in an analogous manner to Example 129 from 3-bromo-2,6-difluorobenzaldehyde and isolated as a beige powder.

$^1$H NMR (DMSO-d6): 11.73 (1H, br s), 7.72 (1H, ddd, J=8.9, 8.1, 5.8 Hz), 7.16 (1H, m), 4.44 (1H, quin, J=8.6 Hz), 4.13 (1H, dd, J=11.5, 9.2 Hz), 3.71 (1H, dd, J=11.6, 7.9 Hz), 3.23 (1H, dd, J=15.5, 9.3 Hz), 2.84 (1H, dd, J=15.4, 8.1 Hz), 1.97 (3H, s).

$^{13}$C NMR (DMSO-d6): 160.8, 160.8, 159.2, 159.1, 157.5, 157.5, 155.9, 155.8, 155, 132.4, 132.4, 127.7, 118.8, 118.7, 118.6, 115.1, 113.8, 113.8, 113.6, 113.6, 104.1, 104, 103.9, 103.9, 48.5, 35.8, 28.7, 9.3.

Example 125: (S)-6-(3-bromo-2,6-difluorophenyl)-1-methyl-2,5,6,7-tetrahydro-3H-pyrrolo[1,2-c]imidazole-3-thione

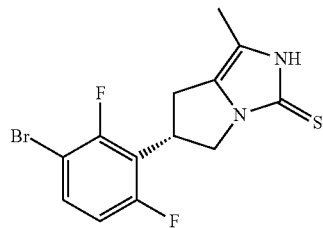

Compound was prepared in an analogous manner to Example 129 from 3-bromo-2,6-difluorobenzaldehyde using 4-((R)-hydroxy((1S,2S,4S,5R)-5-vinylquinuclidin-2-yl)methyl)quinolin-6-ol as catalyst (CAS #524-63-0) and isolated as a beige powder.

$^1$H NMR (DMSO-d6): 11.72 (1H, br s), 7.72 (1H, ddd, J=8.9, 8.1, 5.8 Hz), 7.16 (1H, m), 4.44 (1H, t, J=8.7 Hz), 4.13 (1H, dd, J=11.5, 9.2 Hz), 3.71 (1H, dd, J=11.6, 7.9 Hz), 3.23 (1H, dd, J=15.5, 9.3 Hz), 2.84 (1H, dd, J=15.5, 8.1 Hz), 1.97 (3H, s).

$^{13}$C NMR (DMSO-d6): 160.8, 160.8, 159.2, 159.1, 157.5, 157.5, 155.9, 155.8, 155, 132.4, 132.4, 127.7, 118.8, 118.7, 118.6, 115.1, 113.8, 113.8, 113.6, 113.6, 104.1, 104, 103.9, 103.9, 48.5, 35.8, 28.7, 9.3.

Example 126: (5aS,6aR)-5a-(3-chloro-5-fluorophenyl)-1-methyl-5,5a,6,6a-tetrahydrocyclopropa[3,4]pyrrolo[1,2-c]imidazole-3 (2H)-thione

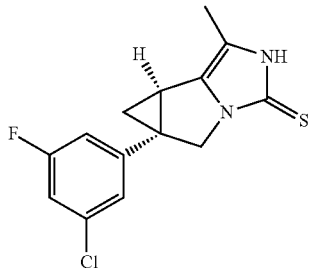 [SMILES: Cc1[nH]c(=S)n2c1[C@@H]1C[C@]1(c1cc(F)cc(Cl)c1)C2]

Compound was prepared in an analogous manner to Example 122 from 2-(3-chloro-5-fluorophenyl)acetonitrile. The product was isolated as a beige solid.

$^1$H NMR (DMSO-d6): 11.64 (1H, s), 7.30 (1H, dt, J=8.7, 2.1 Hz), 7.28 (1H, t, J=1.6 Hz), 7.23 (1H, dt, J=10.0, 1.8 Hz), 4.19 (1H, d, J=12.2 Hz), 3.99 (1H, d, J=12.0 Hz), 3.00 (1H, dd, J=8.3, 4.3 Hz), 2.03 (3H, s), 1.64 (1H, dd, J=8.3, 5.2 Hz), 1.14 (1H, t, J=4.8 Hz).

$^{13}$C NMR (DMSO-d6): 163.1, 161.4, 156, 145, 144.9, 134.1, 134.1, 130.2, 123, 123, 114.5, 114.3, 114.1, 112.9, 112.8, 50.8, 36, 36, 25.2, 22.2, 9.3.

Example 127: (5aS,6aR)-5a-(5-bromo-2-fluorophenyl)-1-(methyl-d$_3$)-5,5a,6,6a-tetrahydrocyclopropa[3,4]pyrrolo[1,2-c]imidazole-3 (2H)-thione

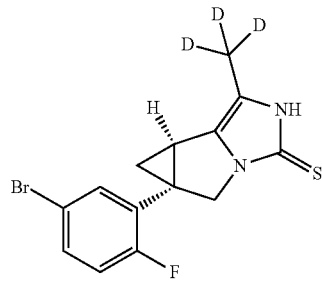 [SMILES: [2H]C([2H])([2H])c1[nH]c(=S)n2c1[C@@H]1C[C@]1(c1cc(Br)ccc1F)C2]

Compound was prepared in an analogous manner to Example 122 from 2-(5-bromo-2-fluorophenyl)acetonitrile. The product was isolated as a beige solid.

$^1$H NMR (DMSO-d6): 11.65 (1H, s), 7.59 (1H, dd, J=6.7, 2.6 Hz), 7.55 (1H, ddd, J=8.7, 4.5, 2.6 Hz), 7.23 (1H, dd, J=10.1, 8.7 Hz), 4.05 (1H, d, J=12.0 Hz), 3.76 (1H, d, J=12.0 Hz), 2.87 (1H, dd, J=8.2, 4.3 Hz), 1.64 (1H, dd, J=8.3, 5.4 Hz), 1.12 (1H, t, J=4.8 Hz).

$^{13}$C NMR (DMSO-d6): 161.8, 160.2, 155.7, 132.9, 132.9, 132.3, 132.2, 130.3, 129.4, 129.3, 118, 117.8, 116.2, 116.2, 114.7, 51.5, 51.5, 32.3, 22.2, 20.2.

Example 128: (S)-6-(5-bromo-2-fluorophenyl)-1-methyl-2,5,6,7-tetrahydro-3H-pyrrolo[1,2-c]imidazole-3-thione

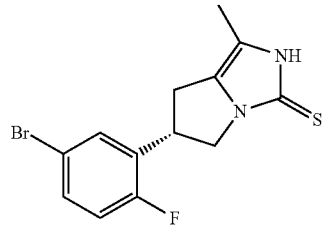

Compound was prepared in an analogous manner to Example 129 from 5-bromo-2-fluorobenzaldehyde using 4-((R)-hydroxy((1S,2S,4S,5R)-5-vinylquinuclidin-2-yl)methyl)quinolin-6-ol as catalyst (CAS #524-63-0) and isolated as an off-white solid.

$^1$H NMR (DMSO-d6): 11.70 (1H, br s), 7.58 (1H, dd, J=6.7, 2.5 Hz), 7.53 (1H, ddd, J=8.7, 4.5, 2.5 Hz), 7.23 (1H, dd, J=10.3, 8.8 Hz), 4.20 (1H, quin, J=8.1 Hz), 4.11 (1H, dd, J=10.9, 8.1 Hz), 3.71 (1H, dd, J=11.3, 7.9 Hz), 3.18 (1H, dd, J=15.2, 8.1 Hz), 2.85 (1H, ddd, J=15.2, 8.3, 1.2 Hz), 1.98 (3H, s).

$^{13}$C NMR (DMSO-d6): 160.3, 158.7, 155.1, 131.8, 131.8, 131.4, 131.4, 130.6, 130.5, 127.5, 118, 117.9, 116.5, 116.4, 115.4, 49, 40.5, 29, 9.3.

149

Example 129: (R)-1-methyl-6-(2,3,6-trifluorophenyl)-6,7-dihydro-2H-pyrrolo[1,2-c]imidazole-3(5H)-thione

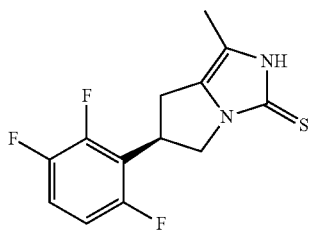 [SMILES: Cc1[nH]c(=S)n2c1C[C@H](c1c(F)ccc(F)c1F)C2]

Step 1: (E)-1,2,4-trifluoro-3-(2-nitrovinyl)benzene

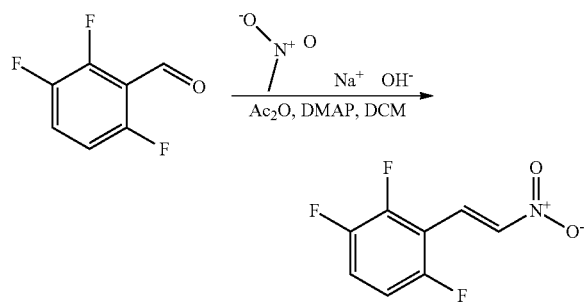

To a solution of methanol (90 mL) and 1.5 M sodium hydroxide (131 mL, 197 mmol) was added a solution of 2,3,6-trifluorobenzaldehyde (30 g, 187 mmol) and nitromethane (16 mL, 299 mmol) in methanol (60 mL) dropwise over 40 min at 5° C., while the internal temperature was maintained between 5 and 10° C. with external cooling. The reaction was then agitated in the cold for 30 min., and then a solution of acetic acid (16 mL, 281 mmol) was added in one portion at 0-10° C. with stirring. The resulting mixture extracted with dichloromethane (ca. 200 mL), the organic phase was washed with brine, dried

150

(MgSO$_4$), filtered to give 1-(3-bromo-2,6-difluorophenyl)-2-nitroethanol solution in dichloromethane. Thereupon, the above solution (ca. 270 mL) was treated with N,N-dimethylpyridin-4-amine (2.289 g, 18.74 mmol) followed by addition of acetic anhydride (21.26 ml, 225 mmol) and the mixture was stirred at room temperature overnight. The reaction mixture was then washed with water and sodium bicarbonate solution, respectively. The organic phase was dried over MgSO4, filtered and evaporated to dryness. The crude product was crystallized from a mixture of isopropanol and water to give a light brownish solid. Yield: 38.1 g, 88%.

Step 2: diethyl (R)-2-(2-nitro-1-(2,3,6-trifluorophenyl)ethyl)malonate

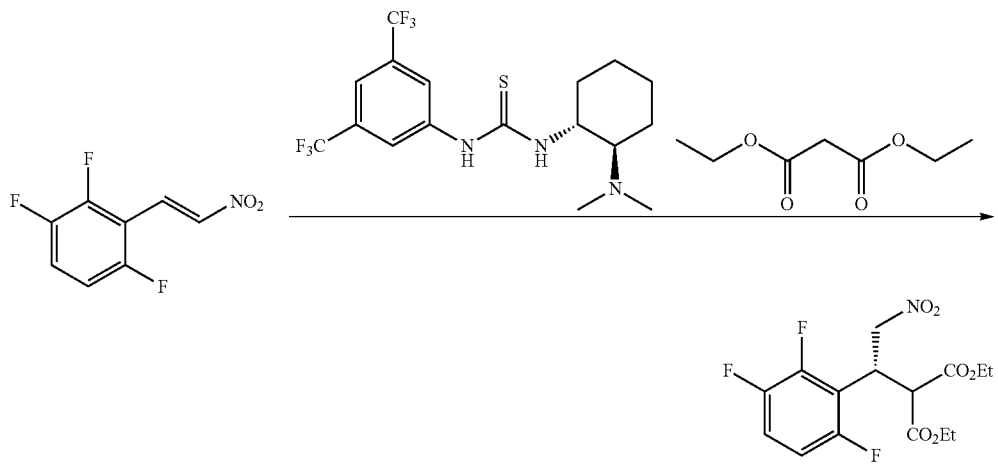

To a cold solution of (E)-1,2,4-trifluoro-3-(2-nitrovinyl) benzene (5 g, 24.62 mmol) and 1-(3,5-bis(trifluoromethyl) phenyl)-3-((1R,2R)-2-(dimethylamino)cyclohexyl)thiourea (CAS #620960-26-1) (0.305 g, 0.738 mmol) in dry toluene (40 ml) was added diethyl malonate (4.88 mL, 32.0 mmol) and the solution was kept for 16 h at −20° C. (in the freezer), the reaction was then warmed up to room temperature, washed with 30 mL of 1 M HCl solution, dried over MgSO$_4$, filtered through a silica pad and evaporated to dryness to give (R)-diethyl 2-(2-nitro-1-(2,3,6-trifluorophenyl)ethyl) malonate as a yellowish oil. Yield: 10.3 g, 98%.

Step 3: ethyl (4R)-2-oxo-4-(2,3,5-trifluorophenyl) pyrrolidine-3-carboxylate

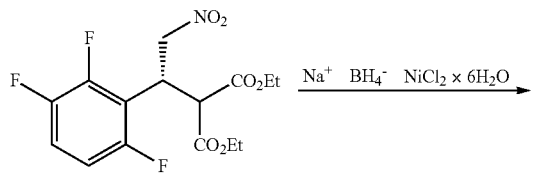

-continued

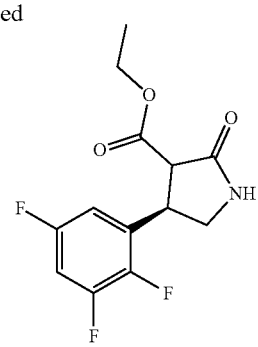

To a suspension of (R)-diethyl 2-(2-nitro-1-(2,3,6-trifluorophenyl)ethyl)malonate (10.3 g, 22.68 mmol) in methanol (115 mL) was added nickel(II) chloride hexahydrate (5.39 g, 22.68 mmol) followed by addition of sodium borohydride (6.86 g, 181 mmol) in portions with ice cooling over 30 min. The mixture was stirred for 5 h at room temperature, then quenched with 2 M HCl solution (60 mL) followed by addition of cc. ammonia (5 mL). The mixture was then diluted with dichloromethane (150 mL), acidified with 6 M HCl to pH=2, and stirred for 16 h to give a clear solution. Thereupon, the mixture was extracted with dichloromethane, the organic phase was dried over MgSO$_4$, filtered and evaporated to dryness. Crystallization from petroleum ether gave the titled product as a light beige powder. (Yield: 6.19 g, 95%).

Step 4: (4R)-2-oxo-4-(2,3,5-trifluorophenyl)pyrrolidine-3-carboxylic acid

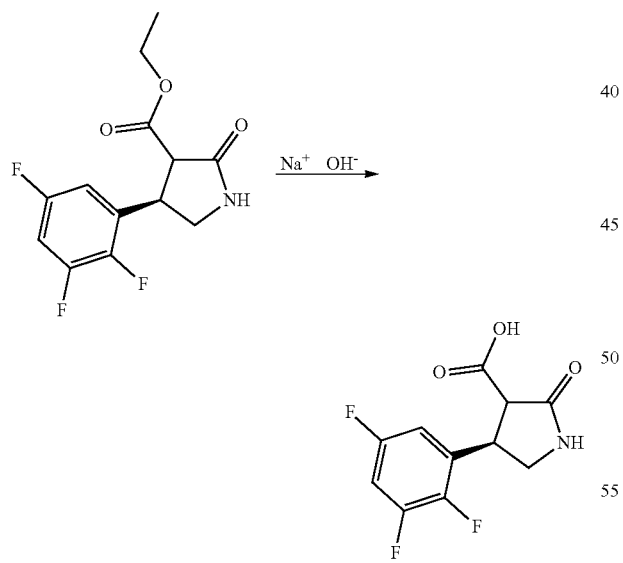

To a stirred solution (4R)-ethyl 2-oxo-4-(2,3,6-trifluorophenyl)pyrrolidine-3-carboxylate (6 g, 20.89 mmol) in ethanol (90 mL) was added 1 M sodium hydroxide (25.1 mL, 25.1 mmol). The resulting suspension was stirred for 2 h at room temperature, the organics were then removed under vacuum, and the residue was dissolved in water (50 mL). The product was crystallized on acidification with 6 M HCl. The resulting crystals were collected, washed with cold water and dried under vacuum at 50° C. to give the product as a beige powder. Yield: 4.75 g, 88%.

Step 5: (R)-4-(2,3,5-trifluorophenyl)pyrrolidin-2-one

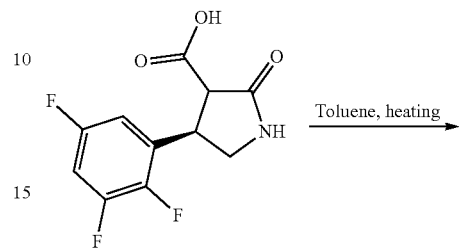

A solution of (4R)-2-oxo-4-(2,3,6-trifluorophenyl)pyrrolidine-3-carboxylic acid (4.64 g, 17.90 mmol) in toluene (150 mL) was stirred under reflux for 3 h, thereupon, the mixture was evaporated to 30 mL followed by addition of petroleum ether afforded the titled product as a beige powder. Yield: 3.45 g, 90%.

Step 6: tert-butyl (R)-2-oxo-4-(2,3,5-trifluorophenyl)pyrrolidine-1-carboxylate

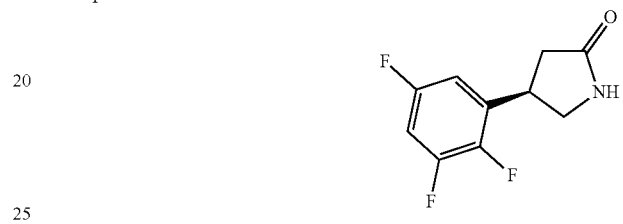

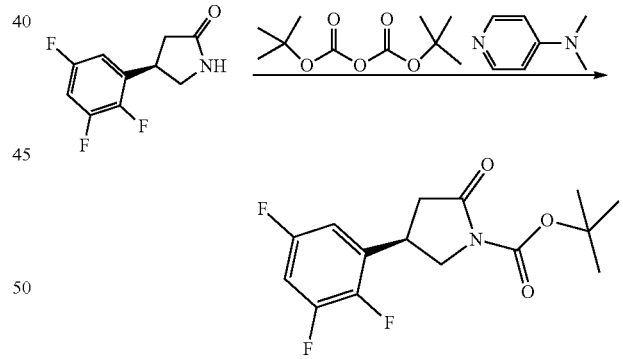

To a stirred solution of (R)-4-(2,3,6-trifluorophenyl)pyrrolidin-2-one (3.35 g, 15.57 mmol)) in dry dichloromethane (14 mL) was added at room temperature di-tert-butyl dicarbonate (5.10 g, 23.35 mmol) followed by addition of N,N-dimethylpyridin-4-amine (1.902 g, 15.57 mmol). The mixture was then stirred at room temperature for 24 h at room temperature, and then diluted with dichloromethane to 80 mL washed with 10% citric acid (80 mL). The organic phase was dried (MgSO$_4$), filtered through silica pad, and then the filtrate was evaporated to dryness. Crystallization from petroleum ether afforded (R)-tert-butyl 2-oxo-4-(2,3,6-trifluorophenyl)pyrrolidine-1-carboxylate as an off-white powder. Yield: 4.15 g, 85%.

Step 7: tert-butyl (4R)-2-hydroxy-4-(2,3,5-trifluoro-phenyl)pyrrolidine-1-carboxylate

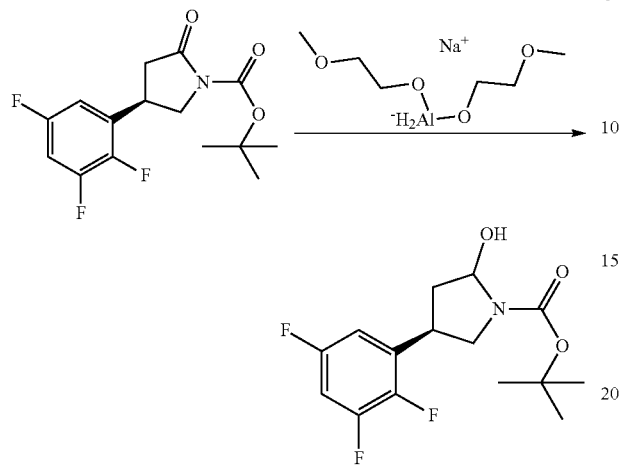

To a stirred solution of (R)-tert-butyl 2-oxo-4-(2,3,6-trifluorophenyl)pyrrolidine-1-carboxylate (4 g, 12.69 mmol) in a mixture of dry diethyl ether (39 mL) and tetrahydrofuran (13 mL) was added dropwise 65% RED-Al (bis(2-methoxy-ethoxy)aluminum(III) sodium hydride) (2.67 mL, 8.88 mmol) in toluene at 5-7° C. under nitrogen and the mixture was stirred for 1 h in the cold. Thereupon, the mixture was quenched with sodium bicarbonate solution (ca. 40 mL) and stirred for 30 min. The organic phase was dried over MgSO₄, filtered and evaporated to dryness to give the product as a yellowish oil. (Yield: 4.55 g, 96%).

Step 8: tert-butyl (4R)-2-cyano-4-(2,3,5-trifluoro-phenyl)pyrrolidine-1-carboxylate

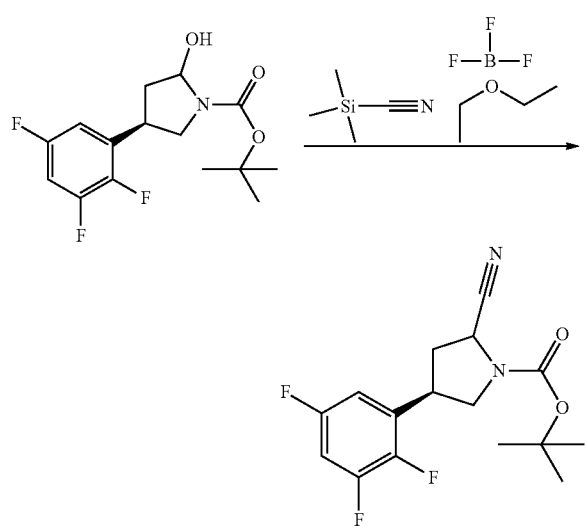

To a stirred solution of (4R)-tert-butyl 2-methoxy-4-(2,3,6-trifluorophenyl)pyrrolidine-1-carboxylate (4.33 g, 11.76 mmol) in dry dichloromethane (90 mL) was added trimethylsilanecarbonitrile (3.15 mL, 23.52 mmol) followed by addition of boron trifluoride diethyl etherate (3.28 mL, 25.9 mmol) at −70° C. The mixture was stirred for 4 h in the cold, quenched with sodium bicarbonate solution, and then allowed to warm up with stirring to room temperature. The organic phase was dried over MgSO₄, filtered and evaporated to dryness under vacuum to give the titled compound as a yellowish oil. (Yield: 4.41 g, 98%).

Step 9: tert-butyl (4R)-2-carbamoyl-4-(2,3,6-trifluo-rophenyl)pyrrolidine-1-carboxylate

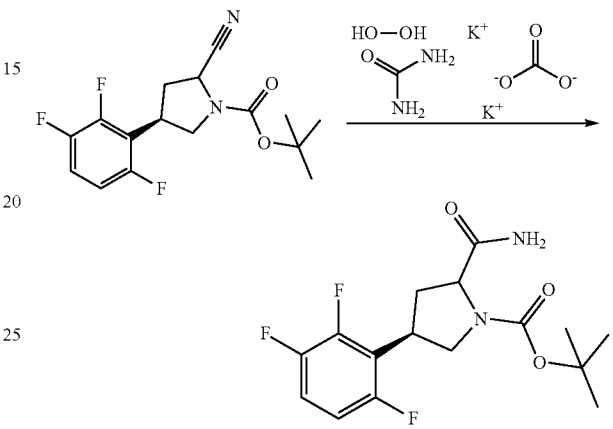

To a stirred solution of (4R)-tert-butyl 2-cyano-4-(2,3,6-trifluorophenyl)pyrrolidine-1-carboxylate (4.4 g, 11.46 mmol) in a mixture of acetone (54 mL) and water (18 mL) was added urea hydrogen peroxide complex (5.39 g, 57.3 mmol) followed by potassium carbonate (0.317 g, 2.292 mmol) and the reaction was stirred at room temperature for 16 h. Acetone was then partially removed under vacuum until oil separation. The mixture was diluted with water and petroleum ether, aged with stirring for 1 h at 5-7° C. (crystallization occurred). The solid was collected, washed with water, petroleum ether and dried to give (4R)-tert-butyl 2-carbamoyl-4-(2,3,6-trifluorophenyl)pyrrolidine-1-carboxylate. Yield: 3.46 g, 88%.

Step 10: (4R)-1-(tert-butoxycarbonyl)-4-(2,3,6-trif-luorophenyl)pyrrolidine-2-carboxylic acid

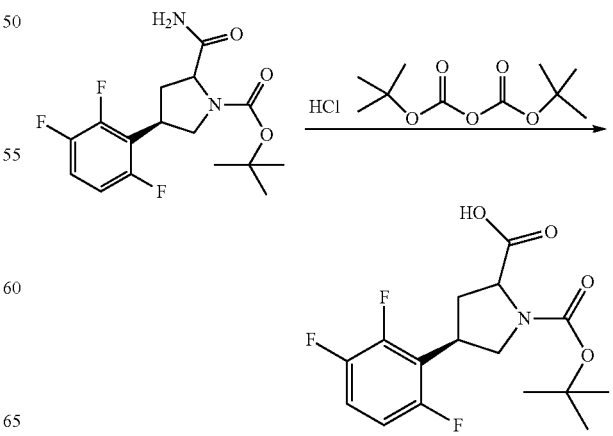

A stirred suspension of (4R)-tert-butyl 2-carbamoyl-4-(2,3,6-trifluorophenyl)pyrrolidine-1-carboxylate (3.36 g, 9.76 mmol) in 2 M HCl (73 mL, 146 mmol) was refluxed for 3 h to give a clear solution with minimum amount of dark insoluble material. After being cooled to room temperature the solid was filtered off and the filtrate was concentrated under vacuum. The residue was dissolved in water (ca. 50 mL), the pH was adjusted to 7 by addition of 1 M NaOH (19.52 mL, 19.52 mmol). The solution was then concentrated to approx. 50 mL and methanol (55 mL) was added followed by addition of di-tert-butyl dicarbonate (2.343 g, 10.73 mmol) and the mixture was stirred for 45 min. Methanol was then removed under vacuum, the residue was diluted with water (25 mL) and washed with petroleum ether. The aqueous phase was acidified to pH=1-2 by addition of 2 M HCl, and then extracted with DCM (50 ml). The organic phase was dried over MgSO$_4$, filtered and evaporated to dryness to give (4R)-1-(tert-butoxycarbonyl)-4-(2,3,6-trifluorophenyl)pyrrolidine-2-carboxylic acid as a light beige powder. Yield: 2.8 g, 83%.

Step 11-14: (R)-1-methyl-6-(2,3,6-trifluorophenyl)-2,5,6,7-tetrahydro-3H-pyrrolo[1,2-c]imidazole-3-thione

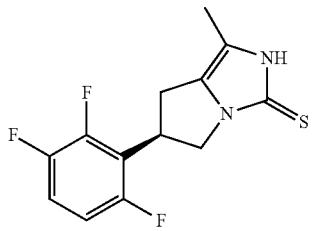 [SMILES: Cc1[nH]c(=S)n2c1C[C@H](c1c(F)ccc(F)c1F)C2]

Compound was prepared in an analogous manner to Example 122 (Steps 6-9) from (4R)-1-(tert-butoxycarbonyl)-4-(2,3,6-trifluorophenyl)pyrrolidine-2-carboxylic acid and isolated as an off-white powder.

$^1$H NMR (DMSO-d6): 11.72 (1H, br s), 7.47 (1H, qd, J=9.4, 5.0 Hz), 7.17 (1H, tdd, J=9.6, 9.6, 3.7, 1.9 Hz), 4.43 (1H, quin, J=8.7 Hz), 4.14 (1H, dd, J=11.3, 9.2 Hz), 3.73 (1H, dd, J=11.5, 8.1 Hz), 3.24 (1H, dd, J=15.6, 9.2 Hz), 2.86 (1H, dd, J=15.4, 8.4 Hz), 1.97 (3H, s).

$^{13}$C NMR (DMSO-d6): 156.9, 156.9, 156.9, 156.9, 155.3, 155.3, 155.3, 155.3, 155, 149.1, 149, 149, 148.9, 147.5, 147.5, 147.4, 147.4, 147.3, 147.3, 145.9, 145.9, 145.8, 145.8, 127.6, 118.9, 118.8, 118.8, 118.7, 116.5, 116.4, 116.3, 116.3, 115.2, 112, 112, 111.9, 111.9, 111.8, 111.8, 111.7, 48.4, 35.7, 28.6, 9.3.

Example 130: (R)-6-(5-bromo-2-fluorophenyl)-1-methyl-2,5,6,7-tetrahydro-3H-pyrrolo[1,2-c]imidazole-3-thione

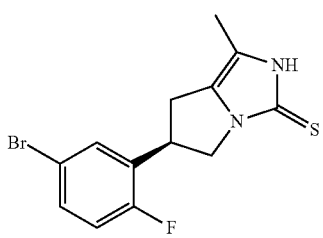 [SMILES: Cc1[nH]c(=S)n2c1C[C@H](c1cc(Br)ccc1F)C2]

Compound was prepared in an analogous manner to Example 129 from 5-bromo-2-fluorobenzaldehyde and isolated as an off-white solid.

$^1$H NMR (DMSO-d6): 11.70 (1H, br s), 7.58 (1H, dd, J=6.6, 2.5 Hz), 7.53 (1H, ddd, J=8.7, 4.5, 2.5 Hz), 7.23 (1H, dd, J=10.3, 8.7 Hz), 4.20 (1H, quin, J=8.1 Hz), 4.11 (1H, dd, J=10.9, 8.2 Hz), 3.71 (1H, dd, J=11.3, 7.9 Hz), 3.18 (1H, dd, J=15.2, 8.1 Hz), 2.85 (1H, ddd, J=15.2, 8.4, 1.1 Hz), 1.98 (3H, s).

$^{13}$C NMR (DMSO-d6): 160.3, 158.7, 155.1, 131.8, 131.8, 131.4, 131.4, 130.6, 130.5, 127.6, 118, 117.9, 116.5, 116.4, 115.4, 49, 40.5, 29, 9.3.

Example 131: (R)-6-(2,6-difluorophenyl)-1-methyl-2,5,6,7-tetrahydro-3H-pyrrolo[1,2-c]imidazole-3-thione

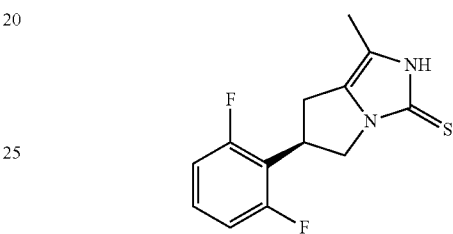

Compound was prepared in an analogous manner to Example 129 from 2,6-difluorobenzaldehyde and isolated as an off-white solid.

$^1$H NMR (DMSO-d6): 11.72 (1H, br s), 7.40 (1H, tt, J=8.4, 6.6 Hz), 7.13 (2H, m), 4.41 (1H, quin, J=8.8 Hz), 4.12 (1H, m), 3.70 (1H, dd, J=11.4, 8.4 Hz), 3.21 (1H, dd, J=15.2, 9.2 Hz), 2.84 (1H, dd, J=15.4, 8.7 Hz), 1.97 (3H, s).

$^{13}$C NMR (DMSO-d6): 161.6, 161.6, 160, 159.9, 155, 129.8, 129.7, 129.7, 127.8, 116.6, 116.5, 116.4, 115.2, 112.3, 112.2, 112.1, 112.1, 48.6, 35.4, 28.8, 9.3.

Example 132: (S)-6-(5-chloro-2-fluorophenyl)-1-methyl-2,5,6,7-tetrahydro-3H-pyrrolo[1,2-c]imidazole-3-thione

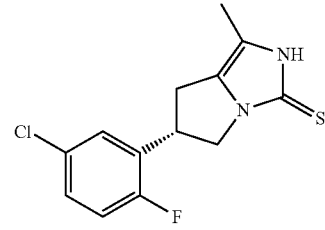 [SMILES: Cc1[nH]c(=S)n2c1C[C@@H](c1cc(Cl)ccc1F)C2]

Compound was prepared in an analogous manner to Example 129 from 5-chloro-2-fluorobenzaldehyde using 4-((R)-hydroxy((1S,2S,4S,5R)-5-vinylquinuclidin-2-yl)methyl)quinolin-6-ol as catalyst (CAS #524-63-0) and isolated as a beige solid.

$^1$H NMR (DMSO-d6): 11.70 (1H, br s), 7.46 (1H, dd, J=6.5, 2.7 Hz), 7.40 (1H, ddd, J=8.8, 4.4, 2.6 Hz), 7.29 (1H, dd, J=10.1, 8.8 Hz), 4.20 (1H, quin, J=8.1 Hz), 4.11 (1H, dd, J=10.8, 8.1 Hz), 3.72 (1H, dd, J=11.3, 7.9 Hz), 3.18 (1H, dd, J=15.1, 8.1 Hz), 2.85 (1H, ddd, J=15.2, 8.3, 1.2 Hz), 1.98 (3H, s).

$^{13}$C NMR (DMSO-d6): 159.8, 158.2, 155.1, 130.2, 130.1, 128.9, 128.8, 128.5, 128.5, 127.6, 117.6, 117.4, 115.5, 49.1, 49.1, 40.5, 29, 9.3.

G. Dopamine-β-Hydroxylase Inhibition Assays

The ability of a compound to inhibit DβH activity may be assessed using the following cell assay. For the purposes of the present invention, a compound is considered to be a "DβH inhibitor" if it exhibits activity in "% of control" of ≤20% at 10 μm in this cell assay. Preferred compounds of the present invention (including most of the specific Examples above) exhibit activity in "% of control" of ≤50% at 1.0 μm in this cell assay. More preferred compounds of the present invention exhibit activity in "% of control" of ≤20% at 1.0 μm in this cell assay. Especially preferred compounds of the present invention exhibit activity in "% of control" of ≤50% at 100 nm in this assay.

SK—N—SH cells (ATCC HTB-11), obtained from LGC Standards (Teddington, UK) were cultured in Eagle's minimum essential medium supplemented with 25 mM Hepes, 100 U/mL penicillin G, 0.25 μg/mL amphotericin B, 100 μg/mL streptomycin and 10% Gibco® fetal bovine serum. Cells were grown in T162 cm flasks (Corning, N.Y.) in a humidified atmosphere of 5% $CO_2$-95% air at 37° C. Fetal bovine serum was removed from cells for 4 h prior to collection.

For the preparation of cellular homogenates, media was removed and cell monolayers were washed with 50 mM Tris-HCl pH 7.4. Cells were subsequently scrapped off the flasks and were resuspended in 50 mM Tris pH 7.4. Cell suspensions were homogenized with SilentCrusher M (Heidolph) for a short stroke and resultant homogenates were aliquoted and stored frozen at −80° C.

Total protein was quantified in cellular homogenates with BioRad Protein Assay (BioRad) using a standard curve of BSA (50-250 μg/mL).

DβH activity was measured by a modification of the method of Nagatsu and Udenfriend (Nagatsu, T. and S. Udenfriend: "Photometric assay of dopamine-hydroxylase activity in human blood." Clin. Chem. 18(9): 980-3, 1972) which is based on the enzymatic hydroxylation of tyramine into octopamine. The octopamine formed is subsequently oxidized to p-hydroxybenzaldehyde and measured by spectrophotometry. In brief, reaction mixture (total volume 500 μl) contained: cellular homogenate (75 μg total protein) sodium acetate pH 5.0 (200 mM), NEM (30 mM), $CuSO_4$ (5 μM), catalase aqueous solution (0.5 mg/mL), pargyline-HCl (1 mM), sodium fumarate (10 mM), ascorbic acid (10 mM), inhibitor or vehicle and tyramine (25 mM). After a 10 min pre-incubation period at 37° C., the reaction was initiated by the addition of tyramine. Reaction was carried out for 45 min at 37° C. before termination with 50 μl PCA (2 M).

Samples were centrifuged for 3 min at 16100 g and supernatants were subjected to solid phase extraction. Solid phase extraction was performed using either SPE cartridges ISOLUTE SCX-3 (100 mg, 1 mL) or SPE 2 mL fixed 96 well plates ISOLUTE SCX-3 (100 mg) previously equilibrated with MilliQ water. Columns/plates were centrifuged at 150 g for 2 min. Eluate was discarded and matrix was washed with 1 mL of MilliQ water after which octopamine was eluted with 2×0.25 mL ammonium hydroxide (4 M). The oxidation of octopamine to p-hydroxybenzaldehyde was carried out for 6 min with 100 μl sodium periodate (2%) and was stopped with 100 μl sodium metabisulfite (10%). Absorbance was measured at 330 nm on a Spectramax microplate reader (Molecular Devices, Sunnyvale, Calif.).

All enzymatic reactions were performed in duplicate. Results are reported in the table below as activity in % of control at the inhibitor concentration tested.

Furthermore, the ability of a compound to inhibit DβH activity may be assessed in human plasma using the following assay. For the purposes of the present invention, a compound is considered to be a "DβH inhibitor" if it exhibits activity in "% of control" of ≤20% at 10 μm in this assay. Preferred compounds of the present invention (including most of the specific Examples above) exhibit activity in "% of control" of ≤50% at 1.0 μm in this cell assay. More preferred compounds of the present invention exhibit activity in "% of control" of ≤20% at 1.0 μm in this cell assay. Especially preferred compounds of the present invention exhibit activity in "% of control" of ≤50% at 100 nm in this assay.

Dopamine beta hydroxylase activity in human plasma was measured by the method previously developed (Nagatsu, T. and Udenfriend, S. Photometric assay of dopamine-β-hydroxylase activity in human blood. Clin. Chem. 18(9) 980-983, 1972) with minor modifications. Catalase, N-ethylmaleimide, tyramine, disodium fumarate, pargyline, sodium acetate, ascorbic acid, copper sulfate and octopamine were obtained from Sigma Chemical Co., St. Louis, Mo. 63178. Human plasma samples were obtained from healthy donors (Instituto Portugues do Sangue Transplantacao, Centro Sangue Transplantacao, Porto, Portugal). From date of collection, plasma was stored at −80° C. until use. Test compounds were initially prepared in dimethyl sulfoxide at a concentration of 10 mM and diluted in dimethyl sulfoxide to the required concentrations. Test compounds were further diluted in ultrapure water to a concentration 20-fold to that of the final concentration to be tested. Final concentrations of test compounds were 10, 100 and 1000 nM. The various reagents used to make up the incubation buffer were pre-mixed and consisted of the following components: sodium acetate buffer (1 M, pH 5.0, 18 ml), sodium fumarate (0.2 M, 4.5 ml), ascorbic acid (0.2 M, 4.5 ml, freshly prepared), pargyline (20 mM, freshly prepared, 4.5 ml), N-ethylmaleimide (0.2 M, 4.5 ml), catalase (10 000 U/ml, 9 ml), copper sulfate (20 μM, 4.5 ml) and 4.5 ultrapure water. The standard incubation mixture (total volume, 950 μl) contained: 50 μL of compound or vehicle (dimethyl sulfoxide 2%); 700 μL of incubation buffer; 125 μl of plasma (or saline for blank reaction or standard curve); 75 μl of saline. The reaction mixture was placed in water bath, shaking at 37° C. and pre-incubated for 10 minutes. Tyramine (0.5 M) was added and incubation proceeded for 45 minutes. The reaction contents were exposed to air. A sample of enzyme preparation (with 125 μl of plasma) that had been added perchloric acid 2 M at the end of the pre-incubation period was used as blank. A blank for each of the tested compounds was used. For octopamine standard curve, perchloric acid 2 M was replaced by increasing concentrations of octopamine prepared in perchloric acid 2 M (0.5, 1, 2.5, 5, 7.5, 10, 15, 20 μg/ml, final concentration). The incubation was stopped by adding 200 μl of 2 M molar perchloric acid, and the mixture was centrifuged at 9000 g for 5 min. The supernatant fluid (800 μL) was transferred to a column (SPE cartridge ISOLUTE SCX-3, 100 mg) and centrifuged at 150 g for 2 min. The column was washed two more times with 0.5 ml of ultrapure water by centrifuging at 150 g for 2 min. The adsorbed octopamine was eluted twice with 0.3 ml of 4 M ammonium hydroxide by centrifuging at 150 g for 2 min. Octopamine in the eluate was then converted to p-hydroxybenzaldehyde by adding 200 μl of sodium periodate (2%) and incubating for 6 min. Excess periodate was than reduced by adding 200 µl of sodium metabisulfite (10%). Absorbance was measured at 330 mm in a 96-well plate by use of a SpectraMAX plus 384 (Molecular Devices) with software SOFTmax® PRO Software 5.3 spectrophotometer. Absorbance was linear with octopamine concentration from 0.5 to 20 µg/ml. Dopamine beta hydroxylase activity is determined as nmol of octopamine formed/ml of plasma/hour and effect of compounds is presented as % control.

Results are reported in the table below (inside brackets) as activity in % of control at the inhibitor concentration tested.

H. MDCK Permeability Screening Assay

Madin-Darby canine kidney (MDCK) is a common cell line to assess membrane permeability of compounds. In this experiment, a value of −6 Log(cm/s) is indicative of a compound which is poorly permeable (e.g. Atenolol Log $P_{app}$=−6.2 Log(cm/s)) whilst a value of −4 Log(cm/s) is indicative of a compound which is highly permeable (e.g. Propranolol Log $P_{app}$=−4.2 Log(cm/s)). Preferred compounds of the present invention (including some of the specific Examples above (other Examples have not been tested)) exhibit a Log $P_{app}$ higher than −6 Log(cm/s) in this assay. More preferred compounds of the present invention exhibit a $P_{app}$ higher than −5 Log(cm/s) in this assay. Especially preferred compounds of the present invention exhibit a Log $P_{app}$ higher than −4.5 Log(cm/s) in this assay.

MDCK-II cells (canine) were grown in MEM supplemented with 100 U/mL penicillin G, 0.25 µg/mL amphotericin B, 100 µg/mL streptomycin, 10% fetal bovine serum and 25 nM Hepes and maintained in a humified atmosphere of 5% $CO_2$-95% air at 37° C. for 4 to 5 days. Transport experiments are performed in collagen treated 0.4 µm polycarbonate filter support (12 mm ID, transwell, Costar-Corning) with compounds being applied from the apical (AP) cell border. The upper and lower chambers contained 400 and 1000 µL of Hank's Balance Salt Solution (HBSS), respectively. On the day of the experiments, cells were washed with HBSS, pH 7.4 and after a 5 min. pre-incubation period under gentle agitation, experiments were started by the addition of test compounds. Compounds are diluted in HBSS in order to have a final concentration of 50 µM with less than 1% DMSO. After 30 min. incubation, 250 µL of medium was taken from the lower side to determine the optical transport. Samples were mixed with equal volume of acetonitrile with 0.1% formic acid and injected directly onto the LC-MS column.

Apparent permeability coefficients ($P_{app}$) were calculated using the following equation:

$$P_{app} = \frac{V}{AC_0} \times \frac{dC}{dt}$$

Where V is the volume of the solution in the receiving compartment, A is the membrane surface area, Co is the initial concentration and dC/dt is the change in the drug concentration in the receiver over time. (Balimane, P. V.; Chong, S and Morrison, R. A.: *J. Pharmacol. Toxicol. Methods*, 44(1), 301-312, 2000). Results are reported as Log $P_{app}$ in Log(cm/s).

I. Evaluation of Pharmacokinetic Profile

Adult male Wistar rats were kept under controlled environmental conditions (12 h light/dark cycle, room temperature 22±1° C. and humidity 50±5%, food and tap water ad libitum). On the day before the experiment, the animals were fasted. In experiments designed to evaluate the pharmacokinetic profile of the compound of Examples 54, 61, 73, 74, 86 and 113, rats (n=4 per group) were administered orally (p.o.) with compounds (10 mg/kg/4 ml; vehicle: 40% kleptose) and plasma and brain samples were collected from anaesthetized animals at 0.5, 1, 2, 4, 8, 15 and 24 h post-dosing. Animals were anaesthetized by intraperitoneal administration of sodium pentobarbital (60 mg/kg). Blood was collected from cardiac punction into heparinised tubes and kept on ice until centrifugation at 1,500 g for 15 min at 4° C. Plasma and brain samples were stored at less than −20° C. until analysis.

After thawing, 200 µl of acetonitrile with 0.1% formic acid was added to 100 µL of plasma. The samples were vortexed and centrifuged for 10 min at 10 000 g. Supernatant was filtered and injected into a mass spectrometer.

After thawing and weighing, water was added to the brain to give a tissue concentration of 0.1 mg/ml. The samples were then homogenized using a Heidolph DIAX 900 mixer and transferred to plastic tubes. Following centrifugation at 10 000 g for 20 min, supernatant was taken and treated as described for plasma.

J. DβH Activity in Rat Adrenal Gland Homogenates

Dopamine beta hydroxylase activity in rat adrenal gland homogenates was measured by the method previously developed (Nagatsu, T. and Udenfriend, S. Photometric assay of dopamine-β-hydroxylase activity in human blood. Clin. Chem. 18(9) 980-983, 1972) with minor modifications. Catalase, N-ethylmaleimide, tyramine, disodium fumarate, pargyline, sodium acetate, ascorbic acid, copper sulfate and octopamine were obtained from Sigma Chemical Co., St. Louis, Mo. 63178. Test compounds were prepared in kleptose 40% at a concentration of 0.75, 2.5 or 7.5 mg/mL to be administered at a dose of 10 mg/kg. Compounds and vehicle (kleptose 40%) were administered to wistar rats and adrenals were collected 0.5 h, 1 h, 2 h, 4 h, 8 h, 15 h and 24 h after administration. Samples were constituted by the right and left adrenals of each animal. Adrenals were stored in 200 µL of 50 mM Tris pH 7.4 at −30° C., from date of collection. The samples were homogenized and homogenates were then quantified for protein. Protein concentration was adjusted to 1.6 mg/ml. The various reagents used to make up the incubation buffer were premixed and consisted of the following components: sodium acetate buffer (1 M, pH 5.0, 6.0 mL), sodium fumarate (0.2 M, 1.5 mL), ascorbic acid (0.2 M, 1.5 mL, freshly prepared), pargyline (20 mM, freshly prepared, 1.5 mL), N-ethylmaleimide (0.2 M, 1.5 mL), catalase (55 000 U/ml, 3 mL), copper sulfate (90 µM, 1.67 mL) and ultrapure water (1.33 mL). The standard incubation mixture (total volume, 500 µL) contained: 350 µL of incubation buffer; 125 µL of protein sample (or buffer for blank reaction or standard curve). The reaction mixture was placed in water bath with shaking at 37° C. and pre-incubated for 10 minutes. Tyramine (0.4 M, 25 µL) was added and incubation proceeded for 45 minutes. The reaction contents were exposed to air. A sample of enzyme preparation (with 125 µL of protein sample) that had been added perchloric acid 2 M at the end of the pre-incubation period was used as blank. A blank for each of the tested compounds was used. For octopamine standard curve, perchloric acid 2 M was replaced by increasing concentrations of octopamine prepared in perchloric acid 2 M (0.5, 1, 2.5, 5, 7.5, 10 µg/mL, final concentration). The incubation was stopped by adding 50 μL of 2 M molar perchloric acid, and the mixture was centrifuged at 16000 g for 3 min. The supernatant fluid (500 μL) was transferred to a column (SPE cartridge ISOLUTE SCX-3, 100 mg) and centrifuged at 150 g for 2 min. The column was washed two more times with 0.5 ml of ultrapure water by centrifuging at 150 g for 2 min. The adsorbed octopamine was eluted twice with 250 μL of 4 M ammonium hydroxide by centrifuging at 150 g for 2 min. Octopamine in the eluate was then converted to p-hydroxybenzaldehyde by adding 100 μL of sodium periodate (2%) and incubating for 6 min. Excess periodate was than reduced by adding 100 μl of sodium metabisulfite (10%). Absorbance was measured at 330 mm in a 96 well plate by use of a SpectraMAX plus 384 (Molecular Devices) with software SOFTmax® PRO Software 5.3 spectrophotometer. Absorbance was linear with octopamine concentration from 0.5 to 10 μg/mL. Dopamine beta hydroxylase activity is determined as nmol of octopamine formed/mg of protein/hour and effect of compounds is presented as % of control.

K. Biological Data

In Vitro Experiments:

| Example | DβH activity in % of Ctrl (0.1 μM) | DβH activity in % of Ctrl (1 μM) | DβH activity in % of Ctrl (10 μM) | MDCK Permeability LogP$_{app}$ (Log(cm/s)) |
|---|---|---|---|---|
| 1 | 75.6 | 42.4 | 4 | −4.2 |
| 2 | 54.9 | | 0 | −3.9 |
| 3 | 89.0 | 53.8 | 3.9 | |
| 4 | | | 18.6 | |
| 5 | 83.2 | | 0.8 | |
| 6 | 97.6 | 50.3 | 3.3 | |
| 7 | 84.8 | 37.7 | 7.5 | −4 |
| 8 | | 14.5 | 2.2 | −3.9 |
| 9 | | 30.9 | 5.3 | −3.6 |
| 10 | 54.9 | 2.7 | 0 | −3.9 |
| 11 | 86.4 | 31.4 | 1.5 | |
| 12 | 63.0 | 11.5 | 0 | −4.1 |
| 13 | | | 7.2 | |
| 14 | | | 13.1 | |
| 15 | 50.1 | 9.3 | | −4.1 |
| 16 | | 55.5 | | |
| 17 | | 56.8 | | −4.1 |
| 18 | 57.0 | 6.4 | | |
| 19 | | 33.4 | | |
| 20 | | 44.8 | | |
| 21 | | 17.5 | | |
| 22 | | 27.4 | | |
| 23 | 5.9 | 0 | | −4 |
| 24 | 40.2 | 15.9 | | −4 |
| 25 | 46.1 | 6.7 | | −4 |
| 26 | | 21.4 | | −4 |
| 27 | | 20.8 | | −3.9 |
| 28 | 0.2 | 3.3 | | |
| 29 | 26.9 | | | |
| 30 | 3.3 | 2.8 | | −3.9 |
| 31 | | | 15.8 | −4.1 |
| 32 | 57.3 | 4.7 | | −4 |
| 33 | 11.8 | 1.0 | | |
| 34 | 12.3 | 0 | | −4.2 |
| 35 | 95.0 | 34.3 | 0 | |
| 36 | 4.0 | 0 | | |
| 37 | 59.7 | 2.4 | | −4.1 |
| 38 | 3.3 | 0 | | −4.1 |
| 39 | 40.4 | 0.3 | | |
| 40 | 87.9 | | | |
| 41 | 29.8 | 0 | | |
| 42 | | 44.1 | | −4 |
| 43 | 43.6 | 0 | | −3.7 |
| 44 | | 70.9 | 13.7 | |
| 45 | | 29.1 | | |
| 46 | | 31.6 | | |
| 47 | | 45.3 | | |
| 48 | | 43.0 | | |
| 49 | | 60.6 | | −4 |
| 50 | 89.3 | 36.6 | 6.8 | −3.9 |
| 51 | | 54.4 | | −4 |
| 52 | | 27.3 | | −4 |
| 53 | 66.5 | 11.8 | | −4.6 |
| 54 | 44.3 | 8.2 | | −4.6 |
| 55 | 61.0 | 0.4 | | −4.1 |
| 56 | 41.7 | 7.8 | | −4.8 |
| 57 | 97.9 | 58.6 | 9.2 | −4.2 |
| 58 | 106.5 | 59.8 | | −3.9 |
| 59 | 100.1 | 27.8 | | −3.6 |
| 60 | | 60.2 | | |
| 61 | 52.2 | 8.4 | | |

-continued

| Example | DβH activity in % of Ctrl (0.1 μM) | DβH activity in % of Ctrl (1 μM) | DβH activity in % of Ctrl (10 μM) | MDCK Permeability LogP$_{app}$ (Log(cm/s)) |
|---|---|---|---|---|
| 62 | 43.1 | 9.8 | | |
| 63 | | 13.9 | | |
| 64 | 39.9 | 7.2 | | |
| 65 | | 17.9 | | |
| 66 | 51.1 | 7.9 | | |
| 67 | | 36.1 | | |
| 68 | | 5.1 | | |
| 69 | | 14.6 | | |
| 70 | | 35.7 | | |
| 71 | | 48.5 | | |
| 72 | | 35.0 | | |
| 73 | 41.7 | 5.1 | | |
| 74 | 21.9 | 1.8 | | |
| 75 | | 18.1 | | |
| 76 | | 17.4 | | |
| 77 | | 23.0 | | |
| 78 | | 10.9 | | |
| 79 | | 13.0 | | |
| 80 | | 56.7 | | |
| 81 | | 59.4 | | |
| 82 | 90.0 | 20.0 | | |
| 83 | 84.0 | 33.1 | | |
| 84 | 96.9 | 41.9 | | |
| 85 | 0 | 0 | | |
| 86 | 25.3 | 0 | | |
| 87 | 36.5 | 0 | | |
| 88 | 45.8 | 6.2 | | |
| 89 | | 29.8 | | |
| 90 | 1.8 | 1.0 | | |
| 91 | 22.0 | 0 | | |
| 92 | 2.0 | 0 | | |
| 93 | 0 | 0 | | |
| 94 | 18.1 | 0 | | |
| 95 | | 28.9 | | |
| 96 | 32.0 (57.3)* | 15.0 | | |
| 97 | 41.9 (74.1)* | 7.9 | | |
| 98 | | 39.9 | | |
| 99 | 31.6 (38.3)* | 1 | | |
| 100 | 0 | 0 | | |
| 101 | 14.5 | 0 | | |
| 102 | 32.0 | 0 | | |
| 103 | 63.4 | 10.3 | | |
| 104 | 47.5 | 6.0 | | |
| 105 | 17.4 | 0 | | |
| 106 | | 16.3 | | |
| 107 | | 54.7 | | |
| 108 | | 38.8 | | |
| 109 | 67.5 | 17.2 | | |
| 110 | 73.8 | 15.9 | | |
| 111 | | 48.3 | | |
| 112 | 70 | 10.1 | | |
| 113 | 39.6 | 0 | | |
| 114 | 70.8 | 15.2 | | |
| 115 | 0.5 | 0 | | |
| 116 | 24.8 | 0 | | |
| 117 | 6.4 | 0 | | |
| 118 | 33.8 | 0 | | |
| 119 | 49.1 | 4.5 | | |
| 120 | 86.4 | 21.8 | | |
| 121 | 5.2 | 0 | | |
| 122 | (9.8)* | | | |
| 123 | (4.7)* | | | |
| 124 | (23.8)* | | | |
| 125 | (12.1)* | | | |
| 126 | (49.9)* | | | |
| 127 | (10.0)* | | | |
| 128 | (39.1)* | | | |
| 129 | (27.7)* | | | |
| 130 | (88.8)* | | | |
| 131 | (0.5)* | | | |
| 132 | (67.0)* | | | |

*numbers in brackets represent activity in % of control in human plasma assay

In Vivo Experiments:

Mean concentration-time profile of the compound of Example 54 in plasma and brain after oral administration of 10 mg/kg, to Wistar rats is shown in FIG. 1. Each point represents mean±SD of 4 rats.

Figure 2:
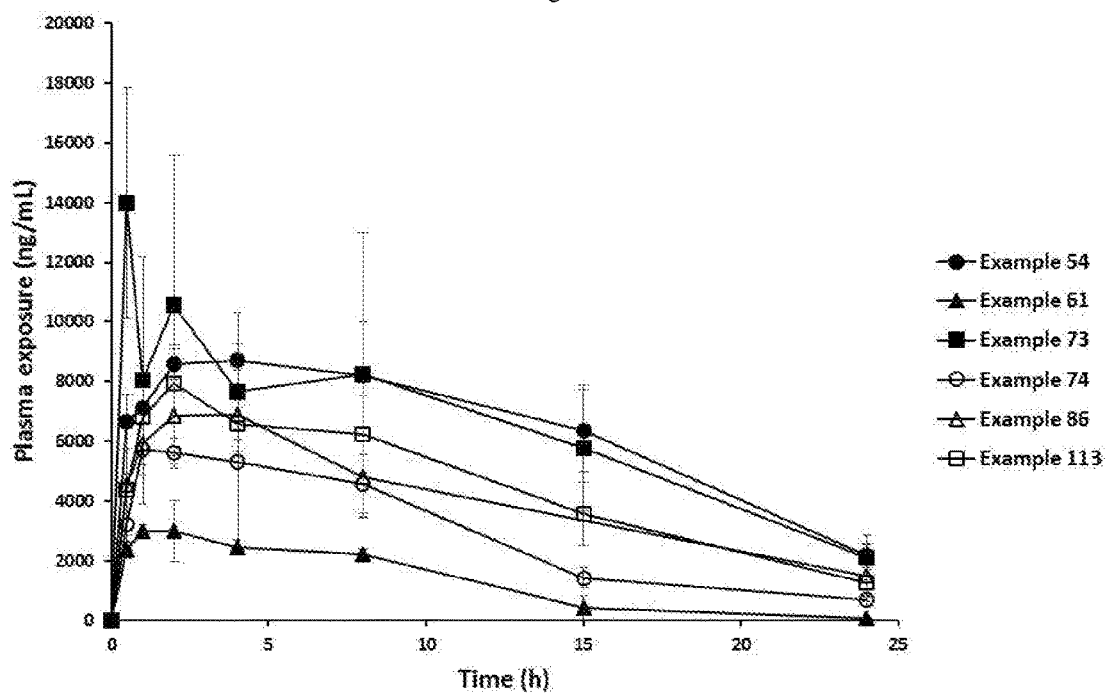
FIG. 2 shows mean concentration-time profile of the compounds of Example 54, 61, 73, 74, 86 and 113 in rat plasma after oral administration of 10 mg/kg to Wistar rats. Each point represents mean±SD of 4 rats.

Mean concentration-time profile of the compounds of Example 54, 61, 73, 74, 86 and 113 in plasma after oral administration of 10 mg/kg to Wistar rats is shown in FIG. 2. Each point represents mean±SD of 4 rats.

Figure 3:
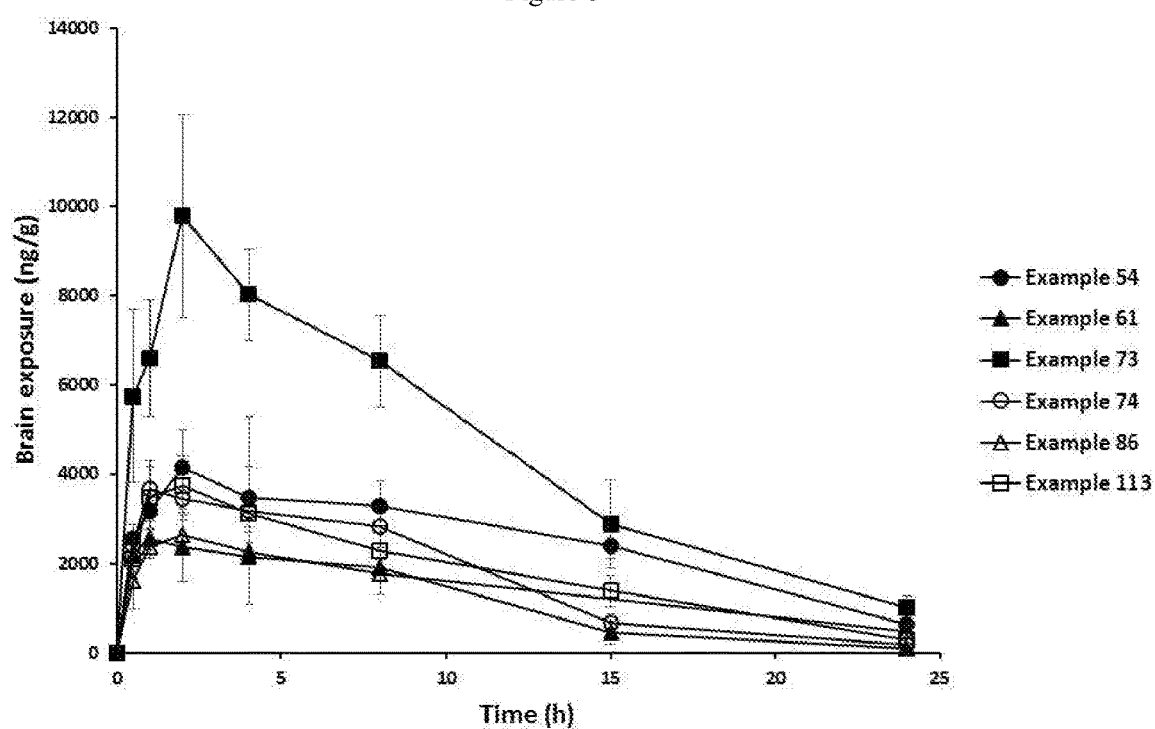
FIG. 3 shows mean concentration-time profile of the compounds of Example 54, 61, 73, 74, 86 and 113 in rat brain after oral administration of 10 mg/kg to Wistar rats. Each point represents mean±SD of 4 rats.

Mean concentration-time profile of the compounds of Example 54, 61, 73, 74, 86 and 113 in brain after oral administration of 10 mg/kg to Wistar rats is shown in FIG. 3. Each point represents mean±SD of 4 rats.

Figure 4:
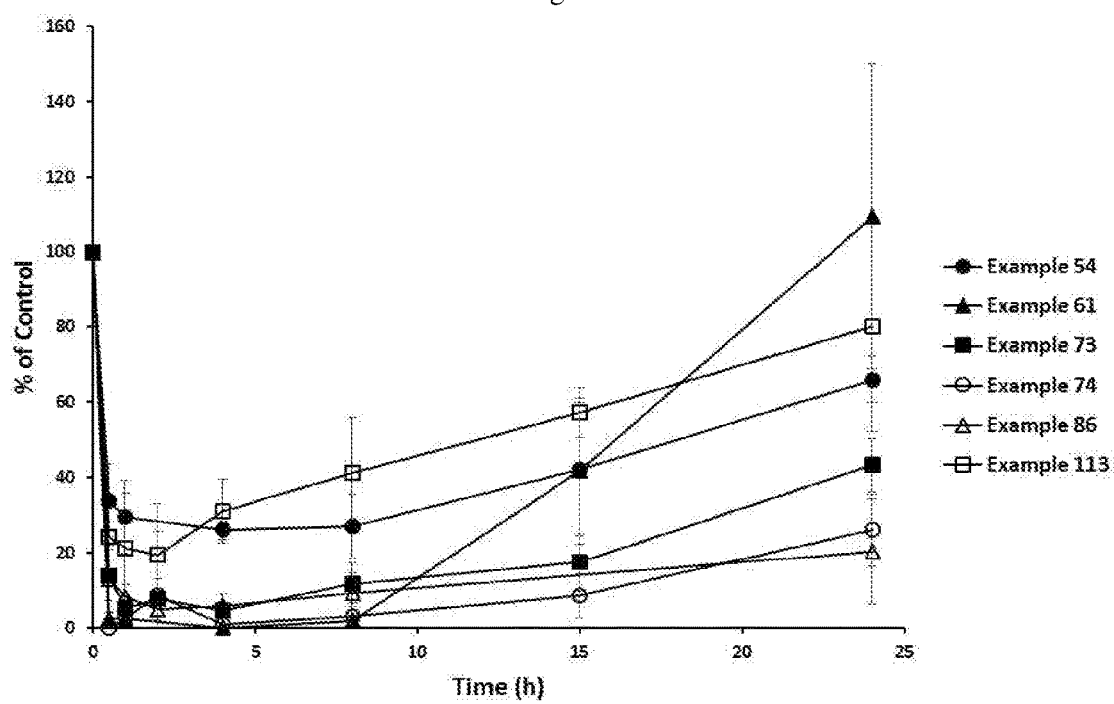
FIG. 4 shows DβH activity in rat ADR after oral administration of 10 mg/kg of compounds of Example 54, 61, 73, 74, 86 and 113. Each point represents mean±SD of 4 rats.

DβH activity in ADR after oral administration of 10 mg/kg of compounds of Example 54, 61, 73, 74, 86 and 113 is shown in FIG. 4. Each point represents mean±SD of 4 rats.

The invention claimed is:
1. A pharmaceutical composition comprising
(i) a compound of formula (Ia), or a pharmaceutically acceptable salt or solvate thereof:

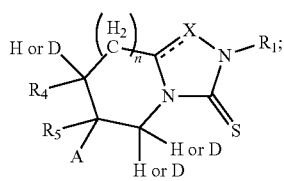

and
(ii) a pharmaceutically acceptable excipient, wherein:
$R_1$ is hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl or amino;
X is $CR_6$;
------ is a double bond;
$R_4$ is hydrogen or $C_1$-$C_3$ alkyl;
$R_5$ is hydrogen or $C_1$-$C_2$ alkyl;
$R_6$ is hydrogen;
A is $C_5$-$C_7$ cycloalkyl, furanyl, thiophenyl, methylthiophenyl or

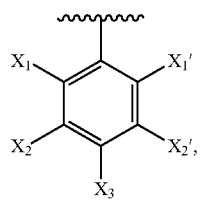

wherein:
$X_1$ is hydrogen, halo or methyl;
$X_1'$ is hydrogen or halo;
$X_2$ is hydrogen, halo or methyl;
$X_2'$ is hydrogen or halo;
$X_3$ is hydrogen or fluoro;
n is 0 or 1, and when n is 0, a single bond joins the carbon atoms to which X and $R_4$ are attached.

2. A pharmaceutical composition according to claim 1, wherein n is 0 and a single bond joins the carbon atoms to which X and $R_4$ are attached.

3. A pharmaceutical composition according to claim 1, wherein A is

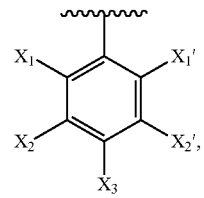

wherein $X_1$, $X_1'$, $X_2$, $X_2'$ and $X_3$ are as defined in claim 1.

4. A pharmaceutical composition according to claim 1, wherein $R_1$ is hydrogen, methyl, d3-methyl, propyl, cyclopropyl, cyanomethyl, mercaptoethyl or amino.

5. A pharmaceutical composition according to claim 1, wherein $R_4$ is hydrogen or methyl.

6. A pharmaceutical composition according to claim 1, wherein $R_5$ is hydrogen or methyl.

7. A pharmaceutical composition according to claim 1, wherein A is

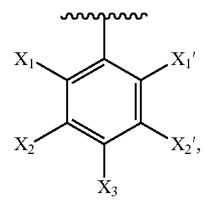

wherein:
$X_1$ is hydrogen, fluoro, chloro or methyl;
$X_1'$ is hydrogen, fluoro or chloro;
$X_2$ is hydrogen, fluoro, chloro, bromo or methyl;
$X_2'$ is hydrogen, fluoro, chloro or bromo;
$X_3$ is hydrogen or fluoro.

8. A compound of formula (Ia), or a pharmaceutically acceptable salt or solvate thereof:

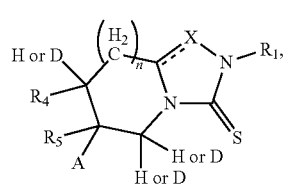

wherein:
$R_1$ is hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl or amino;
X is $CR_6$;
------ is a double bond;
$R_4$ is hydrogen or $C_1$-$C_3$ alkyl;
$R_6$ is hydrogen or $C_1$-$C_2$ alkyl;
$R_6$ is hydrogen;
A is $C_5$-$C_7$ cycloalkyl, furanyl, thiophenyl, methylthiophenyl or

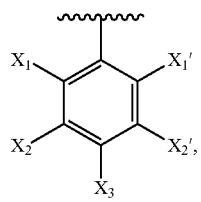

wherein:
- $X_1$ is hydrogen, halo or methyl;
- $X_1'$ is hydrogen or halo;
- $X_2$ is hydrogen, halo or methyl;
- $X_2'$ is hydrogen or halo;
- $X_3$ is hydrogen or fluoro;
- n is 0 or 1, and when n is 0, a single bond joins the carbon atoms to which X and $R_4$ are attached.

9. A compound according to claim 8, wherein n is 0 and a single bond joins the carbon atoms to which X and $R_4$ are attached.

10. A compound according to claim 8, wherein A is

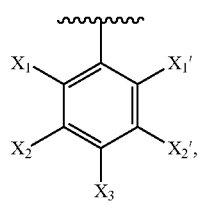

wherein
- $X_1$ is hydrogen, halo or methyl;
- $X_1'$ is hydrogen or halo;
- $X_2$ is hydrogen, halo or methyl;
- $X_2'$ is hydrogen or halo; and
- $X_3$ is hydrogen or fluoro.

11. A compound according to claim 8, wherein $R_1$ is hydrogen, methyl, d3-methyl, propyl, cyclopropyl, cyanomethyl, mercaptoethyl or amino.

12. A compound according to claim 8, wherein $R_4$ is hydrogen or methyl.

13. A compound according to claim 8, wherein $R_5$ is hydrogen or methyl.

14. A compound according to claim 8, wherein A is

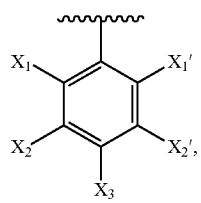

wherein:
- $X_1$ is hydrogen, fluoro, chloro or methyl;
- $X_1'$ is hydrogen, fluoro or chloro;
- $X_2$ is hydrogen, fluoro, chloro, bromo or methyl;
- $X_2'$ is hydrogen, fluoro, chloro or bromo;
- $X_3$ is hydrogen or fluoro.

15. A compound according to claim 8, wherein the compound is selected from the group consisting of:

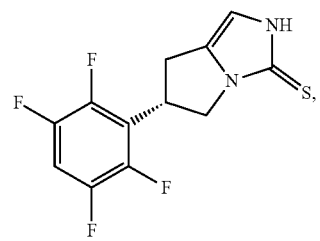 [SMILES: Fc1cc(F)c(F)c([C@@H]2Cc3c[nH]c(=S)n3C2)c1F]

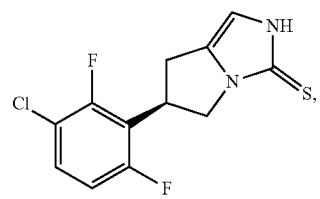

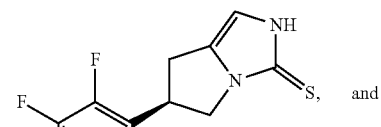

and

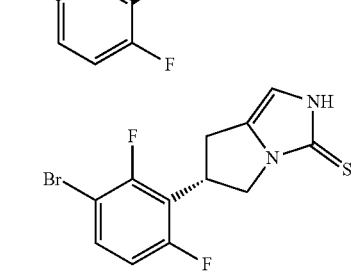

or a pharmaceutically acceptable salt or solvate thereof.

16. A compound according to claim 8, wherein the compound is

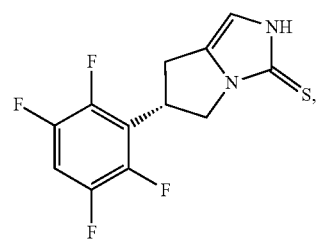

or a pharmaceutically acceptable salt or solvate thereof.

17. A compound according to claim 8, wherein the compound is

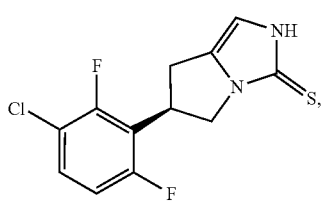 [SMILES: Fc1ccc(Cl)c(F)c1[C@H]1Cc2c[nH]c(=S)n2C1]

or a pharmaceutically acceptable salt or solvate thereof.

18. A compound according to claim 8, wherein the compound is

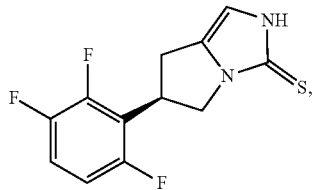 [SMILES: Fc1ccc(F)c([C@H]2Cc3c[nH]c(=S)n3C2)c1F]

or a pharmaceutically acceptable salt or solvate thereof.

19. A compound according to claim 8, wherein the compound is

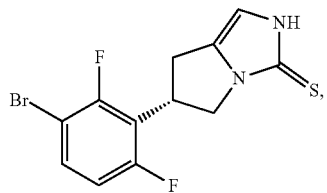 [SMILES: Fc1ccc(Br)c(F)c1[C@@H]1Cc2c[nH]c(=S)n2C1]

or a pharmaceutically acceptable salt or solvate thereof.

20. A method for treating conditions ameliorated by inhibition of dopamine-beta-hydroxylase within the central nervous system comprising administering a therapeutically effective amount of a compound of formula (Ia), as defined in claim 1, or a pharmaceutically acceptable salt or solvate thereof, to a patient in need thereof.

21. The method according to claim 20, wherein the condition is selected from the group consisting of cocaine addiction, alcohol addiction, adjunct opioid addiction, cognition decline in frontotemporal dementia, cognition decline in mild cognitive impairment, cognition decline in Alzheimer's disease, attention deficit-hyperactive disorder, post-traumatic stress disorder and unipolar depression.

* * * * *